(12) United States Patent
Makriyannis et al.

(10) Patent No.: US 11,746,113 B2
(45) Date of Patent: Sep. 5, 2023

(54) LABELLED CANNABINERGIC LIGANDS AND RELATED ANALOGS

(71) Applicants: Alexandros Makriyannis, Watertown, MA (US); Spyridon P. Nikas, Newton, MA (US); Christos Iliopoulos Tsoutsouvas, Allston, MA (US); Shashank Kulkarni, Billerica, MA (US); Lipin Ji, Malden, MA (US)

(72) Inventors: Alexandros Makriyannis, Watertown, MA (US); Spyridon P. Nikas, Newton, MA (US); Christos Iliopoulos Tsoutsouvas, Allston, MA (US); Shashank Kulkarni, Billerica, MA (US); Lipin Ji, Malden, MA (US)

( * ) Notice: Subject to any disclaimer, the term of this patent is extended or adjusted under 35 U.S.C. 154(b) by 40 days.

(21) Appl. No.: 17/205,300

(22) Filed: Mar. 18, 2021

(65) Prior Publication Data
US 2021/0300937 A1    Sep. 30, 2021

Related U.S. Application Data

(60) Provisional application No. 62/992,130, filed on Mar. 19, 2020.

(51) Int. Cl.
| | | |
|---|---|---|
| C07D 491/16 | (2006.01) | |
| C07D 495/04 | (2006.01) | |
| C07D 413/14 | (2006.01) | |
| C07D 407/12 | (2006.01) | |
| C07D 405/06 | (2006.01) | |
| C07D 311/78 | (2006.01) | |
| C07D 405/14 | (2006.01) | |

(52) U.S. Cl.
CPC ......... *C07D 491/16* (2013.01); *C07D 311/78* (2013.01); *C07D 405/06* (2013.01); *C07D 405/14* (2013.01); *C07D 407/12* (2013.01); *C07D 413/14* (2013.01); *C07D 495/04* (2013.01)

(58) Field of Classification Search
None
See application file for complete search history.

(56) References Cited

U.S. PATENT DOCUMENTS

| | | |
|---|---|---|
| 7,183,313 B2 | 2/2007 | Makriyannis et al. |
| 7,923,558 B2 | 4/2011 | Arslantas et al. |
| 9,580,400 B2 | 2/2017 | Makriyannis et al. |
| 2006/0264647 A1 | 11/2006 | Field et al. |
| 2009/0143462 A1 | 6/2009 | Stinchcomb et al. |

FOREIGN PATENT DOCUMENTS

WO    2019195207 A1    10/2019

OTHER PUBLICATIONS

Bruno, Agostino et al., "Beyond radio-displacement techniques for Identification of CB1 Ligands: The First Application of a Fluorescence-quenching Assay," Scientific Reports 4, 3757; DOI:10.1038/srep03757 (2014).
Cooper, Anna G. et al., "Alkyl indole-based cannabinoid type 2 receptor tools: Exploration of linker and fluorophore attachment," European Journal of Medicinal Chemistry 145, 770-789 (2018).
Cooper, Anna et al., "Chemical Tools for Studying Lipid-Binding Class A G Protein-Coupled Receptors," Pharmacological Reviews 69, 316-353 (Jul. 2017).
Cooper, Anna G. et al., "Development of selective, fluorescent cannabinoid type 2 receptor ligands based on a 1,8-naphthyridin-2-(1H)-one-3-carboxamide scaffold," Med. Chem. Commun. 9, 2055-2067 (2018).
Iliopoulos-Tsoutsouvas, Christos et al., "Fluorescent probes for G-protein-coupled receptor drug discovery," Expert Opinion on Drug Discovery, 13:10, 933-947 (2018).
Iliopoulos-Tsoutsouvas, Christos et al., "Natural Compounds and Synthetic Drugs to Target Type-1 Cannabinoid (CB1) Receptor," New Tools to Interrogate Endocannabinoid Signalling: From Natural Compounds to Synthetic Drugs, edited by Mauro Maccarrone, Royal Society of Chemistry (2020).
Ling, Xiaoxi et al., "A novel near-infrared fluorescence imaging probe that preferentially binds to cannabinoid receptors CB2R over CB1R," Biomaterials 57, 169-178 (2015).
Ling, Xiaoxi et al., "Light-activatable cannabinoid prodrug for combined and targetspecific photodynamic and cannabinoid therapy," J. Biomed. Opt. 23(10), 108001 (2018).
Martin, Billy R. et al., "Pharmacological Characterization of Novel Water-Soluble Cannabinoids," Journal of Pharmacology and Experimental Therapeutics, vol. 318, No. 3, 1230-1239 (2006).
Martin-Couce, Lidia et al., "Chemical Probes for the Recognition of Cannabinoid Receptors in Native Systems," Angew. Chem. Int. Ed. 51, 6896-6899 (2012).
Martin-Couce, Lidia et al., "Development of Endocannabinoid-Based Chemical Probes for the Study of Cannabinoid Receptors," J. Med. Chem. 54, 5265-5269 (2011).

(Continued)

*Primary Examiner* — Samantha L Shterengarts
(74) *Attorney, Agent, or Firm* — Alix, Yale & Ristas, LLP

(57) ABSTRACT

Novel cannabinoid ligands represented by the general formulas I, II, and III and methods for preparation and use within which one or more of a fluorescent ligand, nitroxide spin label, metal chelate, biotin moiety, or group with enhanced polarity may be incorporated. The compounds can bind to and modulate the cannabinoid CB1 and CB2 receptors and thereby considered specific ligands for these receptors. Some of the disclosed compounds that bind to cannabinoid CB1 and CB2 receptors can exhibit tight or irreversible binding characteristics for these receptors. Due to the presence of the imaging/diagnostic and/or therapeutic functional groups including fluorescent groups, nitroxide spin labels, metal chelates, biotin moieties, and groups with enhanced polarity, the disclosed compounds may be useful as imaging/diagnostic tools and/or therapeutic agents.

10 Claims, 8 Drawing Sheets
(1 of 8 Drawing Sheet(s) Filed in Color)

(56) References Cited

OTHER PUBLICATIONS

Martin-Fontecha, Mar et al., "A Fluorescent Probe to Unravel Functional Features of Cannabinoid Receptor CB1 in Human Blood and Tonsil Immune System Cells," Bioconjugate Chem. 29, 382-389 (2018).
Pertwee, Roger G. et al., "O-1057, a potent water-soluble cannabinoid receptor agonist with antinociceptive properties," British Journal of Pharmacology 129, 1577-1584 (2000).
Petrov, Ravil R. et al., "Design and evaluation of a novel fluorescent CB2 ligand as probe for receptor visualization in immune cells," Bioorganic & Medicinal Chemistry Letters 21, 5859-5862 (2011).
Sexton, Michelle et al., "NIR-mbc94, a Fluorescent Ligand that Binds to Endogenous CB2 Receptors and Is Amenable to High-Throughput Screening," Chemistry & Biology 18, 563-568 (May 27, 2011).
Wu, Zhiyuan et al., "Molecular imaging of human tumor cells that naturally overexpress type 2 cannabinoid receptors using a quinolone-based near-infrared fluorescent probe," Journal of Biomedical Optics 19(7), 076016 (Jul. 2014).
Wu, Zhiyuan et al., "Targeted zwitterionic near infrared fluorescent probe for improved imaging of type 2 cannabinoid receptors," Journal of Biomedical Optics 19(3), 036006 (Mar. 2014).
Yates, Andrew S. et al., "Chemical modification of the naphthoyl 3-position of JWH-015: In search of a fluorescent probe to the cannabinoid CB2 receptor," Bioorganic & Medicinal Chemistry Letters 15, 3758-3762 (2005).
Zhang, Shaojuan et al., "In vivo inflammation imaging using a CB2R-targeted near infrared fluorescent probe," Am. J. Nucl. Med. Mol. Imaging 5(3), 246-258 (2015).
Zhang, Shaojuan et al., "In Vivo Type 2 Cannabinoid Receptor-Targeted Tumor Optical Imaging Using a Near Infrared Fluorescent Probe," Bioconjugate Chem. 24, 1907-1916 (2013).

LABELLED CANNABINERGIC LIGANDS AND RELATED ANALOGS

CROSS-REFERENCE TO RELATED APPLICATION

This application claims priority from U.S. Provisional Application No. 62/992,130 for "Novel Labelled Cannabinergic Ligands and Related Analogs," filed Mar. 19, 2020, the entire content of which is incorporated herein by reference.

STATEMENT OF FEDERAL GOVERNMENT SUPPORT

This invention was made with government support under NIH Grant Nos. DA045020 and DA009158 awarded by National Institute of Health. The government has certain rights in the invention.

FIELD OF THE INVENTION

The present disclosure relates generally to chemical compounds with cannabinergic activity. More particularly, the present disclosure is concerned with novel ligands that bind to cannabinoid receptors and comprise imaging/diagnostic and/or therapeutic functional groups including fluorescent groups, nitroxide spin labels, metal chelates, biotin moieties, and groups with enhanced polarity. The disclosure is also concerned with pharmaceutical preparations employing these ligands and methods of administering diagnostically effective and/or therapeutically effective amounts of the ligands to allow imaging and/or to provide a physiological effect.

BACKGROUND

The classical cannabinoid $\Delta^9$-tetrahydrocannabinol ($\Delta^9$-THC) is the major active constituent extracted from *Cannabis sativa*. The effects of cannabinoids are due to an interaction with specific high affinity receptors. Presently two $G_{i/o}$ protein coupled cannabinoid receptors (GPCRs), namely CB1 and CB2, have been characterized in mammals and other organisms. The CB1 receptor is very densely distributed through the central nervous system, and at lower levels in various peripheral tissues, including the myocardium, postgangliomic autonomic nerve terminals, and vascular endothelial and smooth muscle cells as well as the liver, skeletal muscle and adipose tissue (Pacher, et al., *Pharmacol. Rev.* (2006) 58:389-462; Batkai, et al., *Circulation* (2004) 110:1996-2002; Bonz, et al., *J. Cardiovasc. Pharmacol.* (2005) 41:657-664; Mukhopadhyay, et al., *J. Am. Coll. Cardiol.* (2007) 50:528-536; Rajesh, et al., *Am. J. Physiol. Heart Circ. Physiol.* (2007) 293:H2210-H2218; Rajesh, et al., *Br. J. Pharmacol.* (2008) 153:347-357; Mallat, et al. *Am. J. Physiol. Gastrointest. Liver Physiol.* (2008) 294:9-12; Osei-Hyiaman, et al., *J. Clin. Invest.* (2005) 115:1298-1305; Engeli, et al., *Diabetes* (2005) 54:2838-2843; Jeong, et al., *Cell. Metab.* (2008) 7:227-235; Pagotto, et al., *Endocr. Rev.* (2006) 27:73-100; Cota, et al., *J. Clin. Invest.* (2003) 112:423-431). The CB2 receptor is present in immune and hematopoietic cells and recently has also been identified in the brain, myocardium, liver, and human coronary endothelial and smooth muscle cells (Van Sickle, et al., *Science* (2005) 310:329-332; Gong, et al., *Brain Res.* (2006) 1071:10-23; Mukhopadhyay, et al., *J. Am. Coll. Cardiol.* (2007) 50:528-536; Mallat, et al., Am. *J. Physiol. Gastrointest. Liver Physiol.* (2008) 294:9-12; Rajesh, et al. Am. *J. Physiol. Heart Circ. Physiol.* (2007) 293:H2210-2218; Rajesh, et al., *Br. J. Pharmacol.* (2008) 153:347-357).

Some compounds (cannabinergic ligands) can bind to the CB1 and/or CB2 receptors in an individual or animal. In vitro methods for assaying the ability of a compound to bind to CB1 and/or CB2 receptors are known. Results from the in vitro assay correlate with and predict the in vivo ability of that compound to bind to CB1 and/or CB2 receptors and modulate their function(s). When introduced in an individual or animal some of these cannabinergic ligands can bind to and modulate (activate or deactivate) the CB1 and/or CB2 receptors. Examples of some cannabinergic ligands include N-arachidonoyl ethanolamine (anandamide, AEA) and 2-arachidonoylglycerol (2-AG) (both endogenous ligands for the cannabinoid CB1 and CB2 receptors), (−)-$\Delta^9$-tetrahydrocannabinol ($\Delta^9$-THC, the principal bioactive constituent of cannabis preparations and exogenous ligand for the cannabinoid CB1 and CB2 receptors) and other synthetic cannabinergic analogs.

Ligands for the CB1/CB2 cannabinoid receptors, such as (−)-$\Delta^9$-tetrahydrocannabinol can bind to and modulate (activate or deactivate) the CB1/CB2 cannabinoid receptors and thereby provide a physiological effect in an individual or animal that is useful to treat a condition in that individual or animal. Conditions that may be treated by modulation of the CB1/CB2 cannabinoid receptors are provided under Summary of the Invention.

Additionally, recent scientific discoveries have demonstrated that the endocannabinoid system is very extensive and is currently under intense investigation. Radiochemical methods have been in use for more than twenty years for studying the complex phenomena associated with the endocannabinoid system and cannabinergic molecules. Despite the usefulness of radiochemical methods, the use of alternative methods such as fluorescent techniques can provide information not readily accessible by conventional radiochemical methods and circumvent certain drawbacks associated with them, such as high cost, special precautions in handling and disposal and potential health hazards. Fluorescent approaches provide great advantages over radiochemical methods in accuracy, sensitivity, efficiency, safety and a wide scope of additional applications, and generally are less costly than radiochemical methods. The state-of-art fluorescence approaches enable researchers to detect particular components of complex biomolecular assemblies, including living cells. In particular, the emission spectrum of a fluorescent molecule is sensitive to its environment. Therefore, fluorescence approaches are extremely useful in providing spatial, dynamic and temporal information about the interactions between macromolecules and their ligands.

With the help of available fluorescent ligands, fluorescence techniques have successfully been applied to study the behavior of a number of biological macromolecules, including dopamine receptors, histamine receptors, muscarinic receptors, adrenergic receptors, glucagon receptors, opioid receptors, adenosine receptors and serotonin receptors. The applications of receptor-specific fluorescent ligands are considerably broad, such as molecular studies on ligand-induced conformational changes within the receptor, rapid kinetics of ligand-receptor interactions, the localization of the ligand-binding site on the receptor and distances between different binding sites on the same receptor. Moreover, fluorescent ligands have been successfully used for studying the mobility of some receptors in both normal and (patho)physiological conditions by fluorescence photobleach recovery techniques, and to localize receptors at tissue and cellular level by fluorescence microscopic techniques. Furthermore, receptor-specific fluorescent ligands have been employed for receptor assays including the determination of the receptor dissociation constant (Kd) and the total receptor content of the tissue (Bmax) by fluorescence titration techniques. They can also be used in the development of competition binding and High-Throughput Screening (HTS) assays to facilitate drug development campaigns.

In summary, fluorescent ligands are powerful experimental tools to study the localization of a receptor on the cell membrane, trafficking and internalization of receptor(s), protein-ligand interactions and binding kinetics as well as conformational changes of a receptor. Such ligands can also be used as in vivo imaging agents for the early diagnosis of diseases that are related to up- or down-regulation of receptors, or for studying receptor expression in specific tissues and also to guide optical imaging during surgical operations. In general, fluorescent ligands are prepared by linking parent ligands with fluorescent moieties to make the newly formed ligands detectable or measurable by fluorescence techniques. Such strategies often face the challenge of reduced potency or efficacy of the parent ligands during interaction with target macromolecules. The broad distribution of cannabinoid receptors and their involvement in many biological and (patho)physiological processes makes them excellent targets for optical imaging. However, as reviewed recently (Christos Iliopoulos-Tsoutsouvas, C. et al. *Expert Opin. Drug Discov.* (2018), 13, 933-947), the discovery of fluorescent ligands for cannabinoid receptors is a challenging task with little success to date, especially with agonist-based fluorescent ligands. Largely, this is due to the low affinity/specificity of the probe for its target protein, inadequate photophysical properties, extensive non-specific binding, and/or low signal-to-noise ratio.

In addition to fluorescent ligands, other labeled chemical compounds/ligands for the cannabinoid receptors can be developed to study the complex pharmacology of these proteins using biochemical, bioanalytical, and biophysical methods including but not limited to: mass spectrometry (MS), nuclear magnetic resonance spectroscopy (NMR), electron paramagnetic resonance spectroscopy (EPR), electron spin labeled spectroscopy (ESP), magnetic resonance imaging (MRI), single photon emission computed tomography (SPECT), positron emission tomography (PET), microscopy including fluorescence microscopy, X-ray crystallography, flow cytometry, computational methods, as well as purification methods such as chromatography including affinity chromatography. Such labeled chemical compounds/ligands include nitroxide spin labeled cannabinoids, metal chelate cannabinoids, and biotinylated cannabinoid ligands. The term "nitroxide spin label" denotes a functional group bearing a nitroxyl radical (N—O). When a "nitroxide spin label" is covalently attached to another molecule (for example a cannabinoid molecule), then the molecule is considered to be "nitroxide spin labelled" or "spin labelled". The term "metal chelate" molecule/cannabinoid refers to a molecule/cannabinoid covalently bonded to a chelate moiety that is complexed with a metal ion. "Biotin labelled" or "biotinylated" molecule/cannabinoid, refers to a molecule/cannabinoid which is covalently bonded to a biotin group.

The nitroxide spin labels are reporter groups carrying an unpaired electron (paramagnetic center) useful in the study of molecular mobility and interactions in biological systems by magnetic resonance spectroscopy. Most of the applications involve electron spin resonance (ESR), which can provide information on dynamic processes in the millisecond to nanosecond range. Systems under investigation are often enzymes, receptors and nucleic acids. The spin-labelled ESR spectroscopy is largely driven by the sensitivity of the spin label to its surroundings. ESR spectroscopy is a useful method to study the role of receptor dynamics in functional processes such as ligand binding, activation, coupling to downstream binding partners (G proteins and arrestins), biased signaling, and allosteric modulation. ESR of nitroxide spin-labels holds a prominent place among the spectroscopic techniques for the investigation of the structure and function of enzymes and proteins, slow translational motions of lipids and proteins (lateral lipid and protein diffusion in membranes, anisotropic protein rotations) and fast anisotropic lipid rotations (long axis rotations, angular motions, chain segmental motions), lipid/protein interactions, and local polarity of membrane and protein regions. In particular, nitroxide spin label studies with high-field/high-frequency ESR and two-dimensional Fourier transform ESR enable one to accurately determine distances in biomolecules, unravel the details of the complex dynamics in proteins, characterize the dynamic structure of membrane domains, and discriminate between bulk lipids and boundary lipids that coat transmembrane peptides or proteins.

The application of spin labels/spin labelled molecules to NMR spectroscopy is based on the increase of relaxation rates of neighboring protons caused by the paramagnetic center, the so-called paramagnetic relaxation enhancement (PRE). This can be used to measure distances up to 20 Angstrom, which are too long to be measured by NOE (Nuclear Overhauser Effect) experiments, or to study the dynamics of peptides or proteins by sampling all conformations that lead to short proton radical distances. Spin labelled molecules/ligands are valuable tools to characterize protein-ligand interactions by NMR, and also, to enhance the sensitivity of NMR spectroscopic screening in drug discovery research.

Chelates are hexa- to octa-dentate moieties containing multiple hard anionic donors. These chelates can be derivatized in order to be incorporated to other molecules (e.g., cannabinoids), followed by complexation with metal ions, thus leading to metal chelate ligands (e.g., metal chelate cannabinoids, meaning compounds consisting of a parent cannabinoid molecule covalently bonded to a chelate group complexed with a metal ion). The hard anionic donors allow the efficient coordination of the metal ion with the chelate. The metal ions that can be complexed include, for example, gadolinium(III), gallium(III), zirconium(IV), indium(III), and yttrium(III). These metal chelates can be used for magnetic resonance imaging (MRI), single photon emission computed tomography (SPECT), and/or positron emission tomography (PET). For example, gadolinium(III) accelerates the Ti relaxation of water protons, resulting in brighter magnetic resonance signals. Thus, gadolinium(III) chelates are used as contrast agents for contrast enhanced magnetic resonance imaging. Cannabinoid gadolinium(III) chelates could be used as targeted contrast agents for the detection of cannabinoid receptors for imaging/diagnostic purposes.

Bioin is a water soluble B vitamin, also called vitamin B7 (formerly known as Vitamin H and Coenzyme R) that is present in small amounts in all living cells and is critical for a number of biological processes. Biotin is abundant in certain plant and animal tissues such as corn kernels, egg yolk, brain, liver and blood. The valeric acid side chain of the biotin molecule can be derivatized in order to incorporate the biotin label to other molecules (e.g., cannabinoids), thus leading to biotinylated ligands (e.g., biotinylated cannabinoids). Avidin and other biotin-binding proteins, including, for example, Streptavidin and NeutrAvidin protein, have the ability to bind to the biotin moiety of the biotinylated ligands, making this interaction ideal for both detection and purification strategies. For example, cannabinoid biotinylated ligands could be tracked using the adequate Avidin or Streptavidin conjugate (such as a fluorophore for visualization or solid support for enrichment/purification and identification).

Moreover, a major problem for developing $\Delta^9$-tetrahydrocannabinol ($\Delta^9$-THC) based pharmacological tools and potential drug candidates is the high lipophilicity of these molecules which is due to their hydrocarbon character. Thus, THC and structurally related classical cannabinoid analogs exhibit a number of undesirable biopharmaceutical properties including extended residency in fatty tissue, high plasma protein binding, and extremely low water solubility that requires solubilization of these molecules with either a surfactant agent or adherence to a water miscible substance (e.g., albumin, emulphor, or Tween). In an effort to address the lipophilicity issue without compromising the CNS activity of the classical cannabinoids, we have incorporated to the classical cannabinoid prototype(s), functional polar groups that encompass nitrogen and/or oxygen atoms. The incorporation of such polar groups took place in judiciously chosen positions within the classical cannabinoid structure that can maintain, or even increase, the bioactivity of the cannabinoid analogs for cannabinoid receptors.

SUMMARY

Novel cannabinoid ligands represented by the general formulas I, II, and III and methods for preparation and use are presented. The disclosed compounds can bind to and modulate the cannabinoid CB1/CB2 receptors and thus, they are specific ligands for these receptors. Some of the disclosed compounds that bind to cannabinoid CB1 and CB2 receptors can also exhibit tight/irreversible binding characteristics for these receptors.

The disclosed compounds comprise imaging/diagnostic and/or therapeutic functional groups including fluorescent groups, nitroxide spin labels, metal chelates, biotin moieties, and groups with enhanced polarity. Thus, the disclosed compounds may be useful as imaging/diagnostic tools and/or therapeutic agents. The disclosed compounds, when administered in a diagnostically effective and/or therapeutically effective amount to an individual or animal, results in a sufficiently high level of that compound in the individual or animal to allow imaging and/or to cause a physiological response. Some of the disclosed compounds may be acting both in the central nervous system and the periphery while the action of some of the disclosed compounds might be restricted in the periphery. The imaging may be useful for diagnosis of pathological and physiological conditions, while the physiological response may be useful to treat a number of (patho)physiological conditions.

Pathological and physiological conditions that may be diagnosed and/or treated by imaging and/or modulation of CB1/CB2 cannabinoid receptors include for example: diabetes, several types of cancer; neurodegenerative diseases including multiple sclerosis, Parkinson's disease, Huntington's chorea, Alzheimer's disease and amyotrophic lateral sclerosis; mental disorders such as schizophrenia and depression; mood disorders; addiction disorders; memory disorders; gastrointestinal motility disorders such as irritable bowel syndrome and diarrhea; dyskinesia; migraine; osteoporosis, osteoarthritis; high blood pressure disease or hypertension; peripheral vascular disease; coronary artery disease; abnormal heart rate; cardiac insufficiency; pulmonary hypertension; ocular hypertension or glaucoma; pain; central pain; peripheral pain; neuropathic pain; neuropathy; inflammatory pain; to prevent or reduce endotoxic shock and hypotensive shock; to modulate appetite; to modulate the immune system; to modulate fertility; to prevent or reduce diseases associated with motor dysfunction such as Tourette's syndrome; to image, prevent, or reduce inflammation; to provide neuroprotection; to produce peripheral vasodilation; to treat epilepsy; to treat nausea such as associated with cancer chemotherapy; AIDS wasting syndrome as well as other ailments in which cannabinoid system is implicated.

In one aspect, a compound of formula I or a pharmaceutically acceptable salt thereof, including all stereoisomers and enantiomers is disclosed:

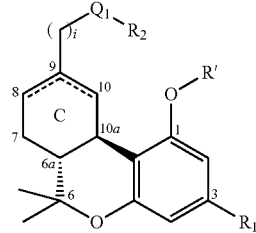

I

Wherein
═══ can be a single or a double bond between $C_8$-$C_9$ or $C_9$-$C_{10}$, provided that no more than one double bond is present in the C-ring of formula I.

$Q_1$ is selected from

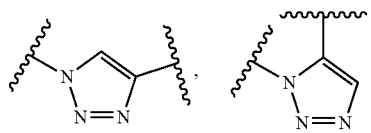 [SMILES: *c1cn(*)nn1 ; *c1cnnn1*]

i is an integer from 0 to about 3.
As used in this disclosure when an integer such as i is 0 the structural portion modified by that integer is absent and the adjacent subunits are directly connected. For example, if i is 0 then $Q_1$ is directly connected to the $C_9$.

$R_1$ is selected from

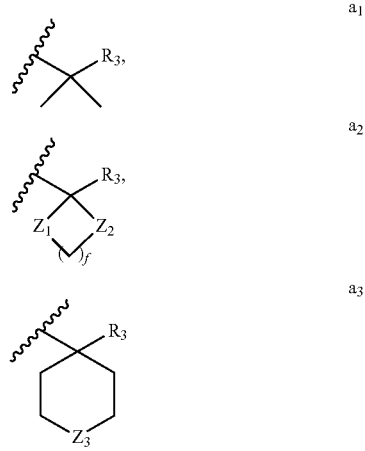

$Z_1$, $Z_2$, and $Z_3$ are independently selected from $CH_2$, O, S, NH, NMe;

$R_3$ is selected from —$(CH_2)_j$—$R_4$, —$(CH_2)_j$—B—$(CH_2)_k$—$R_4$;

B is selected from $CH_2$—$CH_2$, CH=CH, C≡C;

$R_4$ is selected from H, F, Cl, Br, I, NCS, $N_3$, CN, $NO_2$, $ONO_2$, $SO_2F$, OH, SH, $NH_2$, —$N(Alkyl)_2$;

f is an integer from 0 to about 3;

j is an integer from 0 to about 7;

k is an integer from 0 to about 7.

As used in this disclosure when an integer such as f, j, or k is 0, the structural portion modified by that integer is absent and the adjacent subunits are directly connected. For example, when f is 0, structure $a_2$ comprises of 3-member ring.

R is selected from —H, —$C(O)CH_3$,

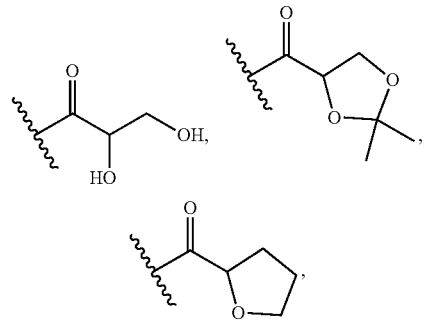

including all enantiomers $R_2$ is selected from $R_5$, T-$R_5$;

T is a tether selected from

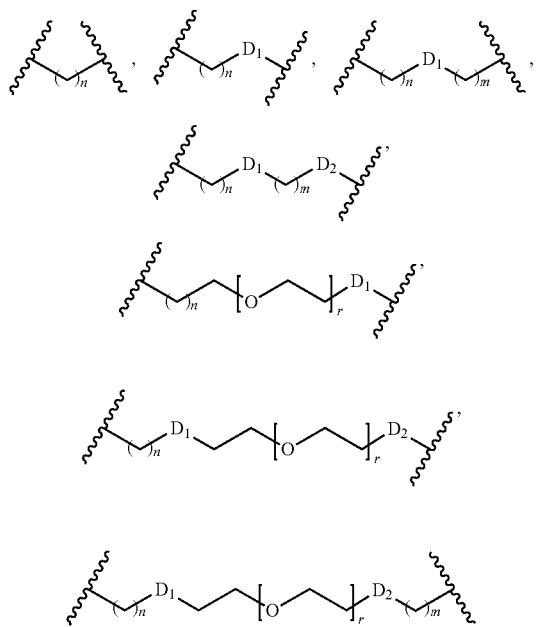

$D_1$ and $D_2$ are independently selected from —O—, —S—, —NH—, —OC(O)—, —C(O)O—, C(O)NH, —NHC(O)—, —$NHSO_2$—, and

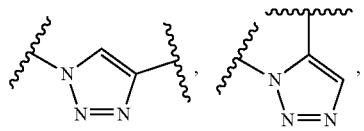 [SMILES: *c1cn(*)nn1 ; *c1cnnn1*]

n is an integer from 0 to about 7;

m is an integer from 1 to about 7;

r is an integer from 1 to about 5.

As used in this disclosure when an integer such as n is 0 the structural portion modified by that integer is absent and the adjacent subunits are directly connected. For example, if n is 0 then $D_1$ is directly connected to the $Q_1$.

$R_5$ is selected from fluorophore moieties, nitroxide spin labels, metal chelates, biotin, heterocyclic moieties, —(NH)-Alkyl, —$N(Alkyl)_2$, —O-Alkyl, F, Cl, Br, I, NCS, $N_3$, CN, $NO_2$, $ONO_2$, $SO_2F$, OH, SH, and $NH_2$. Provided that groups such as fluorophore moieties, nitroxide spin labels, metal chelates, biotin, and heterocyclic moieties can be bonded to $Q_1$ or T from any possible position.

As exemplified in FIGS. 1, 2, 3, and 4, representative fluorophores include, but are not limited to: naphthalimide derivatives, fluorescent coumarin derivatives (e.g., 7-methoxycoumarin-3-carboxylic acid, coumarin 343, 7-hydroxycoumarin-3-carboxylic acid, 7-diethylaminocoumarin-3-carbonyl azide), fluorescent rhodamine derivatives (e.g. rhodamine B, 5-carboxy-X-rhodamine, 6-carboxy-X-rhodamine), fluorescent fluorescein derivatives (e.g. fluorescein carboxylic acid, 5-(iodoacetamido) fluorescein), cyanine dyes (e.g., Cy5, Cy5.5, and Cy7), near infrared (NIR) dyes (e.g., IR 800, NIR641, NIT700), dansyl derivatives, dabcyl derivatives, nitrobenzodiazolamine (NBD) derivatives, Nile Blue, Alexa Fluor 488 derivatives, Texas Red derivatives, Pyrylium/Pyridinium derivatives, etc.

It is understood that these representative fluorophores are exemplary only, and additional derivatives of a common fluorophore structure can also be employed. For example, the Bodipy and Alexa Fluor dye series includes at least 17 and 19 different dyes respectively that are characterized by different emission spectra. These dyes include Bodipy FL, Bodipy 530/550, Bodipy 493/503, Bodipy 558/568, Bodipy 576/589, Bodipy 581/591, Bodipy TR-X, Bodipy TMR-X, Bodipy R6G, Bodipy 630.650-X, Bodipy 650/665-X and Alexa Fluors 350, 405, 430, 488, 500, 514, 532, 546, 555, 568, 594, 610, 633, 635, 647, 660, 80, 700 and 750. Both, Bodipy and Alexa Fluor dyes are available from Fisher Scientific, Sigma-Aldrich and other vendors.

As exemplified in FIG. 5, representative nitroxide spin labels include but are not limited to: TEMPO derivatives (e.g., 4-hydroxy-4-methoxycarbonyl-1-oxyl-2,2,6,6-tetramethylpiperidine, free radical), PROXYL derivatives (e.g. 3-(2-Iodoacetamido)-2,2,5,5-tetramethyl-1-pyrrolidinyloxy free radical) and DOXYL derivatives (e.g. 2-(14-Carboxytetradecyl)-2-ethyl-4,4-dimethyl-3-oxazolidinyloxy, free radical).

As exemplified in FIG. 6, representative chelate moieties capable of complexing with a metal ion to produce metal chelates include but are not limited to: DOTA derivatives (e.g., 2-(4,7,10-tris(2-(tert-butoxy)-2-oxoethyl)-1,4,7,10-tetraazacyclododecan-1-yl)acetic acid, 2,2',2",2'''-(1,4,7,10- tetraazacyclododecane-1,4,7,10-tetrayl)tetraacetic acid, 2-(4,7,10-tris(carboxymethyl)-1,4,7,10-tetraazacyclododecan-1-yl)pentanedioic acid), DO3A derivatives (e.g., 2,2', 2''-(1,4,7,10-tetraazacyclododecane-1,4,7-triyl)triacetic acid, 2,2',2''-(10-(3-carboxypropyl)-1,4,7,10-tetraazacyclododecane-1,4,7-triyl)triacetic acid), and NOTA derivatives (e.g., 2,2',2''-(1,4,7-triazonane-1,4,7-triyl)triacetic acid). The metal ions include but are not limited to gadolinium(III), gallium(III), zirconium(IV), indium(III), and yttrium(III).

In FIG. 7, an example of a metal chelate, which includes a chelate moiety in complex with the metal ion gadolinium (III), is illustrated.

Biotin is represented by the structure bellow.

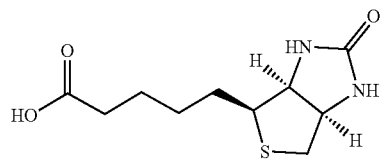 [SMILES: O=C(O)CCCC[C@@H]1SC[C@@H]2NC(=O)N[C@@H]21]

In another aspect, a compound or a pharmaceutically acceptable salt thereof, including all stereoisomers and enantiomers, is disclosed, wherein the compound is selected from the group consisting of:

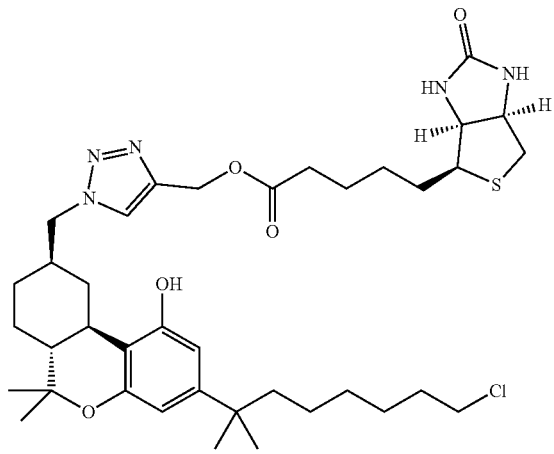

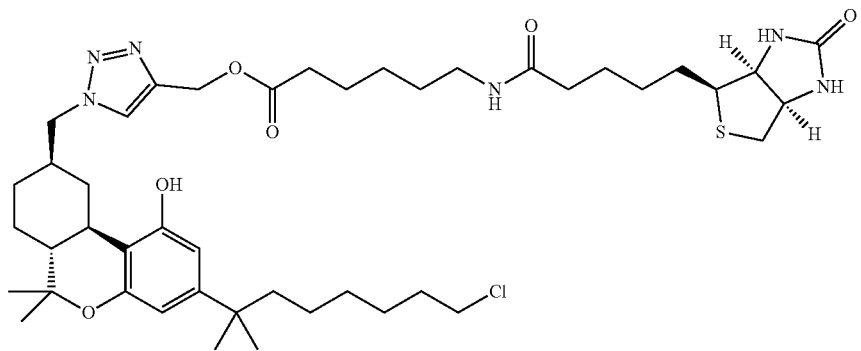

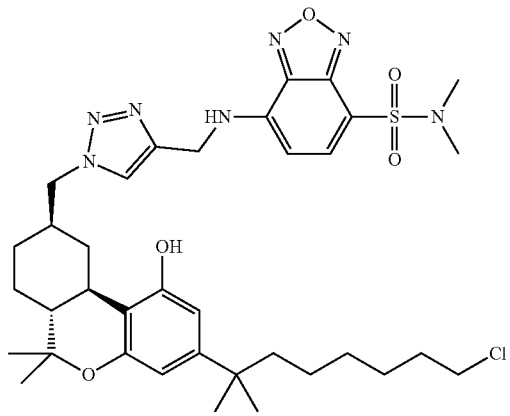

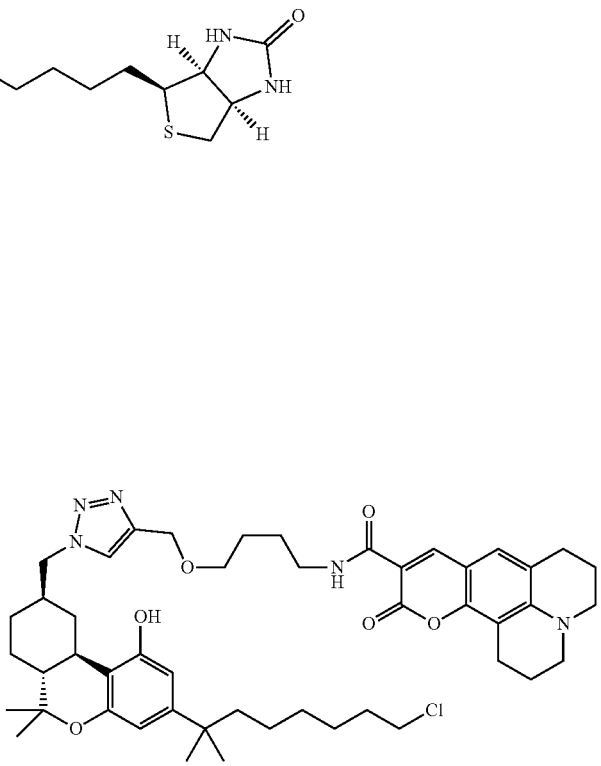

11
-continued
12
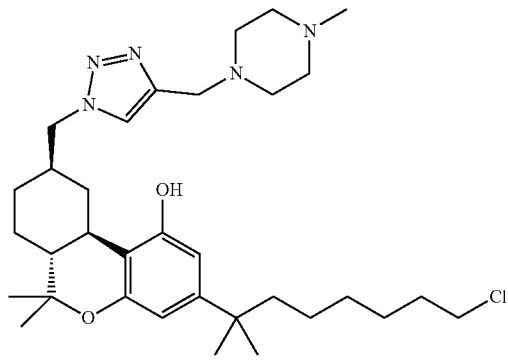
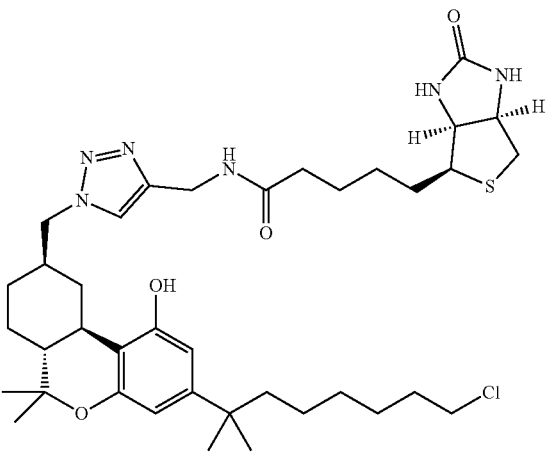
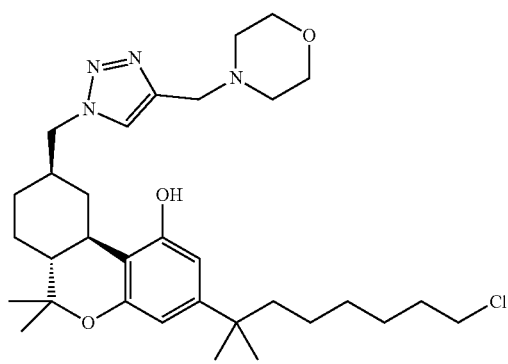
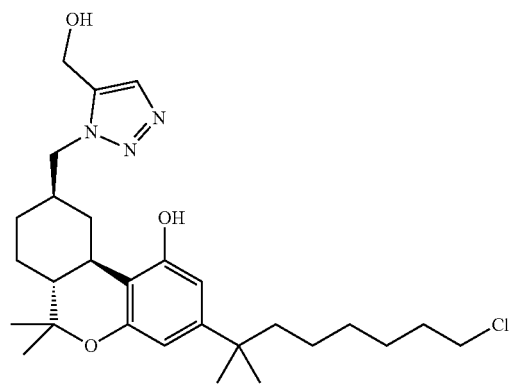
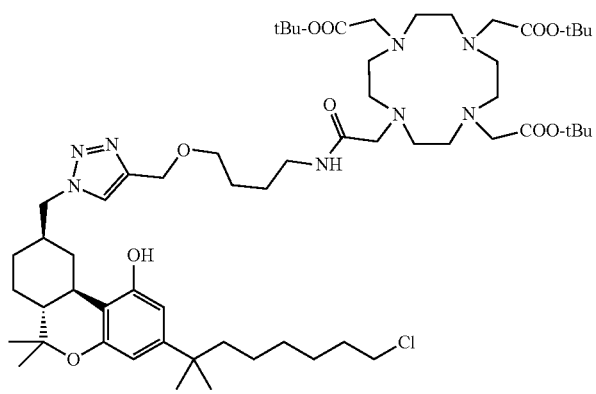
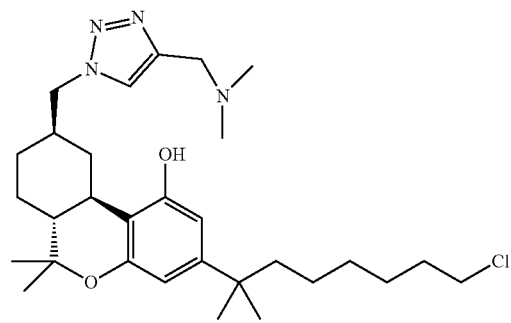
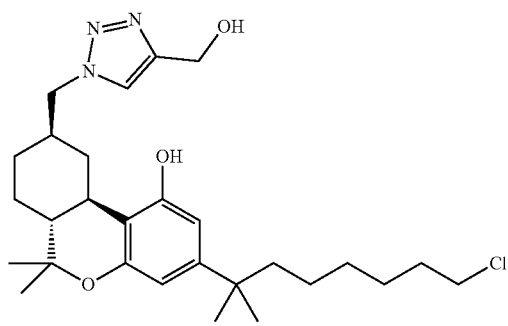
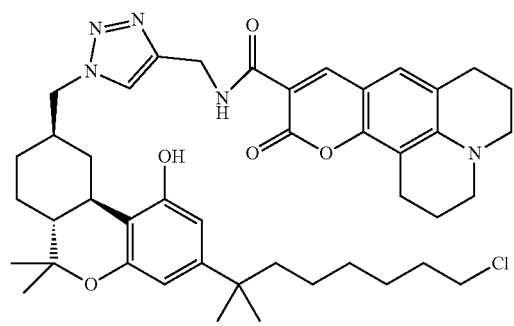

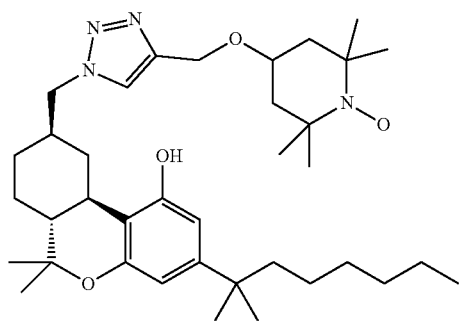

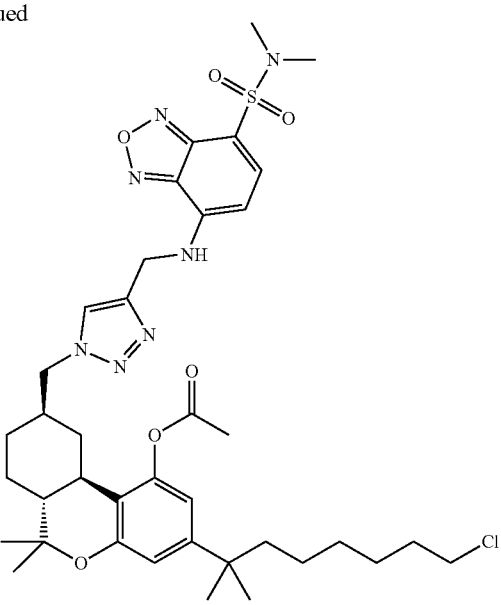

In another aspect, a compound of formula II or a pharmaceutically acceptable salt thereof, including all stereoisomers and enantiomers is disclosed:

II

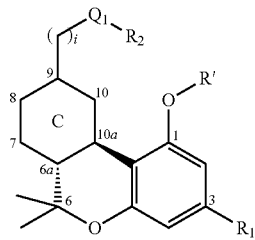

Wherein:

$Q_2$ is selected from —OC(O)—, —C(O)—, and —NHC(O)— i is an integer from 0 to about 3

As used in this disclosure when an integer such as i is 0 the structural portion modified by that integer is absent and the adjacent subunits are directly connected. For example, if i is 0 then $Q_2$ is directly connected to the $C_9$.

$R_1$ is selected from $a_1$

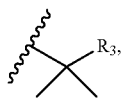

$a_2$

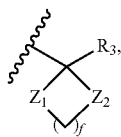

$a_3$

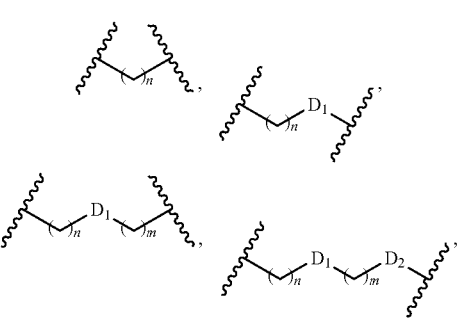

$Z_1$, $Z_2$, and $Z_3$ are independently selected from $CH_2$, O, S, NH, NMe $R_3$ is selected from —$(CH_2)_j$—$R_4$, —$(CH_2)_j$—B—$(CH_2)_k$—$R_4$ B is selected from $CH_2$—$CH_2$, CH=CH, C≡C $R_4$ is selected from H, F, Cl, Br, I, NCS, $N_3$, CN, $NO_2$, $ONO_2$, $SO_2F$, OH, SH, $NH_2$, —N(Alkyl)$_2$ f is an integer from 0 to about 3 j is an integer from 0 to about 7 k is an integer from 0 to about 7

As used in this disclosure when an integer such as f, j, or k is 0, the structural portion modified by that integer is absent and the adjacent subunits are directly connected. For example, when f is 0, structure $a_2$ comprises of 3-member ring.

$R_2$ is selected from $R_5$, T-$R_5$

T is a tether selected from

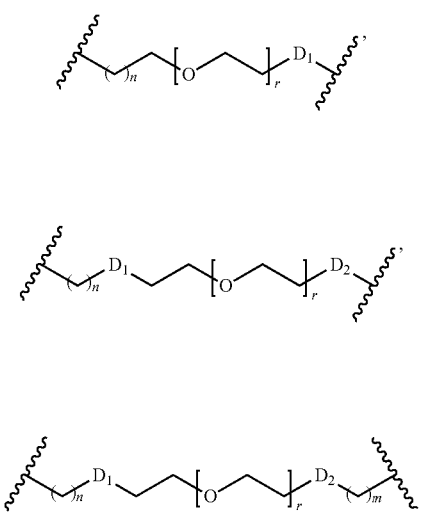

$D_1$ and $D_2$ are independently selected from —O—, —S—, —NH—, —OC(O)—, —C(O)O—, C(O)NH, —NHC(O)—, —NHSO$_2$—, and

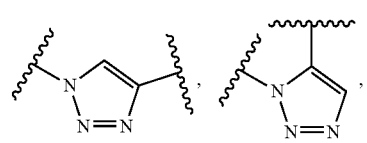 [SMILES: *c1cn(*)nn1 ; *c1cnnn1*]

n is an integer from 0 to about 7
m is an integer from 1 to about 7
r is an integer from 1 to about 5
R' is selected from —H, —C(O)CH$_3$,

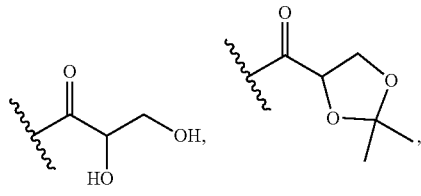

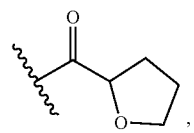, including all enantiomers

R$_5$ is selected from fluorophore moieties, nitroxide spin labels, metal chelates, and biotin as defined above.

In another aspect, a compound or a pharmaceutically acceptable salt thereof, including all stereoisomers and enantiomers, is disclosed, wherein the compound is selected from the group consisting of:

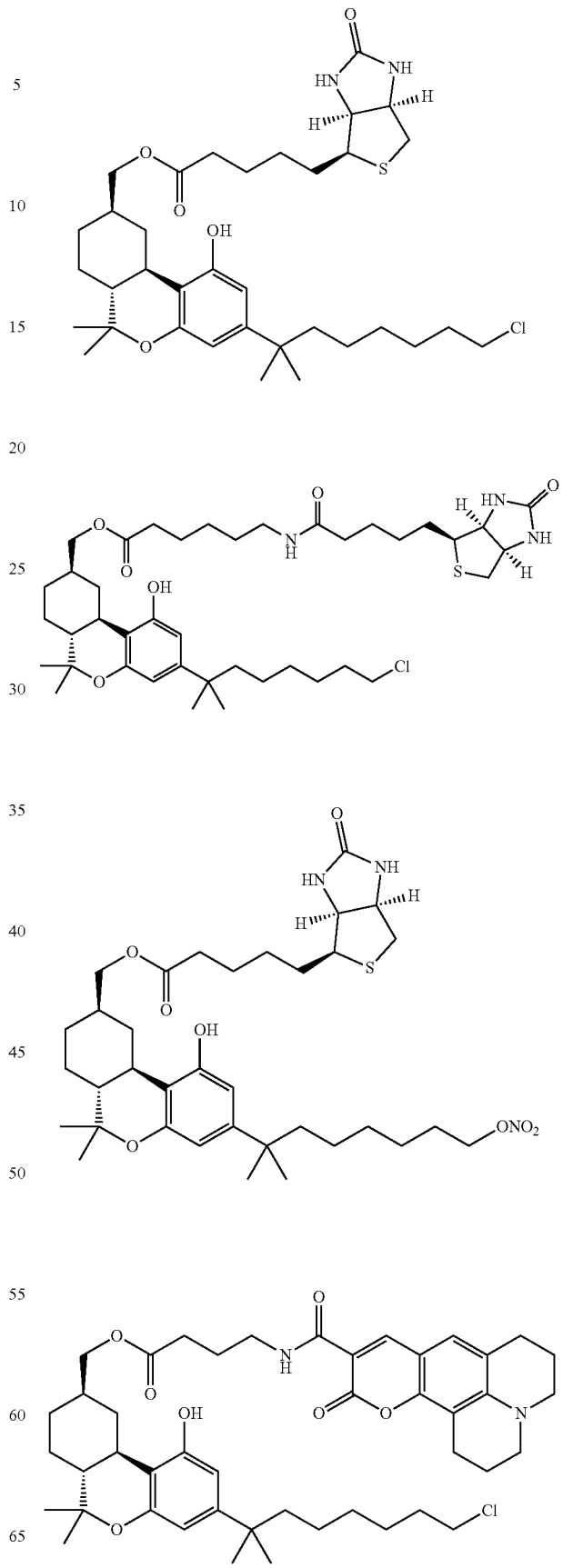

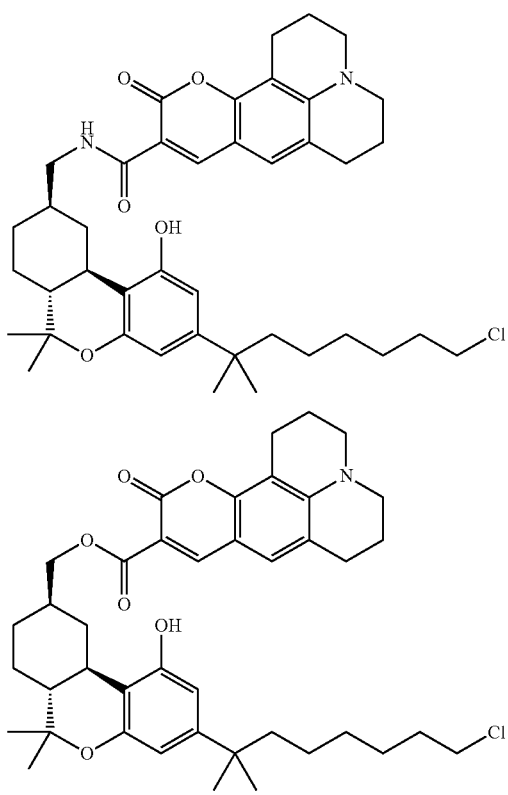

In another aspect, a compound of formula III or a pharmaceutically acceptable salt thereof, including all stereoisomers and enantiomers is disclosed:

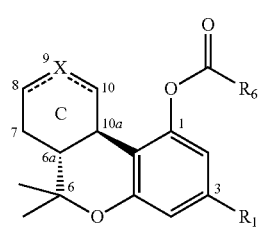

III

Wherein:

=== can be a single or a double bond, provided that no more than one double bond is present in the C-ring of formula III.

when === when between $C_8$-$C_9$ or $C_9$-$C_{10}$ is a single bond, X is >C=O, >CHOH, >CH—$(CH_2)_t$—OH (t=1-3).

when === between $C_8$-$C_9$ or $C_9$-$C_{10}$ is a double bond, X is C—$CH_3$, C—$(CH_2)_t$—OH (t=1-3).

$R_1$ is selected from

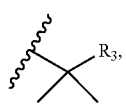

a₁

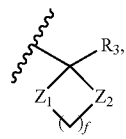

a₂

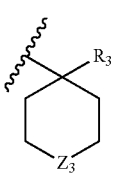

a₃

$Z_1$, $Z_2$, and $Z_3$ are independently selected from $CH_2$, O, S, NH, NMe $R_3$ is selected from —$(CH_2)_j$—$R_4$, —$(CH_2)_j$—B—$(CH_2)_k$—$R_4$ B is selected from $CH_2$—$CH_2$, CH=CH, C≡C $R_4$ is selected from H, F, Cl, Br, I, NCS, $N_3$, CN, $NO_2$, $ONO_2$, $SO_2F$, OH, SH, $NH_2$, —N(Alkyl)$_2$ f is an integer from 0 to about 3 j is an integer from 0 to about 7 k is an integer from 0 to about 7

As used in this disclosure when an integer such as f, j, or k is 0, the structural portion modified by that integer is absent and the adjacent subunits are directly connected. For example, when f is 0, structure a₂ comprises of 3-member ring.

$R_6$ is selected from $R_7$, G-$R_7$, G-T-$R_7$, $R_8$

G is selected from $CH_2$, $CHCH_3$, $C(CH_3)_2$, O, NH, or

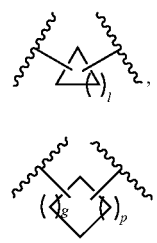

a₄ a₅ l is an integer from 1 to about 4 g is an integer from 1 to about 4 p is an integer from 1 to about 4

Provided that the rings in a₄ and a₅ can be bonded to the main structure and $R_7$ or T from any possible position T is a tether selected from

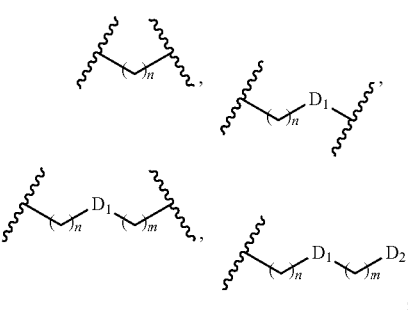

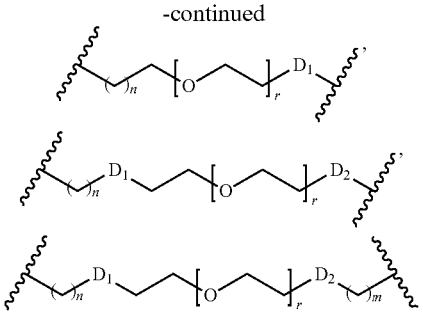

$D_1$ and $D_2$ are independently selected from —NH—, —OC(O)—, —C(O)O—, C(O)NH, —NHC(O)—, —NHSO$_2$—, and

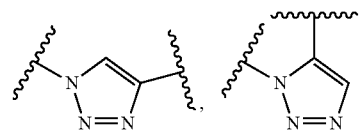 [SMILES: *c1cn(*)nn1 ; *c1cnnn1*]

n is an integer from 0 to about 7
m is an integer from 1 to about 7
r is an integer from 1 to about 5
$R_7$ is selected from fluorophore moieties and nitroxide spin labels as defined above.
$R_8$ is selected from

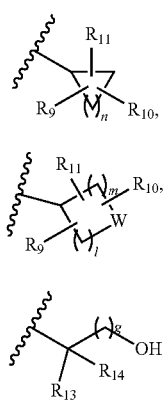

$R_9$ and $R_{10}$ are each independently selected from H, Me, Et, OH, OCH$_3$
$R_{11}$ is selected from —(CH$_2$)$_q$—R$_{12}$, -E-(CH$_2$)$_r$—R$_{12}$
E is selected from O, S, NH, N(Me)
$R_{12}$=H, F, Cl, Br, I, OH, SH, N$_3$, NCS, CN, NO$_2$, ONO$_2$
$R_{13}$=OH, CH$_2$OH
$R_{14}$=H, Me
W is selected from: O, S, O(CH$_2$)$_p$O, O(CH$_2$)$_p$S, and S(CH$_2$)$_p$S
n is an integer from 1 to about 4
m is an integer from 1 to about 5
l is an integer from 0 to about 5
q is an integer from 0 to about 5
r is an integer from 1 to about 5
p is an integer from 1 to about 3
g is an integer from 1 to about 4

Provided that the rings in a$_6$, a$_7$ and a$_8$ can be bonded to the main structure and to substituents R$_9$, R$_{10}$, and R$_{11}$ from any possible position since valency requirements are satisfied.

In another aspect, a compound or a pharmaceutically acceptable salt thereof, including all stereoisomers and enantiomers, is disclosed, wherein the compound is selected from the group consisting of

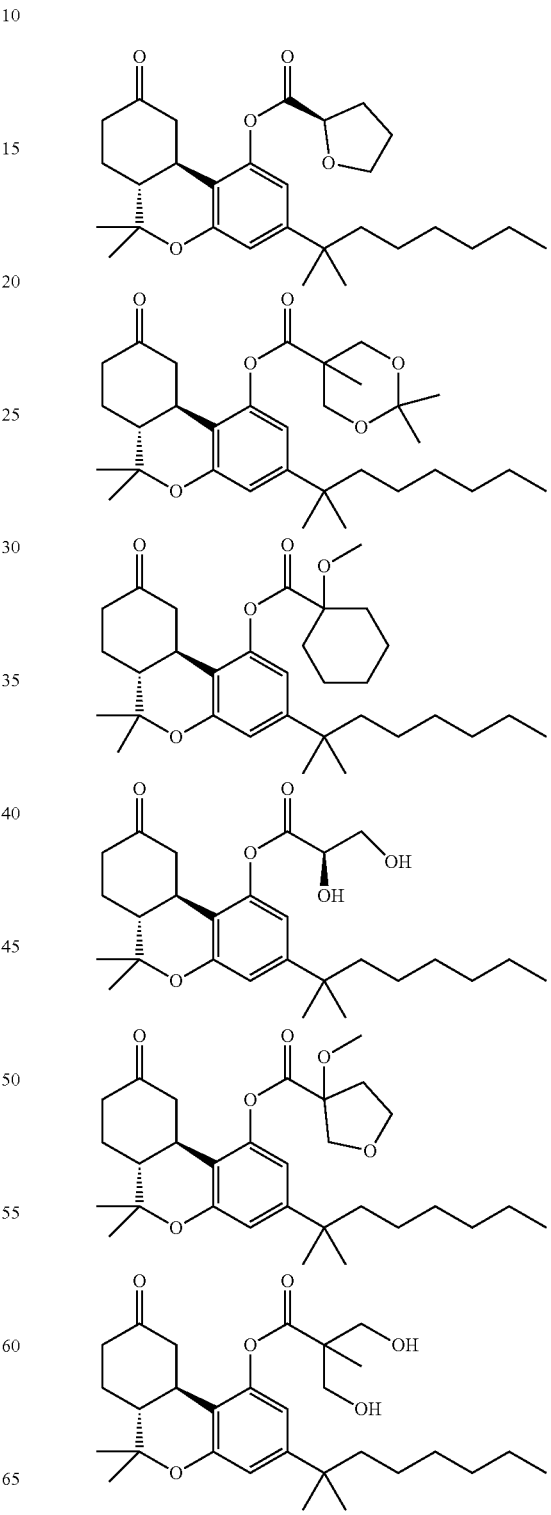

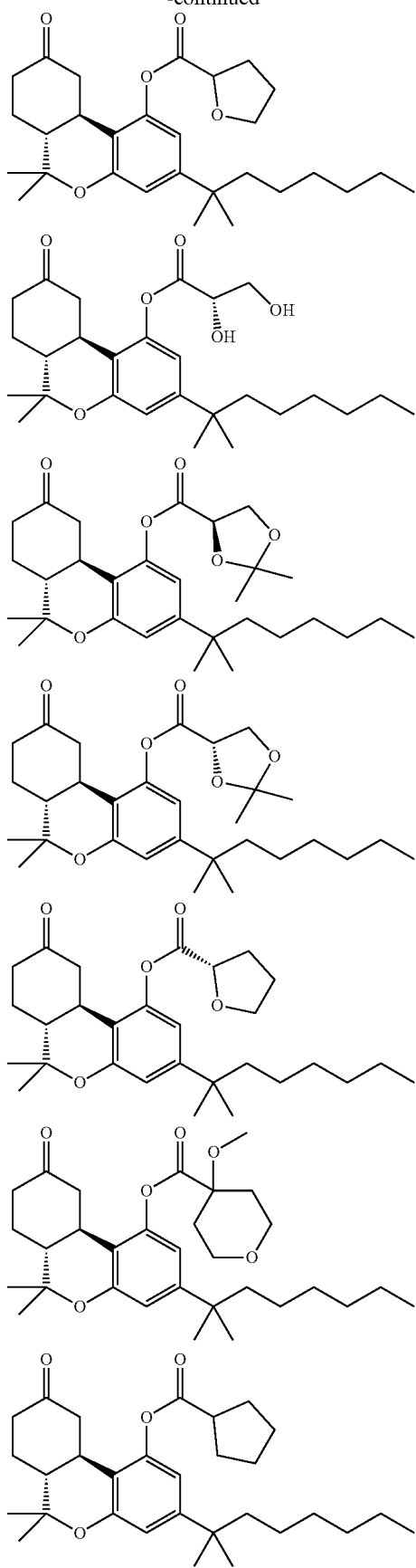
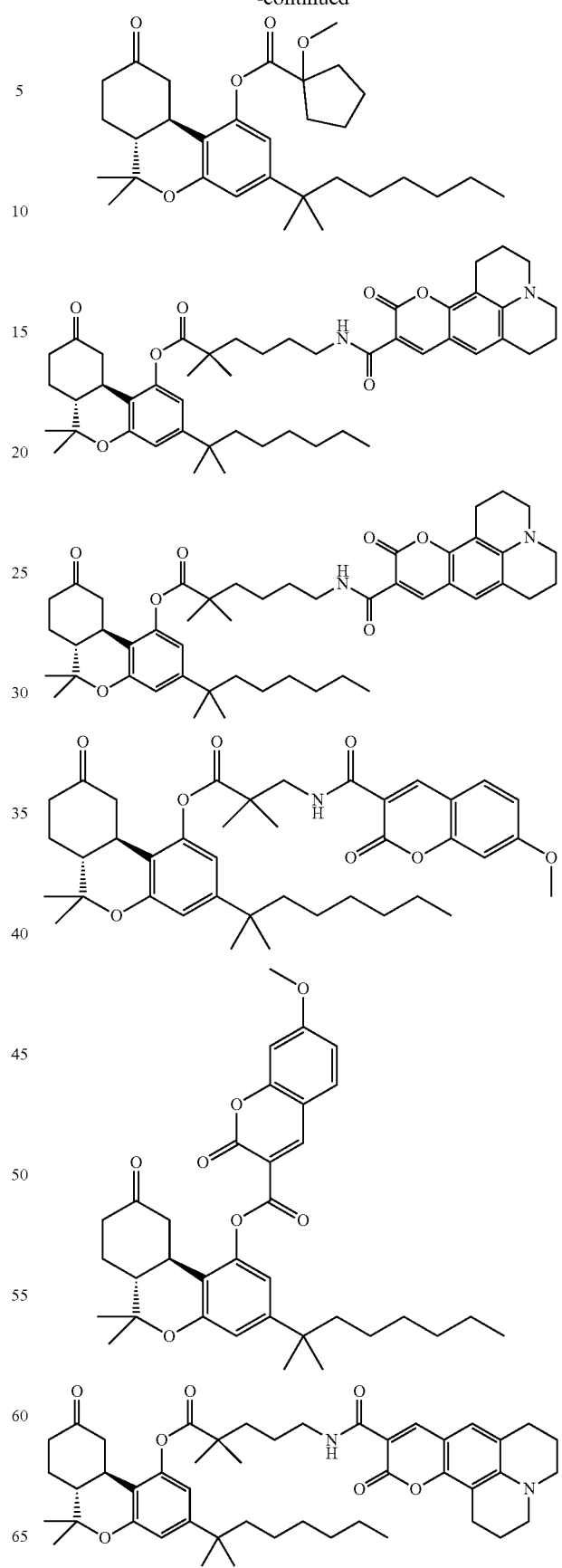

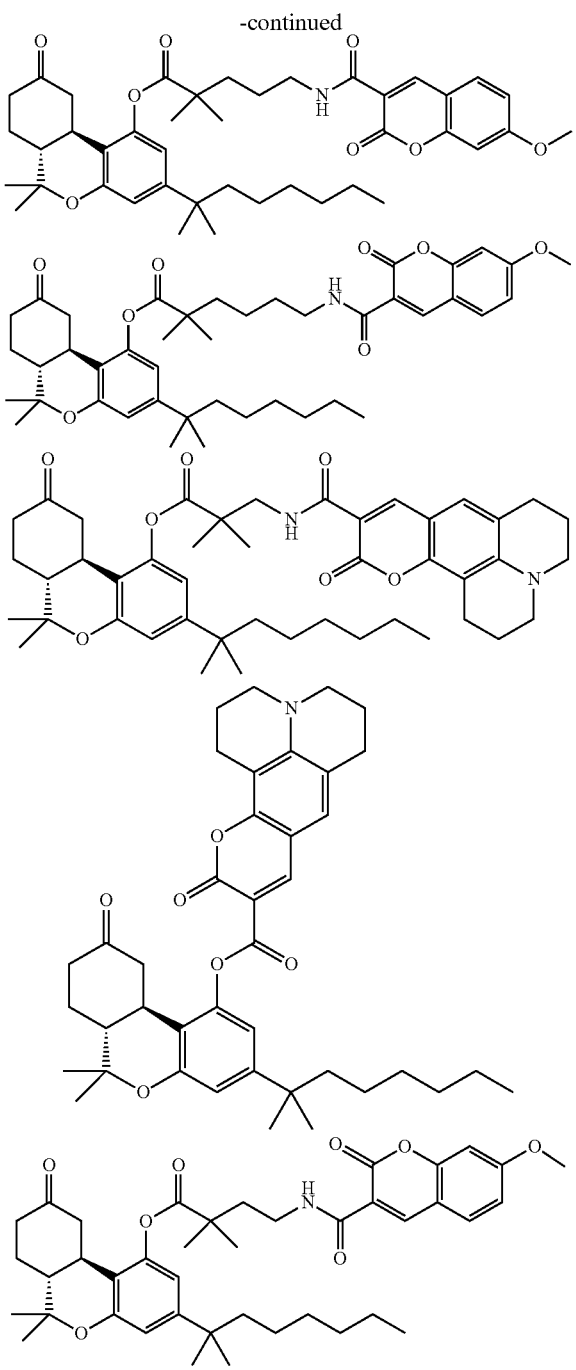

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
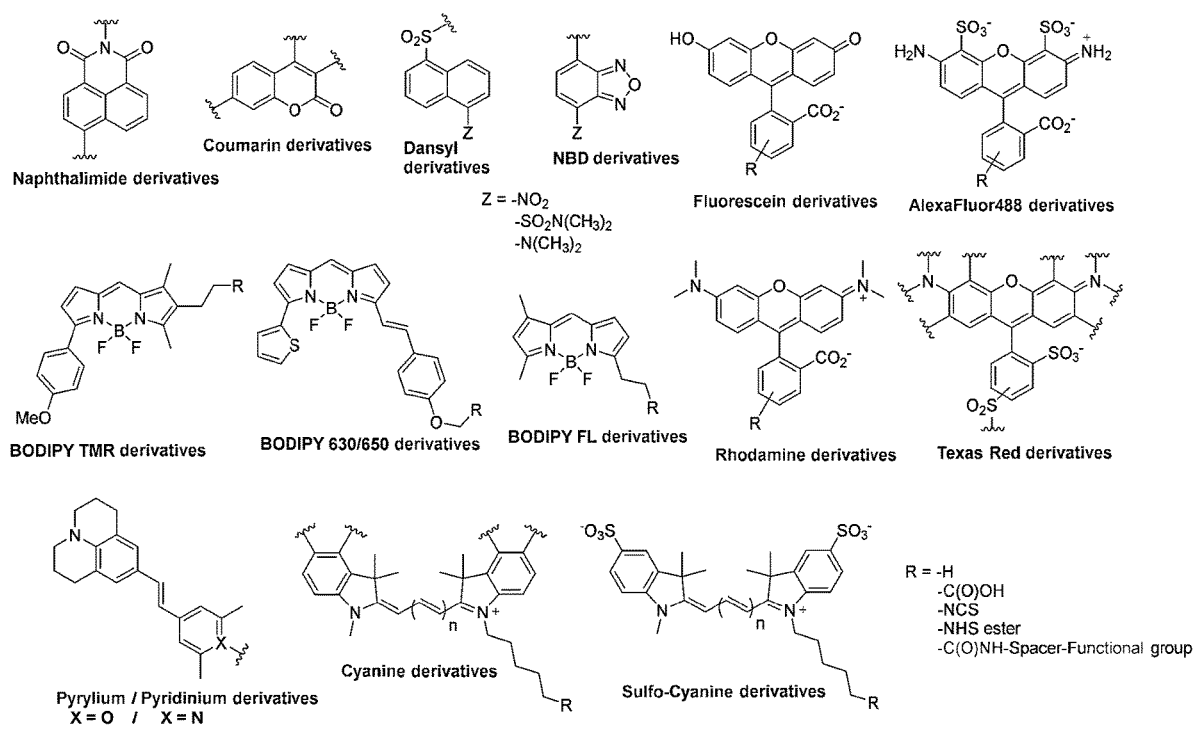
FIG. 1 shows general structures of representative fluorescent moieties, wherein wavy lines represent either substituents determining the photophysical properties of the fluorophores or the attachment point with the tether or with the main structure, the R groups represent reactive groups present in the fluorophore moiety that can be bonded to the main structure or to the tether, and the functional group is selected from carboxylic acids, isothiocynates, NHS esters, alkynes, and azides.
Figure 2:
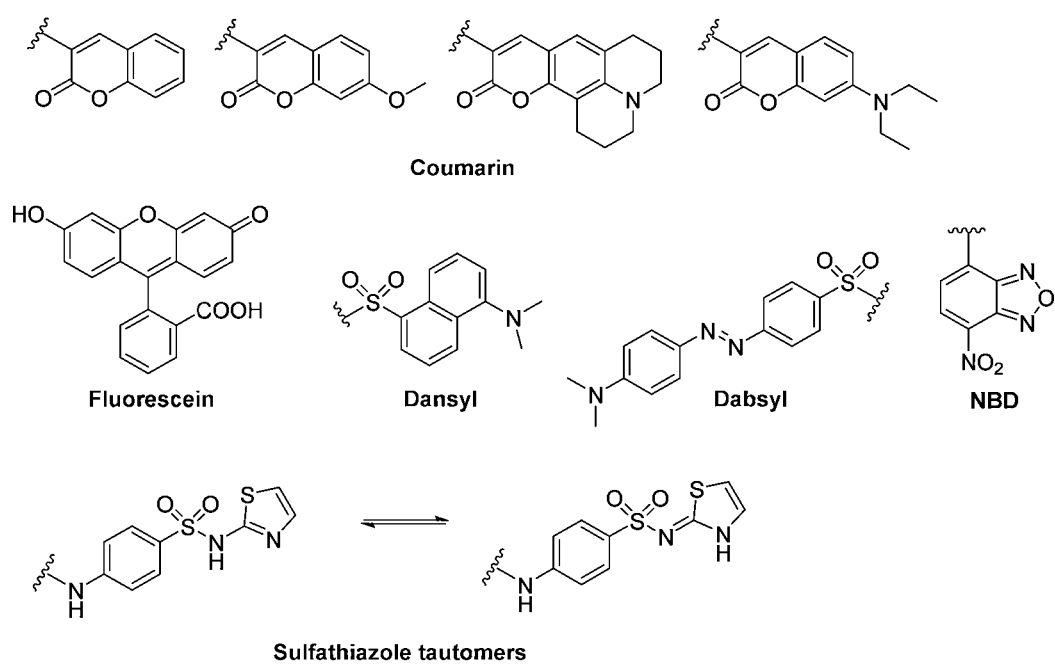
FIG. 2 shows examples of chemical scaffolds for blue, yellow and green fluorophores.
Figure 3:
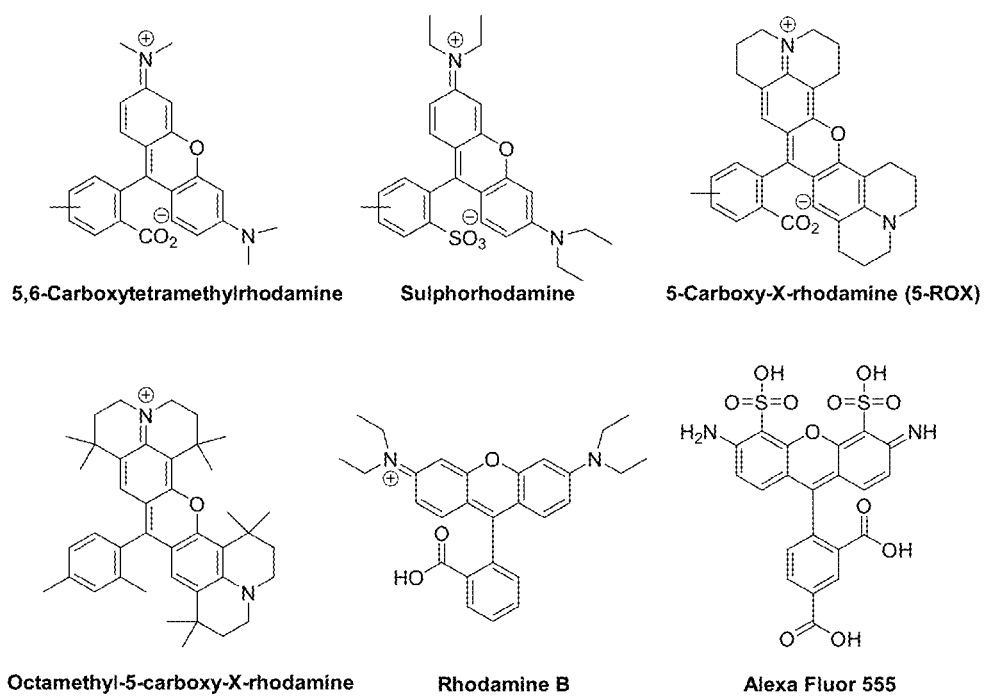
FIG. 3 shows examples of chemical scaffolds for red fluorophores.
Figure 4:
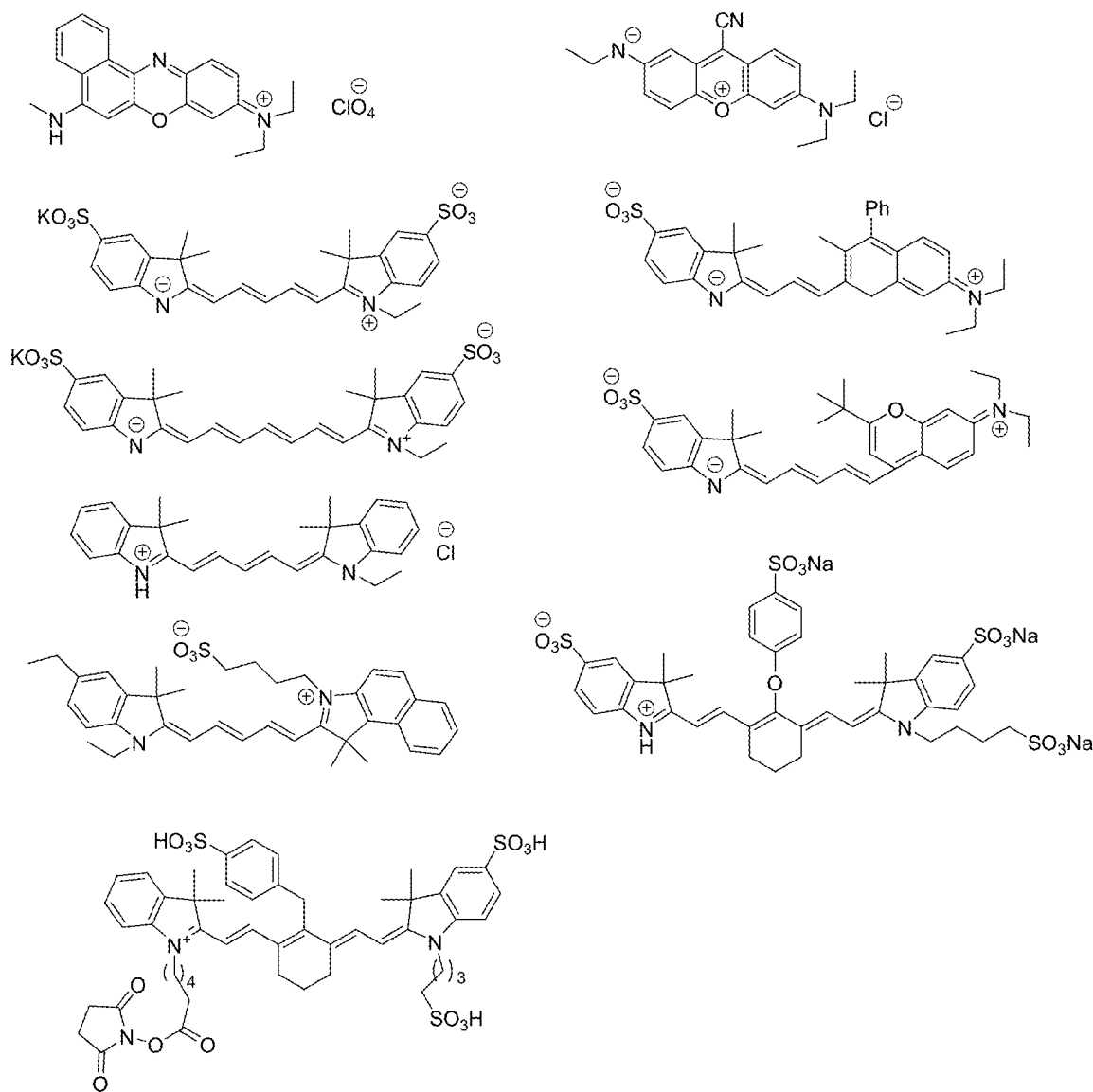
FIG. 4 shows examples of chemical scaffolds for near infrared (NIR) fluorophores.
Figure 5:
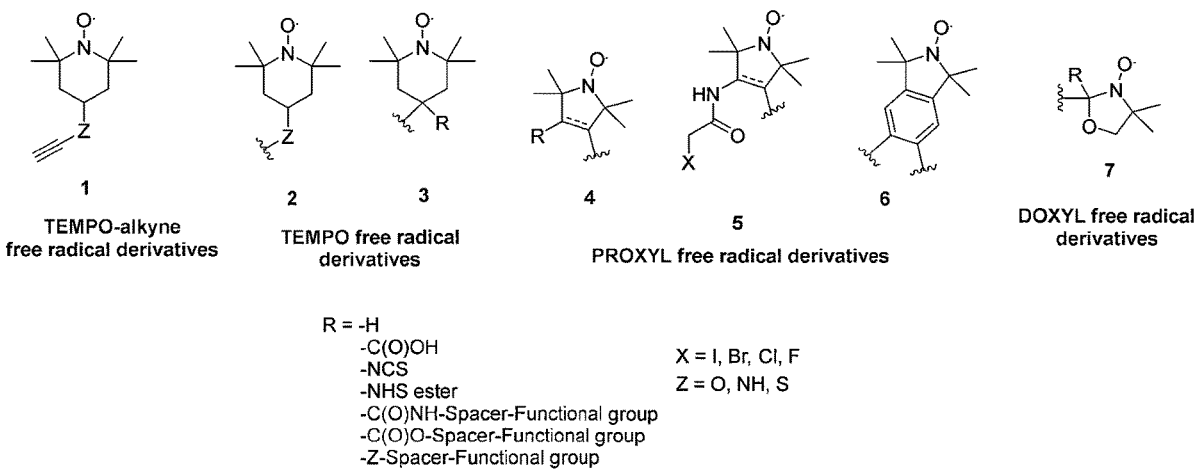
FIG. 5 shows general structures of representative nitroxide spin labels, wherein wavy lines represent either substituents determining the physicochemical properties of the spin labels or the attachment point with the tether and/or with the main structure, the R groups represent reactive groups present in the spin label moiety that can be bonded to the main structure or to the tether, and the functional group is selected from carboxylic acids, isothiocyanates, NHS esters, halogens, alkynes, and azides.
Figure 6:
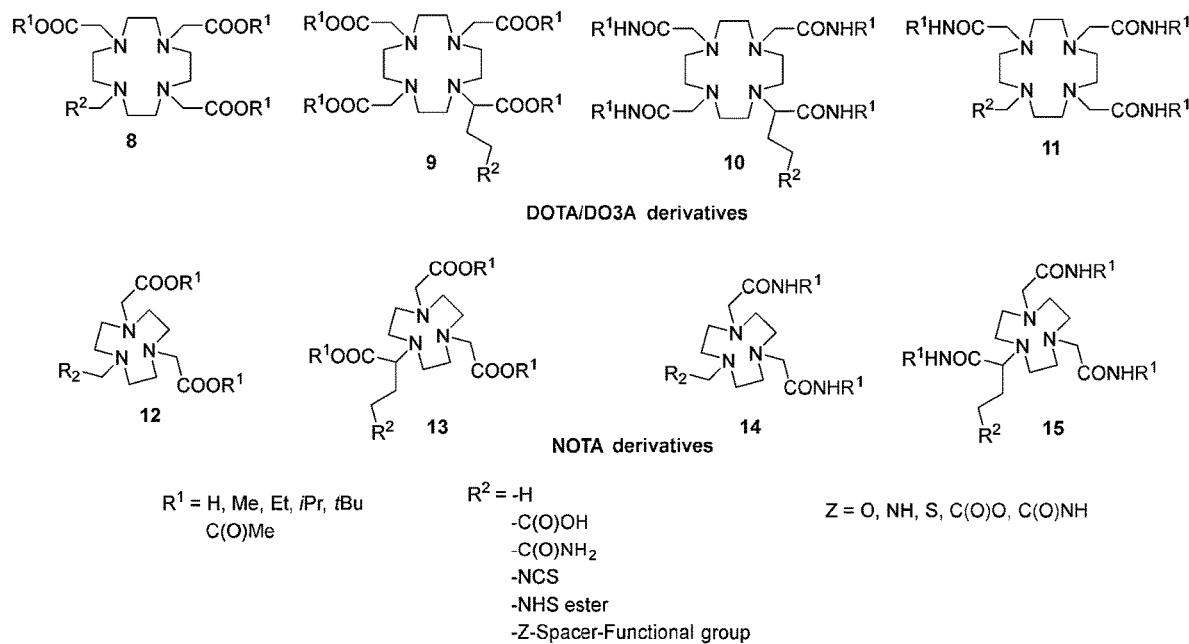
FIG. 6 shows general structures of representative metal chelates. The $R^2$ groups represent reactive groups present in the metal chelate moiety that can be bonded to the main structure or to the tether, the functional group is selected from carboxylic acids, isothiocyanates, NHS esters, halogens, alkynes, and azides.
Figure 7:
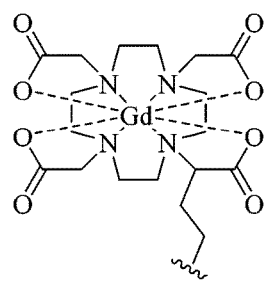
FIG. 7 shows a representative structure of a metal chelate as exemplified by a DOTA derivative and gadolinium(III). Wavy line represents the attachment point with the tether and/or with the main structure.

Unless otherwise defined, all technical and scientific terms used herein have the same meaning as commonly understood by one of ordinary skill in the art to which this invention belongs. Although methods and materials similar or equivalent to those described herein can be used in accordance with the present disclosure, suitable methods and materials are described below. All publications, patent applications, patents, and other references mentioned herein, including GenBank database sequences, are incorporated by reference in their entirety. In case of conflict, the present specification, including definitions, will control. In addition, the materials, methods, and examples are illustrative only and not intended to be limiting. Other features and advantages of the present disclosure will be apparent from the following detailed description, and from the claims.

Definitions

The compounds of this disclosure include any and all possible isomers, stereoisomers, enantiomers diastereomers, tautomers, pharmaceutically-acceptable salts, and solvates thereof. Thus, the terms "compound" and "compounds" as used in this disclosure refer to the compounds of this disclosure and any of all possible isomers, stereoisomers, enantiomers diastereomers, tautomers, pharmaceutically-acceptable salts, and solvates thereof.

Unless otherwise specifically defined, "alkyl" refers to a linear or branched hydrocarbon radical which may be fully saturated, mono- or polyunsaturated and can include divalent radicals, having from 1 to about 15 carbon atoms if it is saturated, or from 2 to about 15 carbon atoms if it is unsaturated. Examples for saturated hydrocarbon radicals include, but are not limited to, groups such as methyl (Me), ethyl (Et), n-propyl, isopropyl, n-butyl, t-butyl, isobutyl, sec-butyl, homologs and isomers of, for example, n-pentyl, n-hexyl, n-heptyl, n-octyl, 1,1-dimethyl-heptyl, 1,2-dimethyl-heptyl, and the like. An unsaturated alkyl group includes one or more double bonds, triple bonds or combinations thereof. Examples of unsaturated alkyl groups include but are not limited to, vinyl, propenyl, isopropenyl, crotyl, 2-isopentenyl, allenyl, butenyl, butadienyl, pentenyl, pentadienyl, 3-(1,4-pentadienyl), hexenyl, hexadienyl, ethynyl, propynyl, butynyl, and higher homologs and isomers. The term "divalent alkyl radicals" unless otherwise specifically defined refers to the general formula: -alkyl-. The term "$C_{1-m}$-alkyl" refers to an alkyl having from 1 to about m carbon atoms.

Unless otherwise specifically defined, "alkoxy" refers to the general formula —O-alkyl.

Unless otherwise specifically defined, "alkylamino" refers to the general formula —(NH)-alkyl.

Unless otherwise specifically defined, "di-alkylamino" refers to the general formula —N-(alkyl)$_2$.

Unless otherwise specifically limited di-alkylamino includes cyclic amine compounds such as piperidine, piperazine, azetidine, pyrrolidine, morpholine and their derivatives.

Unless otherwise specifically defined, "heterocyclic moiety", "heterocyclic" or "heterocyclic ring" refers to a saturated ring structure having about 3 to about 8 ring members that has carbon atoms and one or more heteroatoms, including oxygen, nitrogen and/or sulfur, as ring atoms. The term "heterocyclic moiety", "heterocyclic" or "heterocyclic ring" can include "divalent radicals". The term "divalent heterocyclic radicals" unless otherwise specifically defined refers to the general formula: -heterocyclic-. Examples of heterocyclic moieties include but are not limited to, oxetane, thietane, azetidine, diazetidine, tetrahydrofuran, tetrahydropyran, thiolane, pyrrolidine, dioxolane, oxathiolane, imidazolidine, dioxane, piperidine, morpholine, piperazine, and their derivatives.

The phrase "pharmaceutically acceptable" is employed in this disclosure to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The terms "salt" and "salts", as employed in the disclosure, denotes acidic and/or basic salts formed with inorganic and/or organic acids and bases.

In certain embodiments, the disclosed compounds are isolated from a naturally occurring or synthetic material. In some embodiments, the isolated compound is contemporaneously or subsequently "purified" or "substantially purified". As used herein a "purified" or "substantially purified" compound means a compound that has been processed to a desired purity. A person of ordinary skill can establish the desired purity for a use and method to achieve that purity without undue effort. The purified compound may be used in any disclosed embodiment.

As used herein a "therapeutically effective amount" of a compound, is the quantity of a compound which, when administered to an individual or animal, results in a discernible physiological effect in the individual or animal. The compounds disclosed herein, and pharmaceutically acceptable salts thereof, have pharmacological properties when administered in therapeutically effective amounts for providing a physiological effect useful to treat a number of physiological conditions. Typically, a "therapeutically effective amount" of a compound is believed to range from about 5 mg/day to about 1,000 mg/day.

As used herein, an "individual" refers to a human. An "animal" refers to, for example, veterinary animals, such as dogs, cats, horses and the like, and farm animals, such as cows, pigs and the like.

As used in chemical formulas herein, when an integer is 0, the structural portion modified by that integer is absent and the adjacent subunits are directly connected.

The compositions of the disclosure may be alternately formulated to comprise, consist of, or consist essentially of, any appropriate components herein disclosed. The compositions of the disclosure may additionally, or alternatively, be formulated so as to be devoid, or substantially free, of any components, materials, ingredients, adjuvants or species used in the prior art compositions or that are otherwise not necessary to the achievement of the function and/or objectives of the present disclosure.

The compounds of the present disclosure may have unnatural ratios of atomic isotopes at one or more of their atoms. For example, the compounds may be labeled with isotopes, such as deuterium tritium carbon-11, carbon-14, iodine-123, iodine-125 or fluorine-18. The present disclosure encompasses all isotopic variations of the described compounds, whether radioactive or not.

The disclosed compounds, and pharmaceutically acceptable salts thereof may be used to prepare prodrugs. As used herein, the term "prodrug" refers to any derivative of the compounds of general formulas I, II, and III that are metabolized or otherwise converted into an active form upon introduction into the body of an individual or animal. Prodrugs are well known to those skilled in the art of pharmaceutical chemistry and provide benefits such as increased adsorption and half-life. Those skilled in the art of drug delivery will readily appreciate that the pharmacokinetic properties of general formulas I, II, and III may be controlled by an appropriate choice of moieties to produce prodrug derivatives.

One or more disclosed compounds, typically after purification, can be incorporated into a pharmaceutical composition or medicament. The disclosed compounds can be administered by a variety of known methods, including, for example, orally, rectally, or by parenteral routes (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular, subcutaneous, ocular, intranasal, inhalation-based and transdermal administration) and slow releasing microcarriers (for rectal, intramuscular or intravenous administration). The pharmaceutical composition or medicament can also contain a pharmaceutically acceptable vehicle, diluent, excipient or carrier and optional adjuvants, flavorings, colorants, wetting agents, emulsifying agents, pH buffering agents and preservatives. Some suitable pharmaceutically acceptable vehicles include, for example, saline, sterile water, Ringer's solution and isotonic sodium chloride solutions. The specific dosage level of active ingredient will depend upon a number of factors, including, for example, biological activity of the particular preparation, age, body weight, sex and general health of the individual being treated.

Figure 8A:
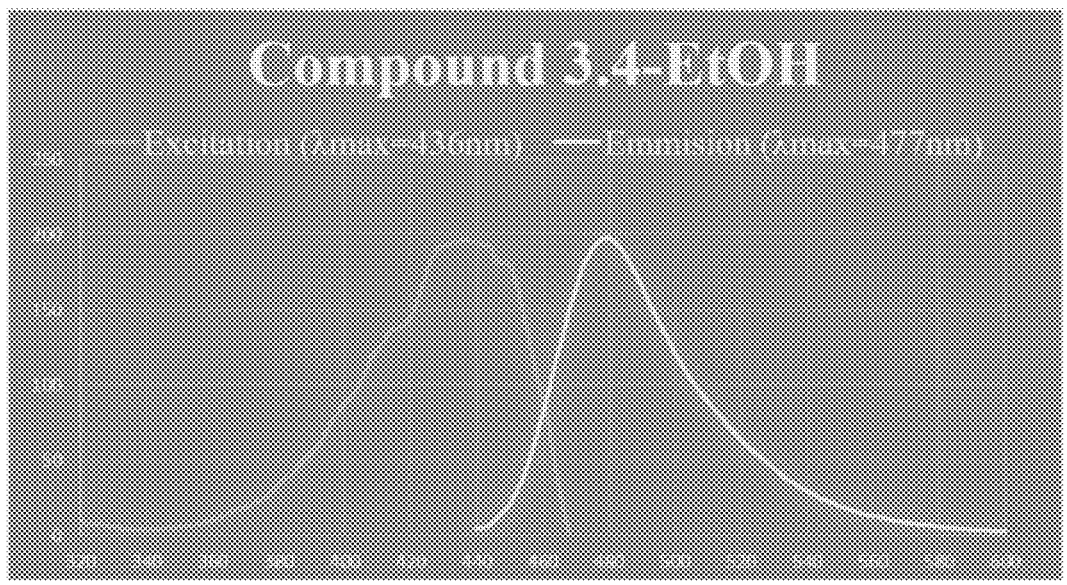
FIG. 8A presents excitation and emission spectra for compound 3.4.
Figure 8B:
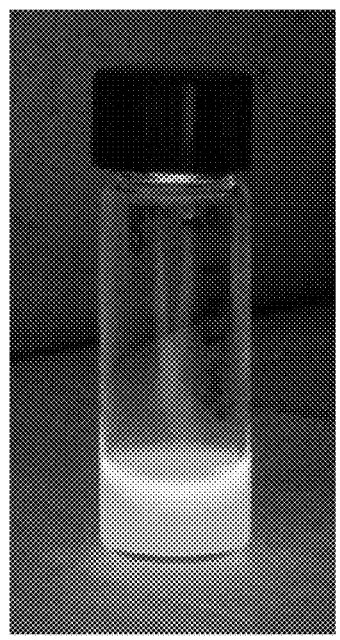
FIG. 8B is a photograph of a fluorescent solution of compound 7.2 in ethanol exposed to a UV light source.
Figure 8C:
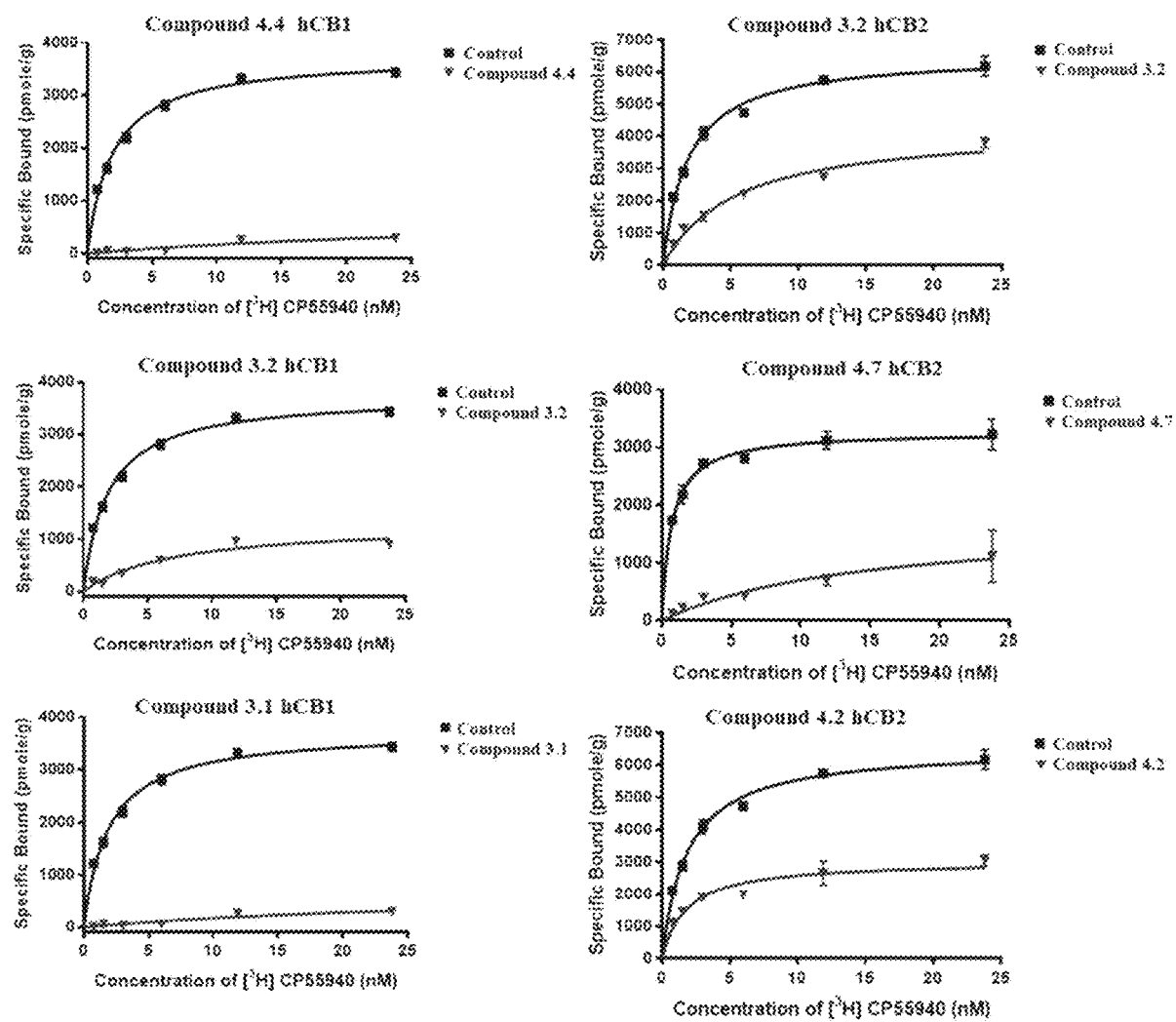
FIG. 8C shows representative saturation binding curves (red) using [3H]CP-55,940 for CB1 (left panel) and CB2 (right panel) receptors preincubated with the tight/irreversible ligands (3.1, 3.2, 4.2, 4.4 and 4.7). Control membranes processed in parallel but without prior exposure to the tight/irreversible are shown in blue.

Some disclosed compounds were tested for CB1 and CB2 receptor binding affinity (Tables 1, 2 and 3). As used herein "binding affinity" is represented by the Ki value. The Ki value is the affinity constant and describes the affinity of the compound for the receptor. The lower the Ki value, the higher the affinity of the compound for the receptor. A detailed description of the methods used to test "binding affinity" of compounds is given in Makriyannis, et al., US 2007, 0135388 and in Papahatjis, et al. *J. Med. Chem.* (2007) 4048, the content of each of which is hereby incorporated by reference. Functional characterization of some of the disclosed compounds was performed by using the cyclic adenosine monophosphate (cAMP) assay. The functional potency of the compound is represented by the $EC_{50}$ value. The lower the $EC_{50}$ value, the higher the functional potency. A detailed description of the cyclic adenosine monophosphate (cAMP) assay is given in Nikas et al. *J. Med. Chem.* (2010) 6996. The ability of some of the ligands to bind to the CB1/CB2 receptors with a tight/irreversible binding mode was determined by measuring reductions in the binding for the radioligand [3H]CP-55,940 when the receptor preparation was pretreated with the tight/irreversible ligand, and comparing it to the untreated sample as disclosed in Ogava et al. *J. Med. Chem.* (2015) 58, 3104. Reductions in the specific binding ($B_{max}$) of [$^3$H]CP-55,940 after ligand pretreatment indicate ability of the ligand to tight/irreversibly bind to the receptor. As detailed in Ogava et al. *J Med. Chem.* (2015) 58, 3104, the experiment was conducted by pretreating the sample with a concentration equal to 10-fold the compound's $K_i$ value for the receptor in question and subsequently measuring the decrease of $B_{max}$ obtained from a saturation curve using [3H]CP-55,940. Testing results for representative ligands with tight/irreversible binding modes are summarized in FIG. 8C.

Those skilled in the art will recognize, or be able to ascertain, using no more than routine experimentation, numerous equivalents to the specific substances and procedures described herein. Such equivalents are intended to be encompassed in the scope of the claims that follow the examples below.

As used herein, when an integer such as f, j, or k is 0, the structural portion modified by that integer is absent and the adjacent subunits are directly connected. For example, when f is 0, structure $a_2$ comprises of 3-member ring and/or when i is 0 then $Q_2$ is directly connected to the $C_9$.

Examples

Synthesis and biological testing of compounds of General Formulas I, II, and III.

Synthesized compounds represented by the general structures I, II, and III are depicted in Tables 1, 2, and 3 respectively, on the following pages. Biological testing results are also provided in Tables 1, 2, and 3 and in FIG. 8C. Fluorescence properties of selected compounds are given in Table 4. Excitation and Emission spectra for compound 3.4 are presented in FIG. 8A and a picture of a fluorescent solution of compound 7.2 in EtOH exposed to UV light is provided in FIG. 8B. Receptor affinities are given as follows:
+: Ki=0.01-10 nM; ++: Ki=10-200 nM; +++: Ki=200-1,000 nM; ++++: Ki>1,000

TABLE 1

Compounds of the general formula I

| Compound number | Structure | CB1 receptor Ki (nM) | CB2 receptor Ki (nM) |
|---|---|---|---|
| 3.1 | 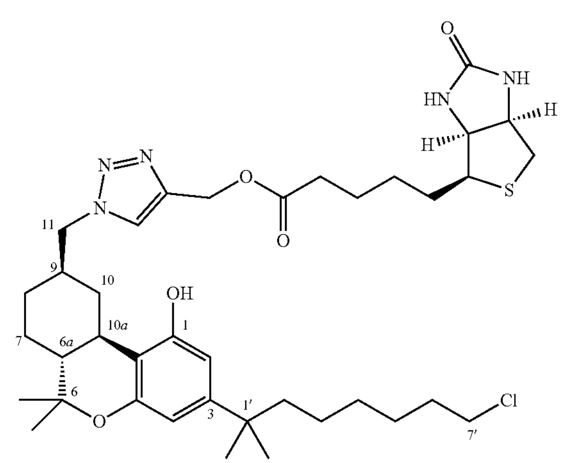 [SMILES: CC(C)(CCCCCCCl)c1cc(O)c2c(c1)OC(C)(C)[C@@H]1CC[C@@H](Cn3cc(COC(=O)CCCC[C@@H]4SC[C@@H]5NC(=O)N[C@@H]54)nn3)C[C@@H]21] | + | + |

TABLE 1-continued

Compounds of the general formula I

| Compound number | Structure | CB1 receptor Ki (nM) | CB2 receptor Ki (nM) |
|---|---|---|---|
| 3.2 | 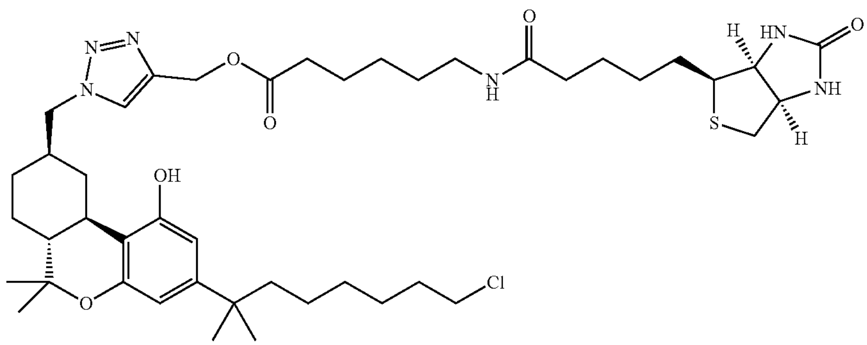 [SMILES: CC(C)(CCCCCCCl)c1cc(O)c2c(c1)OC(C)(C)[C@@H]1CC[C@@H](Cn3cc(COC(=O)CCCCCNC(=O)CCCC[C@@H]4SC[C@@H]5NC(=O)N[C@@H]54)nn3)C[C@@H]21] | + | + |
| 3.3 | 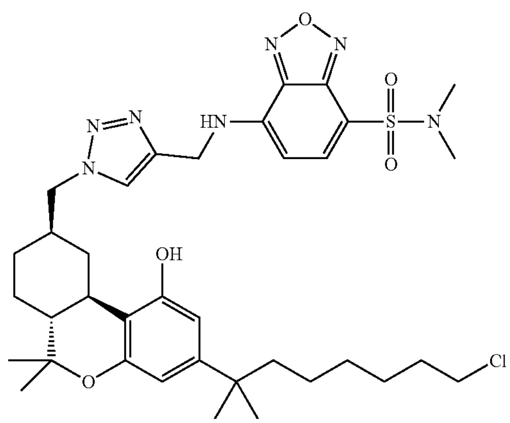 [SMILES: CN(C)S(=O)(=O)c1ccc(NCc2cn(C[C@@H]3CC[C@@H]4[C@@H](C3)c3c(O)cc(C(C)(C)CCCCCCCl)cc3OC4(C)C)nn2)c2nonc12] | + | + |
| 3.4 | 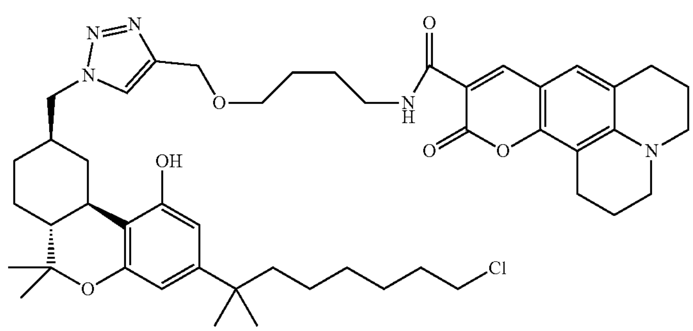 [SMILES: CC(C)(CCCCCCCl)c1cc(O)c2c(c1)OC(C)(C)[C@@H]1CC[C@@H](Cn3cc(COCCCCNC(=O)c4cc5cc6c7c(c5oc4=O)CCCN7CCC6)nn3)C[C@@H]21] | + | + |
| 3.8 | 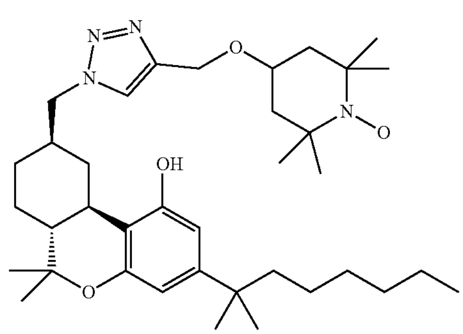 [SMILES: CCCCCCC(C)(C)c1cc(O)c2c(c1)OC(C)(C)[C@@H]1CC[C@@H](Cn3cc(COC4CC(C)(C)N(O)C(C)(C)C4)nn3)C[C@@H]21] | + | + |

TABLE 1-continued

Compounds of the general formula I

| Compound number | Structure | CB1 receptor Ki (nM) | CB2 receptor Ki (nM) |
|---|---|---|---|
| 3.9 | 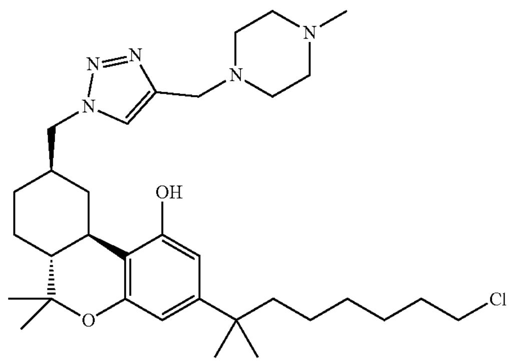 [SMILES: CN1CCN(Cc2cn(C[C@@H]3CC[C@@H]4[C@@H](C3)c3c(O)cc(C(C)(C)CCCCCCCl)cc3OC4(C)C)nn2)CC1] | + | + |
| 3.10 | 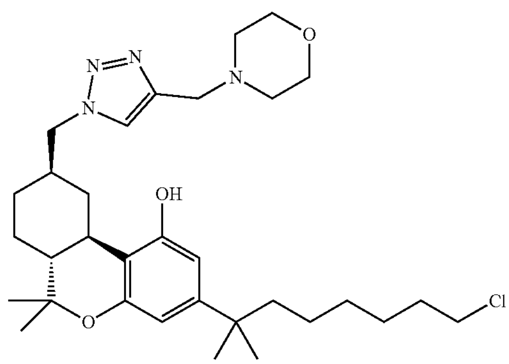 | + | + |
| 3.11 | 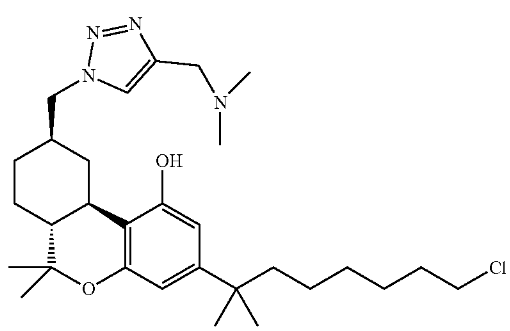 [SMILES: CN(C)Cc1cn(C[C@@H]2CC[C@@H]3[C@@H](C2)c2c(O)cc(C(C)(C)CCCCCCCl)cc2OC3(C)C)nn1] | + | + |
| 3.12 | 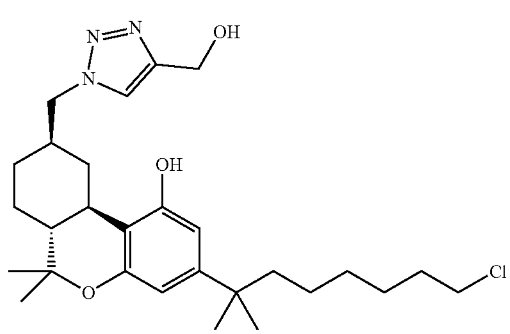 [SMILES: CC(C)(CCCCCCCl)c1cc(O)c2c(c1)OC(C)(C)[C@@H]1CC[C@@H](Cn3cc(CO)nn3)C[C@@H]21] | + | + |

TABLE 1-continued

Compounds of the general formula I

| Compound number | Structure | CB1 receptor Ki (nM) | CB2 receptor Ki (nM) |
|---|---|---|---|
| 3.13 | 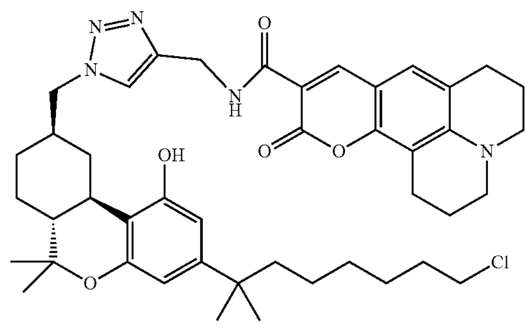 [SMILES: CC(C)(CCCCCCCl)c1cc(O)c2c(c1)OC(C)(C)[C@@H]1CC[C@@H](Cn3cc(CNC(=O)c4cc5cc6c7c(c5oc4=O)CCCN7CCC6)nn3)C[C@@H]21] | + | ++ |
| 3.14 | 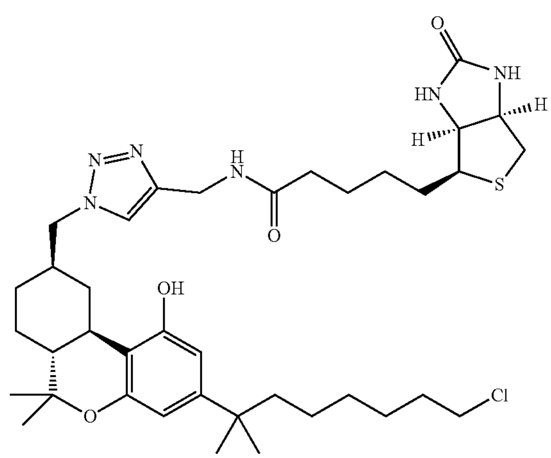 [SMILES: CC(C)(CCCCCCCl)c1cc(O)c2c(c1)OC(C)(C)[C@@H]1CC[C@@H](Cn3cc(CNC(=O)CCCC[C@@H]4SC[C@@H]5NC(=O)N[C@@H]54)nn3)C[C@@H]21] | + | + |
| 3.15 | 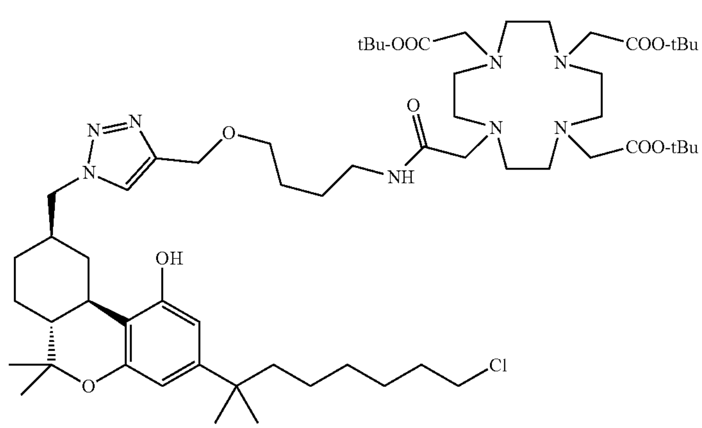 | | |

TABLE 1-continued

Compounds of the general formula I

| Compound number | Structure | CB1 receptor Ki (nM) | CB2 receptor Ki (nM) |
|---|---|---|---|
| 3.16 | 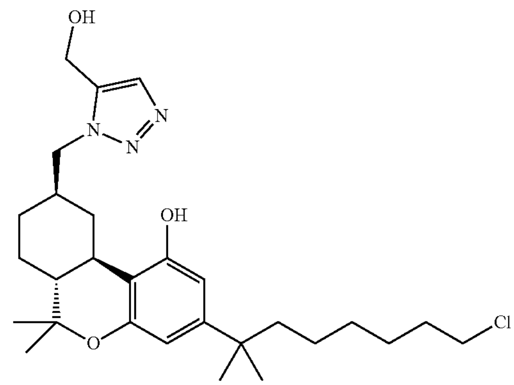 [SMILES: CC(C)(CCCCCCCl)c1cc(O)c2c(c1)OC(C)(C)[C@@H]1CC[C@@H](Cn3nncc3CO)C[C@@H]21] | + | + |
| 11.2 | 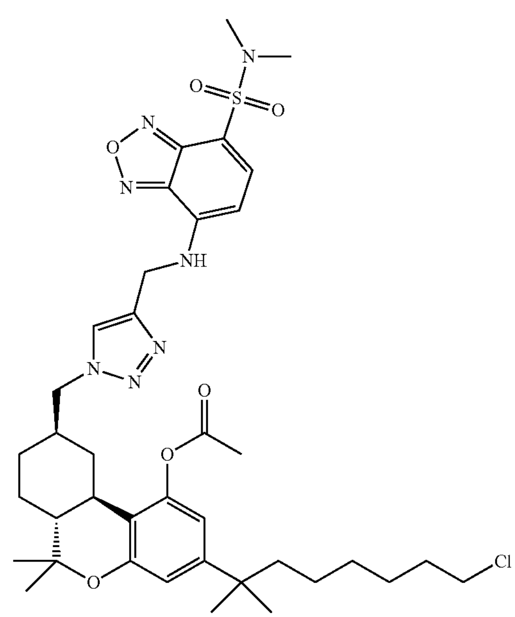 [SMILES: CC(=O)Oc1cc(C(C)(C)CCCCCCCl)cc2c1[C@@H]1C[C@H](Cn3cc(CNc4ccc(S(=O)(=O)N(C)C)c5nonc45)nn3)CC[C@H]1C(C)(C)O2] | ++ | ++ |

TABLE 2

Compounds of the general formula II

| Compound number | Structure | CB1 receptor Ki (nM) | CB2 receptor Ki (nM) |
|---|---|---|---|
| 4.2 | 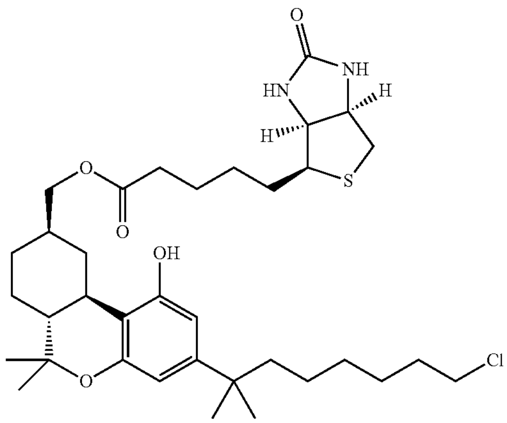 [SMILES: CC(C)(CCCCCCCl)c1cc(O)c2c(c1)OC(C)(C)[C@@H]1CC[C@@H](COC(=O)CCCC[C@@H]3SC[C@@H]4NC(=O)N[C@@H]43)C[C@@H]21] | + | + |
| 4.4 | 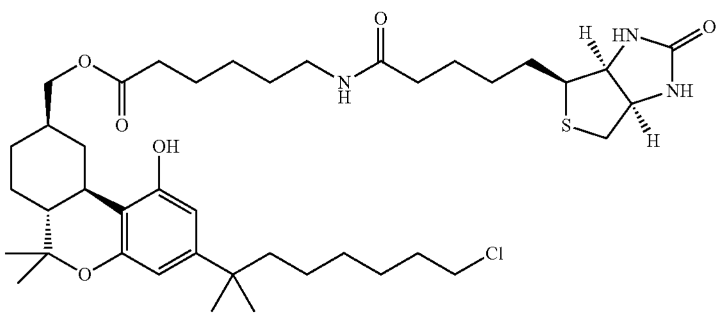 [SMILES: CC(C)(CCCCCCCl)c1cc(O)c2c(c1)OC(C)(C)[C@@H]1CC[C@@H](COC(=O)CCCCCNC(=O)CCCC[C@@H]3SC[C@@H]4NC(=O)N[C@@H]43)C[C@@H]21] | + | + |
| 4.7 | 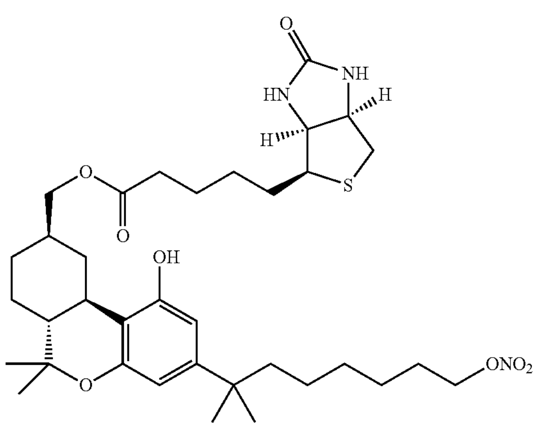 | + | + |

TABLE 2-continued

Compounds of the general formula II

| Compound number | Structure | CB1 receptor Ki (nM) | CB2 receptor Ki (nM) |
|---|---|---|---|
| 5.5 | 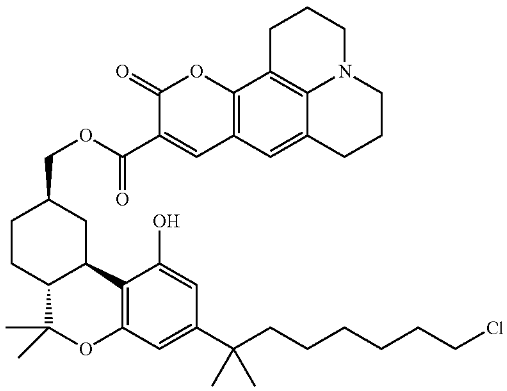 [SMILES: CC(C)(CCCCCCCl)c1cc(O)c2c(c1)OC(C)(C)[C@@H]1CC[C@@H](COC(=O)c3cc4cc5c6c(c4oc3=O)CCCN6CCC5)C[C@@H]21] | ++ | ++ |
| 5.7 | 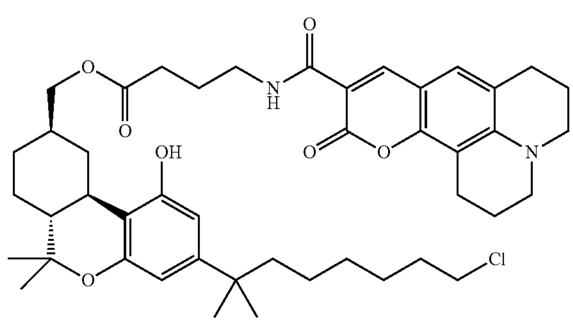 [SMILES: CC(C)(CCCCCCCl)c1cc(O)c2c(c1)OC(C)(C)[C@@H]1CC[C@@H](COC(=O)CCCNC(=O)c3cc4cc5c6c(c4oc3=O)CCCN6CCC5)C[C@@H]21] | ++ | ++ |
| 5.10 | 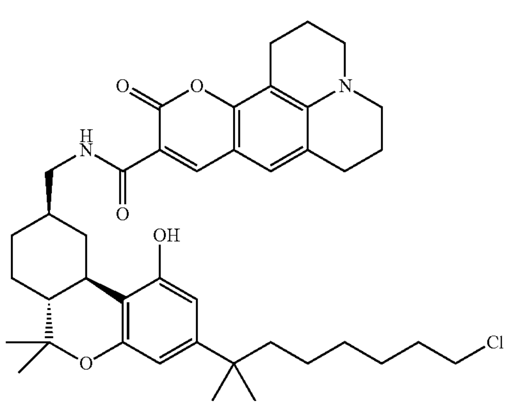 [SMILES: CC(C)(CCCCCCCl)c1cc(O)c2c(c1)OC(C)(C)[C@@H]1CC[C@@H](CNC(=O)c3cc4cc5c6c(c4oc3=O)CCCN6CCC5)C[C@@H]21] | + | + |

TABLE 3

Compounds of the general formula III

| Compound number | Structure | CB1 receptor Ki (nM) | CB2 receptor Ki (nM) |
| --- | --- | --- | --- |
| 7.1 | 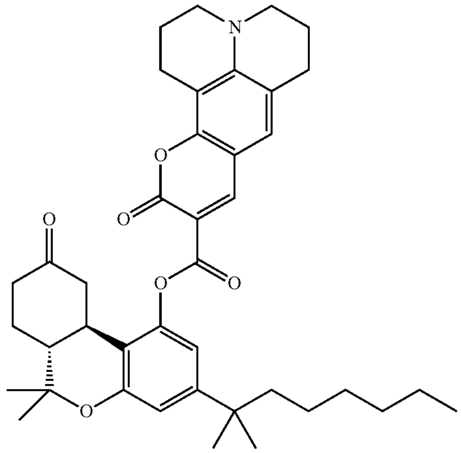 [SMILES: CCCCCCC(C)(C)c1cc(OC(=O)c2cc3cc4c5c(c3oc2=O)CCCN5CCC4)c2c(c1)OC(C)(C)[C@@H]1CCC(=O)C[C@@H]21] | ++ | +++ |
| 7.2 | 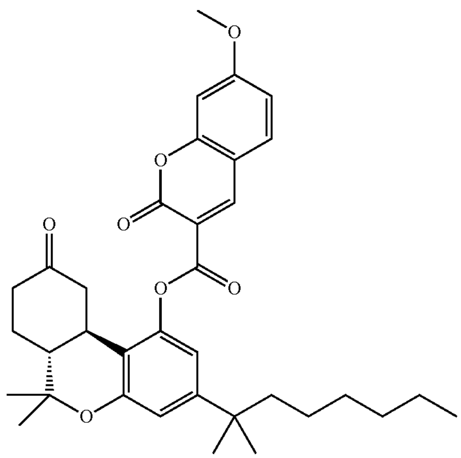 [SMILES: CCCCCCC(C)(C)c1cc(OC(=O)c2cc3ccc(OC)cc3oc2=O)c2c(c1)OC(C)(C)[C@@H]1CCC(=O)C[C@@H]21] | ++ | +++ |
| 9.9 | 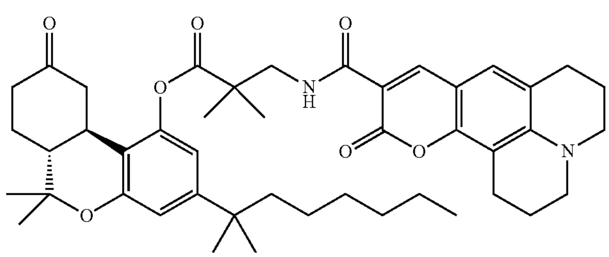 [SMILES: CCCCCCC(C)(C)c1cc(OC(=O)C(C)(C)CNC(=O)c2cc3cc4c5c(c3oc2=O)CCCN5CCC4)c2c(c1)OC(C)(C)[C@@H]1CCC(=O)C[C@@H]21] | +++ | ++ |
| 9.10 | 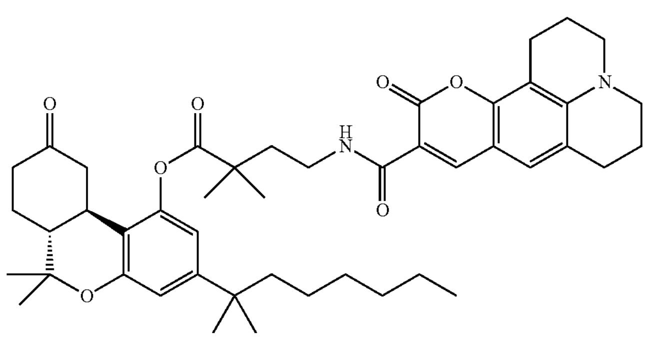 [SMILES: CCCCCCC(C)(C)c1cc(OC(=O)C(C)(C)CCNC(=O)c2cc3cc4c5c(c3oc2=O)CCCN5CCC4)c2c(c1)OC(C)(C)[C@@H]1CCC(=O)C[C@@H]21] | ++++ | ++++ |

TABLE 3-continued
Compounds of the general formula III
| Compound number | Structure | CB1 receptor Ki (nM) | CB2 receptor Ki (nM) |
|---|---|---|---|
| 9.11 | 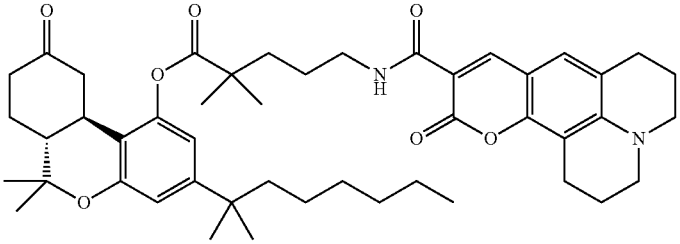 [SMILES: CCCCCCC(C)(C)c1cc(OC(=O)C(C)(C)CCCNC(=O)c2cc3cc4c5c(c3oc2=O)CCCN5CCC4)c2c(c1)OC(C)(C)[C@@H]1CCC(=O)C[C@@H]21] | ++++ | ++++ |
| 9.12 | 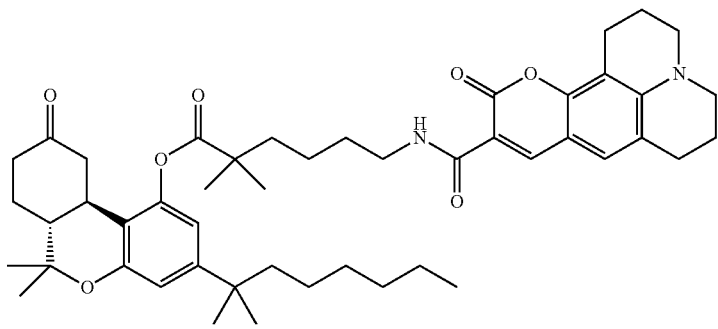 [SMILES: CCCCCCC(C)(C)c1cc(OC(=O)C(C)(C)CCCCNC(=O)c2cc3cc4c5c(c3oc2=O)CCCN5CCC4)c2c(c1)OC(C)(C)[C@@H]1CCC(=O)C[C@@H]21] | ++++ | ++++ |
| 9.13 | 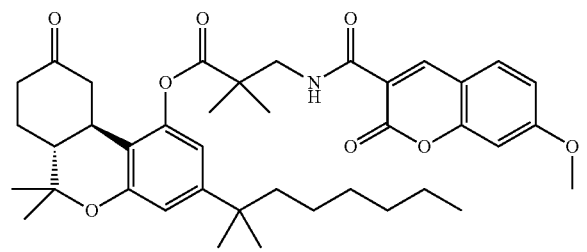 | ++++ | ++++ |
| 9.14 | 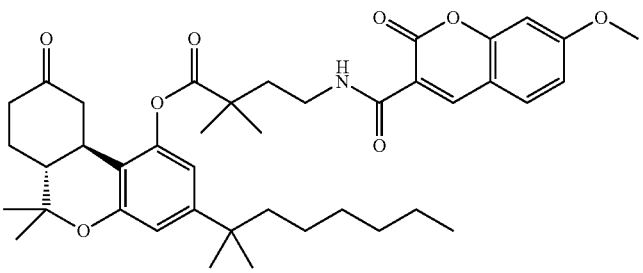 | ++ | ++ |
| 9.15 | 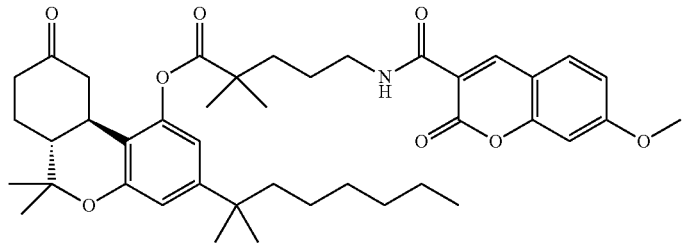 | ++++ | ++++ |

TABLE 3-continued

Compounds of the general formula III

| Compound number | Structure | CB1 receptor Ki (nM) | CB2 receptor Ki (nM) |
|---|---|---|---|
| 9.16 | 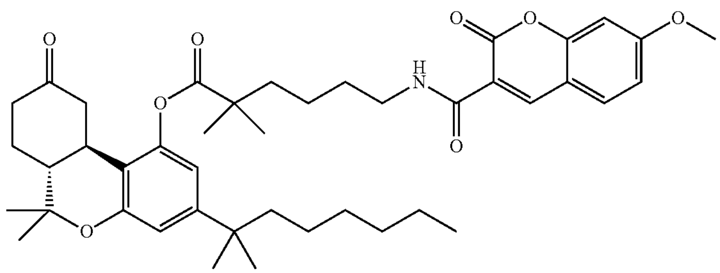 | ++++ | +++ |
| 10.1 | 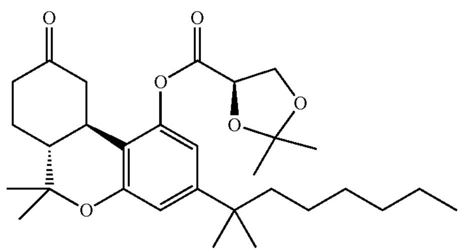 [SMILES: CCCCCCC(C)(C)c1cc(OC(=O)[C@H]2COC(C)(C)O2)c2c(c1)OC(C)(C)[C@@H]1CCC(=O)C[C@@H]21] | ++ | + |
| 10.2 | 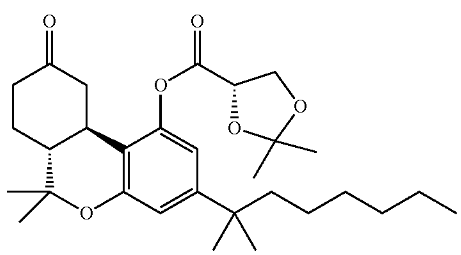 [SMILES: CCCCCCC(C)(C)c1cc(OC(=O)[C@@H]2COC(C)(C)O2)c2c(c1)OC(C)(C)[C@@H]1CCC(=O)C[C@@H]21] | + | ++ |
| 10.3 | 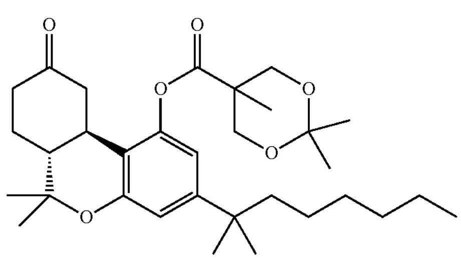 | ++ | +++ |
| 10.4 | 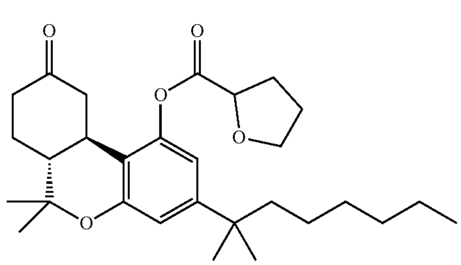 [SMILES: CCCCCCC(C)(C)c1cc(OC(=O)C2CCCO2)c2c(c1)OC(C)(C)[C@@H]1CCC(=O)C[C@@H]21] | + | ++ |

TABLE 3-continued

Compounds of the general formula III

| Compound number | Structure | CB1 receptor Ki (nM) | CB2 receptor Ki (nM) |
|---|---|---|---|
| 10.5 | 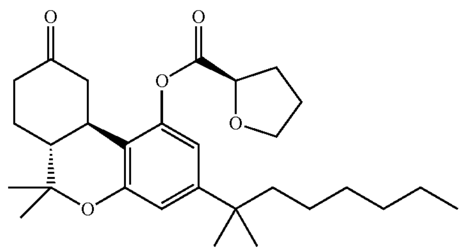 [SMILES: CCCCCCC(C)(C)c1cc(OC(=O)[C@H]2CCCO2)c2c(c1)OC(C)(C)[C@@H]1CCC(=O)C[C@@H]21] | + | ++ |
| 10.6 | 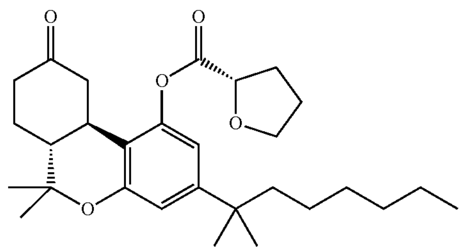 [SMILES: CCCCCCC(C)(C)c1cc(OC(=O)[C@@H]2CCCO2)c2c(c1)OC(C)(C)[C@@H]1CCC(=O)C[C@@H]21] | + | ++ |
| 10.7 | 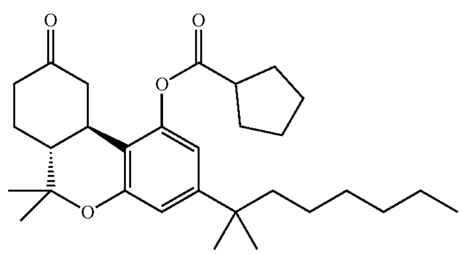 [SMILES: CCCCCCC(C)(C)c1cc(OC(=O)C2CCCC2)c2c(c1)OC(C)(C)[C@@H]1CCC(=O)C[C@@H]21] | ++ | ++++ |
| 10.8 | 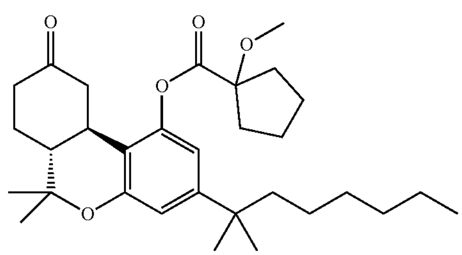 [SMILES: CCCCCCC(C)(C)c1cc(OC(=O)C2(OC)CCCC2)c2c(c1)OC(C)(C)[C@@H]1CCC(=O)C[C@@H]21] | +++ | ++++ |
| 10.9 | 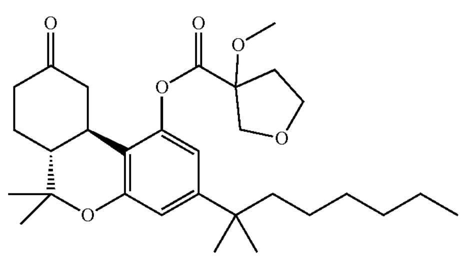 [SMILES: CCCCCCC(C)(C)c1cc(OC(=O)C2(OC)CCOC2)c2c(c1)OC(C)(C)[C@@H]1CCC(=O)C[C@@H]21] | ++ | ++ |
| 10.10 | 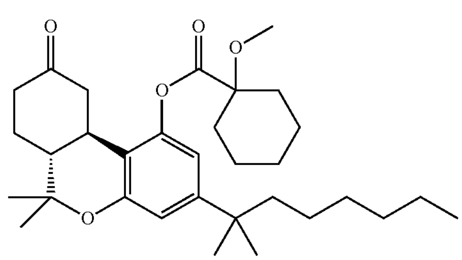 [SMILES: CCCCCCC(C)(C)c1cc(OC(=O)C2(OC)CCOCC2)c2c(c1)OC(C)(C)[C@@H]1CCC(=O)C[C@@H]21] | ++++ | ++++ |

TABLE 3-continued
Compounds of the general formula III
| Compound number | Structure | CB1 receptor Ki (nM) | CB2 receptor Ki (nM) |
|---|---|---|---|
| 10.11 | 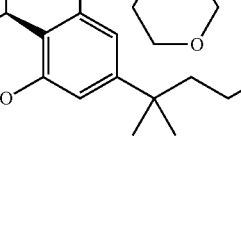 | ++ | +++ |
| 10.12 | 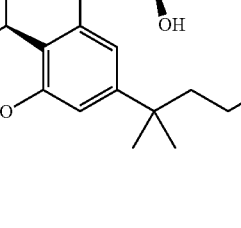 | + | ++ |
| 10.13 | 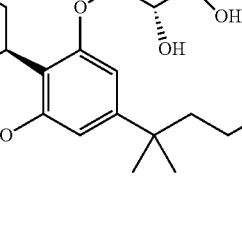 | + | ++ |
| 10.14 | 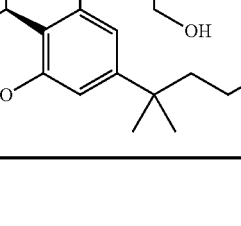 | +++ | +++ |

TABLE 4

Fluorescence properties of selected compounds

| Compound number | Compound | Ethanol Ex $\lambda_{max}$ | Ethanol Em $\lambda_{max}$ | Acetonitrile Ex $\lambda_{max}$ | Acetonitrile Em $\lambda_{max}$ |
|---|---|---|---|---|---|
| 3.3 | | 415 | 581 | 416 | 583 |
| 3.4 | | 436 | 477 | 437 | 488 |
| 3.13 | | 436 | 478 | 435 | 488 |

Syntheses

All reagents and solvents were purchased from Aldrich Chemical Co., unless otherwise specified, and were used without further purification. All anhydrous reactions were performed under a static argon atmosphere in flame-dried glassware using scrupulously dry solvents. Flash column chromatography employed silica gel 60 (230-400 mesh). All compounds were demonstrated to be homogeneous by analytical TLC on precoated silica gel TLC plates (Merck, 60 $F_{245}$ on glass, layer thickness 250 μm), and chromatograms were visualized by phosphomolybdic acid staining. Melting points were determined on a micromelting point apparatus and are uncorrected. IR spectra were recorded on a Perkin Elmer Spectrum One FT-IR spectrometer. NMR spectra were recorded in $CDCl_3$, unless otherwise stated, on a Bruker Ultra Shield 400 WB plus ($^1H$ at 400 MHz, $^{13}C$ at 100 MHz) or on a Varian INOVA-500 ($^1H$ at 500 MHz, $^{13}C$ at 125 MHz) spectrometers and chemical shifts are reported in units of δ relative to internal TMS. Multiplicities are indicated as br (broadened), s (singlet), d (doublet), t (triplet), q (quartet), m (multiplet) and coupling constants (J) are reported in hertz (Hz). Low and high-resolution mass spectra were performed in School of Chemical Sciences, University of Illinois at Urbana-Champaign. Mass spectral data are reported in the form of m/z (intensity relative to base=100). LC/MS analysis was performed by using a Waters Micro-Mass ZQ system [electrospray-ionization (ESI) with Waters-2525 binary gradient module coupled to a Photodiode Array Detector (Waters-2996) and ELS detector (Waters-2424) using a XTerra MS C18, 5 μm, 4.6 mm×50 mm column and acetonitrile/water.

A. Hexahydrocannabinol Synthesis.

Hexahydrocannabinol compound 1.21 (shown in Scheme 1) was synthesized in three steps starting from hexahydrocannabinol compound 1.18 by using the method depicted in Scheme 1. In turn, hexahydrocannabinol compound 1.18 (shown in Scheme 1) was synthesized in twelve steps starting from commercially available 3.5-dimethoxyphenyl acetonitrile (compound 1.6) by a method disclosed in Hua, T. et al., *Nature* (2017), 547: 468-471, the contents of which are hereby incorporated by reference.

Scheme 1

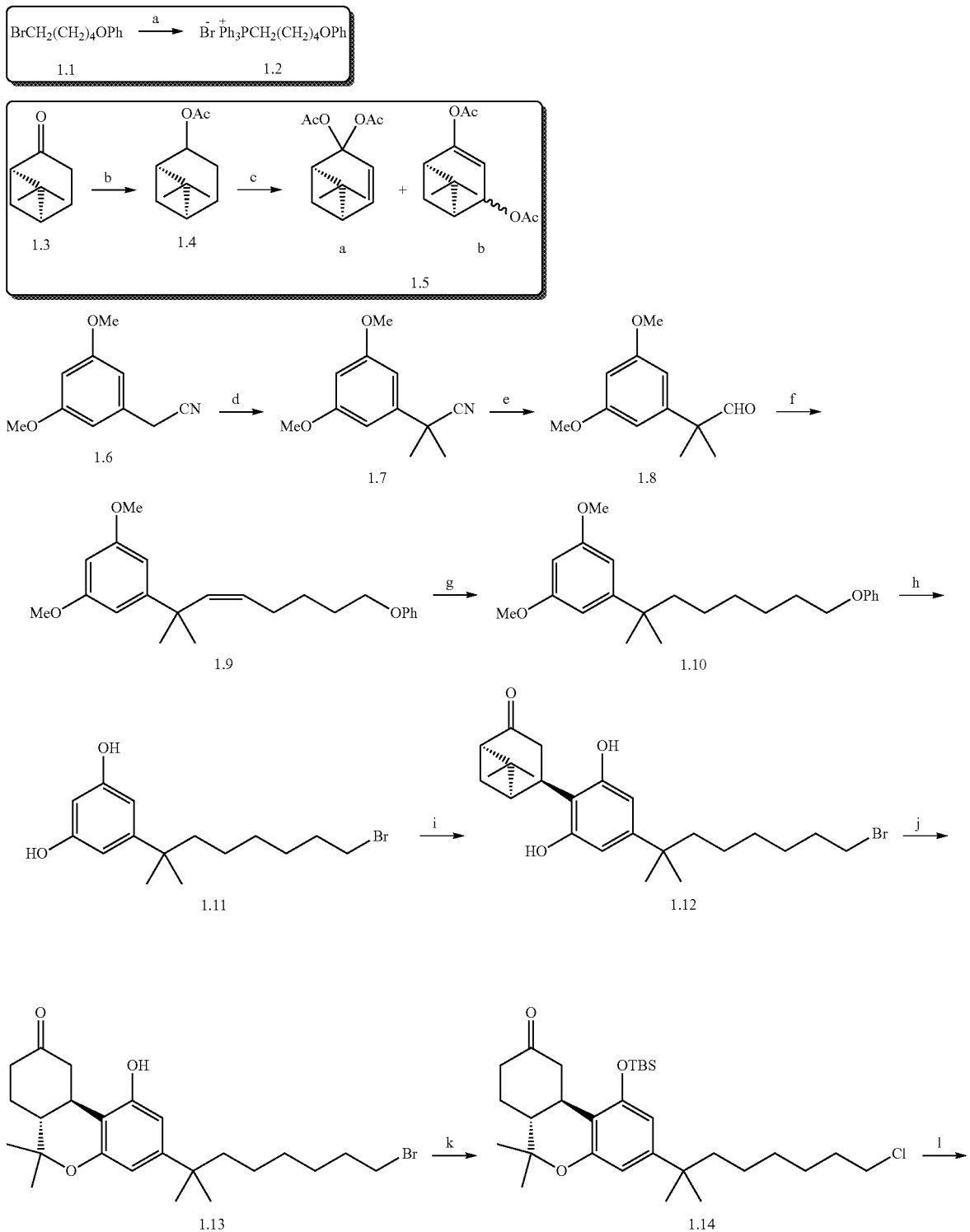

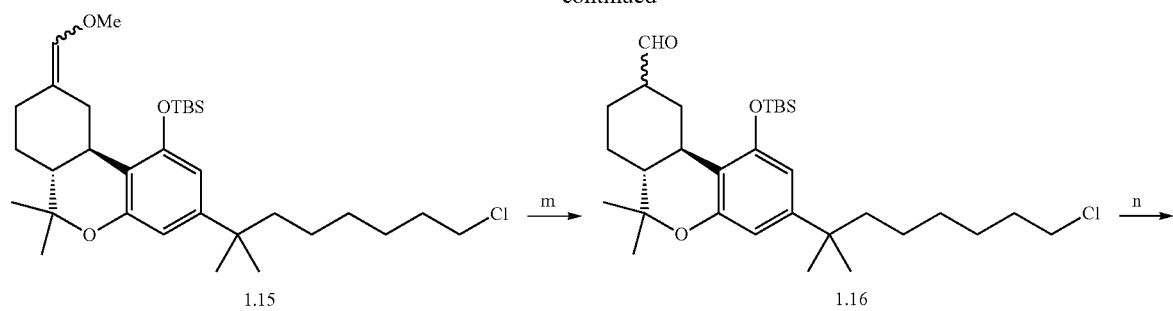
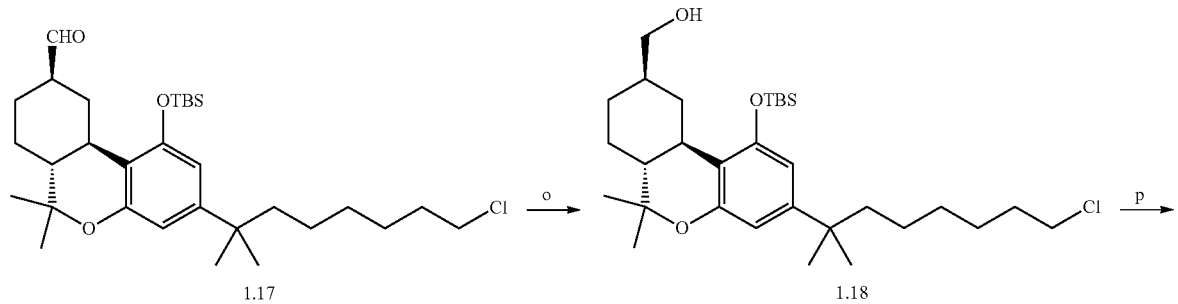
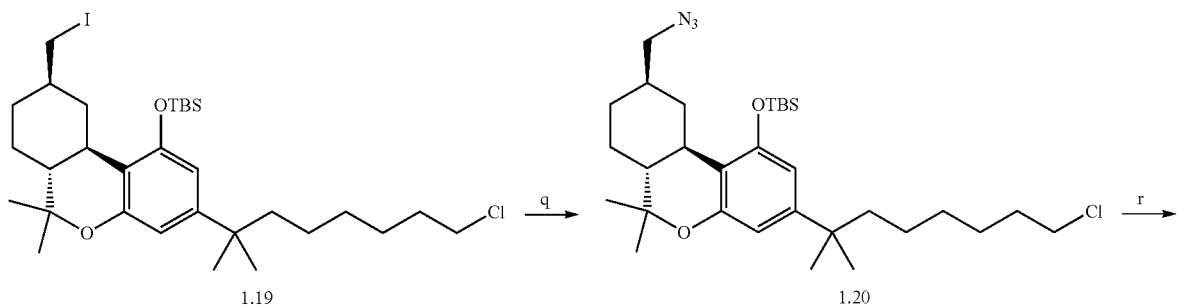
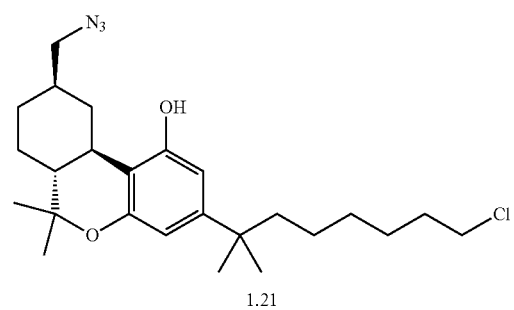

-continued

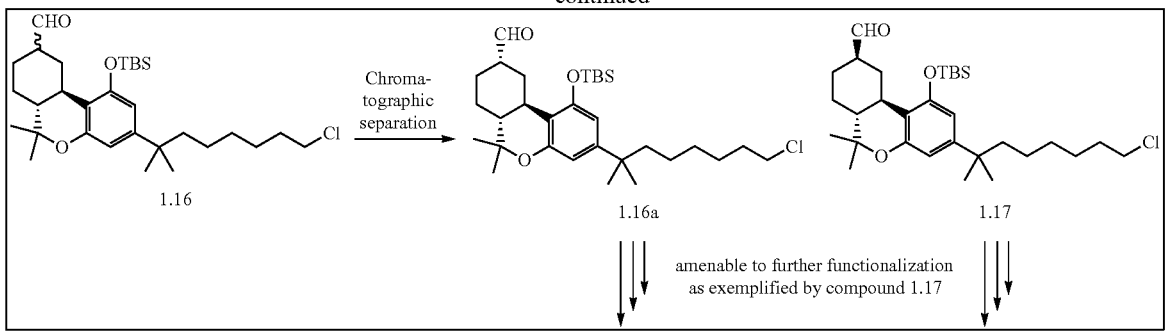

Reagents and Conditions:
(a) PPh₃, benzene, reflux, 72 h, 95%;
(b) isopropenyl acetate, p-TSA, reflux, 5 h, 94%
(c) Pb(OAc)₄, benzene, 78-80° C. 3 h, 90%;
(d) CH₃I, NaH, DMF, 0° C., to r t, 2 h, 96%;
(e) DiBAl-H, CH₂Cl₂, -78° C., 30 min, 92%;
(f) compound 1.2, (Me₃Si)₂N⁻K⁺, THF, 0° C., to r t, 30 min, then addition of compound 1.8, 0° C., to r t, 2 h, 93%;
(g) H₂, 10% Pd on C, AcOEt, r t, 3 h 98%;
(h) BBr₃, CH₂Cl₂, -78° C. to r t, 6 h, 99%;
(i) mixture of compounds 1.5a and 1.5b, p-TSA, wet CHCl₃, 0° C. to r t, 4 days, 64%;
(j) TMSOTf, CH₂Cl₂/MeNO₂, 0° C. to r t, 3 h, 75%;
(k) TBSCl, imidazole, DMAP, DMF, 62° C., 12 h, 93%;
(l) Cl⁻ Ph₃P⁺CH₂OMe, (Me₃Si)₂N⁻K⁺, THF, 0° C. to r t, 40 min, then addition of compound 1.14, 0° C. to r t, 1 h, 93%;
(m) Cl₃CCOOH, CH₂Cl₂, r t, 20 min, 95%;
(n) K₂CO₃, EtOH, r t, 3 h, 84%;
(o) NaBH₄, EtOH, 0° C., 30 min, 98%;
(p) I₂, imidazole, PPh₃, benzene, 50° C., 30 min, 95%;
(q) n-Bu₄NN₃, r t, 30 h, 83%;
(r) n-Bu₄NF, CH₂Cl₂, -70° C., 20 min, 96%.

(5-Phenoxypentyl)triphenyl-phosphonium, bromide (compound 1.2). A mixture of compound 1.1 (6.96 g, 28.6 mmol) and triphenylphosphine (8.25 g, 31.5 mmol) in anhydrous benzene (70 mL) was refluxed with vigorous stirring for 72 hours under argon atmosphere. The reaction mixture was cooled to room temperature, and the precipitating product, compound 1.2 (13.05 g, 95% yield), was isolated by filtration under reduced pressure as a white microcrystalline solid. mp 174-176° C. $^1$H NMR (500 MHz, CDCl₃) δ: 7.86 (dd, J=12.1 Hz, 8.0 Hz, 6H, —PPh₃), 7.78 (td, J=8.0 Hz, 1.5 Hz, 3H, —PPh₃), 7.68 (td, J=8.0 Hz, 3.5 Hz, 6H, —PPh₃), 7.24 (t, J=7.9 Hz, 2H, 3-H, 5-H, -OPh), 6.91 (t, J=7.9 Hz, 1H, 4-H, -OPh), 6.78 (d, J=7.9 Hz, 2H, 2-H, 6-H, -OPh), 3.92 (t, J=5.6 Hz, 2H, —CH₂OPh), 3.85 (dt, J=12.5 Hz, 8.0 Hz, 2H, —CH₂PPh₃), 1.90-1.79 (m, 4H), 1.77-1.69 (m, 2H).

(1R,5S)-6,6-Dimethylbicyclo[3.1.1]hept-2-en-2-yl acetate (compound 1.4). To a stirring solution of compound 1.3 (4.5 g, 32.6 mmol) in isopropenyl acetate (135 mL) was added anhydrous p-toluenesulfonic acid (800 mg, 4.24 mmol) at room temperature under argon atmosphere. The reaction mixture was then heated to reflux and the acetone formed in the reaction was fractionally distilled from the system through a 12-inch column packed with glass helices. After 5 hours, the solvent was evaporated under reduced pressure and the oily residue was diluted with diethyl ether and washed with water. The water layer was back extracted with diethyl ether and the combined organic layer was washed with brine, dried (MgSO₄) and evaporated under reduced pressure. Purification by flash column chromatography on silica gel (0%-5% diethyl ether in hexane) gave the title compound 1.4 (5.45 g, 94% yield) as a colorless liquid. $^1$H NMR (500 MHz, CDCl₃) δ: 5.15 (m, 1H, 3-H), 2.46 (m, 1H, 7-Ha), 2.28 (d, J=16.0 Hz, 1H, 4-Ha), 2.20 (td, J=16.0 Hz, 2.5 Hz, 1H, 4-Hb), 2.09 (m, 2H, 1-, 5-H2), 2.08 (s, 3H, COCH₃), 1.42 (d, J=8.7 Hz, 1H, 7-Hb), 1.28 (s, 3H, 6-CH₃), 0.93 (s, 3H, 6-CH₃) ppm; $^{13}$C NMR (100 MHz CDCl₃) δ: 169.1 (C=O), 156.1 (2-C), 106.3 (3-C), 46.0 (1-C), 40.4 (5-C), 38.9 (6-C), 31.5 (7-C), 28.0 (4-C), 25.8 (6-CH₃), 21.0 (6-CH₃), 20.9 (CH₃CO).

Mixture (1.5) of (+)-6,6-Dimethyl-2,2-diacetoxy-3-norpinene (compound 1.5a) and (−)-6,6-Dimethyl-2,4-diacetoxy-2-norpinene (compound 1.5b). To a solution of compound 1.4 (30 g, 167 mmol) in anhydrous benzene (550 mL) at room temperature, under an argon atmosphere, was added lead(IV) acetate (111 g, 251 mmol) previously dried in vacuo over P₂O₅/KOH. The reaction mixture was heated at 78-80° C. for 3 hours with stirring, then cooled to room temperature, and filtered through a short pad of Celite. The filtrate was diluted with diethyl ether and water was added (formation of brown-black lead oxide). The mixture was stirred vigorously for 10 min, then filtered through a short pad of Celite, and the organic phase was separated. The aqueous layer was extracted with diethyl ether, the combined organic layer was washed with brine, dried (MgSO₄), and the solvent was evaporated under reduced pressure to give 8 (41 g) as a clear liquid. On the basis of $^1$H NMR analysis, this crude product contains approximately 87% diacetates, compound 1.5 (ca. 90% yield) in a ratio 1.63:1 of 1.5a:1.5b respectively, along with small amounts of (+)-apoverbenone [8%, δ: 7.53 (dd, J=9.0, 6.5 Hz, 1H), 5.96 (br d, J=9.0 Hz, 1H)] and traces of unidentified impurities. Compound 1.5a: $^1$H NMR (500 MHz, CDCl₃) δ: 6.55 (dd, J=9.0, 6.7 Hz, 1H), 6.29 (dd, J=9.0, 1.9 Hz, 1H), 3.15 (td, J=6.0, 2.2 Hz, 1H), 2.29-2.21 (m, 3H), 2.04 (s, 6H), 1.40 (s, 3H), 1.01 (s, 3H) ppm. Compound 1.5b: $^1$H NMR (500 MHz, CDCl₃) δ: 5.44 (m as t, J=2.7 Hz, 1H), 5.35 (m, 1H), 2.55-2.49 (m, 2H), 2.47-2.42 (m, 2H), 2.12 (s, 3H), 2.03 (s, 3H), 1.38 (s, 3H), 1.03 (s, 3H).

2-(3,5-Dimethoxyphenyl)-2-methylpropanenitrile (compound 1.7). To a stirring suspension of sodium hydride (5.1 g, 213.4 mmol) in dry DMF (133.4 mL) at 0° C. under an argon atmosphere was added dropwise a solution of 1.6 (11.8 g, 66.7 mmol) and iodomethane (13.2 mL, 213.4 mmol) in dry DMF (6.8 mL). The reaction temperature was rose to 25° C. over a 15 min period and stirring was continued for 2 h. The reaction mixture was quenched with saturated aqueous $NH_4Cl$ solution and diluted with diethyl ether. The organic layer was separated, and the aqueous layer was extracted with diethyl ether. The combined organic layer was washed with water and brine, dried ($MgSO_4$), and concentrated in vacuo. Purification by flash column chromatography on silica gel (25% ethyl acetate in hexane) gave the title compound (13.1 g, 96% yield) as a colorless oil. IR (neat) 2950, 2840, 2234 (w, CN), 1532, 1438, 1319, 1204, 788 $cm^{-1}$. $^1H$ NMR (500 MHz, $CDCl_3$) δ 6.61 (d, J 2.0 Hz, 2H, ArH), 6.40 (t, J 2.0 Hz, 1H, ArH), 3.81 (s, 6H, —$OCH_3$), 1.71 (s, 6H, —$C(CH_3)_2$—); mass spectrum (ESI) m/z (relative intensity) 206 ($M^+$+H, 100). HPLC (4.6 mm×250 mm, Supelco Discovery column, acetonitrile/water) showed purity of 97.6% and retention time of 4.5 min for the title compound.

2-(3,5-Dimethoxyphenyl)-2-methylpropanal (compound 1.8). To a solution of 1.7 (12.9 g, 63.0 mmol) in anhydrous $CH_2Cl_2$ (441 mL) at −78° C., under an argon atmosphere was added 1M solution of DIBAL-H in Hexane (189 mL). The reaction mixture was stirred for 30 min and then quenched by dropwise addition of potassium sodium tartrate (10% solution in water) at −78° C. Following the addition, the mixture was warmed to room temperature, stirred for an additional 50 minutes and then diluted with ethyl acetate. The organic phase was separated, and the aqueous phase was extracted with ethyl acetate. The combined organic layer was washed with brine, dried ($MgSO_4$), and the solvent was evaporated under reduced pressure. The crude product was purified by flash chromatography on silica gel (10-35% ethyl acetate in hexane) to give 12.0 g of 1.8 as viscous oil in 92% yield. IR (neat) 2938, 2838, 2705 (w, CHO), 1725 (s, >C=O), 1595, 1457, 1424, 1314, 1205, 1156, 1066, 835 $cm^{-1}$. $^1H$ NMR (500 MHz, $CDCl_3$) δ 9.46 (s, 1H, —CHO), 6.40 (d, J=2.0 Hz, 2H, 2-H, 6-H, ArH), 6.39 (t, J=2.0 Hz, 1H, 4-H, ArH), 3.78 (s, 6H, OMe), 1.43 (s, 6H, —$C(CH_3)_2$—). $^{13}C$ NMR (100 MHz $CDCl_3$) δ 201.6 (—CHO), 161.1 (ArC), 143.6 (ArC), 105.1 (ArC), 98.6 (ArC), 65.7 (>(C) CHO), 55.2 (—$OCH_3$), 50.5, 22.3. Mass spectrum (EI) m/z (relative intensity) 208 ($M^+$, 25), 196 (16), 179 ($M^+$—CHO), 165 (25), 151 (14), 139 (39), 91 (20), 77 (20). Exact mass (EI) calculated for $C_{12}H_{16}O_3$ ($M^+$), 208.10995; found, 208.11077. HPLC (4.6 mm×250 mm, Supelco Discovery column, acetonitrile/water) showed purity of 97.2% and retention time of 4.4 min for the title compound.

(Z)-3,5-Dimethoxy-1-(2-methyl-8-phenoxyoct-3-en-2-yl)benzene (compound 1.9). To a stirring suspension of (5-phenoxypentyl) triphenylphosphonium bromide (1.2) (74.5 g, 147.4 mmol) in dry THF (895 mL) at 0° C., under an argon atmosphere was added potassium bis(trimethylsilyl)amide (29.0 g, 145.2 mmol). The mixture was stirred for 30 minutes at 10° C. to ensure complete formation of the orange phosphorane. A solution of aldehyde 1.8 (11.4 g, 54.6 mmol) in 8.6 mL THF was added dropwise to the resulting slurry at 0° C. The reaction was stirred for 2 hours at room temperature and upon completion was quenched by the addition of saturated aqueous $NH_4Cl$. The organic layer was separated and the aqueous phase was extracted with diethyl ether. The combined organic layer was washed with brine and dried ($MgSO_4$) and the solvent was evaporated under reduced pressure. The residue was purified on a silica gel (5-15% diethyl ether in hexanes) to give 18.0 g compound 1.9 as colorless oil in 93% yield. IR (neat) 2958, 2835, 1594, 1422, 1243, 1204, 1153, 1052, 753 $cm^1$. $^1H$ NMR (500 MHz, $CDCl_3$) δ 7.26 (m as t, J=7.5 Hz, 2H, 3-H, 5-H, OPh), 6.91 (m as t, J=7.5 Hz, 1H, 4-H, OPh), 6.83 (m as d, J=7.5 Hz, 2H, 2-H, 6-H, OPh), 6.55 (d, J=2.5 Hz, 2H, 2-H, 6-H, ArH), 6.27 (t, J=2.5 Hz, 1H, 4-H, ArH), 5.65 (d t, J=11.1 Hz, J=1.5 Hz, 1H, 2'-H), 5.29 (dt, J=11.1 Hz, J=7.8 Hz, 1H, 3'-H), 3.79-3.73 (t and s overlapping, 8H, OMe and 7'-H), 1.71 (dtd, 2H, 4'-H), 1.56 (qt, 2H, 5'-H), 1.39 (s, 6H, —$C(CH_3)_2$—), 1.31 (qt, 2H, 6'-H). $^{13}C$ NMR (100 MHz $CDCl_3$) δ 160.4 (ArC), 159.0 (ArC), 153.2 (ArC), 139.7 (>C=C<), 130.8 (>C=C<), 129.3 (ArC), 120.4 (ArC), 114.4 (ArC), 104.8 (ArC), 97.0 (ArC), 67.5 (—$CH_2OPh$), 55.2 (—$OCH_3$), 40.3, 31.3, 28.8, 27.9, 25.6. Mass spectrum (ESI) m/z (relative intensity) 377 ($M^+$+Na, 5), 356 ($M^+$+H+1, 30), 355 ($M^+$+H, 100), 261 ($M^+$+H-OPh, 30), 205 (20), 191 (8). 165 (10), 115 (8). HPLC (4.6 mm×250 mm, Supelco Discovery column, acetonitrile/water) showed purity of 98.9% and retention time of 5.8 min for the title compound.

3,5-Dimethoxy-1-(2-methyl-8-phenoxyoctan-2-yl)benzene (compound 1.10). To a solution of 14a (17.9 g, 50.4 mmol) in ethyl acetate (504 mL) was added 10% w/w Pd/C (1.9 g) and the resulting suspension stirred vigorously for 2.5 hours under hydrogen atmosphere at room temperature. The catalyst was removed by filtration through celite, and the filtrate was evaporated under reduced pressure to afford 17.6 g of the crude product 1.10 as colorless oil, in 98% yield which was used in the next step without further purification. IR (neat) 2954, 2853, 1567, 1480, 1241, 1213, 1153, 831, 753 $cm^{-1}$. $^1H$ NMR (500 MHz, $CDCl_3$) δ 7.25 (m as t, J=8.0 Hz, 2H, 3-H, 5-H, OPh), 6.92 (m as t, J=8.0 Hz, 1H, 4-H, OPh), 6.86 (m as d, J=8.0 Hz, 2H, 2-H, 6-H, OPh), 6.49 (d, J=1.5 Hz, 2H, 2-H, 6-H, ArH), 6.30 (t, J=1.5 Hz, 1H, 4-H, ArH), 3.90 (t, J=6.0 Hz, 2H, 7'-H), 3.79 (s, 6H, OMe), 1.75-1.68 (m, 2H, 2'H), 1.59-1.53 (m, 2H, 3'-H), 1.43-1.35 (m, 2H, 4'-H), 1.30-1.22 (m and s overlapping, 8H, 5'-H and —$C(CH_3)_2$—), 1.12-0.60 (m, 2H, 6'-H); Mass spectrum (ESI) m/z (relative intensity) 358 ($M^+$+H+1, 30), 357 ($M^+$+H, 100), 281 (8), 263 ($M^+$+H-OPh, 5). Exact mass (ESI) calculated for $C_{23}H_{33}O_3$ ($M^+$+H), 357.2430; found, 357.2427. HPLC (4.6 mm×250 mm, Supelco Discovery column, acetonitrile/water) showed purity of 98.7% and retention time of 5.9 min for the title compound.

5-(8-Bromo-2-methyloct-2-yl)resorcinol (compound 1.11). To a stirring solution of 1.10 (15.9 g, 44.8 mmol) in dry $CH_2Cl_2$ 448 mL), at −78° C., under an argon atmosphere, was added 1M boron tribromide solution in $CH_2Cl_2$ (197.1 mL, 197.1 mmol). Following the addition, the reaction mixture was gradually warmed to room temperature and the stirring was continued at that temperature until completion of the reaction (6 h). The reaction mixture was then poured into ice-water, warmed to room temperature and volatiles were removed in vacuo. The residue was diluted with ethyl acetate and washed sequentially with saturated aqueous $NaHCO_3$ solution, water and brine. The organic layer was dried over $MgSO_4$, filtered and concentrated under reduced pressure. Purification by flash column chromatography on silica gel (10%-35% ethyl acetate in hexanes) afforded 13.9 g of 1.11 as a white foam in 99% yield. IR (neat) 3343 (br, OH), 2931, 2834, 1601, 1412, 1345, 1235, 1146, 993, 750 $cm^{-1}$; $^1H$ NMR (500 MHz, $CDCl_3$) δ 6.38 (d, J=2.0 Hz, 2H, 2-H, 6-H, ArH) 6.18 (t, J=2.0 Hz, 1H, 4-H, ArH), 4.69 (br s, 2H, —OH), 3.35 (t, J=7.0 Hz, 2H, 7'-H), 1.82-1.75 (m, 2H, 2'-H), 1.55-1.50 (m, 2H, 3'H), 1.40-1.33 (m, 2H, 4'-H), 1.23 (s and m overlapping, 8H, —C(CH$_3$)$_2$—, —CH$_2$— of the side chain, especially 1.23, s, 6H, —C(CH$_3$)$_2$—), 1.10-1.02 (m, 2H, —CH$_2$— of the side chain); Mass spectrum (ESI) m/z (relative intensity) 317 (M$^+$+H+2, 100), 315 (M$^+$+H, 100), 235 (10), 207 (8). Exact mass (ESI) calculated for C$_{15}$H$_{24}$O$_2$Br (M$^+$+H), 315.0960; found, 315.0952. HPLC (4.6 mm×250 mm, Supelco Discovery column, acetonitrile/water) showed purity of 98.6% and retention time of 4.5 min for the title compound.

(1R,4R,5R)-4-[4-(8-Bromo-2-methyloctan-2-yl)-2,6-dihydroxyphenyl]-6,6-dimethylbicyclo[3.1.1]heptan-2-one (compound 1.12). To a degassed solution of 1.11 (11.8 g, 37.4 mmol) and p-toluenesulfonic acid monohydrate (11.4 g, 59.8 mmol) in wet CHCl$_3$ (598 mL) diacetates 1.5 (15.5 g, ca. 90% pure by $^1$H NMR, 59.8 mmol) was added at 0° C., under an argon atmosphere. The mixture was warmed to room temperature and stirred for 4 days to ensure complete formation of the product. The reaction mixture was diluted with diethyl ether and washed sequentially with water, saturated aqueous NaHCO$_3$, and brine. The organic phase was dried over MgSO$_4$ and the solvent was removed under reduced pressure. The residue was chromatographed on silica gel (15%-50% diethyl ether in hexane) and fractions containing almost pure product (TLC) were combined and evaporated. Further purification by recrystallization from CHCl$_3$ and hexane gave 1.12 as a white crystalline solid (10.8 g, 64% yield). m p 83-85° C.; IR (neat) 3349 (br, OH), 2932, 2861, 1683 (s, >C=O), 1621, 1586, 1420, 1267, 1022, 838, 733 cm$^{-1}$. $^1$H NMR (500 MHz, CDCl$_3$) δ 6.22 (s, 2H, ArH), 4.93 (br s, 2H, OH), 3.95 (t, J=8.5 Hz, 1H, 4-H), 3.49 (dd, J=18.5 Hz, J=6.5 Hz, 1H, 3α-H), 3.38 (t, J=7 Hz, 2H, 7'-H), 2.62 (dd, J=18.5 Hz, J=8 Hz, 1H, 3β-H), 2.59 (t, J=5.0 Hz, 1H, 1-H), 2.52 (m, 1H, 7α-H), 2.46 (d, J=10.5 Hz, 1H, 7β-H), 2.32, (t, J=5.5 Hz, 1H, 5-H), 1.85-1.74 (m, 2H, —CH$_2$— of the side chain group), 1.53-1.48 (m, 2H, —CH$_2$— the side chain group), 1.41-1.34 (s and m overlapping, 5H, —CH$_2$— of the side chain, 6-Me, especially 1.36, s, 3H, 6-Me), 1.28-1.18 (s and m overlapping, 8H, —C(CH$_3$)$_2$—, —CH$_2$— of the side chain, especially 1.21, s, 6H, —C(CH$_3$)$_2$—), 1.12-1.04 (m, 2H, —CH$_2$— of the side chain), 1.0 (s, 3H, 6-Me). $^{13}$C NMR (100 MHz CDCl$_3$) δ 217.6 (>C=O), 154.8 (ArC), 149.6 (ArC), 113.4 (ArC), 106.4 (ArC), 46.7, 44.1, 42.2, 42.1, 37.9, 37.1, 34.1, 32.7, 29.5, 29.4, 28.7, 28.0, 26.2, 26.1, 24.4, 22.2. Mass spectrum (ESI) m/z (relative intensity) 451 (M$^+$+H). HPLC (4.6 mm×250 mm, Supelco Discovery column, acetonitrile/water) showed purity of 99.0% and retention time of 5.2 min for the title compound.

(6aR,10aR)-3-(8-Bromo-2-methyloctan-2-yl)-1-hydroxy-6,6-dimethyl-6,6a,7,8,10,10a-hexahydro-9H-benzo[c]chromen-9-one (compound 1.13). To a stirring solution of 1.12 (10.6 g, 23.4 mmol) in anhydrous CH$_2$Cl$_2$/CH$_3$NO$_2$ (3:1 mixture, 780 mL) at 0° C., under an argon atmosphere was added trimethylsilyl trifluoromethanesulfonate (23.4 mL, 0.3M solution in CH$_3$NO$_2$, 7.0 mmol). Stirring was continued for 3 hours after the temperature allowed to rise to 25° C. The reaction was quenched with saturated aqueous NaHCO$_3$/brine (1:1), and diethyl ether was added. The organic phase was separated, the aqueous phase was extracted with diethyl ether, and the combined organic phase was washed with brine and dried over MgSO$_4$. Solvent evaporation and purification by flash column chromatography on silica gel (15%-30% ethyl acetate-hexane) afforded 7.9 g (75% yield) of the title compound 1.13 as white foam. IR (neat) 3298 (br, OH), 2954, 2870, 1696 (s, >C=O), 1575, 1443, 1352, 1134, 1089, 1018, 838, 731 cm$^{-1}$. $^1$H NMR (500 MHz, CDCl$_3$) δ 6.38 (d, J=2 Hz, 1H, ArH), 6.25 (d, J=2 Hz, 1H, ArH), 5.49 (br s, 1H, OH), 3.93 (m as br d, J=15.5 Hz, 1H, 10eq-H), 3.37 (t, J=6.5 Hz, 2H, 7'-H), 2.88 (m as td, J=12.5 Hz, J=3.5 Hz, 1H, 10a-H), 2.62-2.58 (m, 1H, 8eq-H), 2.48-2.41 (m, 1H, 8ax-H), 2.2-2.11 (m, 2H, 10ax-H, 7eq-H), 1.97 (m as td, J=12.0 Hz, J=1.6 Hz, 1H, 6a-H), 1.80-1.74 (m, 2H of —CH$_2$— of the side chain), 1.59-1.45 (m and s overlapping, 6H, 7ax-H, 2'-H, 6-Me, especially 1.47, s, 3H, 6-Me), 1.36 (qt, J=7.5 Hz, 2H, —CH$_2$— of the side chain), 1.28-1.16 (m and s overlapping, 8H, —C(CH$_3$)$_2$—, —CH$_2$— of the side chain, especially, 1.21, s, 6H, —C(CH$_3$)$_2$—), 1.13 (s, 3H, 6-Me), 1.1-1.02 (m, 2H, —CH$_2$— of the side chain). Mass spectrum (ESI) m/z (relative intensity) 451 (M$^+$+H). HPLC (4.6 mm×250 mm, Supelco Discovery column, acetonitrile/water) showed purity of 96.8% and retention time of 5.4 min for the title compound.

(6aR,10aR)-3-(8-Chloro-2-methyloctan-2-yl)-1-[(tert-butyldimethylsilyl)oxy]-6,6-dimethyl-6,6a,7,8,10,10a-hexahydro-9H-benzo[c]chromen-9-one (compound 1.14). To a solution of 1.13 (7.4 g, 16.5 mmol) in anhydrous DMF (110 mL) under an argon atmosphere were added sequentially, imidazole (5.6 g, 82.3 mmol), DMAP (1.0 g, 8.2 mmol) and TBDMSCl (12.1 g, 80.6 mmol). The reaction mixture was stirred at 62° C. for 12 h and then quenched by the addition of brine and extracted with diethyl ether. The organic phase was dried (MgSO$_4$) and evaporated under reduced pressure. Purification by flash column chromatography on silica gel (10%-30% diethyl ether in hexane) afforded 7.9 g (93% yield) of 1.14 as a colorless oil. IR (neat) 2931, 2859, 1713 (s, >C=O), 1613, 1564, 1412, 1332, 1254, 1137, 1096, 1055, 980, 839 cm$^{-1}$; $^1$H NMR (500 MHz, CDCl$_3$) δ 6.41 (d, J=1.5 Hz, 1H, 4-H), 6.33 (br d, J=1.5 Hz, 1H, 2-H), 3.76 (ddd, J=15.0 Hz, J=3.0 Hz, J=2.0 Hz, 1H, 10eq-H), 3.48 (t, J=6.1 Hz, 2H, 7'-H), 2.71 (m as td, J=14.5 Hz, J=3.5 Hz, 1H, 10a-H), 2.59-2.52 (m, 1H, 8eq-H), 2.45-2.36 (m, 1H, 8ax-H), 2.2-2.07 (m, 2H, 10ax-H, 7eq-H), 1.95 (m as td, J=12.5 Hz, J=3.0 Hz, 1H, 6a-H), 1.72-1.64 (m, 2H of —CH$_2$— of the side chain), 1.54-1.47 (m, 3H, 7ax-H, 2H of —CH$_2$— of the side chain —H), 1.47 (s, 3H, 6-Me), 1.38-1.31 (m, 2H, —CH$_2$— of the side chain), 1.26-1.17 (m and s overlapping, 8H, —C(CH$_3$)$_2$—, —CH$_2$— of the side chain, especially, 1.21, s, 6H, —C(CH$_3$)$_2$—), 1.1 (s, 3H, 6-Me), 1.09-1.04 (m, 2H, —CH$_2$— of the side chain), 1.0 (s, 9H, Si(Me)$_2$CMe$_3$), 0.24 (s, 3H, Si(Me)$_2$CMe$_3$), 0.16 (s, 3H, Si(Me)$_2$CMe$_3$). $^{13}$C NMR (100 MHz CDCl$_3$) δ 210.6 (>C=O), 154.2 (ArC-1 or ArC-5), 154.0 (ArC-5 or ArC-1), 149.8 (tertiary aromatic), 111.9 (tertiary aromatic), 109.8 (ArC-2 or ArC-4), 108.3 (ArC-4 or ArC-2), 47.4, 45.5, 45.0, 44.3, 40.7, 37.3, 35.1, 32.5, 29.5, 28.8, 28.6, 27.7, 26.8, 26.7, 25.6, 24.5, 18.6, 18.3, −3.7, −4.1. Exact mass (ESI) calculated for C$_{30}$H$_{50}$O$_3$SiCl (M$^+$+H), 521.3217; found 521.3220. HPLC (4.6 mm×250 mm, Supelco Discovery column, acetonitrile/water) showed purity of 96.8% and retention time of 6.7 min for the title compound.

{[(6aR,10aR)-3-(8-Chloro-2-methyloctan-2-yl)-9-(methoxymethylene)-6,6-dimethyl-6a,7,8,9,10,10a-hexahydro-6H-benzo[c]chromen-1-yl]oxy}(tert-butyl)dimethylsilane (compound 1.15). To a stirring suspension of (methoxymethyl)triphenyl phosphonium chloride (28.5 g, 83.4 mmol) in anhydrous THF (14 mL) under argon atmosphere was added potassium bis(trimethylsilyl)amide (16.3 g, 82.1 mmol) at 0° C., and the reaction mixture was stirred for 10 min at 0° C. and for 30 min at room temperature. Intermediate compound 1.14 (7.8 mg, 13.9 mmol) was dissolved in the minimum amount of anhydrous THF and added dropwise to the solution of the red ylide at 0° C. The reaction mixture was stirred at 0° C. to room temperature for 1 hour, and then quenched with saturated aqueous NH$_4$Cl solution at 0° C. and diluted with ethyl acetate. The organic layer was separated and the aqueous layer was extracted with ethyl acetate. The combined organic layer was washed with brine, dried (MgSO$_4$), and evaporated under reduced pressure. The residue was chromatographed on silica gel (0%-7% diethyl ether in hexane) to give a mixture (compound 1.15) of two geometrical isomers compounds 1.15a and 1.15b (7.6 g, 93% yield) as a colorless oil in the ratio of 2:1 respectively as determined by $^1$H NMR analysis. IR (neat) 2930, 2857, 1674, 1612, 1571, 1418, 1231, 1095, 1049, 835, 743 cm$^{-1}$. $^1$H NMR (500 MHz, CDCl$_3$) δ: 6.38 (d, J=2.0 Hz, 1H, Ar—H, 1.15a), 6.36 (d, J=2.0 Hz, 1H, Ar—H, 1.15b), 6.33 (d, J=2.0 Hz, 1H, Ar—H, 1.15a), 6.31 (d, J=2.0 Hz, 1H, Ar—H, 1.15b), 5.86 (brs, 1H, =CHOMe, 1.15a), 5.82 (brs, 1H, =CHOMe, 1.15b), 4.20-4.15 (m as dd, J=13.5 Hz, J=3.5 Hz, 1H, C-ring, 1.15b), 3.56 (s, 3H, OMe, 1.15a), 3.53 (s, 3H, OMe, 1.15b), 3.48 (t, J=6.5 Hz, 2H, —CH$_2$Cl for 1.15a and 2H, —CH$_2$Cl for 1.15b), 3.46-3.42 (m as dd, J=13.5 Hz, J=3.5 Hz, 1H, C-ring, 1.15a), 2.95-2.89 (m as br d, J=14.0 Hz, 1H, C-ring, 1.15a), 2.35-2.26 (m, 1H, C-ring of 1.15a and 1H, C-ring of 1.15b), 2.22-2.16 (m, 1H, C-ring, 1.15b), 2.09-2.00 (m, 1H, C-ring, 1.15b), 1.91-1.85 (m, 1H, C-ring of 1.15a and 1H, C-ring of 1.15b), 1.82-1.74 (m, 1H, C-ring, 1.15a), 1.73-1.53 (m, 2H, 6'-H of 1.15a, 2H, 6'-H of 1.15b, 2H, C-ring of 1.15a, and 2H, C-ring of 1.15b), 1.52-1.48 (m, 2H, 2'-H of 1.15a, 2H, 2'-H of 1.15b), 1.39 (s, 3H, 6-Me, 1.15a), 1.38 (s, 3H, 6-Me, 1.15b), 1.38-1.30 (m, 2H, —CH$_2$— of the side chain of 1.15a, 2H, —CH$_2$— of the side chain of 1.15b), 1.24-1.16 (m, s and s, overlapping, 2H, —CH$_2$— of the side chain of 1.15a, 2H, —CH$_2$— of the side chain of 1.15b, 6H, —C(CH$_3$)$_2$— of 1.15a, 6H, —C(CH$_3$)$_2$— of 1.15b), 1.11-0.98 (m, s, s, s and s, overlapping, 1H, C-ring of 1.15a, 1H, C-ring of 1.15b, 2H, —CH$_2$— of the side chain of 1.15a, 2H, —CH$_2$— of the side chain of 1.15b, 3H, 6-Me of 1.15a, 3H, 6-Me of 1.15b, 9H, —Si(Me)$_2$CMe$_3$, of 1.15a, 9H, —Si(Me)$_2$CMe$_3$, of 1.15b, especially 1.03, s, —Si(Me)$_2$CMe$_3$, of 1.15a and 1.00, s, —Si(Me)$_2$CMe$_3$, of 1.15b), 0.24 (s, 3H, —Si(Me)$_2$CMe$_3$, 1.15a), 0.23 (s, 3H, —Si(Me)$_2$CMe$_3$, 1.15b), 0.19 (s, 3H, —Si(Me)$_2$CMe$_3$, 1.15b), 0.15 (s, 3H, —Si(Me)$_2$CMe$_3$, 1.15a); Mass spectrum (ESI) m/z (relative intensity) 593 (M$^+$+H). HPLC (4.6 mm×250 mm, Supelco Discovery column, acetonitrile/water) showed purity of 98% and retention time of 7.4 min for the title compound.

(6aR,10aR)-3-(8-Chloro-2-methyloctan-2-yl)-1-[(tert-butyldimethylsilyl)oxy]-6,6-dimethyl-6a,7,8,9,10,10a-hexahydro-6H-benzo[c]chromene-9-carbaldehyde (compound 1.16). To a stirring solution of compound 1.15 (5.7 g, 9.6 mmol) in wet CH$_2$Cl$_2$ (320 mL) under argon atmosphere, was added trichloroacetic acid (7.8 g, 48 mmol). The reaction mixture was stirred at room temperature for 20 min and then quenched with saturated aqueous NaHCO$_3$ solution and diluted with diethyl ether. The organic layer was separated and the aqueous layer was extracted with diethyl ether. The combined organic phase was washed with water and brine, dried (MgSO$_4$) and evaporated under reduced pressure. The residue consisted of a mixture of epimeric aldehydes, compound 1.16a and compound 1.17 (5.3 g, 95% yield) in the ratio of 2:1 respectively as determined by $^1$H NMR analysis, and it was used into the next step as such. $^1$H NMR (500 MHz, CDCl$_3$) δ: 9.89 (d, J=1.5 Hz, 1H, 9α-CHO, 1.16a), 9.63 (d, J=1.5 Hz, 1H, 9β-CHO, 1.17), 6.38 (d, J=2.0 Hz, 1H, Ar—H, 1.17), 6.36 (d, J=2.0 Hz, 1H, Ar—H, 1.16a), 6.33 (d, J=2.0 Hz, 1H, Ar—H, 1.16a), 6.32 (d, J=2.0 Hz, 1H, Ar—H, 1.17), 3.69-3.63 (m as br d, J=14.0 Hz, 1H, C-ring, 1.16a), 3.52-3.46 (t and m as br d overlapping, t, J=6.5 Hz, 2H, —CH$_2$Cl for 1.17 and 2H, —CH$_2$Cl for 1.16a, m as br d, J=13.5 Hz, 1H, C-ring, 1.17), 2.66-2.61 (m, 1H, C-ring, 1.16a), 2.46-2.33 (m, 2H, C-ring, 1.17 and 2H, C-ring, 1.16a), 2.31-2.24 (m, 1H, C-ring, 1.16a), 2.14-2.06 (m, 1H, C-ring, 1.17), 2.02-1.96 (m, 1H, C-ring, 1.17), 1.78-1.73 (m, 1H, C-ring, 1.16a), 1.68 (sextet, J=6.7 Hz, 2H, 6'-H of 1.17 and 2H, 6'-H of 1.16a), 1.58-1.42 (m, 2H, 2'-H of 1.17, 2H, 2'-H of 1.16a, 2H, C-ring of 1.17, 2H, C-ring of 1.16a), 1.42-130 (m, s, and s, overlapping, 2H, —CH$_2$— of the side chain of 1.17, 2H, —CH$_2$— of the side chain of 1.16a, 1.39, s, 3H, 6-Me of 1.17, 1.36, s, 3H, 6-Me of 1.16a), 1.26-1.10 (m, 2H, —CH$_2$— of the side chain of 1.17, 2H, —CH$_2$— of the side chain of 1.16a, 2H, C-ring of 1.17, 1H, C-ring of 1.16a, 6H, —C(CH$_3$)$_2$— of 1.16a, 6H, —C(CH$_3$)$_2$— of 1.17), 1.09-1.02 (m and s, overlapping, 2H, —CH$_2$— of the side chain of 1.17, 2H, —CH$_2$— of the side chain of 1.16a, 1.08, s, 3H, 6-Me, 1.17), 1.01-1.00 (s and s overlapping, 3H, 6-Me of 1.16a and 9H, —Si(Me)$_2$CMe$_3$ of 1.17), 0.97 (s, 9H, —Si(Me)$_2$CMe$_3$, 1.16a), 0.28 (s, 3H, —Si(Me)$_2$CMe$_3$, 1.16a), 0.26 (s, 3H, Si(Me)$_2$CMe$_3$, 1.17), 0.25 (s, 3H, Si(Me)$_2$CMe$_3$, 1.16a), 0.15 (s, 3H, Si(Me)$_2$CMe$_3$, 1.17); Mass spectrum (ESI) m/z (relative intensity) 565 (M$^+$+H). HPLC (4.6 mm×250 mm, Supelco Discovery column, acetonitrile/water) showed purity of 98% and retention time of 6.7 min for the title compound.

(6aR,9R,10aR)-3-(8-Chloro-2-methyloctan-2-yl)-1-[(tert-butyldimethylsilyl)oxy]-6,6-dimethyl-6a,7,8,9,10,10a-hexahydro-6H-benzo[c]chromene-9-carbaldehyde (compound 1.17). To a solution of 1.16 (4.7 g, 8.8 mmol) in ethanol (176.5 mL) under an argon atmosphere, was added potassium carbonate powder (6.1 g, 44.1 mmol) and the mixture was stirred at room temperature for 3 h. The reaction mixture was quenched by the dropwise addition of 1M aqueous acetic acid solution (pH of 5). The volatiles were evaporated under reduced pressure. The water layer was extracted with diethyl ether. The organic layer was washed with brine, dried (MgSO$_4$), and concentrated under reduced pressure. Purification by flash column chromatography on silica gel (5%-25% diethyl ether in hexane) gave 1.17 (3.9 g, 84% yield) as a colorless oil. IR (neat) 2931, 2859, 2713 (w, CHO), 1727 (s, >C=O), 1613, 1564, 1412, 1331, 1254, 1064, 841, 780 cm$^{-1}$. $^1$H NMR (500 MHz, CDCl$_3$) δ 9.63 (d, J=1.5 Hz, 1H, 9β-CHO), 6.38 (d, J=2.0 Hz, 1H, Ar—H), 6.32 (d, J=2.0 Hz, 1H, Ar—H), 3.52-3.46 (t and m as br d overlapping, t, J=6.5 Hz, 2H, —CH$_2$Cl, m as br d, J=13.5 Hz, 1H, C-ring), 2.46-2.33 (m, 2H, C-ring), 2.14-2.06 (m, 1H, C-ring), 2.02-1.96 (m, 1H, C-ring), 1.69 (sextet, J=6.7 Hz, 2H, 6'-H), 1.52-1.42 (m, 4H, 2'-H, C-ring), 1.42-130 (m and s, overlapping, 5H, —CH$_2$— of the side chain and 1.39, s, 6-Me), 1.26-1.10 (m, 10H, —CH$_2$— of the side chain, C-ring and —C(CH$_3$)$_2$—), 1.09-1.00 (m, s and s, overlapping, 14H as follows: 2H, —CH$_2$— of the side chain, 1.08, s, 3H, 6-Me, 1.01, s, 9H, —Si(Me)$_2$CMe$_3$), 0.26 (s, 3H, Si(Me)$_2$CMe$_3$), 0.15 (s, 3H, Si(Me)$_2$CMe$_3$). $^{13}$C NMR (100 MHz CDCl$_3$) δ 203.5 (—CHO), 154.5 (ArC-1 or ArC-5), 154.2 (ArC-5 or ArC-1), 149.3 (tertiary aromatic), 111.4 (tertiary aromatic), 109.5 (ArC-2 or ArC-4), 108.4 (ArC-4 or ArC-2), 50.5, 49.0, 45.6, 45.0, 44.4, 37.3, 37.2, 35.4, 32.6, 30.2, 29.5, 28.8, 28.6, 27.6, 26.9, 26.8, 25.9, 24.5, 18.8, 18.2, −3.6, −4.2. Mass spectrum (ESI) m/z (relative intensity) 535 (M$^+$+H). HPLC (4.6 mm×250 mm, Supelco Discovery column, acetonitrile/water) showed purity of 96.5% and retention time of 7.0 min for the title compound.

{(6aR,9R,10aR)-3-(8-Chloro-2-methyloctan-2-yl)-1-[(tert-butyldimethylsilyl)oxy]-6,6-dimethyl-6a,7,8,9,10,10a-hexahydro-6H-benzo[c]chromen-9-yl}methanol (compound 1.18). Sodium borohydride (2.1 g, 56.1 mmol) was added to a stirred solution of aldehyde 1.17 (3.7 g, 7.0 mmol) in ethanol (175 mL) at 0° C. under argon. After 30 min, the reaction was quenched with saturated ammonium chloride solution and volatiles were removed in vacuo. The residue was dissolved in ethyl acetate and water was added. The organic layer was separated and the aqueous layer was extracted with ethyl acetate. The combined organic phase was washed with water and brine, dried ($MgSO_4$), and evaporated. Purification by flash column chromatography on silica gel (15%-50% diethyl ether in hexane) gave 1.18 (3.7 g, 98% yield) as a colorless viscous oil. IR (neat) 3354 (br, OH), 2930, 2858, 1612, 1562, 1464, 1411, 1253, 1140, 1064, 1047, 835, 779 $cm^{-1}$; $^1H$ NMR (500 MHz, $CDCl_3$) δ 6.37 (d, J=2.0 Hz, 1H, Ar—H), 6.30 (d, J=2.0 Hz, 1H, Ar—H), 3.54 (dd, J=10.5 Hz, J=5.5 Hz, half of an AB system, 1H, —$CH_2OH$), 3.50-3.43 (dd and t overlapping, especially, 3.48, t, J=6.5, 7'-H, dd, J=10.0 Hz, J=6.5 Hz, half of an AB system, 1H, —$CH_2OH$), 3.18-3.16 (m as br d, J=13.0 Hz, 1H, C-ring), 2.40-2.32 (m as td, J=11.0 Hz, J=3.0 Hz, 1H, C-ring), 2.04-1.97 (m, 1H, C-ring), 1.94-1.88 (m, 1H, C-ring), 1.8-1.64 (m, 3H, 1H of C-ring, 2H, 6'-H), 1.52-1.44 (m, 3H, 2'-H, C-ring), 1.4-1.3 (m and s overlapping, 5H, —$CH_2$— of the side chain, 6-Me, especially 1.25, s, 3H, 6-Me), 1.24-1.1 (m, s, and s overlapping, 10H, —$C(CH_3)_2$—, —$CH_2$— of the side chain, C-ring, especially, 1.20, s, 3H, —$C(CH_3)_2$—, and 1.19, s, 3H, —$C(CH_3)_2$—), 1.09-1.02 (s and m overlapping, 5H, 6-Me, —$CH_2$— of the side chain, especially, 1.06, s, 3H, 6-Me), 1.0 (s, 9H, $Si(Me)_2CMe_3$), 0.82-0.7 (m, 1H, C-ring), 0.23 (s, 3H, $Si(Me)_2CMe_3$), 0.12 (s, 3H, $Si(Me)_2CMe_3$). $^{13}C$ NMR (100 MHz $CDCl_3$) δ 154.5 (ArC-1 or ArC-5), 154.3 (ArC-5 or ArC-1), 149.0 (tertiary aromatic), 113.5 (tertiary aromatic), 109.7 (ArC-2 or ArC-4), 108.4 (ArC-4 or ArC-2), 68.5 (—$CH_2OH$), 49.6, 45.1, 44.4, 41.8, 40.5, 37.2, 35.5, 33.2, 32.6, 29.8, 29.5, 28.8, 28.6, 27.6, 27.5, 26.8, 25.9, 24.5, 18.8, 18.2, −3.6, −4.3. Mass spectrum (ESI) m/z (relative intensity) 537 ($M^+$+H, 100). HPLC (4.6 mm×250 mm, Supelco Discovery column, acetonitrile/water) showed purity of 97.9% and retention time of 6.7 min for the title compound.

{[(6aR,9R,10aR)-3-(8-Chloro-2-methyloctan-2-yl)-9-(iodomethyl)-6,6-dimethyl-6a,7,8,9,10,10a-hexahydro-6H-benzo[c]chromen-1-yl]oxy}(tert-butyl)dimethylsilane (compound 1.19). To a stirring solution of compound 1.18 (429 mg, 0.8 mmol) in anhydrous benzene (16 mL), under argon atmosphere, were added imidazole (217 mg, 3.2 mmol) and triphenylphosphine (419.7 mg, 1.6 mmol), then the reaction mixture was heated to 50° C., followed by a dropwise addition of a solution of iodine (406 mg, 1.6 mmol) in benzene (8 mL). The reaction mixture was stirred for 30 min at 50° C. The reaction was quenched by addition of aqueous sodium sulfite solution and diluted with diethyl ether. The two layers were separated and the water layer was extracted with diethyl ether. The combined organic layer was washed with brine, dried ($MgSO_4$) and evaporated under reduced pressure. Purification by flash column chromatography on silica gel (0%-15% diethyl ether in hexane) gave compound 1.19 (491 mg, 95% yield) as a white oil. IR (neat) 2929, 2857, 1612, 1562, 1411, 1361, 1324, 1253, 1058, 835, 779 $cm^{-1}$; $^1H$ NMR (500 MHz, $CDCl_3$) δ: 6.38 (d, J=2.0 Hz, 1H, Ar—H), 6.31 (d, J=2.0 Hz, 1H, Ar—H), 3.48 (t, J=6.5 Hz, 8'-H), 3.26-3.19 (dd and m as d overlapping, 2H, 1H of C-ring, 1H of —$CH_2I$, especially, m as br d, J=13.0 Hz, 1H, C-ring, 3.21, dd, J=10.0 Hz, J=5.0 Hz, half of an AB system, 1H, —$CH_2I$) 3.08 (dd, J=10.0 Hz, J=5.0 Hz, half of an AB system, 1H, —$CH_2I$), 2.40-2.33 (m as td, J=10.5 Hz, J=2.5 Hz, 1H, C-ring), 2.12-2.08 (m, 1H, C-ring), 1.93-1.87 (m, 1H, C-ring), 1.76-1.58 (m, 3H, 2H of —$CH_2$— of the side chain group, 1H of C-ring), 1.52-1.44 (m, 3H, 2'-H, C-ring), 1.38 (s, 3H, 6Me), 1.36-1.29 (m, 2H, —$CH_2$— of the side chain), 1.22-1.10 (m, 12H, 4H of —$CH_2$— of the side chain, 2H of C-ring, 1.20, s 3H, $C(CH_3)_2$, 1.19, s, 3H, $C(CH_3)_2$), 1.05 (s, 3H, 6-Me), 1.02-0.93 (s and m overlapping, 11H, 2H of —$CH_2$— of the side chain, $Si(Me)_2CMe_3$, especially, 1.01, s, 9H, $Si(Me)_2CMe_3$), 0.89-0.82 (m, 1H, C-ring), 0.23 (s, 3H, $Si(Me)_2CMe_3$), 0.14 (s, 3H, $Si(Me)_2CMe_3$).

{[(6aR,9R,10aR)-3-(8-Chloro-2-methyloctan-2-yl)-9-(azidomethyl)-6,6-dimethyl-6a,7,8,9,10,10a-hexahydro-6H-benzo[c]chromen-1-yl]oxy}(tert-butyl)dimethylsilane (compound 1.20). To a stirring solution of compound 1.19 (497 mg, 0.77 mmol) in anhydrous $CH_2Cl_2$ (15.5 mL) at r t, under argon atmosphere, was added tetra-n-butylammonium azide (1.6 g, 7.7 mmol). The reaction mixture was stirred for 30 h at the same temperature, then quenched by brine and diluted with diethyl ether. The two layers were separated and the water layer was extracted with diethyl ether. The combined organic layer was washed with brine, dried ($MgSO_4$) and evaporated under reduced pressure. Purification by flash column chromatography on silica gel (0%-10% diethyl ether in hexane) gave compound 1.20 (359 mg, 83% yield) as a white foam. IR (neat) 2929, 2858, 2097 (s, $N_3$), 1612, 1563, 1463, 1411, 1342, 1254 1138, 1062, 873 $cm^{-1}$; $^1H$ NMR (500 MHz, $CDCl_3$) δ: 6.37 (d, J=2.0 Hz, 1H, Ar—H), 6.31 (d, J=2.0 Hz, 1H, Ar—H), 3.48 (t, J=7.0 Hz, 7'-H) 3.22-3.18 (dd and m as d overlapping, 2H, 1H of C-ring, 1H of —$CH_2N_3$, especially, m, 1H, C-ring, dd, J=12.0 Hz, J=7.0 Hz, half of an AB system, 1H, —$CH_2N_3$) 3.14 (dd, J=12.0 Hz, J=7.0 Hz, half of an AB system, 1H, —$CH_2N_3$), 2.38-2.32 (m as td, J=11.5 Hz, J=2.5 Hz, 1H, C-ring), 2.02-1.97 (m, 1H, C-ring), 1.92-1.88 (m, 1H, C-ring), 1.78-1.73 (m, 1H of C-ring), 1.69 (quintet, J=7.0 Hz, 2H of —$CH_2$— of the side chain group), 1.51-1.43 (m, 3H, 2'-H, C-ring), 1.38 (s, 3H, 6-Me), 1.38-1.31 (m, 2H, —$CH_2$— of the side chain), 1.24-1.10 (m, 12H, 4H of —$CH_2$— of the side chain, 2H of C-ring, 1.20, 3H of $C(CH_3)_2$, 1.19, 3H of $C(CH_3)_2$), 1.06 (s, 3H, 6-Me), 1.02-0.91 (s and m overlapping, 11H, 2H of —$CH_2$— of the side chain, $Si(Me)_2CMe_3$, especially, 1.01, s, 9H, $Si(Me)_2CMe_3$), 0.84-0.76 (m as q, J=12 Hz, 1H, C-ring), 0.24 (s, 3H, $Si(Me)_2CMe_3$), 0.13 (s, 3H, $Si(Me)_2CMe_3$).

(6aR,9R,10aR)-9-(Azidomethyl)-3-(8-chloro-2-methyloctan-2-yl)-6,6-dimethyl-6a,7,8,9,10,10a-hexahydro-6H-benzo[c]chromen-1-ol (compound 1.21). To a stirring solution of compound 1.20 (404 mg, 0.72 mmol) in anhydrous THF (18 mL) at −70° C., under argon atmosphere, was added tetra-n-butylammonium fluoride (1.4 mL, 1.4 mmol, 1M solution in anhydrous THF). The reaction mixture was stirred for 20 min at the same temperature, then quenched using a saturated aqueous $NH_4Cl$ solution and diluted with diethyl ether. The two layers were separated and the water layer was extracted with diethyl ether. The combined organic layer was washed with brine, dried ($MgSO_4$) and evaporated under reduced pressure. Purification by flash column chromatography on silica gel (10%-40% ethyl acetate in hexane) gave compound 1.21 (309 mg, 96% yield) as a white solid. $^1H$ NMR (500 MHz, $CDCl_3$) δ: 6.35 (d, J=2.0 Hz, 1H, Ar—H), 6.18 (d, J=2.0 Hz, 1H, Ar—H), 4.81 (br, 1H, —OH), 3.48 (t, J=7.0 Hz, 7'-H) 3.28-3.18 (dd and m overlapping, 2H, 1H of C-ring, 1H of —$CH_2N_3$, especially, m, 1H, C-ring, dd, J=12.5 Hz, J=6.5 Hz, half of an AB system, 1H, —$CH_2N_3$) 3.15 (dd, J=12.5 Hz, J=6.5 Hz, half of an AB system, 1H, —$CH_2N_3$), 2.50-2.45 (m as td, J=11.5 Hz, J=3.0 Hz, 1H, C-ring), 2.01-1.96 (m, 1H, C-ring), 1.94-1.90 (m, 1H, C-ring), 1.88-1.80 (m, 1H of C-ring), 1.69 (quintet, J=7.0 Hz, 2H of —CH$_2$— of the side chain group), 1.52-1.45 (m, 3H, 2'-H, C-ring), 1.39 (s, 3H, 6-Me), 1.39-1.31 (m, 2H, —CH$_2$— of the side chain), 1.24-1.10 (m, 12H, 4H of —CH$_2$— of the side chain, 2H of C-ring), 1.20, 6H of C(CH$_3$)$_2$), 1.06 (s, 3H, 6-Me), 1.02-0.91 (m, 2H of —CH$_2$— of the side chain), 0.84-0.76 (m, 1H, C-ring).

B. Alkyne Synthons Synthesis

Alkyne compounds 2.2, 2.3, 2.5, 2.11 and 2.13 (shown in Scheme 2) were synthesized in by the methods depicted in Scheme 2 starting from commercially available D-(+)-Biotin (compound 2.1), or D-(+)-Biotin-ε-aminocaproic acid (compound 2.4), or Coumarin343 (compound 2.10) or 7-fluoro-N,N-dimethylbenzo[c][1,2,5]oxadiazole-4-sulfonamide (compound 2.12).

Scheme 2
Reagents and Conditions: (a) propargyl alcohol, EDCI, DMAP, DMF, rt, 12 h, 62%; (b) propargyl amine, CDI, DMF, rt, 14 h, 75%; (c) propargyl alcohol, EDCI, DMAP, DMSO, rt, 12 h, 84%; (d) Boc$_2$O, TEA, CH$_2$Cl$_2$, 0° C. to rt, 3 h, 99%; (e) NaH, propargyl bromide, DMF/THF, 0° C. to rt, 14 h, 70%; (f) TFA, CH$_2$Cl$_2$, 0° C. to rt, 1 h, 93%; (g) 2.9, CDI, THF/CH$_2$Cl$_2$, 0° C. to rt, 10 h, 80%; (h) propargyl amine, Et$_3$N, THF, rt, 30 min, 98%.

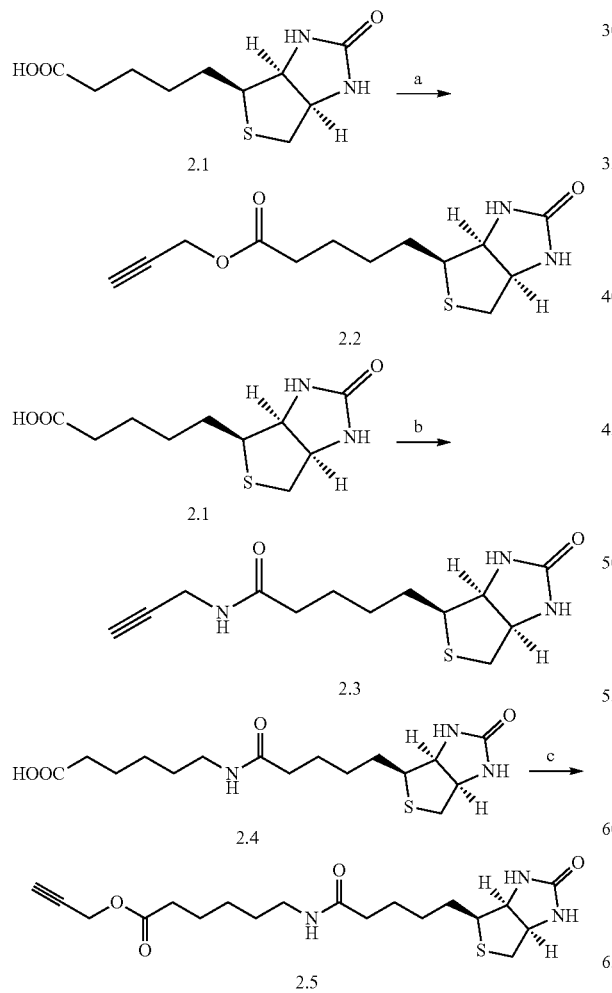

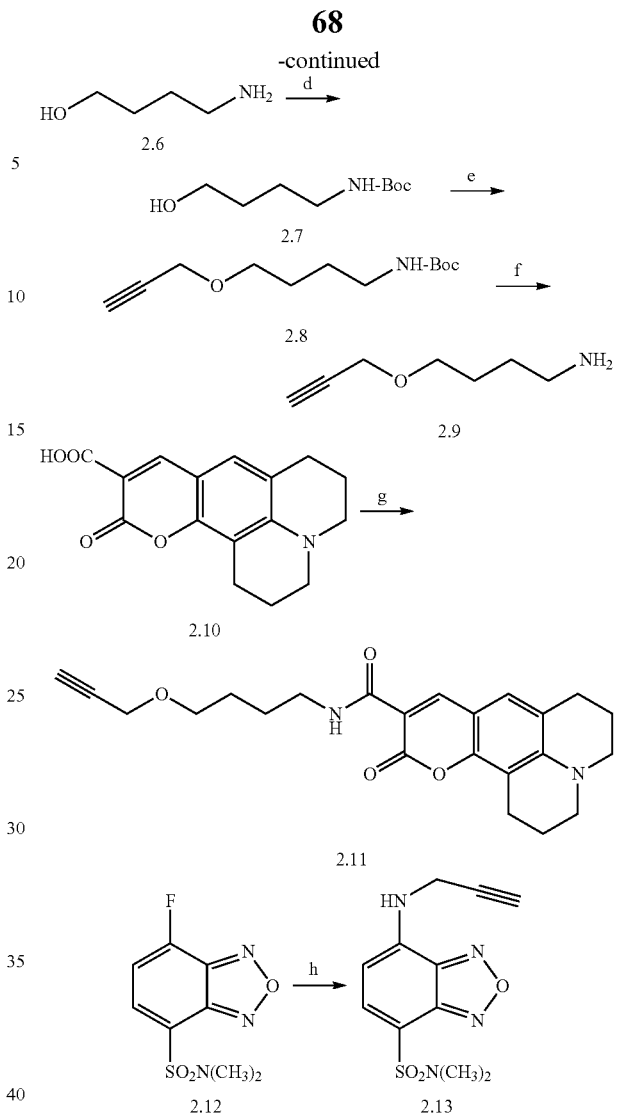

Prop-2-yn-1-yl 5-[(3aS,4S,6aR)-2-oxohexahydro-1H-thieno[3,4-d]imidazol-4-yl]pentanoate (compound 2.2). To a stirring solution of DMAP (366 mg, 3 mmol) and EDCI (382 mg, 2 mmol) in anhydrous DMF (5 mL) at 0° C. under argon atmosphere, D-(+)-Biotin (compound 2.1) (112 mg, 0.5 mmol) was added. The reaction was stirred for 20 min at 0° C. and then propargyl alcohol (0.1 mL, 2 mmol) was added. The mixture was warmed to room temperature and stirred for 14 h to ensure complete formation of the product. The reaction mixture was diluted with diethyl ether and washed sequentially with 5% HCl aqueous solution, saturated aqueous NaHCO$_3$ solution, and brine. The organic phase was dried over MgSO$_4$, and the solvent was evaporated under reduced pressure. Purification by flash column chromatography on silica gel (5%-30% methanol in dichloromethane) afforded compound 2.2 (81 mg, 62% yield) as a white solid. $^1$H NMR (500 MHz, CDCl$_3$) δ: 5.69 (s, 1H, NH), 5.17 (s, 1H, NH), 4.68 (d, J=2.5 Hz, 2H, —OCH$_2$CCH), 4.54-4.50 (m, 1H, —NHCHCH$_2$—), 4.34-4.30 (m, 1H, —NHCHCH$_2$—), 3.20-3.14 (m, 1H, —SCHCH$_2$—), 2.92 (dd, J=13 Hz, 5 Hz, 1H, —SCH$_2$—), 2.75 (d, J=13 Hz, 1H, —SCH$_2$—), 2.49 (t, J=2.5 Hz, 1H, —CCH), 2.40 (t, J=7.5 Hz, 2H, —CH$_2$COO—), 1.78-1.64 (m, 4H, —CH$_2$— of chain), 1.53-1.41 (m, 4H, —CH$_2$— of chain).

5-((3aS,4S,6aR)-2-Oxohexahydro-1H-thieno[3,4-d]imidazol-4-yl)-N-(prop-2-yn-1-yl)pentanamide (compound 2.3). To a stirring solution of compound 2.1 (120 mg, 0.5 mmol) in anhydrous DMF (5 mL), was added CDI (240 mg, 1.5 mmol) and propargyl amine (0.15 mL, 2 mmol) at room temperature under argon atmosphere and the reaction mixture was stirred for 15 hours. Then it was extracted again with ethyl acetate and this organic layer was washed with brine, dried (MgSO$_4$) and evaporated under reduced pressure. Recrystallization in chloroform and hexanes afforded the title compound 2.3 (105 mg, 75%) as white solid.

Prop-2-yn-1-yl 6-{5-[(3aS,4S,6aR)-2-oxohexahydro-1H-thieno[3,4-d]imidazol-4-yl]pentanamido}hexanoate (compound 2.5). The synthesis was carried out as described for compound 2.2 using compound 2.4 (72 mg, 0.2 mmol), EDCI (153 mg, 0.8 mmol), DMAP (146 mg, 1.2 mmol) and propargyl alcohol (0.04 mL, 0.8 mmol) in anhydrous DMSO (2 mL) and afforded compound 2.5 (67 mg, 84% yield) as a white solid. $^1$H NMR (500 MHz, CDCl$_3$) δ: 7.75 (t, J=5.5 Hz, 1H, —CH$_2$NHCO), 6.44 (s, 1H, NH), 6.37 (s, 1H, NH), 4.68 (d, J=2.5 Hz, 2H, —OCH$_2$CCH), 4.54-4.50 (m, 1H, —NHCHCH$_2$—), 4.34-4.30 (m, 1H, —NHCHCH$_2$—), 3.12-3.07 (m, 1H, —SCHCH$_2$—), 3.00 (q, J=6.5 Hz, 2H, —CH$_2$NHCO—) 2.82 (dd, J=13 Hz, 5 Hz, 1H, —SCH$_2$—), 2.57 (d, J=13 Hz, 1H, —SCH$_2$—), 2.54 (t, J=2.5 Hz, 1H, —CCH), 2.33 (t, J=7.5 Hz, 2H, —CH$_2$COO—), 2.04 (t, J=7.5 Hz, 2H, —CH$_2$COO—), 1.58-1.43 (m, 4H, —CH$_2$— of chain), 1.32-1.21 (m, 8H, —CH$_2$— of chain).

tert-Butyl (4-hydroxybutyl)carbamate (compound 2.7). To a stirring mixture of compound 2.6 (1 g, 11.22 mmol) and triethylamine (3.45 mL, 2.2 mmol) in anhydrous dichloromethane (11 mL), was added di-tert-butyl-dicarbonate (2.7 g, 12.34 mmol) at 0° C. under argon atmosphere and the reaction mixture was stirred for 12 hours at room temperature. The reaction was diluted with diethyl ether and the organic layer was washed with saturated aqueous NH$_4$Cl solution, saturated aqueous NaHCO$_3$ solution and brine and was evaporated under reduced pressure. Purification by flash column chromatography on silica gel (40%-80% ethyl acetate in hexane) afforded the title compound 2.7 (2.1 g, 99% yield) as colorless oil. IR (neat) 3352, 2935, 1690, 1366, 1252, 1173 cm$^{-1}$; $^1$H (400 MHz, CDCl$_3$) δ: 4.68 (s, 1H, NH), 3.66 (t, J=6.5 Hz, 2H, H-2), 3.14 (t, J=6.5 Hz, 2H, H-4), 2.00 (s, 1H, OH), 1.55-1.58 (m, 4H, H-2, H-3), 1.43 (s, 9H, C(CH$_3$)$_3$) ppm; $^{13}$C (100 MHz, CDCl$_3$) δ: 156.1 79.2, 62.3, 41.0, 29.7, 26.6, 28.6.

tert-Butyl [4-(prop-2-yn-1-yloxy)butyl]carbamate (compound 2.8). To a stirring solution of compound 2.7 (900 mg, 5 mmol) in anhydrous THF/DMF (1:1 mixture, 25 mL) was added sodium hydride (280 mg, 12 mmol) at 0° C. under argon atmosphere and the reaction mixture was stirred for 30 minutes. Then was added a solution of propargyl bromide (1.5 mL, 7.5 mmol, 5 M in toluene) in anhydrous THF (5 mL) and the reaction mixture was warmed up at room temperature and was stirred for additional 12 hours. The reaction mixture was quenched by the addition of water and extracted with diethyl ether. The combined organic layer was washed with brine, dried (MgSO$_4$) and evaporated under reduced pressure. Purification by flash column chromatography on silica gel (5%-30% ethyl acetate in hexane) afforded the title compound 2.8 (790 mg, 70% yield) as white oil. IR (neat) cm$^{-1}$: 3256, 2158, 1720; $^1$H NMR (400 MHz, CDCl$_3$) δ: 4.66 (s, (br), 1H, NH), 3.51 (t, J=6.1 Hz, 2H, H-1), 3.12 (t, J=6.6 Hz, 2H, H-4), 2.41 (t, J=2.4 Hz, 1H, CCH), 1.65-1.51 (m, 4H, H-2, H-3), 1.42 (s, 9H, C(CH$_3$)$_3$) ppm; $^{13}$C NMR (100 MHz, CDCl$_3$): δ: 155.9, 79.7, 78.4, 74.2, 69.1, 60.1, 57.7, 40.1, 28.2, 26.5.

4-(Prop-2-yn-1-yloxy)butan-1-amine (compound 2.9). To a stirring solution of compound 2.8 (1.7 g, 7.45 mmol) in anhydrous dichloromethane (74 mL), was added trifluoroacetic acid (4 mL, 37.28 mmol) at 0° C. under argon atmosphere and the reaction mixture was then warmed at room temperature and was stirred for 2 hours. The reaction was quenched by dropwise addition of saturated aqueous NaHCO$_3$ solution at 0° C. and the water layer was first extracted with diethyl ether. Then it was extracted again with ethyl acetate and this organic layer was washed with brine, dried (MgSO$_4$) and evaporated under reduced pressure to afford the title compound 2.9 (930 mg, 93%) as yellow oil. $^1$H NMR (400 MHz, CDCl$_3$) δ: 4.15 (d, J=2.4 Hz, 2H, —OCH$_2$CCH), 3.57 (t, J=6.5 Hz, 2H, H-1), 3.00 (t, J=8 Hz, 2H, H-4), 2.46 (t, J=2.4 Hz, 1H, —CCH), 1.81 (quintet, J=7 Hz, 2H, H-2), 1.72 (quintet, J=7 Hz, 2H, H-3).

11-Oxo-N-[4-(prop-2-yn-1-yloxy)butyl]-2,3,6,7-tetrahydro-1H, 5H, 11H-pyrano[2,3-f]pyrido[3,2,1-ij]quinoline-10-carboxamide (compound 2.11). The synthesis was carried out as described for compound 2.3 using compound 2.10 (40 mg, 0.14 mmol), CDI (91 mg, 0.56 mmol), and compound 2.9 (80 mg, 0.63 mmol) in anhydrous THF/dichloromethane (1:1 mixture, 2.4 mL) and afforded compound 2.11 (44 mg, 80% yield) as a yellow solid. $^1$H NMR (500 MHz, CDCl$_3$) δ: 8.87 (t, J=5.0 Hz, 1H, NHCO), 8.60 (s, Ar-Coumarin), 7.00 (s, Ar-Coumarin), 4.14 (d, J=2 Hz, 2H, —OCH$_2$CCH), 3.58-3.54 (m, 2H, —OCH$_2$CH$_2$CH$_2$CH$_2$N—), 3.49-3.44 (m, 2H, —CH$_2$NHCO), 3.36-3.30 (m, 4H, CH$_2$N—), 2.91-2.86 (m, 2H, —CH$_2$CH$_2$CH$_2$N—), 2.79-2.74 (m, 2H, —CH$_2$CH$_2$CH$_2$N—), 2.41 (t, J=2 Hz, 1H, CCH), 2.01-1.94 (m, 2H, —CH$_2$— of chain), 1.73-1.68 (m, 2H, —CH$_2$— of chain).

N,N-Dimethyl-7-(prop-2-yn-1-ylamino)benzo[c][1,2,5]oxadiazole-4-sulfonamide (compound 2.13). To a stirring solution of compound 2.12 (40 mg, 0.16 mmol) in anhydrous acetonitrile (2 mL), was added propargyl amine (0.07 mL, 0.48 mmol) and triethylamine (0.04 mL, 0.48 mmol) at room temperature under argon atmosphere and the reaction was stirred for 20 minutes The solvent was evaporated and the residue was chromatographed on silica gel (20%-90% ethyl acetate in hexane) to afford the title compound 2.13 (45 mg, 98%). $^1$H NMR (400 MHz, CDCl$_3$) δ 7.95 (d, J=8 Hz, 1H Ar—H), 6.30 (d, J=8 Hz, 1H, Ar—H) 5.82 (br, NH), 4.23-21 (m, 2H, NHCH$_2$CCH), 2.89 (s, 6H, CH$_3$), 2.39 (t, J=3 Hz, 1H, CCH).

C. Hexahydrocannabinol Triazoles Synthesis

Hexahydrocannabinol triazole compounds 3.1, 3.2, 3.3, 3.4, 3.8, 3.9, 3.10, and 3.15 (shown in Table 1) were synthesized from hexahydrocannabinol compound 1.21 by the method depicted in Scheme 3. Hexahydrocannabinol Triazole compound 3.16 (shown in Table 1) was synthesized from hexahydrocannabinol compound 1.21 by the method depicted in Scheme 3.

Scheme 3
Reagents and Conditions: (a) R-CH₂CCH, CuSO₄·5H₂O, sodium ascorbate, tert-BuOH/H₂O, rt, 12-24 h, 79-93%; b) propargyl alcohol, Cp*RuCl(PPh₃)₂, 1,4-dioxane, 60° C., 12 h, 54%.

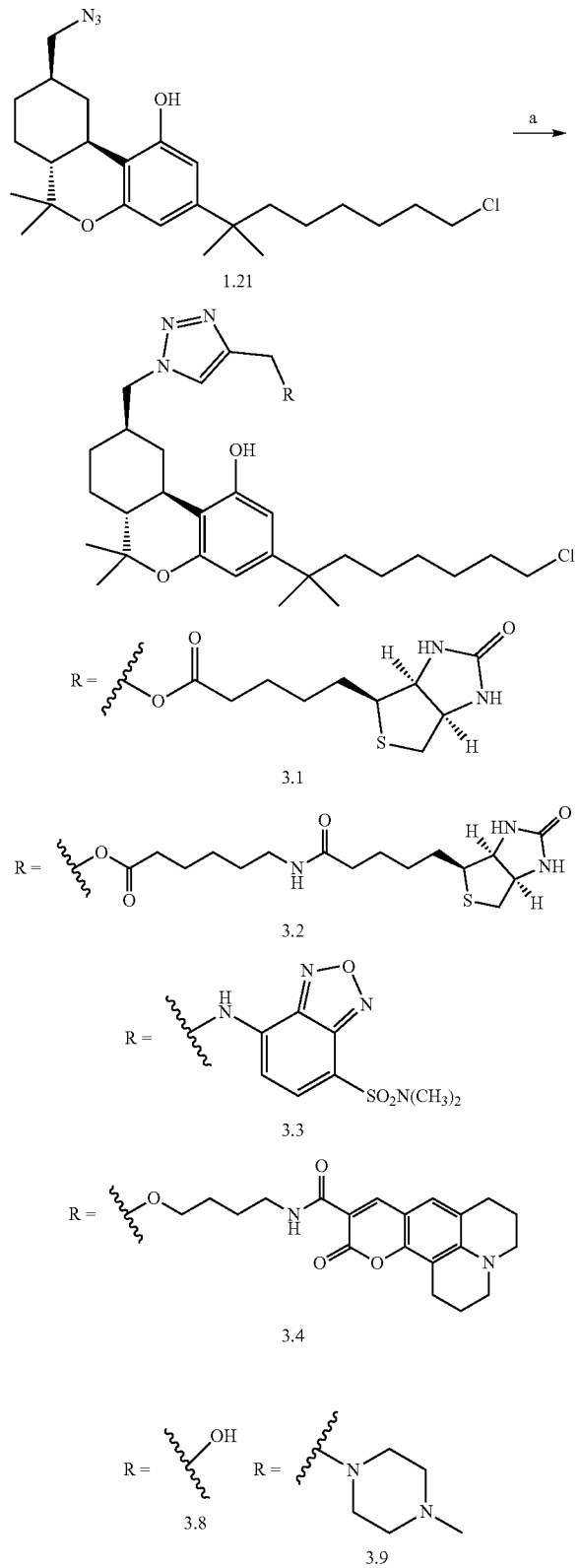

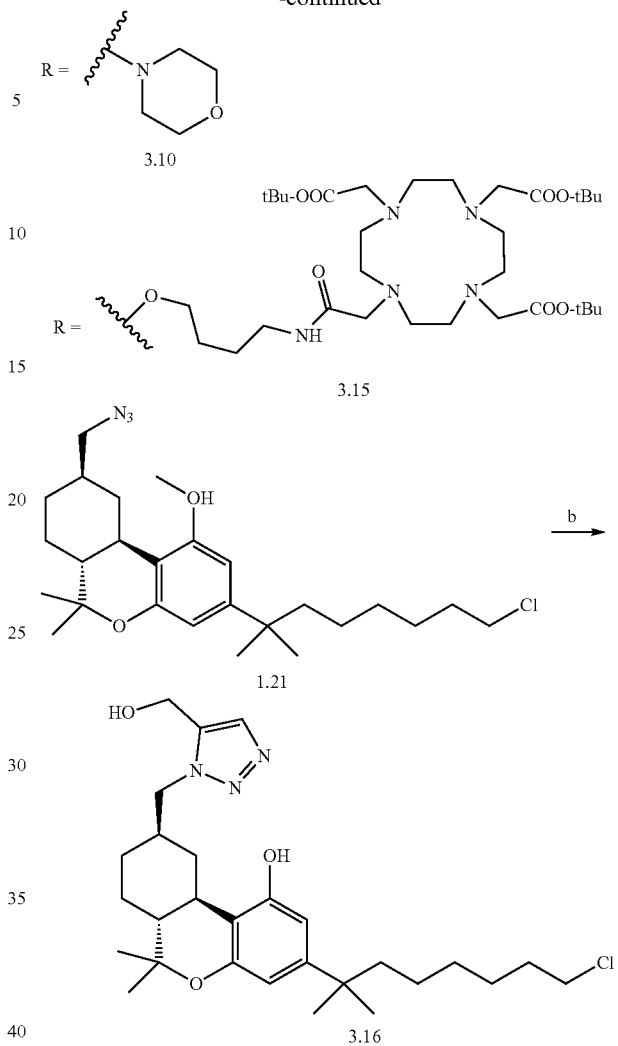

General Procedure for the Synthesis of 1,4-triazole Derivatives

To a stirring solution of alkyne (1 equivalent) and azide (1 equivalent) in tert-butanol at room temperature under argon atmosphere, were added a mixture of copper sulfate pentahydrate (0.05 equivalent) and sodium ascorbate (0.1 equivalent) in water and the reaction mixture was stirred for 12-24 hours. Then the reaction mixture was diluted with dichloromethane and the organic layer was washed with brine, dried (MgSO₄) and evaporated under reduced pressure.

(1-{[(6aR,9R,10aR)-3-(8-Chloro-2-methyloctan-2-yl)-1-hydroxy-6,6-dimethyl-6a,7,8,9,10,10a-hexahydro-6H-benzo[c]chromen-9-yl]methyl}-1H-1,2,3-triazol-4-yl) methyl 5-[(3aS,4S,6aR)-2-oxohexahydro-1H-thieno[3,4-d]imidazol-4-yl]pentanoate (compound 3.1). The synthesis was carried out based on the general procedure described above using compound 1.21 (22 mg, 0.05 mmol), compound 2.2 (14 mg, 0.05 mmol) copper sulfate pentahydrate (0.2 mg, 0.005 mmol), sodium ascorbate (2 mg, 0.01 mmol) in tert-butanol/water (1:1 mixture, 1 mL). Purification by flash column chromatography on silica gel (5%-30% methanol in dichloromethane) afforded the title compound 3.1 (26 mg, 87% yield) as white solid. ¹H NMR (500 MHz, CDCl₃) δ: 7.63 (s, 1H, Ar-triazole), 6.48 (s, (br), 1H NH), 6.27 (d, J=2.0 Hz, 1H, Ar—H), 6.22 (d, J=2.0 Hz, 1H, Ar—H), 5.33

(d, J=7.5 Hz, 1H, CH$_2$O), 5.13 (d, J=7.5 Hz, 1H, CH$_2$O), 4.96 (s, (br), 1H NH), 4.60-4.56 (m, 1H, —CHNHCO—), 4.38-4.36 (m, 1H, —CHNHCO—), 4.36-4.32 (m, 1H, —CH$_2$N—), 4.10-4.05 (m, 1H, —CH$_2$N—), 3.49 (t, J=7.0 Hz, 2H, H-7'), 3.17-3.14 (m, 1H, —CHS—), 3.08-3.02 (m, 1H, C-ring), 2.95 (dd, J=13.0 Hz, 6.5 Hz, 1H, —CH$_2$S—), 2.87 (d, J=13.0 Hz, 1H, —CH$_2$S—), 2.45-2.37 (m, 3H, 2H, —CH$_2$COO—, 1H, C-ring), 2.28-2.19 (m, 1H, C-ring), 1.92-1.87 (m, 2H, C-ring), 1.90-1.58 (m, 7H, 4H, —CH$_2$— of biotin chain, 2H, H-6', 1H, C-ring), 1.53-1.40 (m, 5H, 2H, H-2', 2H, —CH$_2$— of side chain, 1H, C-ring), 1.39-1.31 (s and m overlapping, 5H, 2H, —CH$_2$— of side chain, 1.36, s, 3H, 6b-Me), 1.31-1.01 (s, s and m overlapping, 14H, 1H, C-ring, 4H—CH2- of side chain, 1.16, s 6H, C(CH$_3$)$_2$, 1.03, 3H, 6a-Me), 0.82-0.73 (m, 1H, C-ring).

(1-{[(6aR,9R,10aR)-3-(8-Chloro-2-methyloctan-2-yl)-1-hydroxy-6,6-dimethyl-6a,7,8,9,10,10a-hexahydro-6H-benzo [c]chromen-9-yl]methyl}-1H-1,2,3-triazol-4-yl) methyl 6-{5-[(3aS,4S,6aR)-2-oxohexahydro-1H-thieno[3,4-d]imidazol-4-yl]pentanamido}hexanoate (compound 3.2). The synthesis was carried out based on the general procedure described above using compound 1.21 (22 mg, 0.05 mmol), compound 2.5 (15 mg, 0.05 mmol) copper sulfate pentahydrate (0.2 mg, 0.005 mmol), sodium ascorbate (2 mg, 0.01 mmol) in tert-butanol/water (1:1 mixture, 1 mL). Purification by flash column chromatography on silica gel (5%-30% methanol in dichloromethane) afforded the title compound 3.2 (35 mg, 79% yield) as white solid. $^1$H NMR (500 MHz, CDCl$_3$) δ: 8.00 (s, 1H, Ar-triazole), 6.27 (d, J=2.0 Hz, 1H, Ar—H), 6.19 (d, J=2.0 Hz, 1H, Ar—H), 5.19 (s, 2H, CH$_2$O), 4.48-4.45 (m, 1H, —CHNHCO—), 4.33-4.26 (m, 3H, 1H, —CHNHCO—, 2H, —CH$_2$N—), 3.49 (t, J=7.0 Hz, 2H, H-7'), 3.26-3.11 (m, 5H, 1H, —CHS—, 1H, C-ring, 2H, CH$_2$NHCO—), 2.91 (dd, J=13.0 Hz, 6.5 Hz, 1H, —CH$_2$S—), 2.68 (d, J=13.0 Hz, 1H, —CH$_2$S—), 2.41 (td, J=9 Hz, 1.5 Hz, 1H, C-ring), 2.36 (t, J=7.5 Hz, 2H, —CH$_2$COO—), 2.22-2.09 (m and s overlapping, 3H, especially 2.18, t, J=7.5 Hz, 2H—CH$_2$CO—, 1H, C-ring), 1.92-1.87 (m, 1H, C-ring), 1.79-1.54 (m, 9H, 6H, —CH$_2$— of biotin chain, 2H, H-6', 1H, C-ring), 1.52-1.39 (m, 7H, 2H, H-2', 4H, —CH$_2$— of side and biotin chain, 1H, C-ring), 1.39-1.28 (s and m overlapping, 5H, 2H, —CH$_2$— of side chain, 1.33, s, 3H, 6b-Me), 1.27-1.12 (s, s and m overlapping, 14H, 1H, C-ring, 4H—CH2- of side chain, 1.18, s 6H, C(CH$_3$)$_2$), 1.11-1.01 (m and s overlapping, 5H, 2H, —CH$_2$— of side chain, 1.03, s, 3H, 6a-Me), 0.83-0.74 (m, 1H, C-ring).

7-(((1-(((6aR,9R,10aR)-3-(8-Chloro-2-methyloctan-2-yl)-1-hydroxy-6,6-dimethyl-6a,7,8,9,10,10a-hexahydro-6H-benzo [c]chromen-9-yl)methyl)-1H-1,2,3-triazol-4-yl) methyl)amino)-N,N-dimethylbenzo[c][1,2,5]oxadiazole-4-sulfonamide (compound 3.3). The synthesis was carried out based on the general procedure described above using compound 1.21 (22 mg, 0.05 mmol), compound 2.13 (14 mg, 0.05 mmol) copper sulfate pentahydrate (0.2 mg, 0.005 mmol), sodium ascorbate (2 mg, 0.01 mmol) in tert-butanol/water (1:1 mixture, 1 mL). Purification by flash column chromatography on silica gel (5%-30% methanol in dichloromethane) afforded the title compound 3.3 (29 mg, 80% yield) as yellow solid. $^1$H NMR (400 MHz, CDCl$_3$) δ 7.95, 7.93, 7.62, 6.38-28, 5.88, 5.63, 4.78-67, 4.44-36, 4.23-14, 3.48, 3.06-2.98, 2.89, 2.46-38, 2.19-08 1.96-82, 1.88, 1.69, 1.54-45, 1.40-30, 1.29-14, 1.14-02, 0.89-80.

N-{4-[(1-{[(6aR,9R,10aR)-3-(8-Chloro-2-methyloctan-2-yl)-1-hydroxy-6,6-dimethyl-6a,7,8,9,10,10a-hexahydro-6H-benzo[c]chromen-9-yl]methyl}-1H-1,2,3-triazol-4-yl) methoxy]butyl}-11-oxo-2,3,6,7-tetrahydro-1H, 5H, 11H-pyrano[2,3-f]pyrido[3,2,1-ij]quinoline-10-carboxamide (compound 3.4). The synthesis was carried out based on the general procedure described above using compound 1.21 (22 mg, 0.05 mmol), compound 2.11 (19 mg, 0.05 mmol) copper sulfate pentahydrate (0.2 mg, 0.005 mmol), sodium ascorbate (2 mg, 0.01 mmol) in tert-butanol/water (1:1 mixture, 1 mL). Purification by flash column chromatography on silica gel (5%-30% methanol in dichloromethane) afforded the title compound 3.4 (42 mg, 91% yield) as a yellow solid. $^1$H NMR (500 MHz, CDCl$_3$) δ: 9.02 (t, J=5.5 Hz, 1H, —NHCO), 8.54 (s, 1H, Ar-Coumarin), 7.58 (s, 1H, Ar-triazole), 6.82 (s, 1H, Ar-Coumarin), 6.43 (d, J=2.0 Hz, Ar—H), 6.30 (s, J=2.0 Hz, 1H, Ar—H), 4.68-4.61 (m, 2H, triazole-CH$_2$O—), 4.33 (dd, J=13.5 Hz, 5 Hz, 1H, —CH$_2$-triazole, half part of an AB system), 4.11 (dd, J=13.5 Hz, 8.5 Hz, 1H, —CH2-triazole, half part of an AB system), 3.58 (t, J=5.5 Hz, 2H, —OCH$_2$CH$_2$—), 3.52-3.38 (m, 4H, especially 2 of C-ring and 3.45, t, J=6.5 Hz, 2H, 7'-H), 3.36-3.26 (m, 4H, —NCH$_2$CH$_2$CH$_2$—), 2.85 (t, J=6 Hz, 2H, —NCH$_2$CH$_2$CH$_2$—), 2.72 (t, J=6.5 Hz, 2H, —NCH$_2$CH$_2$CH$_2$—), 2.49-2.43 (m as td, J=10.5 Hz, J=2.5 Hz, 1H, C-ring), 2.21-2.13 (m, 1H, C-ring), 1.99-1.89 (m, 5H, 1H, C-ring, 4H, —CH$_2$CH$_2$CH$_2$N—), 1.76-1.61 (m, 5H, 1H, C-ring, 4H, —CH$_2$— of chain), 1.52-1.44 (m, 3H, 1H, C-ring, 2H, 6'-H), 1.37 (s, 3H, 6-Me), 1.35-1.22 (m, 7H, 2H, 2'-H, 1H, C-ring, 4H—CH$_2$— of chain), 1.22-1.11 (m, s, and s overlapping, 10H, —C(CH$_3$)$_2$—, 4H, —CH$_2$— of the side chain, C-ring, especially, 1.16, s, 3H, —C(CH$_3$)$_2$—, 1.15, s, 3H, —C(CH$_3$)$_2$—), 1.09-1.02 (s and m overlapping, 5H, 6-Me, especially, 1.07, s, 3H, 6-Me, 2H, —CH$_2$— of the side chain), 0.92-0.84 (m, 3H, 1H, C-ring, 2H, —CH$_2$— of the chain).

(6aR,9R,10aR)-3-(8-Chloro-2-methyloctan-2-yl)-9-{[4-(hydroxymethyl)-1H-1,2,3-triazol-1-yl]methyl}-6,6-dimethyl-6a,7,8,9,10,10a-hexahydro-6H-benzo[c]chromen-1-ol (compound 3.8). The synthesis was carried out based on the general procedure described above using compound 1.21 (22 mg, 0.05 mmol), commercially available propargyl alcohol (0.003 mL, 0.05 mmol) copper sulfate pentahydrate (0.2 mg, 0.005 mmol), sodium ascorbate (2 mg, 0.01 mmol) in tert-butanol/water (1:1 mixture, 1 mL). Purification by flash column chromatography on silica gel (5%-30% methanol in dichloromethane) afforded the title compound 3.9 (27 mg, 93% yield) as white solid. %). $^1$H NMR (500 MHz, CDCl$_3$) δ 7.48 (s, 1H, triazole), 6.31 (d, J=2.0 Hz, 1H, Ar—H), 6.22 (d, J=2.0 Hz, 1H, Ar—H), 4.75 (s, 2H, —CH$_2$OH), 4.27-19 (m, 2H, H—11), 3.46 (t, J=6.5 Hz, 2H, H-7'3.11-07 (m, 1H, C-ring), 2.42 (td, J=11 Hz, 2.5 Hz, 1H, C-ring), 2.30-20 (m, 1H, C-ring), 1.90-77 (m, 2H, C-ring) 1.70-62, (m, 1H, C-ring, 2H, —CH$_2$— of the side chain group) 1.50-41 (m, 3H, 2'-H, C-ring), 1.37-27 (m, 3H, 6-Me, 2H—CH$_2$— of chain), 1.25-09 (m, 9H, 4H of —CH$_2$— of the side chain, 1H of C-ring, 6H of C(CH$_3$)$_2$), 1.09-0.99 (m, 3H, 6-Me, 2H of —CH$_2$— of the side chain), 0.90-82 (m, 1H, C-ring).

(6aR,9R,10aR)-3-(8-Chloro-2-methyloctan-2-yl)-6,6-dimethyl-9-((4-((4-methylpiperazin-1-yl)methyl)-1H-1,2,3-triazol-1-yl)methyl)-6a,7,8,9,10,10a-hexahydro-6H-benzo[c]chromen-1-ol (compound 3.9). The synthesis was carried out based on the general procedure described above using compound 1.21 (22 mg, 0.05 mmol), commercially available 1-methyl-4-(prop-2-yn-1-yl)piperazine (7 mg, 0.05 mmol) copper sulfate pentahydrate (0.2 mg, 0.005 mmol), sodium ascorbate (2 mg, 0.01 mmol) in tert-butanol/water (1:1 mixture, 1 mL). Purification by flash column chromatography on silica gel (5%-30% methanol in dichloromethane) afforded the title compound 3.9 (27 mg, 93% yield) as white solid. ¹H NMR (500 MHz, CDCl₃) δ 7.40, 6.19, 5.95, 4.55, 4.16, 3.97, 3.87, 3.44, 3.07, 2.91-50, 2.39, 2.25, 2.16-07, 2.06-1.96, 1.94-87, 1.65, 1.50-26, 1.25-08, 1.07-0.97, 0.72-62.

(6aR,9R,10aR)-3-(8-Chloro-2-methyloctan-2-yl)-6,6-dimethyl-9-((4-(morpholinomethyl)-1H-1,2,3-triazol-1-yl)methyl)-6a,7,8,9,10,10a-hexahydro-6H-benzo[c]chromen-1-ol (compound 3.10). The synthesis was carried out based on the general procedure described above using compound 1.21 (22 mg, 0.05 mmol), commercially available 4-(prop-2-yn-1-yl)morpholine (6 mg, 0.05 mmol) copper sulfate pentahydrate (0.2 mg, 0.005 mmol), sodium ascorbate (2 mg, 0.01 mmol) in tert-butanol/water (1:1 mixture, 1 mL). Purification by flash column chromatography on silica gel (5%-30% methanol in dichloromethane) afforded the title compound 3.10 (26 mg, 90% yield) as white solid. ¹H NMR (500 MHz, CDCl₃) δ 7.43, 6.26, 6.06, 4.50, 4.04, 3.96-86, 3.80, 3.45, 2.89, 2.70-61, 2.58-47, 2.33, 2.21-19, 2.00-1.87, 1.66, 1.51-39, 1.34-08, 1.07-0.97, 0.79-69.

tri-tert-butyl 2,2',2''-(10-(2-((4-(((1-(((6aR,9R,10aR)-3-(8-chloro-2-methyloctan-2-yl)-1-hydroxy-6,6-dimethyl-6a,7,8,9,10,10a-hexahydro-6H-benzo [c]chromen-9-yl)methyl)-1H-1,2,3-triazol-4-yl)methoxy)butyl)amino)-2-oxoethyl)-1,4,7,10-tetraazacyclododecane-1,4,7-triyl)triacetate (compound 3.15). The synthesis was carried out based on the general procedure described above using compound 1.21 (22 mg, 0.05 mmol), tri-tert-butyl 2,2',2''-(10-(2-oxo-2-((4-(prop-2-yn-1-yloxy)butyl)amino)ethyl)-1,4,7,10-tetraazacyclododecane-1,4,7-triyl)triacetate (34 mg, 0.05 mmol), copper sulfate pentahydrate (0.2 mg, 0.005 mmol), sodium ascorbate (2 mg, 0.01 mmol) in tert-butanol/water (1:1 mixture, 1 mL). Purification by flash column chromatography on silica gel (5%-30% methanol in dichloromethane) afforded the title compound 3.15 (45 mg, 80% yield) as white solid.

(6aR,9R,10aR)-3-(8-Chloro-2-methyloctan-2-yl)-9-((5-(hydroxymethyl)-1H-1,2,3-triazol-1-yl)methyl)-6,6-dimethyl-6a,7,8,9,10,10a-hexahydro-6H-benzo[c]chromen-1-ol (compound 3.16).

To a stirring degassed mixture of compound 1.21 (22 mg, 0.05 mmol) and propargyl alcohol (0.003 mL, 0.05 mmol) in dry 1,4-dioxane (0.06 mL), was added a solution of Cp*RuCl(PPh₃)₂ (0.8 mg, 0.001 mmol) in 1,4-dioxane (0.3 mL) and the reaction mixture was stirred under argon atmosphere at 60° C. for 12 hours. Purification by flash column chromatography on silica gel (Ethyl Acetate) afforded the title compound 3.16 (9 mg, 54%). ¹H NMR (500 MHz, CDCl₃) δ 7.52 (s, 1H, triazole), 6.31 (d, J=2.0 Hz, 1H, Ar—H), 6.22 (d, J=2.0 Hz, 1H, Ar—H), 4.75 (s, 2H, —CH₂OH), 4.27-19 (m, 2H, H-11), 3.46 (t, J=6.5 Hz, 2H, H-7'3.11-07 (m, 1H, C-ring), 2.42 (td, J=11 Hz, 2.5 Hz, 1H, C-ring), 2.30-20 (m, 1H, C-ring), 1.90-77 (m, 2H, C-ring) 1.70-62, (m, 1H, C-ring, 2H, —CH₂— of the side chain group) 1.50-41 (m, 3H, 2'-H, C-ring), 1.37-27 (m, 3H, 6-Me, 2H—CH₂— of chain), 1.25-09 (m, 9H, 4H of —CH₂— of the side chain, 1H of C-ring, 6H of C(CH₃)₂), 1.09-0.99 (m, 3H, 6-Me, 2H of —CH₂— of the side chain), 0.90-82 (m, 1H, C-ring).

D. Hexahydrocannabinol Biotin Synthesis

Hexahydrocannabinol Biotin compounds 4.2, 4.4 and 4.7 (shown in Table 2) were synthesized from hexahydrocannabinol compound 1.18 by the method depicted in Scheme 4.

Scheme 4
Reagents and Conditions: (a) D-(+)-Biotin (compound 2.1), EDCI, DMAP, DMF, rt, 14 h, 83%; (b) n-Bu₄NF, CHCl₂, -70° C. to rt, 1 h, 95%; (c) (+)-Biotin-ε-aminocaproic acid (compound 2.4), EDCI, DMAP, DMF, rt, 16 h, 74%; (d) n-Bu₄NF, CH₂Cl₂, -70° C. to rt, 1 h, 78%; (e) AgNO₃, MeCN, reflux, 48 h, 84%; (f) D-(+)-Biotin, EDCI, DMAP, DMF, rt, 14 h, 90%; (g) n-Bu₄NF, CH₂Cl₂, -70° C. to rt, 1 h, 78%.

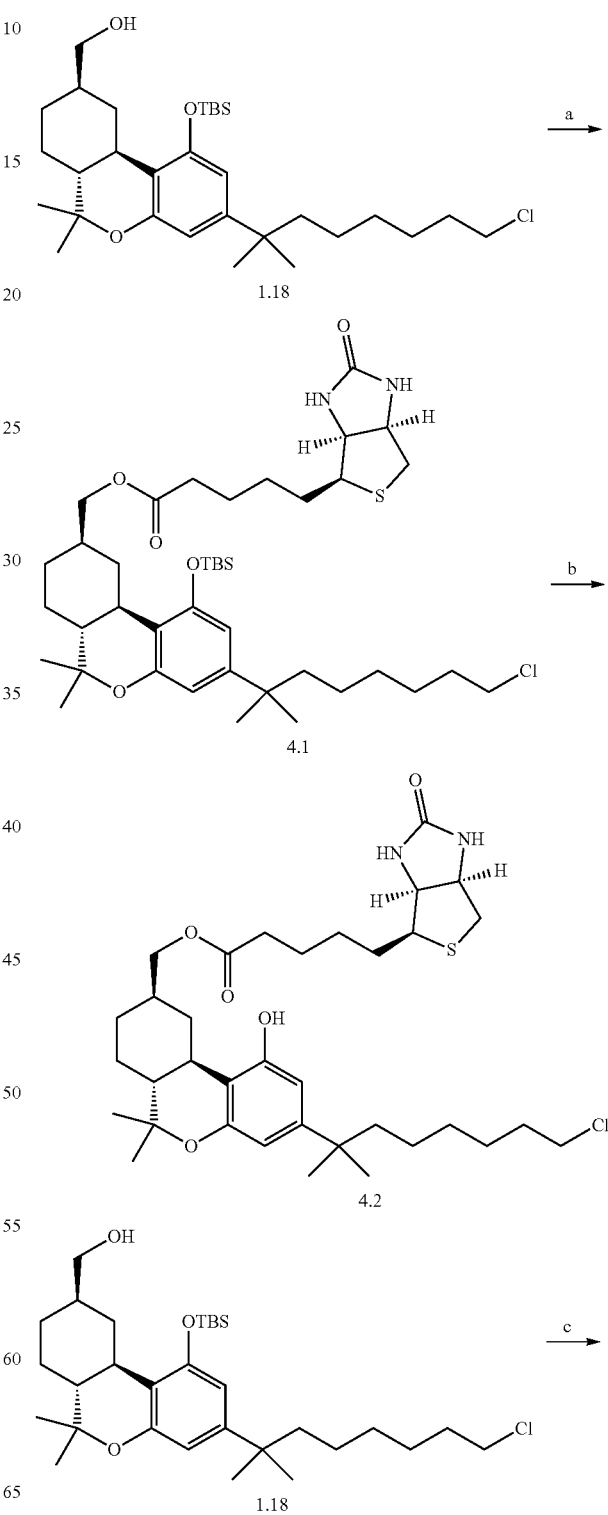

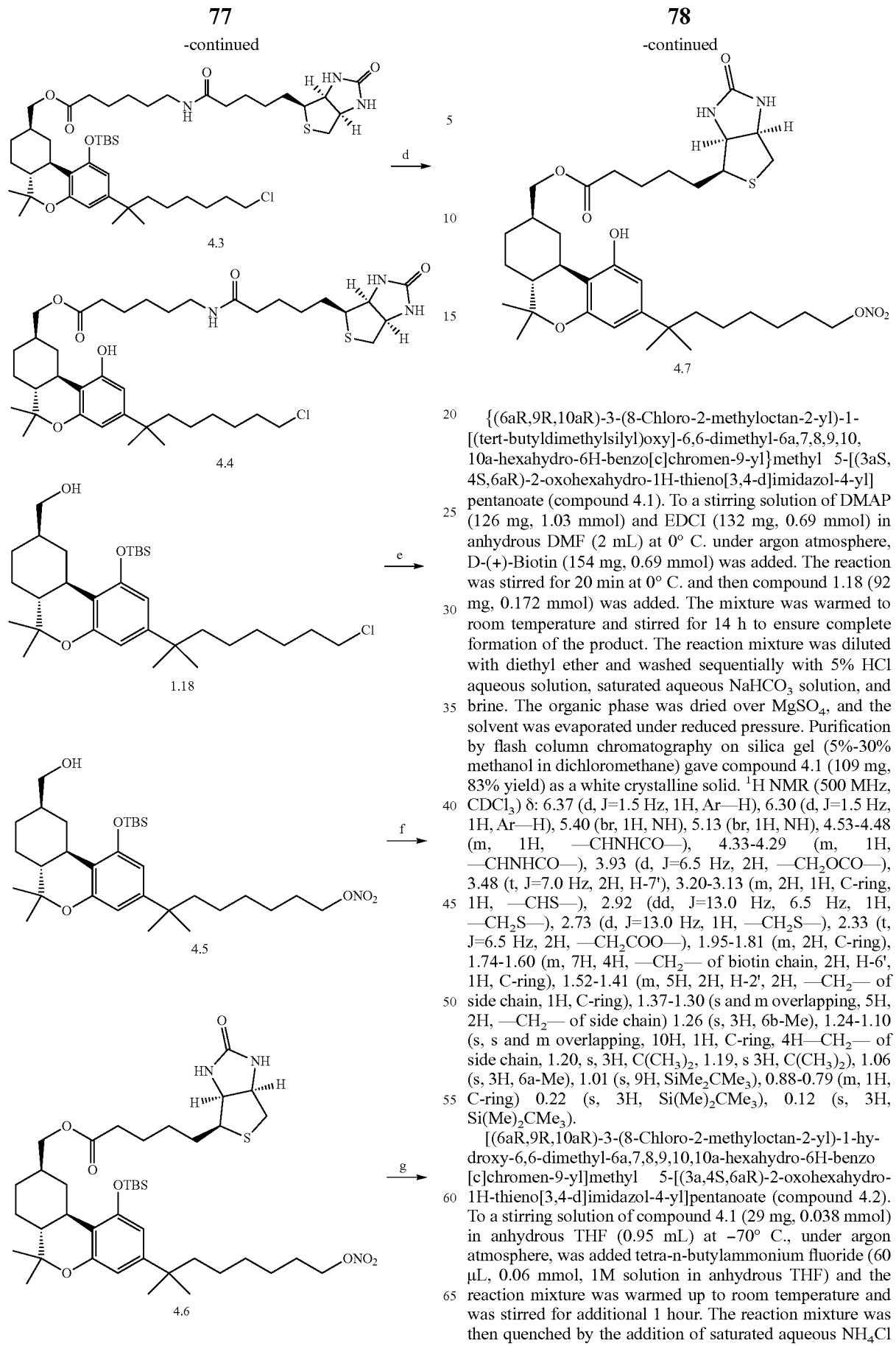

{(6aR,9R,10aR)-3-(8-Chloro-2-methyloctan-2-yl)-1-[(tert-butyldimethylsilyl)oxy]-6,6-dimethyl-6a,7,8,9,10,10a-hexahydro-6H-benzo[c]chromen-9-yl}methyl 5-[(3aS,4S,6aR)-2-oxohexahydro-1H-thieno[3,4-d]imidazol-4-yl]pentanoate (compound 4.1). To a stirring solution of DMAP (126 mg, 1.03 mmol) and EDCI (132 mg, 0.69 mmol) in anhydrous DMF (2 mL) at 0° C. under argon atmosphere, D-(+)-Biotin (154 mg, 0.69 mmol) was added. The reaction was stirred for 20 min at 0° C. and then compound 1.18 (92 mg, 0.172 mmol) was added. The mixture was warmed to room temperature and stirred for 14 h to ensure complete formation of the product. The reaction mixture was diluted with diethyl ether and washed sequentially with 5% HCl aqueous solution, saturated aqueous NaHCO₃ solution, and brine. The organic phase was dried over MgSO₄, and the solvent was evaporated under reduced pressure. Purification by flash column chromatography on silica gel (5%-30% methanol in dichloromethane) gave compound 4.1 (109 mg, 83% yield) as a white crystalline solid. ¹H NMR (500 MHz, CDCl₃) δ: 6.37 (d, J=1.5 Hz, 1H, Ar—H), 6.30 (d, J=1.5 Hz, 1H, Ar—H), 5.40 (br, 1H, NH), 5.13 (br, 1H, NH), 4.53-4.48 (m, 1H, —CHNHCO—), 4.33-4.29 (m, 1H, —CHNHCO—), 3.93 (d, J=6.5 Hz, 2H, —CH₂OCO—), 3.48 (t, J=7.0 Hz, 2H, H-7'), 3.20-3.13 (m, 2H, 1H, C-ring, 1H, —CHS—), 2.92 (dd, J=13.0 Hz, 6.5 Hz, 1H, —CH₂S—), 2.73 (d, J=13.0 Hz, 1H, —CH₂S—), 2.33 (t, J=6.5 Hz, 2H, —CH₂COO—), 1.95-1.81 (m, 2H, C-ring), 1.74-1.60 (m, 7H, 4H, —CH₂— of biotin chain, 2H, H-6', 1H, C-ring), 1.52-1.41 (m, 5H, 2H, H-2', 2H, —CH₂— of side chain, 1H, C-ring), 1.37-1.30 (s and m overlapping, 5H, 2H, —CH₂— of side chain) 1.26 (s, 3H, 6b-Me), 1.24-1.10 (s, s and m overlapping, 10H, 1H, C-ring, 4H—CH₂— of side chain, 1.20, s, 3H, C(CH₃)₂, 1.19, s 3H, C(CH₃)₂), 1.06 (s, 3H, 6a-Me), 1.01 (s, 9H, SiMe₂CMe₃), 0.88-0.79 (m, 1H, C-ring) 0.22 (s, 3H, Si(Me)₂CMe₃), 0.12 (s, 3H, Si(Me)₂CMe₃).

[(6aR,9R,10aR)-3-(8-Chloro-2-methyloctan-2-yl)-1-hydroxy-6,6-dimethyl-6a,7,8,9,10,10a-hexahydro-6H-benzo[c]chromen-9-yl]methyl 5-[(3a,4S,6aR)-2-oxohexahydro-1H-thieno[3,4-d]imidazol-4-yl]pentanoate (compound 4.2). To a stirring solution of compound 4.1 (29 mg, 0.038 mmol) in anhydrous THF (0.95 mL) at −70° C., under argon atmosphere, was added tetra-n-butylammonium fluoride (60 μL, 0.06 mmol, 1M solution in anhydrous THF) and the reaction mixture was warmed up to room temperature and was stirred for additional 1 hour. The reaction mixture was then quenched by the addition of saturated aqueous NH₄Cl solution and diluted with ethyl acetate. The two layers were separated and the water layer was extracted with ethyl acetate. The combined organic layer was washed with brine, dried (MgSO$_4$) and evaporated under reduced pressure. Purification by flash column chromatography on silica gel (5%-30% methanol in dichloromethane) gave compound 4.2 (23 mg, 95% yield) as a white solid. $^1$H NMR (500 MHz, CDCl$_3$) δ: 7.54 (br, 1H, NH), 6.58 (br, 1H, NH), 6.31 (s, 2H, Ar—H), 4.92 (br, 1H, OH), 4.49-4.44 (m, 1H, —CHNHCO—), 4.32-4.26 (m, 1H, —CHNHCO—), 4.05 (dd, J=12.0 Hz, 6.5 Hz, 1H, —CH$_2$OCO—), 3.81 (t, J=12.0 Hz, 1H, —CH$_2$OCO—), 3.49 (t, J=7.0 Hz, 2H, H-7'), 3.40-3.34 (m, 1H, C-ring), 3.17-3.11 (m, 1H, —CHS—), 2.90 (dd, J=13.0 Hz, 6.5 Hz, 1H, —CH$_2$S—), 2.70 (d, J=13.0 Hz, 1H, —CH$_2$S—), 2.47-2.36 (m, 2H, —CH$_2$COO—), 2.34-2.28 (m, 1H, C-ring), 2.01-1.92 (m, 2H, C-ring), 1.90-1.58 (m, 7H, 4H, —CH$_2$— of biotin chain, 2H, H-6', 1H, C-ring), 1.53-1.40 (m, 5H, 2H, H-2', 2H, —CH$_2$— of side chain, 1H, C-ring), 1.39-1.31 (s and m overlapping, 5H, 2H, —CH$_2$— of side chain, 1.39, s, 3H, 6b-Me), 1.31-1.01 (s, s and m overlapping, 14H, 1H, C-ring, 4H—CH$_2$— of side chain, 1.19, s 6H, C(CH$_3$)$_2$, 1.08, 3H, 6a-Me), 0.82-0.73 (m, 1H, C-ring).

{(6aR,9R,10aR)-3-(8-Chloro-2-methyloctan-2-yl)-1-[(tert-butyldimethylsilyl)oxy]-6,6-dimethyl-6a,7,8,9,10,10a-hexahydro-6H-benzo[c]chromen-9-yl}methyl 6-{5-[(3aS,4S,6aR)-2-oxohexahydro-1H-thieno[3,4-d]imidazol-4-yl]pentanamido}hexanoate (compound 4.3). The synthesis was carried out as described for compound 4.1 using compound 1.18 (150 mg, 0.28 mmol), EDCI (260 mg, 1.27 mmol), DMAP (250 mg, 1.66 mmol) and (+)-Biotin-ε-aminocaproic acid (490 mg, 1.27 mmol) in anhydrous DMF (8.5 mL) and afforded compound 4.3 (181 mg, 74% yield) as a white solid. $^1$H NMR (500 MHz, CDCl$_3$) δ: 8.29 (br, 1H, —CH$_2$NHCO—), 6.39 (d, J=1.5 Hz, 1H, Ar—H), 6.33 (br, 1H, NH), 6.34 (d, J=1.5 Hz, 1H, Ar—H), 6.01 (br, 1H, NH), 4.48-4.44 (m, 1H, —CHNHCO—), 4.30-4.26 (m, 1H, —CHNHCO—), 4.06 (dd, J=12.0 Hz, 6.5 Hz, 1H, —CH$_2$OCO—), 3.79 (t, J=9.0 Hz, 1H, —CH$_2$OCO—), 3.49 (t, J=7.0 Hz, 2H, H-7'), 3.39-3.33 (m, 1H, C-ring), 3.31-3.25 (m, 2H, CH$_2$NHCO), 3.16-3.11 (m, 1H, —CHS—), 2.87 (dd, J=13.0 Hz, 6.5 Hz, 1H, —CH$_2$S—), 2.70 (d, J=13.0 Hz, 1H, —CH$_2$S—), 2.45 (td, J=8 Hz, 2.0 Hz, 1H, C-ring), 2.33 (t, J=6.5 Hz, 2H, —CH$_2$COO—), 2.25 (t, J=6.5 Hz, 2H, —CH$_2$COO—), 1.92-1.87 (m, 1H, C-ring), 1.85-1.80 (m, 1H, C-ring), 1.77-1.53 (m, 11H, 8H, —CH$_2$— of biotin chain, 2H, H-6', 1H, C-ring), 1.53-1.41 (m, 7H, 2H, H-2', 2H, —CH$_2$— of side chain, 1H, C-ring, 2H, —CH$_2$— of biotin chain), 1.40-1.04 (s, s, s and m overlapping, 19H, 2H, —CH$_2$— of side chain, 1.35, s, 3H, 6b-Me, 1H, C-ring, 4H—CH2- of side chain, 1.19, s 6H, C(CH$_3$)$_2$, 1.07, 3H, 6a-Me), 1.01 (s, 9H, SiMe$_2$CMe$_3$), 0.80-0.71 (m, 1H, C-ring), 0.22 (s, 3H, Si(Me)$_2$CMe$_3$), 0.12 (s, 3H, Si(Me)$_2$CMe$_3$).

[(6aR,9R,10aR)-3-(8-Chloro-2-methyloctan-2-yl)-1-hydroxy-6,6-dimethyl-6a,7,8,9,10,10a-hexahydro-6H-benzo[c]chromen-9-yl]methyl 6-{5-[(3aS,4S,6aR)-2-oxohexahydro-1H-thieno[3,4-d]imidazol-4-yl]pentanamido}hexanoate (compound 4.4). The synthesis was carried out as described for compound 4.2 using compound 4.3 (27 mg, 0.031 mmol) and tetra-n-butylammonium fluoride (47 μL, 0.047 mmol, 1M solution in anhydrous THF) in anhydrous THF (0.8 mL) and afforded compound 4.4 (18 mg, 78% yield) as a white solid. $^1$H NMR (500 MHz, CDCl$_3$) δ: 8.29 (br, 1H, —CH$_2$NHCO—), 6.49 (d, J=1.5 Hz, 1H, Ar—H), 6.33 (br, 1H, NH), 6.28 (d, J=1.5 Hz, 1H, Ar—H), 6.01 (br, 1H, NH), 5.21 (br, 1H, OH), 4.48-4.44 (m, 1H, —CHNHCO—), 4.30-4.26 (m, 1H, —CHNHCO—), 4.06 (dd, J=12.0 Hz, 6.5 Hz, 1H, —CH$_2$OCO—), 3.79 (t, J=9.0 Hz, 1H, —CH$_2$OCO—), 3.49 (t, J=7.0 Hz, 2H, H-7'), 3.39-3.33 (m, 1H, C-ring), 3.31-3.25 (m, 2H, CH$_2$NHCO), 3.16-3.11 (m, 1H, —CHS—), 2.87 (dd, J=13.0 Hz, 6.5 Hz, 1H, —CH$_2$S—), 2.70 (d, J=13.0 Hz, 1H, —CH$_2$S—), 2.45 (td, J=8 Hz, 2.0 Hz, 1H, C-ring), 2.33 (t, J=6.5 Hz, 2H, —CH$_2$COO—), 2.25 (t, J=6.5 Hz, 2H, —CH$_2$COO—), 1.92-1.87 (m, 1H, C-ring), 1.85-1.80 (m, 1H, C-ring), 1.77-1.53 (m, 11H, 8H, —CH$_2$— of biotin chain, 2H, H-6', 1H, C-ring), 1.53-1.41 (m, 7H, 2H, H-2', 2H, —CH$_2$— of side chain, 1H, C-ring, 2H, —CH$_2$— of biotin chain), 1.40-1.04 (s, s, s and m overlapping, 19H, 2H, —CH$_2$— of side chain, 1.35, s, 3H, 6b-Me, 1H, C-ring, 4H—CH2- of side chain, 1.19, s 6H, C(CH$_3$)$_2$, 1.07, 3H, 6a-Me), 0.80-0.71 (m, 1H, C-ring).

7-{(6aR,9R,10aR)-1-[(tert-Butyldimethylsilyl)oxy]-9-(hydroxymethyl)-6,6-dimethyl-6a,7,8,9,10,10a-hexahydro-6H-benzo[c]chromen-3-yl}-7-methyloctyl nitrate (compound 4.5). To a stirring solution of compound 1.18 (107 mg, 0.2 mmol) in anhydrous MeCN (4 mL) under argon atmosphere was added silver nitrate (272 mg, 1.6 mmol). The reaction mixture was refluxed for 48 h, then cooled to room temperature and solid materials were filtered off through Celite. The filtrate was evaporated under reduced pressure and purified by flash column chromatography on silica gel (15%-50% diethyl ether in hexane) which afforded the title compound compound 4.5 (94 mg, 84% yield) as white foam. IR (neat) 3355 (br, OH), 2931, 2860, 1628 (s, ONO$_2$), 1562, 1471, 1411, 1329, 1278 (s, ONO$_2$), 1140, 1063, 976, 844, 779 cm$^{-1}$; $^1$H NMR (500 MHz, CDCl$_3$) δ: 6.37 (d, J=2.0 Hz, 1H, Ar—H), 6.30 (d, J=2.0 Hz, 1H, Ar—H), 4.39 (t, J=6.5 Hz, 2H, 7'-H)3.54 (dd, J=10.5 Hz, J=5.5 Hz, half of an AB system, 1H, —CH$_2$OH), 3.46 (dd, J=10.0 Hz, J=6.5 Hz, 1H, half of an AB system, —CH$_2$OH), 3.19-3.13 (m as br d, J=13.0 Hz, 1H, C-ring), 2.40-2.32 (m as td, J=11.0 Hz, J=3.0 Hz, 1H, C-ring), 2.04-1.97 (m, 1H, C-ring), 1.94-1.88 (m, 1H, C-ring), 1.78-1.68 (m, 1H, C-ring), 1.67-1.60 (m, 2H, 6'-H), 1.52-1.44 (m, 3H, 2'-H, C-ring), 1.38 (s, 3H, 6Me), 1.34-1.24 (m, 4H, —CH$_2$— of the side chain, 1.24-1.17 (s and s overlapping, 6H, —C(CH$_3$)$_2$—, especially, 1.20, s, 3H, —C(CH$_3$)$_2$—, and 1.19, s, 3H, —C(CH$_3$)$_2$—), 1.16-1.10 (m, 2H, C-ring), 1.09-1.02 (s and m overlapping, 5H, 6-Me, —CH$_2$— of the side chain, especially, 1.06, s, 3H, 6-Me), 1.00 (s, 9H, Si(Me)$_2$CMe$_3$), 0.82-0.7 (m, 1H, C-ring), 0.23 (s, 3H, Si(Me)$_2$CMe$_3$), 0.12 (s, 3H, Si(Me)$_2$CMe$_3$) ppm; $^{13}$C NMR (100 MHz CDCl$_3$) δ: 154.5 (ArC-1 or ArC-5), 154.3 (ArC-5 or ArC-1), 148.9 (tertiary aromatic), 113.6 (tertiary aromatic), 109.7 (ArC-2 or ArC-4), 108.4 (ArC-4 or ArC-2), 73.4 (—CH$_2$ONO$_2$), 68.5 (—CH$_2$OH), 49.6, 44.3, 40.5, 37.2, 35.5, 33.2, 29.8, 29.7, 28.8, 28.7, 27.6, 27.5, 26.6, 25.9, 25.5, 24.4, 18.8, 18.2, −3.6, −4.3. Mass spectrum (ESI) m/z (relative intensity) 564 (M$^+$+H, 100). HPLC (4.6 mm×250 mm, Supelco Discovery column, acetonitrile/water) showed purity of 96.5% and retention time of 6.5 min for the title compound.

{(6aR,9R,10aR)-1-[(tert-Butyldimethylsilyl)oxy]-6,6-dimethyl-3-[2-methyl-8-(nitrooxy)octan-2-yl]-6a,7,8,9,10,10a-hexahydro-6H-benzo[c]chromen-9-yl}methyl 5-[(3aS,4S,6aR)-2-oxohexahydro-1H-thieno[3,4-d]imidazol-4-yl]pentanoate (compound 4.6). The synthesis was carried out as described for compound 4.1 using compound 4.5 (30 mg, 0.053 mmol), EDCI (41 mg, 0.212 mmol), DMAP (39 mg, 0.318 mmol) and D-(+)-Biotin (compound 2.1) (48 mg, 0.212 mmol) in anhydrous DMF (0.53 mL) and afforded compound 4.6 (36 mg, 90% yield) as a white solid. $^1$H NMR (500 MHz, CDCl₃) δ: 6.37 (d, J=1.5 Hz, 1H, Ar—H), 6.30 (d, J=1.5 Hz, 1H, Ar—H), 5.44 (br, 1H, NH), 5.17 (br, 1H, NH), 4.53-4.48 (m, 1H, —CHNHCO—), 4.39 (t, J=7.0 Hz, 2H, H-7'), 4.33-4.28 (m, 1H, —CHNHCO—), 3.92 (d, J=6.5 Hz, 2H, —CH₂OCO—), 3.20-3.13 (m, 2H, 1H, C-ring, 1H, —CHS—), 2.91 (dd, J=13.0 Hz, 6.5 Hz, 1H, —CH₂S—), 2.73 (d, J=13.0 Hz, 1H, —CH₂S—), 2.32 (t, J=6.5 Hz, 2H, —CH₂COO—), 1.95-1.81 (m, 2H, C-ring), 1.76-1.58 (m, 7H, 4H, —CH₂— of biotin chain, 2H, H-6', 1H, C-ring), 1.52-1.41 (m, 5H, 2H, H-2', 2H, —CH₂— of side chain, 1H, C-ring), 1.37 (s, 3H, 6b-Me), 1.35-1.09 (s, s and m overlapping, 14H, 2H, C-ring, 6H—CH₂— of side chain, 1.20, s, 3H, C(CH₃)₂, 1.19, s 3H, C(CH₃)₂), 1.05 (s, 3H, 6a-Me), 1.00 (s, 9H, SiMe₂CMe₃), 0.87-0.78 (m, 1H, C-ring) 0.22 (s, 3H, Si(Me)₂CMe₃), 0.11 (s, 3H, Si(Me)₂CMe₃).

{(6aR,9R,10aR)-1-Hydroxy-6,6-dimethyl-3-[2-methyl-8-(nitrooxy)octan-2-yl]-6a,7,8,9,10,10a-hexahydro-6H-benzo[c]chromen-9-yl}methyl 5-[(3aS,4S,6aR)-2-oxohexahydro-1H-thieno[3,4-d]imidazol-4-yl]pentanoate (compound 4.7). The synthesis was carried out as described for compound 4.2 using compound 4.6 (18 mg, 0.031 mmol) and tetra-n-butylammonium fluoride (47 μL, 0.047 mmol, 1M solution in anhydrous THF) in anhydrous THF (0.8 mL) and afforded compound 4.7 (10 mg, 78% yield) as a white solid. ¹H NMR (500 MHz, CDCl₃) δ: 6.41 (s, (br), 1H, NH), 5.16 (s, (br), 1H, NH), 6.30 (s, 2H, Ar—H), 4.50-4.45 (m, 1H, —CHNHCO—), 4.40 (t, J=7.0 Hz, 2H, H-7'), 4.30-4.27 (m, 1H, —CHNHCO—), 4.04 (dd, J=12.0 Hz, 6.5 Hz, 1H, —CH₂OCO—), 3.83 (t, J=12.0 Hz, 1H, —CH₂OCO—), 3.38-3.32 (m, 1H, C-ring), 3.17-3.12 (m, 1H, —CHS—), 2.90 (dd, J=13.0 Hz, 6.5 Hz, 1H, —CH₂S—), 2.72 (d, J=13.0 Hz, 1H, —CH₂S—), 2.37 (t, J=7.0 Hz, 2H, —CH₂COO—), 2.35-2.27 (m, 1H, C-ring), 1.98-1.81 (m, 2H, C-ring), 1.81-1.57 (m, 7H, 4H, —CH₂— of biotin chain, 2H, H-6', 1H, C-ring), 1.52-1.40 (m, 5H, 2H, H-2', 2H, —CH₂— of side chain, 1H, C-ring), 1.38 (s, 3H, 6b-Me), 1.35-1.12 (s, s and m overlapping, 14H, 1H, C-ring, 4H—CH2- of side chain, 1.25, s 3H, C(CH₃)₂, 1.18, s 3H, C(CH₃)₂, 1.07, 3H, 6a-Me), 0.82-0.73 (m, 1H, C-ring).

E. Hexahydrocannabinol Coumarin Synthesis

Coumarin compound 5.3 (shown in Scheme 5) was synthesized from commercially available Coumarin343 (compound 5.1) by the method depicted in Scheme 5.

Hexahydrocannabinol Coumarin compounds 5.5 and 5.7 (shown in Table 2) were synthesized in two steps starting from hexahydrocannabinol compound 1.18 by the method depicted in Scheme 5.

Hexahydrocannabinol Coumarin compound 5.10 (shown in Table 2) was synthesized starting from hexahydrocannabinol compound 1.20 by the method depicted in Scheme 5.

Scheme 5

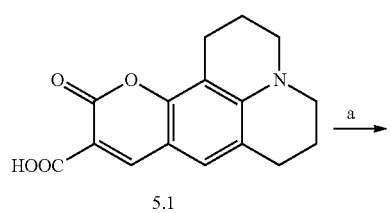

5.1

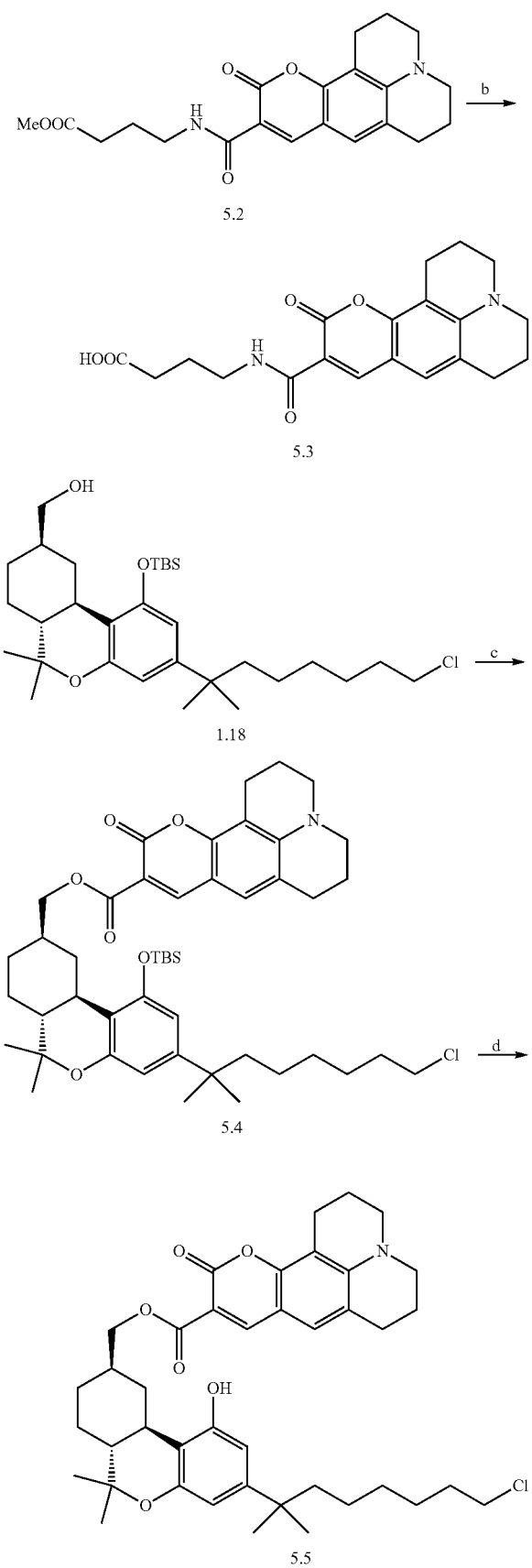

83
-continued

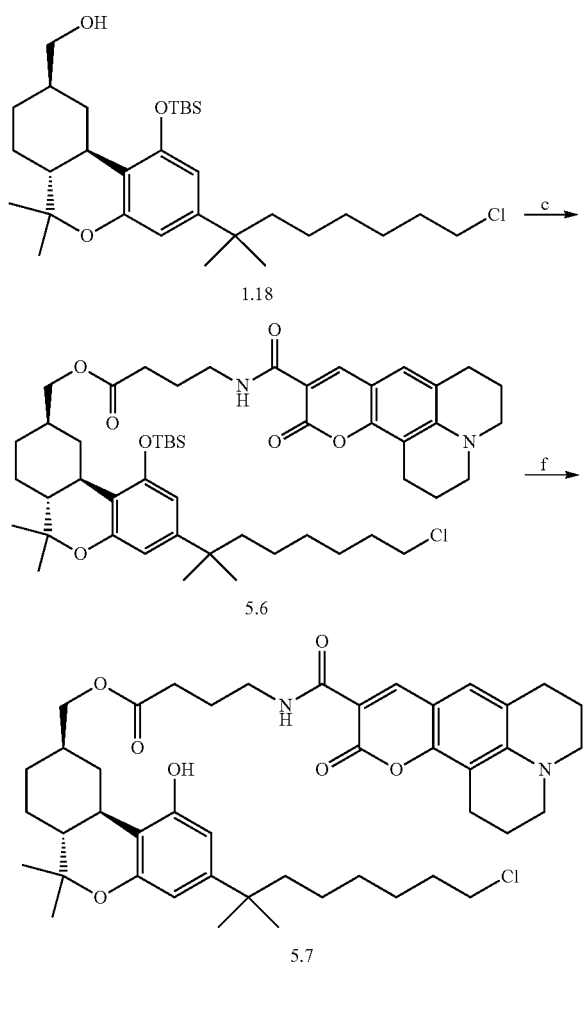

84
-continued

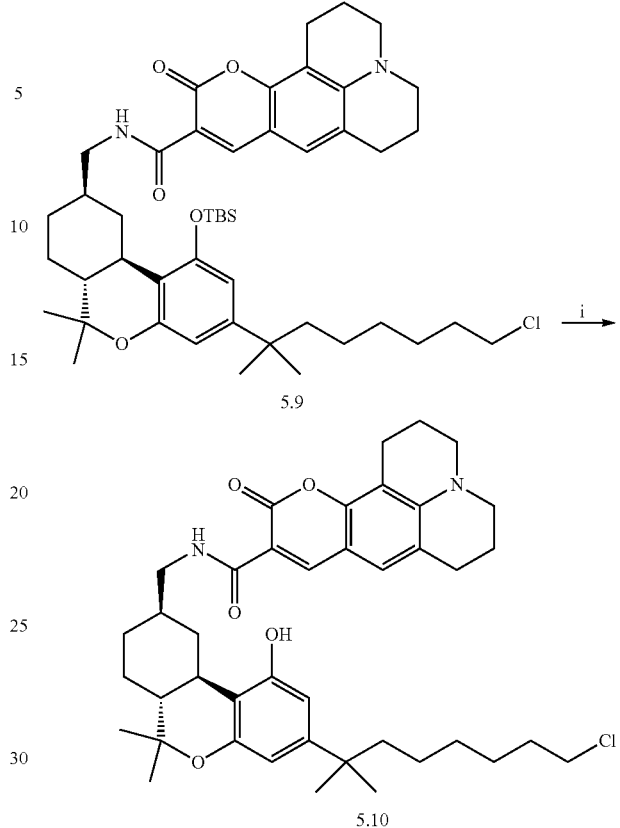

Reagents and Conditions:
(a) CDI, methyl 4-aminobutyrate hydrochloride, pyridine, THF/CH₂Cl₂, r t, 13 h, 84%;
(b) Me₃SnOH, 1,2-DCE, 60° C., 12 h, 99%;
(c) 5.1 EDCI, DMAP, CH₂Cl₂, r t, 14 h, 62%;
(d) n-Bu₄NF, CH₂Cl₂, -70° C. to r t, 1 h, 92%;
(e) 5.3, EDCI, DMAP, DMF, r t, 16 h, 81%;
(f) n-Bu₄NF, CH₂Cl₂, -70° C. to r t, 1 h, 82%;
(g) Ph₃P, MeOH, 50° C., 1 h, 67%;
(h) 5.1, CDI, CH₂Cl₂/THF, r t, 12 h, 86%;
(i) n-Bu₄NF, CH₂Cl₂, -70° C., 20 min, 79%

Methyl 4-(11-oxo-2,3,6,7-tetrahydro-1H, 5H, 11H-pyrano[2,3-f]pyrido[3,2,1-ij]quinoline-10-carboxamido)butanoate (compound 5.2). To a stirring solution of compound 5.1 (285 mg, 1 mmol) in anhydrous THF/dichloromethane (2:1 mixture, 16 mL) at room temperature under argon atmosphere was added CDI (649 mg, 4 mmol) and the reaction mixture was stirred for 10 hours. Then, a solution of methyl 4-aminobutyrate hydrochloride (920 mg, 6 mmol) in anhydrous pyridine (8.5 mL) was added and the reaction mixture was stirred for additional 3 hours. The reaction mixture was evaporated under reduced pressure. Purification by flash column chromatography on silica gel (10%-50% dichloromethane in hexane) afforded the title compound 5.2 (323 mg, 84% yield) as yellow solid. $^1$H NMR (500 MHz, CDCl₃) δ: 8.90 (s, (br), 1H, NHCO), 8.60 (s, 1H, Ar-Coumarin), 7.00 (s, 1H, Ar-Coumarin), 3.68 (s, 3H, —OCH₃), 3.48 (q, J=6.5 Hz, 2H, CH₂NHCO), 3.35-3.31 (m, 4H, —NCH₂CH₂CH₂—), 2.89 (t, J=6 Hz, 2H—CH₂CH₂CH₂N—), 2.77 (t, J=6.5 Hz, 2H—CH₂CH₂CH₂N—), 2.42 (t, J=7.5 Hz, 2H, —CH₂COOCH₃), 2.02-1.91 (m, 6H, 4H, —CH₂CH₂CH₂N—, 2H, —CH₂— of chain).

4-(11-Oxo-2,3,6,7-tetrahydro-1H, 5H, 11H-pyrano[2,3-f] pyrido[3,2,1-ij]quinoline-10-carboxamido)butanoic acid

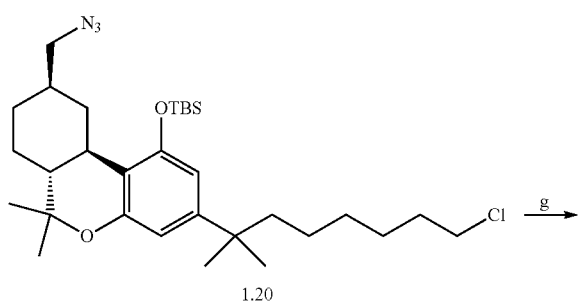

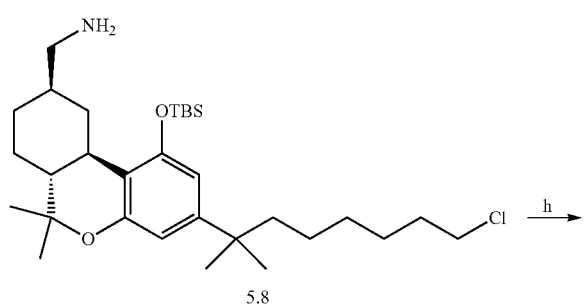

(compound 5.3). To a stirring solution of compound 5.2 (180 mg, 0.47 mmol) in anhydrous 1,2-dichloroethane at room temperature under argon atmosphere, was added trimethyltinhydroxide (850 mg, 4.7 mmol) and the reaction mixture was heated at 60° C. for 12 hours.

The reaction mixture was cooled to room temperature, filtered through Celite and the filtrate was evaporated under reduced pressure. Purification by flash column chromatography on silica gel (5%-35% methanol in ethyl acetate) afforded the title compound 5.3 (171 mg, 99% yield) as yellow solid. $^1$H NMR (500 MHz, DMSO-d6) δ: 8.94 (s, (br), 1H, NHCO), 8.62 (s, 1H, Ar-Coumarin), 7.07 (s, 1H, Ar-Coumarin), 3.53 (q, J=6.5 Hz, 2H, CH$_2$NHCO), 3.41-3.35 (m, 4H, —NCH$_2$CH$_2$CH$_2$—), 2.94 (t, J=6 Hz, 2H—CH$_2$CH$_2$CH$_2$N—), 2.79 (t, J=6.5 Hz, 2H—CH$_2$CH$_2$CH$_2$N—), 2.47 (t, J=7.5 Hz, 2H, —CH$_2$COOCH$_3$), 2.08-1.94 (m, 6H, 4H, —CH$_2$CH$_2$CH$_2$N—, 2H, —CH$_2$— of chain).

{(6aR,9R,10aR)-3-(8-Chloro-2-methyloctan-2-yl)-1-[(tert-butyldimethylsilyl)oxy]-6,6-dimethyl-6a,7,8,9,10,10a-hexahydro-6H-benzo[c]chromen-9-yl}methyl 11-oxo-2,3,6,7-tetrahydro-1H, 5H, 11H-pyrano[2,3-f]pyrido[3,2,1-ij]quinoline-10-carboxylate (compound 5.4). The synthesis was carried out as described for compound 4.1 using compound 1.18 (97 mg, 0.18 mmol), EDCI (105 mg, 0.55 mmol), DMAP (100 mg, 0.82 mmol) and compound 5.1 (156 mg, 0.55 mmol) in anhydrous dichloromethane (1.4 mL) and afforded compound 5.4 (89 mg, 62% yield) as a yellow solid. $^1$H NMR (500 MHz, CDCl$_3$) δ: 8.29 (s, 1H, Ar-Coumarin), 6.95 (s, 1H, Ar-Coumarin), 6.38 (d, J=2.0 Hz, 1H, Ar—H), 6.30 (d, J=2.0 Hz, 1H, Ar—H), 4.26 (dd, J=10.5 Hz, J=4.5 Hz, half of an AB system, 1H, —CH$_2$O—), 4.07 (dd J=10.0 Hz, J=5.5 Hz, half of an AB system, 1H, —CH$_2$O—), 3.4 (t, J=6.5 Hz, 2H, 7'-H), 3.36-3.30 (t and t overlapping, especially, 3.33, t, J=5.5 Hz, 2H, —NCH$_2$CH$_2$CH$_2$—, t, 3.32, J=5.5 Hz, 2H, —NCH$_2$CH$_2$CH$_2$—), 3.21-3.14 (m, 1H, C-ring), 2.87 (t, J=6.5 Hz, 2H, —NCH$_2$CH$_2$CH$_2$—), 2.77 (t, J=6.5 Hz, 2H, —NCH$_2$CH$_2$CH$_2$—), 2.52-2.47 (m as td, J=10.5 Hz, 1.5 Hz, 1H, C-ring), 2.12-2.04 (m, 1H, C-ring), 2.03-1.88 (m, 5H, 4H, —CH$_2$CH$_2$CH$_2$N—, 1H, C-ring), 1.72-1.64 (m, 3H, 1H, C-ring, 2H, 6'-H), 1.52-1.44 (m, 2H, 2'-H, 1H, C-ring), 1.40-1.29 (m and s overlapping, 5H, 4H, —CH$_2$— of the side chain, 6-Me, especially 1.39, s, 3H, 6-Me), 1.26 (t, J=6.5 Hz, 2H, —CH$_2$— of the side chain), 1.22-1.11 (m, s, and s overlapping, 10H, —C(CH$_3$)$_2$—, —CH$_2$— of the side chain, C-ring, especially, 1.20, s, 3H, —C(CH$_3$)$_2$—, 1.19, s, 3H, —C(CH$_3$)$_2$—), 1.09-1.02 (s and m overlapping, 5H, 6-Me, —CH$_2$— of the side chain, especially, 1.07, s, 3H, 6-Me), 0.98 (s, 9H, Si(Me)$_2$CMe$_3$), 0.92-0.84 (m, 1H, C-ring), 0.20 (s, 3H, Si(Me)$_2$CMe$_3$), 0.12 (s, 3H, Si(Me)$_2$CMe$_3$).

[(6aR,9R,10aR)-3-(8-Chloro-2-methyloctan-2-yl)-1-hydroxy-6,6-dimethyl-6a,7,8,9,10,10a-hexahydro-6H-benzo[c]chromen-9-yl]methyl 11-oxo-2,3,6,7-tetrahydro-1H, 5H, 11H-pyrano[2,3-f]pyrido[3,2,1-ij]quinoline-10-carboxylate (compound 5.5). The synthesis was carried out as described for compound 4.2 using compound 5.4 (32 mg, 0.04 mmol) and tetra-n-butylammonium fluoride (60 µL, 0.06 mmol, 1M solution in anhydrous THF) in anhydrous THF (1 mL) and afforded compound 5.5 (25 mg, 92% yield) as a yellow solid. $^1$H NMR (500 MHz, CDCl$_3$) δ: 8.31 (s, 1H, Ar-Coumarin), 6.95 (s, 1H, Ar-Coumarin), 6.3 (d, J=2.0 Hz, 1H, Ar—H), 6.21 (d, J=2.0 Hz, 1H, Ar—H), 5.15 (br, 1H, —OH), 4.18 (d, J=6 Hz, 2H, —CH$_2$O—), 3.49 (t, J=6.5 Hz, 2H, 7'-H), 3.37-3.29 (m, 5H, 4H, —NCH$_2$CH$_2$CH$_2$—, 1H, C-ring), 2.85 (t, J=6.5 Hz, 2H, —NCH$_2$CH$_2$CH$_2$—), 2.76 (t, J=6.5 Hz, 2H, —NCH$_2$CH$_2$CH$_2$—), 2.52-2.47 (m as td, J=11.0 Hz, J=2.5 Hz, 1H, C-ring), 2.09-1.90 (m, 6H, 1H, C-ring, 4H, —CH$_2$CH$_2$CH$_2$N—, 1H, C-ring), 1.72-1.64 (m, 3H, 1H, C-ring, 2H, 6'-H), 1.52-1.44 (m, 3H, 2'-H, 1H, C-ring), 1.40-1.29 (m and s overlapping, 5H, 4H, —CH$_2$— of the side chain, 6-Me, especially 1.39, s, 3H, 6-Me), 1.22-1.11 (m, 10H, —C(CH$_3$)$_2$—, —CH$_2$— of the side chain, C-ring, especially, 1.19, s, 6H, —C(CH$_3$)$_2$—), 1.09-1.02 (s and m overlapping, 5H, 6-Me, —CH$_2$— of the side chain, especially, 1.07, s, 3H, 6-Me), 0.90-0.84 (m, 1H, C-ring).

{(6aR,9R,10aR)-3-(8-Chloro-2-methyloctan-2-yl)-1-[(tert-butyldimethylsilyl)oxy]-6,6-dimethyl-6a,7,8,9,10,10a-hexahydro-6H-benzo[c]chromen-9-yl}methyl 4-(11-oxo-2,3,6,7-tetrahydro-1H, 5H, 11H-pyrano[2,3-f]pyrido[3,2,1-ij]quinoline-10-carboxamido)butanoate (compound 5.6). The synthesis was carried out as described for compound 4.1 using compound 1.18 (27 mg, 0.05 mmol), EDCI (38 mg, 0.2 mmol), DMAP (37 mg, 0.3 mmol) and compound 5.3 (74 mg, 0.2 mmol) in anhydrous DMF (1 mL) and afforded compound 5.6 (36 mg, 81% yield) as a yellow solid. $^1$H NMR (500 MHz, CDCl$_3$) δ: 8.90 (t, J=6 Hz, 1H, NHCO), 8.60 (s, 1H, Ar-Coumarin), 7.00 (s, 1H, Ar-Coumarin), 6.37 (d, J=1.5 Hz, 1H, Ar—H), 6.30 (d, J=1.5 Hz, 1H, Ar—H), 3.96-3.88 (m, 2H, —CH$_2$OCO), 3.51-3.45 (m, 4H, 2H, 7'-H, 2H, —NCH$_2$CH$_2$CH$_2$—), 3.36-3.30 (m, 4H, 2H, —CH$_2$NHCO, 2H, —NCH$_2$CH$_2$CH$_2$—), 3.19-3.14 (m, 1H, C-ring), 2.89 (t, J=6.0 Hz, 2H, —NCH$_2$CH$_2$CH$_2$—), 2.77 (t, J=6.0 Hz, 2H, —NCH$_2$CH$_2$CH$_2$—), 2.41 (t, J=7 Hz, 2H, —CH$_2$CO), 2.37-2.31 (m as td, J=11.0 Hz, J=2.0 Hz, 1H, C-ring), 2.02-1.84 (m, 7H, 4H, —CH$_2$CH$_2$CH$_2$N—, 1H, C-ring, 2H, COCH$_2$CH$_2$CH$_2$NHCO), 1.72-1.64 (m, 3H, 1H, C-ring, 2H, 6'-H), 1.52-1.44 (m, 2H, 2'-H, 1H, C-ring), 1.39-1.30 (m and s overlapping, 5H, 4H, —CH$_2$— of the side chain, 6-Me, especially 1.37, s, 3H, 6-Me), 1.24-1.11 (m, s, and s overlapping, 10H, —C(CH$_3$)$_2$—, —CH$_2$— of the side chain, C-ring, especially, 1.20, s, 3H, —C(CH$_3$)$_2$—, 1.19, s, 3H, —C(CH$_3$)$_2$—), 1.10-0.96 (s and m overlapping, 5H, 6-Me, —CH$_2$— of the side chain, especially, 1.07, s, 3H, 6-Me, 1.00, s, 9H, Si(Me)$_2$CMe$_3$), 0.90-0.84 (m, 1H, C-ring), 0.20 (s, 3H, Si(Me)$_2$CMe$_3$), 0.12 (s, 3H, Si(Me)$_2$CMe$_3$).

[(6aR,9R,10aR)-3-(8-Chloro-2-methyloctan-2-yl)-1-hydroxy-6,6-dimethyl-6a,7,8,9,10,10a-hexahydro-6H-benzo[c]chromen-9-yl]methyl 4-(11-oxo-2,3,6,7-tetrahydro-1H, 5H, 11H-pyrano[2,3-f]pyrido[3,2,1-ij]quinoline-10-carboxamido)butanoate (compound 5.7). The synthesis was carried out as described for compound 4.2 using compound 5.6 (15 mg, 0.017 mmol) and tetra-n-butylammonium fluoride (26 µL, 0.026 mmol, 1M solution in anhydrous THF) in anhydrous THF (0.34 mL) and afforded compound 5.7 (11 mg, 82% yield) as a yellow solid. $^1$H NMR (500 MHz, CDCl$_3$) δ: 9.00 (t, J=5.5 Hz, 1H, NHCO), 8.64 (s, 1H, Ar-Coumarin), 7.92 (s, (br), —OH), 6.98 (s, 1H, Ar-Coumarin), 6.42 (d, J=2.0 Hz, 1H, Ar—H), 6.28 (d, J=2.0 Hz, 1H, Ar—H), 4.01-3.96 (m, 2H, —CH$_2$OCO), 3.54-3.42 (m, 5H, 2H, 7'-H, 2H, —NCH$_2$CH$_2$CH$_2$—, 1H, C-ring), 3.37-3.31 (m, 4H, 2H, —CH$_2$NHCO, 2H, —NCH$_2$CH$_2$CH$_2$—), 2.89 (t, J=6.0 Hz, 2H, —NCH$_2$CH$_2$CH$_2$—), 2.78 (t, J=6.0 Hz, 2H, —NCH$_2$CH$_2$CH$_2$—), 2.44-2.41 (m, 3H, 2H, —CH$_2$CO, 1H, C-ring), 2.12-1.96 (m, 7H, 4H, —CH$_2$CH$_2$CH$_2$N—, 1H, C-ring, 2H, COCH$_2$CH$_2$CH$_2$NHCO), 1.93-1.87 (m, 1H, C-ring), 1.84-1.78 (m, 1H, C-ring), 1.69-1.62 (m, 3H, 1H, C-ring, 2H, 6'-H), 1.52-1.44 (m, 2H, 2'-H, 1H, C-ring), 1.37 (s, 3H, 6-Me), 1.36-1.20 (m, s, and s overlapping, 10H, —C(CH$_3$)$_2$—, 4H—CH$_2$— of the side chain, especially, 1.22, s, 3H, —C(CH$_3$)$_2$—, 1.21, s, 3H, —C(CH$_3$)$_2$—), 1.19-1.04 (s and m overlapping, 5H, 6-Me, —CH$_2$— of the side chain, especially, 1.09, s, 3H, 6-Me), 0.76-0.68 (m, 1H, C-ring).

{(6aR,9R,10aR)-3-(8-Chloro-2-methyloctan-2-yl)-1-[(tert-butyldimethylsilyl)oxy]-6,6-dimethyl-6a,7,8,9,10,10a-hexahydro-6H-benzo[c]chromen-9-yl}methanamine (compound 5.8). To a stirring solution of compound 1.20 (56 mg, 0.1 mmol) in anhydrous methanol was added triphenylphosphine (130 mg, 0.5 mmol) at room temperature under argon, the reaction mixture was heated at 50° C. for 60 minutes and then the solvent was evaporated under reduced pressure. Purification by flash column chromatography on silica gel (5%-35% methanol in dichloromethane with saturated aqueous ammonia 28%) afforded the title compound 5.8 (36 mg, 67% yield) as yellow solid. $^1$H NMR (500 MHz, CDCl$_3$) δ: 6.37 (d, J=1.5 Hz, 1H, Ar—H), 6.30 (d, J=1.5 Hz, 1H, Ar—H), 3.48 (d, J=7.0 Hz, 2H, 7'-H), 3.16-3.14 (m as d, J=12.0 Hz, 1H, C-ring), 2.77 (dd, J=12.0 Hz, J=5.0 Hz, half of an AB system, 1H, —CH$_2$NH$_2$), 2.62 (dd, J=12.0 Hz, J=5.0 Hz, half of an AB system, 1H, —CH$_2$NH$_2$), 2.40-2.34 (m as td, J=11.0 Hz, J=2.5 Hz, 1H, C-ring), 2.12-2.07 (m, 1H, C-ring), 1.95-1.91 (m, 1H, C-ring), 1.75-1.66 (m, 3H, 1H of C-ring, 2H of —CH$_2$— of the side chain), 1.52-1.44 (m, 3H, 2'-H, C-ring), 1.37 (s, 3H, 6-Me), 1.37-1.31 (m, 2H, —CH$_2$— of the side chain), 1.26-1.11 (m, 12H, 4H of —CH$_2$— of the side chain, 2H of C-ring, 1.20, 3H of C(CH$_3$)$_2$, 1.19, 3H of C(CH$_3$)$_2$), 1.11-1.03 (s and m overlapping, 5H, 2H of —CH$_2$— of the side chain, 1.05, s, 3H, 6-Me), 1.00 (s, 9H, Si(Me)$_2$CMe$_3$), 0.84-0.76 (m as q, J=11.5 Hz, 1H, C-ring), 0.23 (s, 3H, Si(Me)$_2$CMe$_3$), 0.13 (s, 3H, Si(Me)$_2$CMe$_3$).

N-({(6aR,9R,10aR)-3-(8-Chloro-2-methyloctan-2-yl)-1-[(tert-butyldimethylsilyl)oxy]-6,6-dimethyl-6a,7,8,9,10,10a-hexahydro-6H-benzo[c]chromen-9-yl}methyl)-11-oxo-2,3,6,7-tetrahydro-1H, 5H, 11H-pyrano[2,3-f]pyrido[3,2,1-ij]quinoline-10-carboxamide (compound 5.9). To a stirring solution of compound 5.8 (107 mg, 0.2 mmol) in anhydrous THF/dichloromethane (2:1 mixture, 3 mL) was added CDI (24 mg, 0.15 mmol) at room temperature under argon atmosphere and the reaction mixture was stirred for 12 hours. Then, a solution of compound 5.1 (22 mg, 0.05 mmol) in anhydrous THF (0.7 mL) was added and the reaction mixture was stirred for additional 3 hours. Then, the reaction mixture was diluted with diethyl ether and the organic layer was washed with saturated aqueous NaHCO$_3$ and brine and was evaporated under reduced pressure. Purification by flash column chromatography on silica gel (40%-80% ethyl acetate in hexane) afforded the title compound compound 5.9 (138 mg, 86% yield) as yellow solid. $^1$H NMR (500 MHz, CDCl$_3$) δ: 8.94 (t, J=5.5 Hz, 1H, NH), 8.61 (s, 1H, Ar-Coumarin), 7.00 (s, 1H, Ar-Coumarin), 6.36 (d, J=1.5 Hz, 1H, Ar—H), 6.29 (d, J=1.5 Hz, 1H, Ar—H), 3.48 (t, J=7 Hz, 2H, 7'-H), 3.45-3.39 (m, 1H, —CH$_2$NHCO, half of an AB system), 3.36-3.25 (m, 5H, 4H, —NCH$_2$CH$_2$CH$_2$—, 1H, —CH$_2$NHCO, half of an AB system), 3.22-3.16 (m as d, J=12 Hz, 1H, C-ring) 2.89 (t, J=6.0 Hz, 2H, —NCH$_2$CH$_2$CH$_2$—), 2.78 (t, J=6.0 Hz, 2H, —NCH$_2$CH$_2$CH$_2$—), 2.39-2.32 (m as td, J=11.0 Hz, J=2.5 Hz, 1H, C-ring), 2.02-1.95 (m, 5H, 1H, C-ring, 4H, —CH$_2$CH$_2$CH$_2$N—), 1.91-1.86 (m, 1H, C-ring), 1.73-1.65 (m, 3H, 1H, C-ring, 2H, 6'-H), 1.52-1.45 (m, 2H, 2'-H, 1H, C-ring), 1.38-1.31 (m and s overlapping, 5H, 4H, —CH$_2$— of the side chain, 6-Me, especially 1.37, s, 3H, 6-Me), 1.22-1.11 (m, s, and s overlapping, 10H, —C(CH$_3$)$_2$—, —CH$_2$— of the side chain, C-ring, especially, 1.20, 3H, —C(CH$_3$)$_2$—, 1.19, s, 3H, —C(CH$_3$)$_2$—), 1.09-1.02 (s and m overlapping, 5H, 6-Me, —CH$_2$— of the side chain, especially, 1.07, s, 3H, 6-Me), 0.97 (s, 9H, Si(Me)$_2$CMe$_3$) 0.92-0.84 (m, 1H, C-ring), 0.19 (s, 3H, Si(Me)$_2$CMe$_3$), 0.11 (s, 3H, Si(Me)$_2$CMe$_3$).

N-{[(6aR,9R,10aR)-3-(8-Chloro-2-methyloctan-2-yl)-1-hydroxy-6,6-dimethyl-6a,7,8,9,10,10a-hexahydro-6H-benzo[c]chromen-9-yl]methyl}-11-oxo-2,3,6,7-tetrahydro-1H, 5H, 11H-pyrano[2,3-f]pyrido[3,2,1-ij]quinoline-10-carboxamide (compound 5.10). The synthesis was carried out as described for compound 4.2 using compound 5.9 (21 mg, 0.026 mmol) and tetra-n-butylammonium fluoride (40 μL, 0.04 mmol, 1M solution in anhydrous THF) in anhydrous THF (0.5 mL) and afforded compound 5.10 (14 mg, 79% yield) as a yellow solid. $^1$H NMR (500 MHz, CDCl$_3$) δ: 9.04 (t, J=5.5 Hz, 1H, NH), 8.60 (s, 1H, Ar-Coumarin), 6.98 (s, 1H, Ar-Coumarin), 6.31 (d, J=0.5 Hz, 1H, Ar—H), 6.23 (d, J=0.5 Hz, 1H, Ar—H), 5.93 (br, 1H, OH), 3.47 (t, J=7 Hz, 2H, 7'-H), 3.44-3.39 (m, 1H, C-ring), 3.34-3.31 (t and t overlapping, especially, 3.33, t, J=5.5 Hz, 2H, —NCH$_2$CH$_2$CH$_2$—, t, 3.32, J=5.5 Hz, 2H, —NCH$_2$CH$_2$CH$_2$—), 2.87 (t, J=6.5 Hz, 2H, —NCH$_2$CH$_2$CH$_2$—), 2.77 (t, J=6.5 Hz, 2H, —NCH$_2$CH$_2$CH$_2$—), 2.52-2.47 (m as td, J=11.5 Hz, J=2.5 Hz, 1H, C-ring), 2.02-1.97 (m, 5H, 1H, C-ring, 4H, —CH$_2$CH$_2$CH$_2$N—), 1.91-1.89 (m, 1H, C-ring), 1.72-1.64 (m, 3H, 1H, C-ring, 2H, 6'-H), 1.52-1.44 (m, 2H, 2'-H, 1H, C-ring), 1.38-1.30 (m and s overlapping, 5H, 4H, —CH$_2$— of the side chain, 6-Me, especially 1.37, s, 3H, 6-Me), 1.26 (t, J=6.5 Hz, 2H, —CH$_2$— of the side chain), 1.22-1.11 (m, s, and s overlapping, 10H, —C(CH$_3$)$_2$—, —CH$_2$— of the side chain, C-ring, especially, 1.18, s, 6H, —C(CH$_3$)$_2$—), 1.09-1.02 (s and m overlapping, 5H, 6-Me, —CH$_2$— of the side chain, especially, 1.07, s, 3H, 6-Me), 0.92-0.84 (m, 1H, C-ring).

F. 9-Keto-Hexahydrocannabinol Starting Material 6.3.

The preparation of the 9-keto-hexahydrocannabinol 6.3 which serves as a starting material for the synthesis of analogs carrying fluorescent moieties at the phenolic hydroxy group is depicted in Scheme 6 [Archer, R. A. et al., J. Org. Chem., (1977) 42: 2277-2284; Nikas, S. P. et al., J. med. Chem., (2010) 53: 6996-7010]

Scheme 6
Reagents and conditions: (a) compoounds 1.5a and 1.5b, p-TSA, CHCl$_3$, 0° C. to rt, 4 days, 55%; (b) TMSOTf, CH$_2$Cl$_2$, MeNO$_2$, 0° C. to rt, 7 h, 65%.

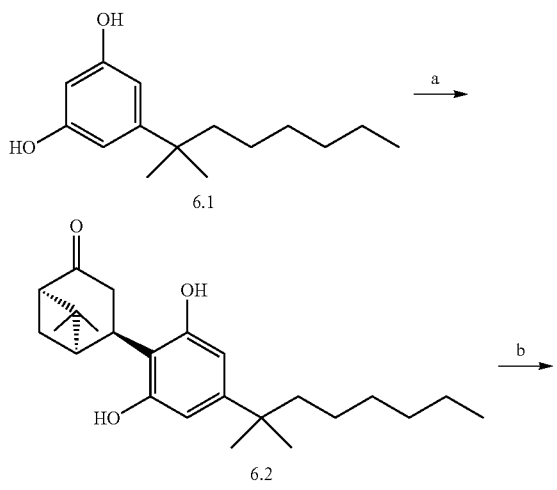

-continued

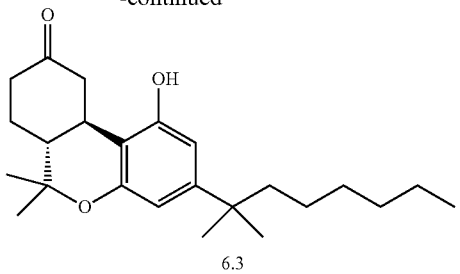

6.3

(1R,4R,5R)-4-(2,6-dihydroxy-4-(2-methyloctan-2-yl) phenyl)-6,6-dimethylbicyclo[3.1.1]heptan-2-one (compound 6.2). The synthesis was carried out as described for compound 1.12 using compound 6.1 (2.36 g, 10 mmol), p-toluenesulfonic acid monohydrate (3.05 g, 16 mmol) and diacetates compounds 1.5a and 1.5b (4.15 g, ca. 90% pure by $^1$H NMR, 16 mmol) in wet CHCl$_3$ (5 mL). The residue was chromatographed on silica gel (15%-50% diethyl ether in hexane) and fractions containing almost pure product (TLC) were combined and evaporated. Further purification by recrystallization from CHCl$_3$ and hexane gave compound 6.2 (2.05 g, 5.5 mmol, 55%) as a white crystalline solid.

(6aR,10aR)-1-hydroxy-6,6-dimethyl-3-(2-methyloctan-2-yl)-6,6a,7,8,10,10a-hexahydro-9H-benzo[c]chromen-9-one (compound 6.3). The synthesis was carried out as described for compound 1.13 using compound 6.2 (1.86 g, 5 mmol), and trimethylsilyltrifluoromethanesulfonate (5 mL, 0.3M solution in CH$_3$NO$_2$, mmol) in anhydrous CH$_2$Cl$_2$/CH$_3$NO$_2$ (3:1 mixture, 167 mL). Purification by flash column chromatography on silica gel (15%-30% ethyl acetate-hexane) afforded 1.21 g (65% yield) of the title compound 6.3 as white foam. mp=158-160° C.

G. Fluorescent 9-Keto-hexahydrocannabinols.

Fluorescent 9-Keto-hexahydrocannabinols 7.1, 7.2, 7.3, and 9.9-9.16 (shown in Table 3) were synthesized by methods depicted in Schemes 7, 8, and 9.

Scheme 7
Reagents and conditions: (a) R-COOH, EDCI, DMAP, CH$_2$Cl$_2$ or DMF, 0° C. to rt, 24 h, 52-73%

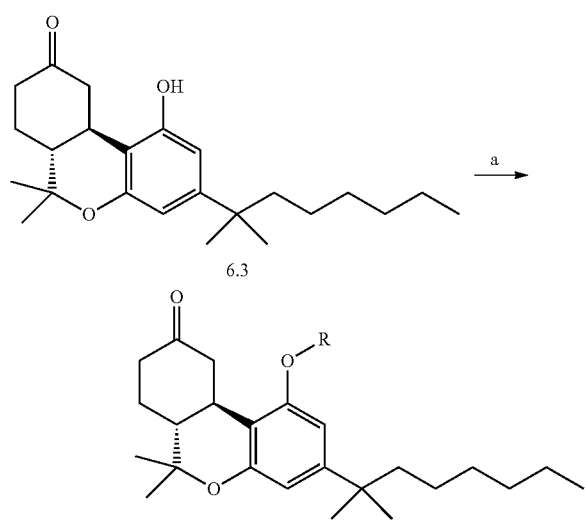

-continued

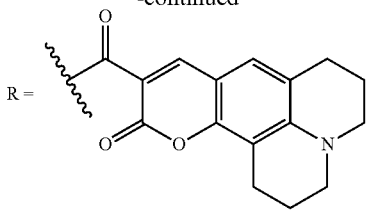

7.1

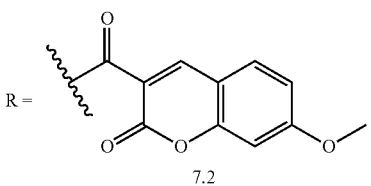

7.2

Standard Procedure for the Steglich Esterification:

To a stirring solution of 4-dimethylaminopyridine (DMAP) (6 equivalents) and N-(3-dimethylaminopropyl)-N'-ethylcarbodiimide hydrochloride (EDCI) (4 equivalents) in dry CH$_2$Cl$_2$ at 0° C., carboxylic acid (4 equivalents) was added. The reaction was stirred for 20 min at 0° C. and then compound 6.3 (1 equivalents) was added under argon atmosphere. The mixture was warmed to room temperature and stirred for 24 h to ensure complete formation of the product. The reaction mixture was diluted with diethyl ether and washed sequentially with 5% HCl, saturated aqueous NaHCO$_3$, and brine. The organic phase was dried over MgSO$_4$, and the solvent was removed under reduced pressure. The residue was purified by flash column chromatography to give the product.

(6aR,10aR)-6,6-Dimethyl-3-(2-methyloctan-2-yl)-9-oxo-6a,7,8,9,10,10a-hexahydro-6H-benzo[c]chromen-1-yl 11-oxo-2,3,6,7-tetrahydro-1H, 5H, 11H-pyrano[2,3-f]pyrido[3,2,1-ij]quinoline-10-carboxylate (compound 7.1). The reaction was performed using the standard procedure reported above using DMAP (99 mg, 0.80 mmol), EDCI (103 mg, 0.53 mmol), Coumarin 343 (151 mg, 0.53 mmol) and compound 6.3 (50 mg, 0.134 mmol) in dry CH$_2$Cl$_2$ (2 ml). The residue was chromatographed on silica gel (50% AcOEt in hexane) to give compound 7.1 as a yellow crystalline solid (45 mg, 52% yield). mp=132-133° C. IR (neat): 2927, 1762, 1710, 1619, 1588, 1442, 1366, 1235, 1197, 1108 cm$^{-1}$. $^1$H NMR (500 MHz, CDCl$_3$) δ 8.51 (s, 1H, ArH-Coumarin), 7.01 (s, 1H, ArH-Coumarin), 6.70 (d, J=1.5 Hz, 1H, ArH), 6.65 (d, J=2.0 Hz, 1H, ArH), 3.42-3.33 (overlapping multiples, 5H, 10eq-H, Coumarin —N—CH$_2$—), 2.92-2.85 (Overlapping multiples, 3H, 10a-H, Coumarin —N—CH$_2$—CH$_2$—CH$_2$—), 2.77 (t, J=6.0 Hz, Coumarin N—CH$_2$—CH$_2$—CH$_2$—), 2.55-2.49 (m, 1H, 8eq-H), 2.41-2.33 (m, 1H, 8ax-H), 2.26-2.17 (m, 1H, 10ax-H), 2.13-2.09 (m, 1H, 7eq-H), 1.99-1.91 (overlapping multiples, 5H, Coumarin N—CH$_2$—CH$_2$—CH$_2$—, 6a-H), 1.53-1.46 (m, 6H, 7ax-H, 2'-H, 6-Me, especially 1.48, s, 6-Me), 1.25-1.15 (m, 12H, 3'-H, 4'-H, 5'-H, —C(CH$_3$)$_2$—, especially 1.22, s, —C(CH$_3$)$_2$—), 1.16 (s, 3H, 6-Me), 1.07 (sextet, J=7.5 Hz, 2H, 6'-H), 0.84 (t, J=6.5 Hz, 3H, 7'-H). $^{13}$C NMR (100 MHz, CDCl$_3$) δ 209.53 (>C=O), 161.99 (—C(O)—O), 158.31 (—C(O)—O), 153.78 (ArC-1 or ArC-5), 153.73 (ArC-5 or ArC-1), 150.59 (tertiary aromatic), 149.96 (ArC-Coumarin), 149.30 (ArC-Coumarin), 149.00 (ArC-Coumarin), 127.33 (ArC-Coumarin), 119.28 (ArC-Coumarin), 114.28 (tertiary aromatic), 112.74 (ArC-2 and ArC-4), 107.68 (ArC-Coumarin), 105.63 (ArC-Coumarin), 105.50 (ArC-Coumarin), 50.23, 49.86, 47.33, 45.84, 44.28, 40.33, 37.44, 34.44, 31.62, 30.20, 29.85, 28.47, 27.60, 27.30, 26.19, 24.44, 22.54, 21.01, 20.03, 19.93, 18.86, 13.96. Mass spectrum (ESI) m/z (relative intensity) 640 (M$^+$+H, 100). Exact mass (ESI) calculated for $C_{40}H_{50}NO_6$ (M$^+$+H), 640.3638; found 640.3631. LC/MS analysis (Waters MicroMass ZQ system) showed purity of 99.7% and retention time of 6.3 min for the title compound.

(6aR,10aR)-6,6-Dimethyl-3-(2-methyloctan-2-yl)-9-oxo-6a,7,8,9,10,10a-hexahydro-6H-benzo[c]chromen-1-yl 7-methoxy-2-oxo-2H-chromene-3-carboxylate (compound 7.2). The reaction was performed using the standard procedure reported above using DMAP (37 mg, 0.30 mmol), EDCI (38 mg, 0.20 mmol), 7-Methoxycoumarin-3-carboxylic acid (33 mg, 0.15 mmol) and compound 6.3 (50 mg, 0.134 mmol) in dry $CH_2Cl_2$ (0.8 ml). The residue was chromatographed on silica gel (50% AcOEt in hexane) to give compound 7.2 as a white crystalline solid (25 mg, 66% yield). mp=122-123° C. IR (neat): 2929, 1746, 1713, 1604, 1556, 1412, 1373, 1200, 1100, 1026 cm$^{-1}$. $^1$H NMR (500 MHz, CDCl$_3$) δ 8.74 (s, 1H, ArH-Coumarin), 7.63 (d, J=9.0 Hz, 1H, ArH-Coumarin), 6.93 (dd, J=9.0 Hz, J=2.5 Hz, 1H, ArH-Coumarin), 6.85 (d, J=2.5 Hz, 1H, ArH-Coumarin), 6.74 (d, J=1.5 Hz, 1H, ArH), 6.67 (d, J=2.0 Hz, 1H, ArH), 3.93 (s, 3H, O—CH$_3$), 3.35 (ddd, J=15.0 Hz, J=3.5 Hz, J=2.0 Hz, 1H, 10eq-H), 2.86 (m as td, J=12.4 Hz, J=3.4 Hz, 1H, 10a-H), 2.56-2.50 (m, 1H, 8eq-H), 2.44-2.35 (m, 1H, 8ax-H), 2.31-2.24 (m, 1H, 10ax-H), 2.16-2.10 (m, 1H, 7eq-H), 2.02-1.94 (m as td, J=12 Hz, J=3 Hz, 1H, 6a-H), 1.55-1.47 (m, 6H, 7ax-H, 2'-H, 6-Me, especially 1.49, s, 6-Me), 1.27-1.17 (m, 12H, 3'-H, 4'-H, 5'-H, —C(CH$_3$)$_2$—, especially 1.24, s, —C(CH$_3$)$_2$—), 1.16 (s, 3H, 6-Me), 1.07 (sextet, J=7.5 Hz, 2H, 6'-H), 0.84 (t, J=6.5 Hz, 3H, 7'-H). $^{13}$C NMR (100 MHz, CDCl$_3$) δ 209.43 (>C=O), 165.63 (—C(O)—O), 161.08 (—C(O)—O), 157.88 (ArC-Coumarin), 156.73 (ArC-Coumarin), 153.94 (ArC-1 or ArC-5), 150.88 (ArC-5 or ArC-1), 148.90 (tertiary aromatic), 131.14 (ArC-Coumarin), 113.93 (tertiary aromatic), 113.83 (ArC-Coumarin), 113.21 (ArC-Coumarin), 112.58 (ArC-2 or ArC-4), 112.43 (ArC-4 or ArC-2), 111.60 (ArC-Coumarin), 100.27 (ArC-Coumarin), 77.04, 55.96, 47.42, 46.00, 44.26, 40.42, 37.50, 34.60, 31.62, 29.83, 28.46, 27.58, 26.38, 24.44, 22.53, 18.81, 13.96. Mass spectrum (ESI) m/z (relative intensity) 575 (M$^+$+H, 100). Exact mass (ESI) calculated for $C_{35}H_{43}O_7$ (M$^+$+H), 575.3009; found 575.3007. LC/MS analysis (Waters MicroMass ZQ system) showed purity of 99.3% and retention time of 6.0 min for the title compound.

Scheme 8
Reagents and conditions: (a) CsCO$_3$, CH$_3$I, DMF, rt, 20 h, 78%; (b) LDA, CH$_3$I, THF, -78° C., 6 h, 70%; (c) MeOH, NaOH, 50° C., 3 h, 85% (compound 8.7) 88% (compound 8.8).

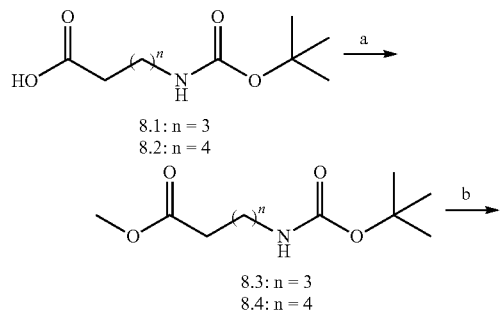

8.1: n = 3
8.2: n = 4

8.3: n = 3
8.4: n = 4

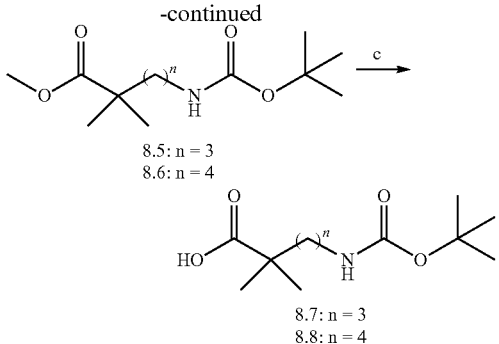

8.5: n = 3
8.6: n = 4

8.7: n = 3
8.8: n = 4

Methyl 5-((tert-butoxycarbonyl)amino)pentanoate (compound 8.3). To a stirred solution of compound 8.1 (600 mg, 2.76 mmol) in dry DMF (15 ml) at room temperature, CsCO$_3$ (900 mg, 2.76 mmol) and CH$_3$I (400 mg, 2.76 mmol) were added under an argon atmosphere. The mixture was stirred for 20 h to ensure complete formation of the product. The reaction mixture was diluted with ethyl acetate and quenched using water. The organic phase was dried over MgSO$_4$, and the solvent was removed under reduced pressure. The residue was chromatographed on silica gel (40% ethyl acetate in hexane) to give compound 8.3 as a colorless oil (500 mg, 78% yield). IR (neat): 3362, 2935, 1737, 1690, 1516, 1452, 1438, 1365, 1246, 1160, 1098 cm$^{-1}$. $^1$H NMR (500 MHz, CDCl$_3$) δ 4.28 (s, 1H, NH), 3.67 (s, 3H, O—CH$_3$), 3.16-3.10 (m, 2H, —NH—CH$_2$—), 2.33 (t, J 7.0 Hz, 2H, —C(O)O—CH$_2$—), 1.70-1.62 (m, 2H, —C(O)O—CH$_2$—CH$_2$—), 1.56-1.46 (m, 2H, —C(O)O—CH$_2$—CH$_2$—CH$_2$—), 1.43 (s, 9H, t-Butyl). $^{13}$C NMR (100 MHz, CDCl$_3$) δ 173.71 (>C=O), 155.81 (>C=O), 78.87, 77.22, 76.90, 76.58, 51.32, 39.92, 33.38, 29.30, 28.21, 21.87. LC/MS analysis (Waters MicroMass ZQ system) showed purity of 98.6% and retention time of 4.0 min for the title compound.

Methyl 6-((tert-butoxycarbonyl)amino)hexanoate (compound 8.4). The reaction was performed similar to as described for compound 8.3 using compound 8.2 (600 mg, 2.6 mmol), dry DMF (15 ml), CsCO$_3$ (845 mg, 2.6 mmol) and CH$_3$I (370 mg, 2.6 mmol). The residue was chromatographed on silica gel (40% ethyl acetate in hexane) to give compound 8.4 as a colorless oil (500 mg, 78% yield). IR (neat): 3364, 2934, 1736, 1692, 1517, 1454, 1437, 1365, 1247, 1155, 1092 cm$^{-1}$. $^1$H NMR (500 MHz, CDCl$_3$) δ 4.58 (s, 1H, NH), 3.66 (s, 3H, O—CH$_3$), 3.15-3.07 (m, 2H, —NH—CH$_2$—), 2.31 (t, J 7.5 Hz, 2H, —C(O)O—CH$_2$—), 1.69-1.60 (m, 2H, —C(O)O—(CH$_2$)$_3$—CH$_2$—), 1.54-1.43 (m, 11H, —C(O)O—CH$_2$—CH$_2$—, especially 1.44 s, t-Butyl), 1.39-1.30 (m, 2H, —C(O)O—(CH$_2$)$_2$—CH$_2$—). $^{13}$C NMR (100 MHz, CDCl$_3$) δ 173.48 (>C=O), 155.46 (>C=O), 78.41, 76.87, 76.55, 76.23, 50.88, 39.77, 33.33, 29.14, 27.82, 25.69, 23.97. LC/MS analysis (Waters MicroMass ZQ system) showed purity of 99.2% and retention time of 4.3 min for the title compound.

Methyl 5-((tert-butoxycarbonyl)amino)-2,2-dimethylpentanoate (compound 8.5). To a stirred solution of compound 8.3 (500 mg, 2.16 mmol) in dry THF (30 ml) at −78° C., LDA (930 mg, 8.6 mmol) was added under an argon atmosphere. The reaction mixture was stirred at the same temperature for 15 min followed by addition of CH$_3$I (3.0 g, 21.6 mmol). The mixture was stirred for additional 30 min to ensure complete formation of the product. The reaction mixture was diluted with diethyl ether and quenched using saturated solution of ammonium chloride. The organic phase was dried over MgSO$_4$, and the solvent was removed under reduced pressure. The residue was chromatographed on silica gel (30% ethyl acetate in hexane) to give compound 8.5 as brown oil (300 mg, 70% yield). IR (neat): 3378, 2951, 1712, 1693, 1517, 1474, 1452, 1365, 1247, 1165, 984 cm$^{-1}$. $^1$H NMR (500 MHz, CDCl$_3$) δ 4.28 (s, 1H, NH), 3.66 (s, 3H, O—CH$_3$), 3.13-3.05 (m, 2H, —NH—CH$_2$—), 1.56-1.50 (m, 2H, —NH—CH$_2$—CH$_2$—CH$_2$—), 1.45-1.38 (m, 11H, —NH—CH$_2$—CH$_2$—, especially 1.44, s, t-Butyl), 1.17 (s, 6H, —C(CH$_3$)$_2$—). $^{13}$C NMR (100 MHz, CDCl$_3$) δ 178.12 (>C=O), 155.81 (>C=O), 78.98, 51.63, 41.93, 40.72, 37.52, 28.31, 25.54, 25.04. LC/MS analysis (Waters Micro-Mass ZQ system) showed purity of 98.5% and retention time of 4.5 min for the title compound.

Methyl 6-((tert-butoxycarbonyl)amino)-2,2-dimethyl-hexanoate (compound 8.6). The synthesis was carried out as described for compound 8.5 using compound 8.4 (500 mg, 2.04 mmol), dry THF (15 ml), LDA (873 mg, 8.16 mmol) and CH$_3$I (2.9 g, 20.4 mmol). The residue was chromatographed on silica gel (30% ethyl acetate in hexane) to give compound 8.6 as brown oil (300 mg, 70% yield). IR (neat): 3377, 2974, 1720, 1680, 1521, 1474, 1456, 1365, 1250, 1173, 1082 cm$^{-1}$. $^1$H NMR (500 MHz, CDCl$_3$) δ 4.28 (s, 1H, NH), 3.65 (s, 3H, O—CH$_3$), 3.22-3.13 (m, 2H, —NH—CH$_2$—), 1.56-1.42 (m, 13H, —NH—CH$_2$—CH$_2$—CH$_2$—, —NH—CH$_2$—CH$_2$—, especially 1.45, s, t-Butyl), 1.24-1.13 (m, 8H, —NH—(CH$_2$)$_3$—CH$_2$—, especially 1.16, s, —C(CH$_3$)$_2$—). $^{13}$C NMR (100 MHz, CDCl$_3$) δ 178.27 (>C=O), 155.82 (>C=O), 78.92, 51.56, 42.13, 40.21, 40.15, 30.29, 28.30, 25.04, 22.06. LC/MS analysis (Waters MicroMass ZQ system) showed purity of 99.4% and retention time of 4.7 min for the title compound.

5-((tert-butoxycarbonyl)amino)-2,2-dimethylpentanoic acid (compound 8.7). To a stirred solution of compound 8.5 (300 mg, 1.10 mmol) in dry methanol (12 ml) at 50° C., NaOH (88 mg, 2.2 mmol) was added under an argon atmosphere. The mixture was stirred for 4 h to ensure complete formation of the product. Upon completion, the mixture was diluted with diethyl ether and quenched using water. The organic phase was dried over MgSO$_4$, and the solvent was removed under reduced pressure. The residue was chromatographed on silica gel (30% ethyl acetate in hexane) to give compound 8.7 as colorless oil (250 mg, 85% yield). IR (neat): 3312, 2941, 1730, 1646, 1477, 1457, 1409, 1371, 1283, 1153, 1059 cm$^{-1}$. $^1$H NMR (500 MHz, CDCl$_3$) δ 5.78 (s, 1H, OH), 4.62 (s, 1H, NH), 3.08-3.00 (m, 2H, —NH—CH$_2$—), 1.58-1.51 (m, 2H, —NH—CH$_2$—CH$_2$—), 1.50-1.42 (m, 11H, —NH—CH$_2$—CH$_2$—, especially 1.44, s, t-Butyl), 1.20 (s, 6H, —C(CH$_3$)$_2$). $^{13}$C NMR (100 MHz, CDCl$_3$) δ 183.65 (>C=O), 155.89 (>C=O), 79.08, 41.74, 40.77, 37.33, 28.31, 25.49, 24.90. LC/MS analysis (Waters MicroMass ZQ system) showed purity of 98.8% and retention time of 4.0 min for the title compound.

6-((tert-butoxycarbonyl)amino)-2,2-dimethylhexanoic acid (compound 8.8). The reaction was performed similar to as described for compound 8.7 using compound 8.6 (400 mg, 1.54 mmol), dry methanol (10 ml) and NaOH (123 mg, 3.0 mmol). The residue was chromatographed on silica gel (30% ethyl acetate in hexane) to give compound 8.8 as colorless oil (350 mg, 88% yield). IR (neat): 3133, 2945, 1722, 1659, 1472, 1449, 1403, 1367, 1228, 1149, 1066 cm$^{-1}$. $^1$H NMR (500 MHz, CDCl$_3$) δ 5.65 (s, 1H, OH), 4.58 (s, 1H, NH), 3.10-3.00 (m, 2H, —NH—CH$_2$—), 1.58-1.51 (m, 2H, —NH—CH$_2$—CH$_2$—CH$_2$—), 1.50-1.41 (m, 11H, —NH—(CH$_2$)$_2$—CH$_2$—, especially 1.44, s, t-Butyl), 1.33-1.16 (m, 8H, —NH—(CH$_2$)$_3$—CH$_2$—, especially 1.18, s, —C(CH$_3$)$_2$). $^{13}$C NMR (100 MHz, CDCl$_3$) δ 183.69 (>C=O), 155.90 (>C=O), 79.02, 41.95, 40.24, 39.94, 30.33, 28.32, 24.90, 22.02. LC/MS analysis (Waters Micro-Mass ZQ system) showed purity of 99.6% and retention time of 4.5 min for the title compound.

Scheme 8
Reagents and conditions: (a) X-COOH, HBTU, DIPEA, DMF, 50° C., 24 h, 80-82% (b) TFA, CH$_2$Cl$_2$, 1 h, 89-95%, (c) CDI, R$_1$ or R$_2$, DMF, 0° C.-rt, 21 h, 75-81%.

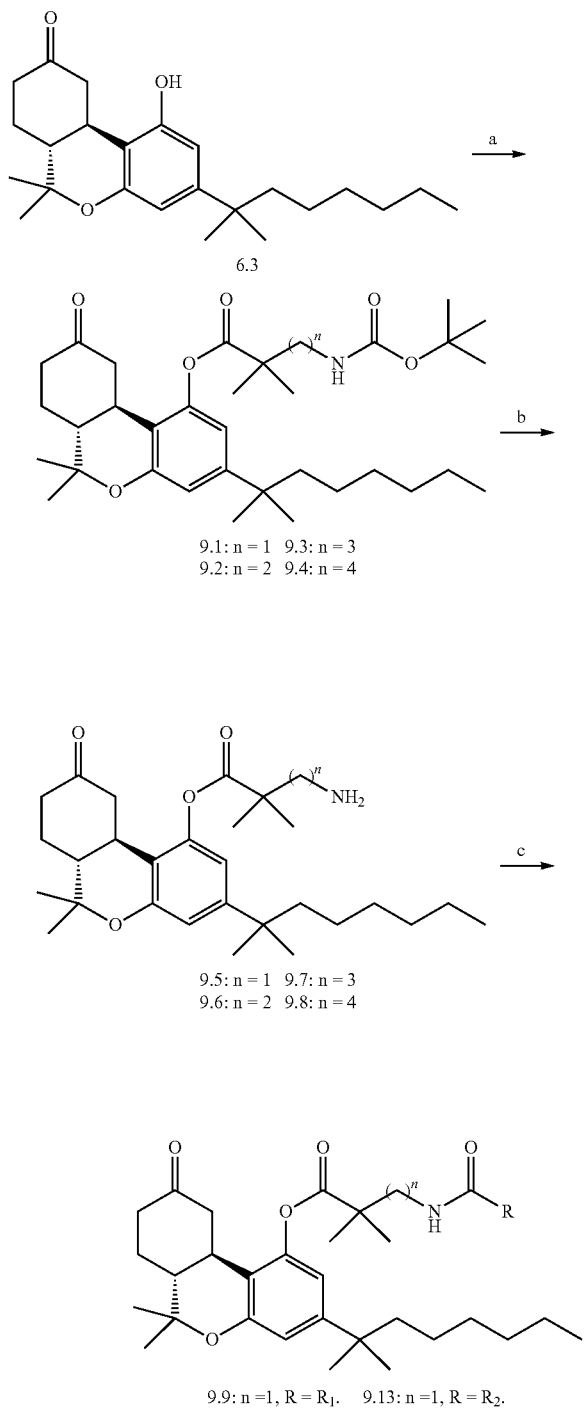

6.3

9.1: n = 1   9.3: n = 3
9.2: n = 2   9.4: n = 4

9.5: n = 1   9.7: n = 3
9.6: n = 2   9.8: n = 4

9.9: n = 1, R = R$_1$.    9.13: n = 1, R = R$_2$.
9.10: n = 2, R = R$_1$.   9.14: n = 2, R = R$_2$.
9.11: n = 3, R = R$_1$.   9.15: n = 3, R = R$_2$.
9.12: n = 4, R = R$_1$.   9.16: n = 4, R = R$_2$.

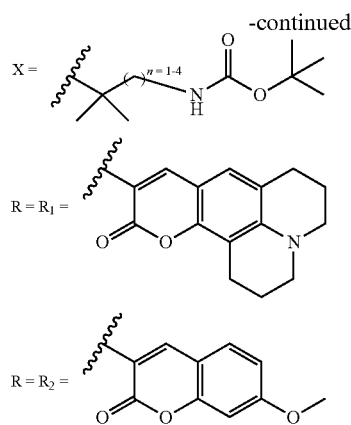

(6aR,10aR)-6,6-Dimethyl-3-(2-methyloctan-2-yl)-9-oxo-6a,7,8,9,10,10a-hexahydro-6H-benzo[c]chromen-1-yl 3-((tert-butoxycarbonyl)amino)-2,2-dimethylpropanoate (compound 9.1). To a stirred suspension of 3-((tert-butoxycarbonyl)amino)-2,2-dimethylpropanoic acid (250 mg, 1.2 mmol) in dry DMF (6 ml) at 50° C., DIPEA (416 mg, 3.22 mmol) and HBTU (522 mg, 1.37 mmol) was added under an argon atmosphere. The mixture was stirred for 3 h followed by the addition of compound 6.3 (200 mg, 0.53 mmol) and stirring continued for additional 21 h. Upon completion the reaction was diluted with ethyl acetate and quenched using water. The organic phase was dried over MgSO$_4$, and the solvent was removed under reduced pressure. The residue was chromatographed on silica gel (25% ethyl acetate in hexane) to give compound 9.1 as colorless oil (300 mg, 82% yield). IR (neat): 3179, 2930, 1710, 1623, 1506, 1459, 1413, 1388, 1365, 1248, 1168, 1044 cm$^{-1}$. $^1$H NMR (500 MHz, CDCl$_3$) δ 6.71 (d, J=2.0 Hz, 1H, ArH), 6.43 (d, J=1.5 Hz, 1H, ArH), 5.07 (t, J=4.5 Hz, 1H, NH), 3.44-3.29 (m, 2H, —NH—CH$_2$—), 3.23 (ddd, J=15.0 Hz, J=3.5 Hz, J=2.0 Hz, 1H, 10eq-H), 2.68 (m as td, J=12.4 Hz, J=3.4 Hz, 1H, 10a-H), 2.59-2.52 (m, 1H, 8eq-H), 2.46-2.36 (m, 1H, 8ax-H), 2.24-2.12 (m, 2H, 10ax-H, 7eq-H), 2.10-1.93 (m as td, J=12 Hz, J=3 Hz, 1H, 6a-H), 1.54-1.46 (m, 6H, 7ax-H, 2'-H, 6-Me, especially 1.48, s, 6-Me), 1.43 (s, 9H, t-Butyl), 1.41 (s, 3H, —C(O)O—C(CH$_3$)$_2$—), 1.39 (s, 3H, —C(O)O—C(CH$_3$)$_2$—), 1.24-1.16 (m, 12H, 3'-H, 4'-H, 5'-H, —C(CH$_3$)$_2$—, especially 1.22, s, —C(CH$_3$)$_2$—), 1.13 (s, 3H, 6-Me), 1.06 (sextet, J=7.5 Hz, 2H, 6'-H), 0.84 (t, J=7.0 Hz, 3H, 7'-H). $^{13}$C NMR (100 MHz, CDCl$_3$) δ 209.51 (>C=O), 202.07 (—C(O)—O), 183.66 (>C=O), 154.17 (ArC-1 or ArC-5), 151.20 (ArC-5 or ArC-1), 149.39 (tertiary aromatic), 114.20 (tertiary aromatic), 113.34 (ArC-2 or ArC-4), 112.16 (ArC4 or ArC-2), 79.37, 48.52, 48.01, 46.32, 44.43, 44.20, 40.82, 37.67, 35.07, 31.83, 30.03, 28.63, 28.49, 27.74, 26.96, 24.64, 23.16, 22.75, 18.92, 14.18. LC/MS analysis (Waters MicroMass ZQ system) showed purity of 99.2% and retention time of 6.3 min for the title compound.

(6aR,10aR)-6,6-Dimethyl-3-(2-methyloctan-2-yl)-9-oxo-6a,7,8,9,10,10a-hexahydro-6H-benzo[c]chromen-1-yl 4-((tert-butoxycarbonyl)amino)-2,2-dimethylbutanoate (compound 9.2). The synthesis was performed similar to as described for compound 9.1 using 4-((tert-butoxycarbonyl)amino)-2,2-dimethylbutanoic acid (250 mg, 1.06 mmol), dry DMF (6 ml), DIPEA (416 mg, 3.22 mmol), HBTU (522 mg, 1.37 mmol) and compound 6.3 (200 mg, 0.53 mmol). The residue was chromatographed on silica gel (25% ethyl acetate in hexane) to give compound 9.2 as colorless oil (290 mg, 80% yield). IR (neat): 3185, 2931, 1710, 1623, 1512, 1457, 1413, 1366, 1228, 1136, 1027 cm$^{-1}$. $^1$H NMR (500 MHz, CDCl$_3$) δ 6.70 (d, J=1.5 Hz, 1H, ArH), 6.46 (d, J=1.5 Hz, 1H, ArH), 5.10 (s, 1H, NH), 3.27 (multiplet overlapping, 2H, 10eq-H, —NH—CH$_2$—), 3.12-3.02 (m, 1H, —NH—CH$_2$—), 2.69 (m as td, J=12.4 Hz, J=3.4 Hz, 1H, 10a-H), 2.60-2.52 (m, 1H, 8eq-H), 2.47-2.33 (m, 1H, 8ax-H), 2.26-2.11 (m, 2H, 10ax-H, 7eq-H), 2.10-1.90 (multiplets overlapping, 3H, 6a-H, —NH—CH$_2$—CH$_2$—), 1.53-1.47 (m, 6H, 7ax-H, 2'-H, 6-Me, especially 1.48, s, 6-Me), 1.45 (s, 9H, t-Butyl), 1.39 (s, 3H, —C(O)O—C(CH$_3$)$_2$—), 1.38 (s, 3H, —C(O)O—C(CH$_3$)$_2$—), 1.24-1.18 (m, 12H, 3'-H, 4'-H, 5'-H, —C(CH$_3$)$_2$—, especially 1.22, s, —C(CH$_3$)$_2$—), 1.13 (s, 3H, 6-Me), 1.06 (sextet, J=7.5 Hz, 2H, 6'-H), 0.84 (t, J=7.0 Hz, 3H, 7'-H). $^{13}$C NMR (100 MHz, CDCl$_3$) δ 210.47 (>C=O), 208.51 (—C(O)—O), 179.45 (>C=O), 154.55 (ArC-1 or ArC-5), 151.63 (ArC-5 or ArC-1), 150.18 (tertiary aromatic), 114.58 (tertiary aromatic), 113.59 (ArC-2 or ArC-4), 112.71 (ArC4 or ArC-2), 83.29, 48.50, 46.88, 44.82, 43.28, 42.78, 41.36, 40.68, 38.09, 35.60, 33.41, 32.26, 30.46, 29.14, 28.99, 28.59, 28.19, 27.41, 26.10, 25.07, 24.87, 23.18, 19.35, 14.61. LC/MS analysis (Waters MicroMass ZQ system) showed purity of 98.2% and retention time of 6.4 min for the title compound.

(6aS,10aR)-6,6-Dimethyl-3-(2-methyloctan-2-yl)-9-oxo-6a,7,8,9,10,10a-hexahydro-6H-benzo[c]chromen-1-yl 5-((tert-butoxycarbonyl)amino)-2,2-dimethylpentanoate (compound 9.3). The synthesis was performed similar to as described for compound 9.1 using compound 8.7 (250 mg, 1.06 mmol), dry DMF (6 ml), DIPEA (416 mg, 3.22 mmol), HBTU (522 mg, 1.37 mmol) and compound 6.3 (200 mg, 0.53 mmol). The residue was chromatographed on silica gel (25% ethyl acetate in hexane) to give compound 9.3 as colorless oil (292 mg, 81% yield). IR (neat): 3403, 2930, 1709, 1622, 1510, 1457, 1413, 1364, 1247, 1120, 1027 cm$^{-1}$. $^1$H NMR (500 MHz, CDCl$_3$) δ 6.72 (d, J=2.0 Hz, 1H, ArH), 6.42 (d, J=1.5 Hz, 1H, ArH), 4.92 (s, 1H, NH), 3.31 (ddd, J=15.0 Hz, J=3.5 Hz, J=2.0 Hz, 1H, 10eq-H), 3.23-3.14 (m, 2H, —NH—CH$_2$—), 2.71 (m as td, J=12.4 Hz, J=3.4 Hz, 1H, 10a-H), 2.62-2.54 (m, 1H, 8eq-H), 2.48-2.38 (m, 1H, 8ax-H), 2.26-2.13 (m, 2H, 10ax-H, 7eq-H), 2.04-1.95 (m as td, J=12 Hz, J=3 Hz, 1H, 6a-H), 1.79-1.71 (m, 2H, —NH—CH$_2$—CH$_2$—), 1.57-1.50 (m, 8H, 7ax-H, 2'-H, —NH—CH$_2$—CH$_2$—, 6-Me, especially 1.51, s, 6-Me), 1.46 (s, 9H, t-Butyl), 1.38 (s, 6H, —C(O)O—C(CH$_3$)$_2$—), 1.27-1.18 (m, 12H, 3'-H, 4'-H, 5'-H, —C(CH$_3$)$_2$—, especially 1.24, s, —C(CH$_3$)$_2$—), 1.15 (s, 3H, 6-Me), 1.09 (sextet, J=7.5 Hz, 2H, 6'-H), 0.87 (t, J=7.0 Hz, 3H, 7'-H). $^{13}$C NMR (100 MHz, CDCl$_3$) δ 209.58 (>C=O), 175.97 (—C(O)—O), 155.92 (—C(O)—NH—), 153.92 (ArC-1 or ArC-5), 150.87 (ArC-5 or ArC-1), 149.55 (tertiary aromatic), 114.13 (tertiary aromatic), 112.93 (ArC-2 or ArC-4), 111.94 (ArC4 or ArC-2), 47.85, 46.15, 44.22, 42.37, 40.72, 37.41, 34.87, 31.63, 29.84, 28.54, 28.34, 27.55, 26.73, 25.56, 25.01, 24.88, 24.43, 22.56, 18.72, 13.99. LC/MS analysis (Waters MicroMass ZQ system) showed purity of 99.7% and retention time of 6.4 min for the title compound.

(6aS,10aR)-6,6-Dimethyl-3-(2-methyloctan-2-yl)-9-oxo-6a,7,8,9,10,10a-hexahydro-6H-benzo[c]chromen-1-yl 6-((tert-butoxycarbonyl)amino)-2,2-dimethylhexanoate (compound 9.4). The synthesis was performed similar to as described for compound 9.1 using compound 8.8 (250 mg, 1.06 mmol), dry DMF (6 ml), DIPEA (416 mg, 3.22 mmol), HBTU (522 mg, 1.37 mmol) and compound 6.3 (200 mg, 0.53 mmol). The residue was chromatographed on silica gel (25% ethyl acetate in hexane) to give compound 9.4 as colorless oil (300 mg, 82% yield). IR (neat): 3394, 2930, 1710, 1622, 1512, 1457, 1413, 1364, 1250, 1171, 1085 cm$^{-1}$. $^1$H NMR (500 MHz, CDCl$_3$) δ 6.69 (d, J=1.5 Hz, 1H, ArH), 6.39 (d, J=1.5 Hz, 1H, ArH), 4.64 (s, 1H, NH), 3.29 (ddd, J=15.0 Hz, J=3.5 Hz, J=2.0 Hz, 1H, 10eq-H), 3.20-3.08 (m, 2H, —NH—CH$_2$—), 2.68 (m as td, J=12.4 Hz, J=3.4 Hz, 1H, 10a-H), 2.59-2.51 (m, 1H, 8eq-H), 2.45-2.34 (m, 1H, 8ax-H), 2.23-2.10 (m, 2H, 10ax-H, 7eq-H), 2.01-1.92 (m as td, J=12 Hz, J=3 Hz, 1H, 6a-H), 1.78-1.62 (m, 2H, —NH—CH$_2$—CH$_2$—), 1.57-1.46 (m, 10H, 7ax-H, 2'-H, —NH—(CH$_2$)$_2$—CH$_2$—, —NH—(CH$_2$)$_3$—CH$_2$—, 6-Me, especially 1.48, s, 6-Me), 1.43 (s, 9H, t-Butyl), 1.36 (s, 3H, —C(O)O—C(CH$_3$)$_2$—), 1.34 (s, 3H, —C(O)O—C(CH$_3$)$_2$—), 1.24-1.15 (m, 12H, 3'-H, 4'-H, 5'-H, —C(CH$_3$)$_2$—, especially 1.22, s, —C(CH$_3$)$_2$—), 1.13 (s, 3H, 6-Me), 1.06 (sextet, J=7.5 Hz, 2H, 6'-H), 0.84 (t, J=6.5 Hz, 3H, 7'-H). $^{13}$C NMR (100 MHz, CDCl$_3$) δ 209.42 (>C=O), 175.99 (—C(O)—O), 155.87 (—C(O)—NH—), 153.91 (ArC-1 or ArC-5), 150.81 (ArC-5 or ArC-1), 149.54 (tertiary aromatic), 114.14 (tertiary aromatic), 112.88 (ArC-2 or ArC-4), 111.95 (ArC4 or ArC-2), 47.79, 46.08, 44.23, 42.57, 40.67, 40.38, 40.14, 37.40, 34.88, 31.62, 30.35, 29.84, 28.53, 28.41, 28.34, 27.54, 26.73, 25.21, 24.82, 24.42, 22.56, 22.24, 18.72, 13.99. LC/MS analysis (Waters MicroMass ZQ system) showed purity of 99.1% and retention time of 6.5 min for the title compound.

(6aR,10aR)-6,6-Dimethyl-3-(2-methyloctan-2-yl)-9-oxo-6a,7,8,9,10,10a-hexahydro-6H-benzo[c]chromen-1-yl 3-amino-2,2-dimethylpropanoate (compound 9.5). To a stirred solution of compound 9.1 (150 mg, 0.26 mmol) in CH$_2$Cl$_2$ (5 ml) at room temperature under an argon atmosphere was added TFA (2.5 ml). The reaction was stirred for 1 h to ensure complete formation of the product. The reaction was quenched using saturated aqueous NaHCO$_3$ and extracted using AcOEt. The organic phase was dried over MgSO$_4$, and the solvent was removed under reduced pressure. The residue was chromatographed on silica gel (10% MeOH in CH$_2$Cl$_2$) to give compound 9.5 as white solid (110 mg, 95% yield). mp=68-69° C. IR (neat): 2929, 1737, 1672, 1526, 1413, 1365, 1245, 1135, 1110 cm$^{-1}$. $^1$H NMR (500 MHz, CDCl$_3$) δ 6.75 (d, J=1.5 Hz, 1H, ArH), 6.41 (d, J=2.0 Hz, 1H, ArH), 3.16-3.00 (multiplet overlapping, 3H, 10eq-H, —NH$_2$—CH$_2$—), 2.67 (m as td, J=12.4 Hz, J=3.4 Hz, 1H, 10a-H), 2.58-2.50 (m, 1H, 8eq-H), 2.47-2.37 (m, 1H, 8ax-H), 2.28 (t, J 9.0 Hz, 1H, 10ax-H), 2.16-2.12 (m, 1H, 7eq-H), 2.10-1.94 (m as td, J=12 Hz, J=3 Hz, 1H, 6a-H), 1.58 (s, 3H, —C(O)O—C(CH$_3$)$_2$—), 1.54 (s, 3H, —C(O)O—C(CH$_3$)$_2$—), 1.53-1.46 (m, 6H, 7ax-H, 2'-H, 6-Me, especially 1.48, s, 6-Me), 1.29-1.14 (m, 12H, 3'-H, 4'-H, 5'-H, —C(CH$_3$)$_2$—, especially 1.22, s, —C(CH$_3$)$_2$—), 1.11 (s, 3H, 6-Me), 1.05 (sextet, J=7.5 Hz, 2H, 6'-H), 0.84 (t, J=7.0 Hz, 3H, 7'-H). $^{13}$C NMR (100 MHz, CDCl$_3$) δ 210.68 (>C=O), 175.18 (>C=O), 154.65 (ArC-1 or ArC-5), 151.77 (ArC-5 or ArC-1), 149.26 (tertiary aromatic), 114.38 (tertiary aromatic), 114.10 (ArC-2 or ArC-4), 112.19 (ArC4 or ArC-2), 66.30, 48.34, 47.38, 46.81, 44.75, 41.66, 41.07, 38.04, 35.15, 32.17, 30.35, 30.16, 28.95, 28.05, 27.10, 24.97, 23.84, 23.23, 23.09, 19.15, 14.51. LC/MS analysis (Waters MicroMass ZQ system) showed purity of 98.3% and retention time of 5.5 min for the title compound.

(6aR,10aR)-6,6-Dimethyl-3-(2-methyloctan-2-yl)-9-oxo-6a,7,8,9,10,10a-hexahydro-6H-benzo[c]chromen-1-yl 4-amino-2,2-dimethylbutanoate (compound 9.6). The reaction was performed as described for compound 9.5 using compound 9.2 (200 mg, 0.34 mmol), CH$_2$Cl$_2$ (6 ml) and TFA (3 ml). The residue was chromatographed on silica gel (10% MeOH in CH$_2$Cl$_2$) to give compound 9.6 as white solid (155 mg, 92% yield). mp=69-70° C. IR (neat): 2929, 1678, 1624, 1563, 1456, 1414, 1365, 1226, 1140, 1029 cm$^{-1}$. $^1$H NMR (500 MHz, CDCl$_3$) δ 6.69 (d, J=1.5 Hz, 1H, ArH), 6.35 (d, J=2.0 Hz, 1H, ArH), 3.20-3.00 (multiplet overlapping, 3H, 10eq-H, —NH$_2$—CH$_2$—), 2.65 (m, 1H, 10a-H, 8eq-H), 2.44-2.30 (m, 1H, 8ax-H), 2.31-2.23 (m, 1H, 10ax-H), 2.15-2.03 (m, 3H, 7eq-H, —NH$_2$—CH$_2$—CH$_2$—), 2.00-1.95 (m as td, J=12 Hz, J=3 Hz, 1H, 6a-H), 1.51-1.38 (m, 9H, 7ax-H, 2'-H, —C(O)O—C(CH$_3$)$_2$—), 1.30 (s, 3H, 6-Me), 1.27-1.16 (m, 12H, 3'-H, 4'-H, 5'-H, —C(CH$_3$)$_2$—, especially 1.20, s, —C(CH$_3$)$_2$—), 1.09 (s, 3H, 6-Me), 1.06 (sextet, J=7.5 Hz, 2H, 6'-H), 0.83 (t, J=7.0 Hz, 3H, 7'-H). $^{13}$C NMR (100 MHz, CDCl$_3$) δ 211.72 (>C=O), 175.61 (>C=O), 154.64 (ArC-1 or ArC-5), 149.62 (ArC-5 or ArC-1), 147.66 (tertiary aromatic), 115.01 (tertiary aromatic), 114.65 (ArC-2 or ArC-4), 111.18 (ArC4 or ArC-2), 48.35, 47.61, 47.24, 44.70, 41.57, 39.84, 31.90, 31.52, 30.10, 29.92, 28.77, 27.78, 25.89, 24.74, 23.01, 22.83, 21.69, 18.79, 14.65. LC/MS analysis (Waters MicroMass ZQ system) showed purity of 98.8% and retention time of 5.6 min for the title compound.

(6aR,10aR)-6,6-Dimethyl-3-(2-methyloctan-2-yl)-9-oxo-6a,7,8,9,10,10a-hexahydro-6H-benzo[c]chromen-1-yl 5-amino-2,2-dimethylpentanoate (compound 9.7). The reaction was performed similar to as described for compound 9.5 using compound 9.3 (260 mg, 0.42 mmol), CH$_2$Cl$_2$ (7 ml) and TFA (3.5 ml). The residue was chromatographed on silica gel (10% MeOH in CH$_2$Cl$_2$) to give compound 9.7 as white solid (195 mg, 91% yield). mp=68-69° C. IR (neat): 2930, 1747, 1675, 1566, 1457, 1413, 1365, 1222, 1113, 1032 cm$^{-1}$. $^1$H NMR (500 MHz, CDCl$_3$) δ 6.69 (d, J=1.5 Hz, 1H, ArH), 6.35 (d, J=2.0 Hz, 1H, ArH), 3.16 (ddd, J=15.0 Hz, J=3.5 Hz, J=2.0 Hz, 1H, 10eq-H), 3.12-3.00 (m, 2H, —NH$_2$—CH$_2$—), 2.70 (m as td, J=12.4 Hz, J=3.4 Hz, 1H, 10a-H), 2.65-2.52 (m, 1H, 8eq-H), 2.46-2.34 (m, 1H, 8ax-H), 2.33-2.21 (m, 1H, 10ax-H), 2.18-2.08 (m, 1H, 7eq-H), 2.01-1.92 (m as td, J=12 Hz, J=3 Hz, 1H, 6a-H), 1.86-1.76 (m, 4H, —NH$_2$—CH$_2$—CH$_2$—CH$_2$—, —NH$_2$—CH$_2$—CH$_2$—), 1.54-1.44 (m, 9H, 7ax-H, 2'-H, —C(O)O—C(CH$_3$)$_2$—), 1.38 (s, 3H, 6-Me), 1.25-1.15 (m, 12H, 3'-H, 4'-H, 5'-H, —C(CH$_3$)$_2$—, especially 1.20, s, —C(CH$_3$)$_2$—), 1.11 (s, 3H, 6-Me), 1.06 (sextet, J=7.5 Hz, 2H, 6'-H), 0.83 (t, J=7.0 Hz, 3H, 7'-H). $^{13}$C NMR (100 MHz, CDCl$_3$) δ 213.06 (>C=O), 176.38 (>C=O), 154.63 (ArC-1 or ArC-5), 151.67 (ArC-5 or ArC-1), 150.32 (tertiary aromatic), 115.20 (tertiary aromatic), 114.62 (ArC-2 or ArC-4), 112.35 (ArC4 or ArC-2), 48.36, 46.81, 44.79, 42.97, 41.20, 41.06, 38.03, 36.67, 35.65, 32.23, 30.44, 30.24, 29.16, 28.99, 28.13, 27.29, 27.14, 25.86, 25.03, 24.70, 23.56, 23.17, 19.22, 14.59. LC/MS analysis (Waters MicroMass ZQ system) showed purity of 98.6% and retention time of 5.5 min for the title compound.

(6aR,10aR)-6,6-Dimethyl-3-(2-methyloctan-2-yl)-9-oxo-6a,7,8,9,10,10a-hexahydro-6H-benzo[c]chromen-1-yl 6-amino-2,2-dimethylhexanoate (compound 9.8). The reaction was performed similar to as described for compound 9.5 using compound 9.4 (240 mg, 0.40 mmol), CH$_2$Cl$_2$ (7 ml) and TFA (3.5 ml). The residue was chromatographed on silica gel (10% MeOH in CH$_2$Cl$_2$) to give compound 9.8 as white solid (180 mg, 89% yield). mp=67-68° C. IR (neat): 2933, 1671, 1563, 1458, 1413, 1389, 1326, 1187, 1100, 1029 cm$^{-1}$. $^1$H NMR (500 MHz, CDCl$_3$) δ 6.73 (d, J=1.5 Hz, 1H, ArH), 6.34 (d, J=2.0 Hz, 1H, ArH), 3.92-3.72 (multiplet overlapping, 3H, 10eq-H, —NH$_2$—CH$_2$—), 3.37 (m as td, J=12.4 Hz, J=3.4 Hz, 1H, 10a-H), 3.12-2.86 (m, 3H, 8eq-H, —NH$_2$—CH$_2$—CH$_2$—), 2.74-2.51 (m, 2H, 10ax-H, 8ax-H), 2.31-2.06 (m, 5H, 7eq-H, —NH$_2$—CH$_2$—CH$_2$—CH$_2$—, —NH$_2$—CH$_2$—CH$_2$—CH$_2$—CH$_2$—), 2.00-1.86 (m as td, J=12 Hz, J=3 Hz, 1H, 6a-H), 1.55-1.42 (m, 9H, 7ax-H, 2'-H, —C(O)O—C(CH$_3$)$_2$—), 1.27-1.14 (m, 15H, 3'-H, 4'-H, 5'-H, —C(CH$_3$)$_2$—, 6-Me, especially 1.22, s, —C(CH$_3$)$_2$—), 1.11 (s, 3H, 6-Me), 1.05 (sextet, J=7.5 Hz, 2H, 6'-H), 0.93 (t, J=7.0 Hz, 3H, 7'-H). $^{13}$C NMR (100 MHz, CDCl$_3$) δ 212.06 (>C=O), 175.94 (>C=O), 154.59 (ArC-1 or ArC-5), 151.46 (ArC-5 or ArC-1), 150.24 (tertiary aromatic), 118.12 (tertiary aromatic), 114.58 (ArC-2 or ArC-4), 112.32 (ArC4 or ArC-2), 48.42, 44.77, 43.11, 38.14, 38.02, 35.93, 35.52, 32.22, 30.41, 29.31, 29.15, 29.00, 28.14, 27.71, 27.10, 25.59, 25.38, 25.03, 23.16, 22.88, 20.33, 19.25, 19.01, 14.59. LC/MS analysis (Waters MicroMass ZQ system) showed purity of 98.9% and retention time of 5.5 min for the title compound.

(6aR,10aR)-6,6-Dimethyl-3-(2-methyloctan-2-yl)-9-oxo-6a,7,8,9,10,10a-hexahydro-6H-benzo[c]chromen-1-yl 2,2-dimethyl-3-(11-oxo-2,3,6,7-tetrahydro-1H, 5H, 11H-pyrano[2,3-f]pyrido[3,2,1-ij]quinoline-10-carboxamido) propanoate (compound 9.9). To a stirred solution of coumarin 343 (10 mg, 0.03 mmol) in dry DMF (1 ml) at 50° C., CDI (17 mg, 010 mmol) was added under an argon atmosphere. The reaction mixture was stirred at same temperature for 15 h followed by addition of compound 9.5 (28 mg, 0.06 mmol) and stirring continued for additional 6 h. Upon completion, the mixture was diluted with diethyl ether and quenched using water. The organic phase was dried over MgSO$_4$, and the solvent was removed under reduced pressure. The residue was chromatographed on silica gel (30% ethyl acetate in hexane) to give compound 9.9 as yellow solid (15 mg, 75% yield). mp=131-132° C. IR (neat): 3854, 2931, 1704, 1618, 1522, 1447, 1376, 1309, 1184, 1120 cm$^{-1}$. $^1$H NMR (500 MHz, CDCl$_3$) δ 9.23 (t, J=4.5 Hz, 1H, NH), 8.61 (s, 1H, ArH-Coumarin), 7.00 (s, 1H, ArH-Coumarin), 6.69 (d, J=2.0 Hz, 1H, ArH), 6.55 (d, J=2.0 Hz, 1H, ArH), 3.78-3.69 (m, 2H, —CH$_2$—N—C(O)—), 3.33-3.28 (m, 4H, Coumarin N—CH$_2$—), 3.22 (ddd, J=15.0 Hz, J=3.5 Hz, J=2.0 Hz, 1H, 10eq-H), 2.87-2.73 (Overlapping multiples, 5H, 10a-H, Coumarin N—CH$_2$—CH$_2$—CH$_2$—), 2.52-2.44 (m, 1H, 8eq-H), 2.39-2.28 (m, 1H, 8ax-H), 2.21-2.08 (m, 2H, 7eq-H, 10ax-H), 2.02-1.90 (overlapping multiples, 5H, Coumarin N—CH$_2$—CH$_2$—CH$_2$—, 6a-H), 1.54-1.37 (m, 14H, 7ax-H, 2'-H, —C(CH$_3$)$_2$—CH$_2$—NH—, —C(O)O—C(CH$_3$)$_2$—, 6-Me, especially 1.48, s, 6-Me), 1.28-1.20 (m, 12H, 3'-H, 4'-H, 5'-H, —C(CH$_3$)$_2$—, especially 1.22, s, —C(CH$_3$)$_2$—), 1.17 (s, 3H, 6-Me), 1.07 (sextet, J=7.5 Hz, 2H, 6'-H), 0.84 (t, J=6.5 Hz, 3H, 7'-H). $^{13}$C NMR (100 MHz, CDCl$_3$) δ 209.33 (>C=O), 175.10 (—C(O)—O), 164.09 (—C(O)—NH), 163.10 (—C(O)—O), 152.89 (ArC-1 or ArC-5), 151.20 (ArC-5 or ArC-1), 149.73 (tertiary aromatic), 148.43 (ArC-Coumarin), 127.28 (ArC-Coumarin), 119.71 (ArC-Coumarin), 114.72 (ArC-Coumarin), 113.26 (ArC-Coumarin), 112.57 (tertiary aromatic), 109.45 (ArC-2 and ArC-4), 108.55 (ArC-Coumarin), 105.79 (ArC-Coumarin), 50.44, 50.02, 48.18, 47.28, 46.32, 44.67, 44.55, 40.91, 37.78, 34.79, 31.96, 30.16, 28.74, 27.88, 27.69, 26.68, 24.76, 24.01, 22.99, 22.88, 21.41, 20.50, 20.27, 19.07, 14.30. Mass spectrum (ESI) m/z (relative intensity) 739 (M$^+$+H, 100). Exact mass (ESI) calculated for C$_{45}$H$_{49}$N$_2$O$_7$ (M$^+$+H), 739.4322; found 739.4314. LC/MS analysis (Waters MicroMass ZQ system) showed purity of 99.3% and retention time of 6.5 min for the title compound.

(6aR,10aR)-6,6-Dimethyl-3-(2-methyloctan-2-yl)-9-oxo-6a,7,8,9,10,10a-hexahydro-6H-benzo[c]chromen-1-yl 2,2-dimethyl-4-(11-oxo-2,3,6,7-tetrahydro-1H, 5H, 11H-pyrano[2,3-f]pyrido[3,2,1-ij]quinoline-10-carboxamido)butanoate (compound 9.10). The reaction was performed similar to as described for compound 9.9 using coumarin 343 (10 mg, 0.03 mmol), CDI (17 mg, 0.10 mmol), compound 9.6 (29 mg, 0.06 mmol) in dry DMF (1 ml) and gave 14 mg (78% yield) of compound 9.10 as a yellow solid. mp=132-133° C. IR (neat): 3728, 2931, 1747, 1706, 1618, 1588, 1510, 1444, 1366, 1309, 1175, 1110 cm$^{-1}$. $^1$H NMR (500 MHz, CDCl$_3$) δ 8.92 (t, J=4.5 Hz, 1H, NH), 8.59 (s, 1H, ArH-Coumarin), 7.00 (s, 1H, ArH-Coumarin), 6.70 (d, J=2.0 Hz, 1H, ArH), 6.52 (d, J=2.0 Hz, 1H, ArH), 3.61-3.45 (m, 2H, —CH$_2$—NH—C(O)—), 3.37-3.25 (overlapping multiples, 5H, 10eq-H, Coumarin —N—CH$_2$—), 2.88 (t, J=6.5 Hz, 2H, Coumarin —N—CH$_2$—CH$_2$—CH$_2$—), 2.80-2.68 (Overlapping multiples, 3H, 10a-H, Coumarin —N—CH$_2$—CH$_2$—CH$_2$—), 2.45-2.33 (m, 1H, 8eq-H), 2.45-2.20 (m, 5H, 8ax-H, 7eq-H, 10ax-H, —NH—CH$_2$—CH$_2$—), 2.10-1.93 (overlapping multiples, 5H, Coumarin N—CH$_2$—CH$_2$—CH$_2$—, 6a-H), 1.55-1.46 (m, 9H, 7ax-H, 2'-H, —C(O)O—C(CH$_3$)$_2$—), 1.42 (s, 3H, 6-Me), 1.26-1.17 (m, 12H, 3'-H, 4'-H, 5'-H, —C(CH$_3$)$_2$—, especially 1.22, s, —C(CH$_3$)$_2$—), 1.14 (s, 3H, 6-Me), 1.07 (sextet, J=7.5 Hz, 2H, 6'-H), 0.83 (t, J=6.5 Hz, 3H, 7'-H). $^{13}$C NMR (100 MHz, CDCl$_3$) δ 209.14 (>C=O), 175.50 (—C(O)—O), 163.33 (—C(O)—NH), 162.90 (—C(O)—O), 152.56 (ArC-1 or ArC-5), 150.94 (ArC-5 or ArC-1), 149.53 (tertiary aromatic), 147.86 (ArC-Coumarin), 126.88 (ArC-Coumarin), 119.42 (ArC-Coumarin), 114.14 (ArC-Coumarin), 112.89 (ArC-Coumarin), 112.24 (tertiary aromatic), 109.22 (ArC-2 and ArC-4), 108.20 (ArC-Coumarin), 105.63 (ArC-Coumarin), 50.13, 49.73, 47.88, 46.19, 44.23, 41.73, 40.63, 39.64, 37.47, 35.97, 34.78, 31.65, 30.24, 29.86, 28.52, 28.45, 27.56, 27.38, 26.67, 25.21, 24.97, 24.46, 22.57, 21.10, 20.16, 20.05, 18.75, 14.00. LC/MS analysis (Waters MicroMass ZQ system) showed purity of 98.7% and retention time of 6.7 min for the title compound.

(6aS,10aR)-6,6-Dimethyl-3-(2-methyloctan-2-yl)-9-oxo-6a,7,8,9,10,10a-hexahydro-6H-benzo[c]chromen-1-yl 2,2-dimethyl-5-(11-oxo-2,3,6,7-tetrahydro-1H, 5H, 11H-pyrano[2,3-f]pyrido[3,2,1-ij]quinoline-10-carboxamido)pentanoate (compound 9.11). The reaction was performed similar to as described for compound 9.9 using coumarin 343 (10 mg, 0.03 mmol), CDI (17 mg, 0.10 mmol), compound 9.7 (30 mg, 0.06 mmol) in dry DMF (1 ml) and gave 15 mg (80% yield) of compound 9.11 as a yellow solid. mp=130-131° C. IR (neat): 3747, 2930, 1693, 1617, 1587, 1505, 1476, 1366, 1308, 1174, 1109 cm$^{-1}$. $^1$H NMR (500 MHz, CDCl$_3$) δ 8.93 (t, J=4.5 Hz, 1H, NH), 8.60 (s, 1H, ArH-Coumarin), 7.00 (s, 1H, ArH-Coumarin), 6.68 (d, J=2.0 Hz, 1H, ArH), 6.42 (d, J=2.0 Hz, 1H, ArH), 3.54-3.42 (m, 2H, —CH$_2$—NH—C(O)—), 3.36-3.25 (overlapping multiples, 5H, 10eq-H, Coumarin —N—CH$_2$—), 2.88 (t, J=7.0 Hz, 2H, Coumarin —N—CH$_2$—CH$_2$—CH$_2$—), 2.77 (t, J=7.0 Hz, 2H, Coumarin —N—CH$_2$—CH$_2$—CH$_2$—), 2.70 (m as td, J=12.4 Hz, J=3.0 Hz, 1H, 10a-H), 2.59-2.53 (m, 1H, 8eq-H), 2.44-2.34 (m, 1H, 8ax-H), 2.24-2.10 (m, 2H, 10ax-H, 7eq-H), 2.10-1.92 (overlapping multiples, 5H, Coumarin —N—CH$_2$—CH$_2$—CH$_2$—, 6a-H), 1.85-1.65 (m, 4H, —NH—CH$_2$—CH$_2$—CH$_2$—), 1.54-1.47 (m, 6H, 7ax-H, 2'-H, especially 1.48, s, 6-Me), 1.39 (s, 3H, —C(O)O—C(CH$_3$)$_2$—), 1.35 (s, 3H, —C(O)O—C(CH$_3$)$_2$—), 1.24-1.14 (m, 12H, 3'-H, 4'-H, 5'-H, —C(CH$_3$)$_2$—, especially 1.22, s, —C(CH$_3$)$_2$—), 1.13 (s, 3H, 6-Me), 1.06 (sextet, J=7.5 Hz, 2H, 6'-H), 0.83 (t, J=6.5 Hz, 3H, 7'-H). $^{13}$C NMR (100 MHz, CDCl$_3$) δ 210.33 (>C=O), 176.60 (—C(O)—O), 163.75 (—C(O)—NH), 162.59 (—C(O)—O), 153.31 (ArC-1 or ArC-5), 150.79 (ArC-5 or ArC-1), 151.68 (tertiary aromatic), 148.75 (ArC-Coumarin), 127.66 (ArC-Coumarin), 119.81 (ArC-Coumarin), 114.79 (ArC-Coumarin), 113.20

(ArC-Coumarin), 112.50 (tertiary aromatic), 110.10 (ArC-2 and ArC-4), 109.05 (ArC-Coumarin), 106.23 (ArC-Coumarin), 50.97, 50.56, 48.70, 46.96, 45.08, 43.24, 41.49, 40.55, 38.66, 38.26, 35.65, 32.48, 30.69, 29.36, 29.25, 28.40, 28.22, 27.51, 26.00, 25.65, 25.28, 23.40, 21.94, 21.00, 20.89, 19.59, 14.83. Mass spectrum (ESI) m/z (relative intensity) 767 (M$^+$+H, 100). Exact mass (ESI) calculated for $C_{47}H_{63}N_2O_7$ (M$^+$+H), 767.4635; found 767.4636. LC/MS analysis (Waters MicroMass ZQ system) showed purity of 99.3% and retention time of 6.7 min for the title compound.

(6aS,10aR)-6,6-Dimethyl-3-(2-methyloctan-2-yl)-9-oxo-6a,7,8,9,10,10a-hexahydro-6H-benzo[c]chromen-1-yl 2,2-dimethyl-6-(11-oxo-2,3,6,7-tetrahydro-1H, 5H, 11H-pyrano[2,3-f]pyrido[3,2,1-ij]quinoline-10-carboxamido)hexanoate (compound 9.12). The reaction was performed similar to as described for compound 9.9 using coumarin 343 (10 mg, 0.03 mmol), CDI (17 mg, 0.10 mmol), compound 9.8 (31 mg, 0.06 mmol) in dry DMF (1 ml) and gave 14 mg (78% yield) of compound 9.12 as a yellow solid. mp=133-134° C. IR (neat): 3723, 2961, 1709, 1619, 1517, 1418, 1260, 1141 cm$^{-1}$. $^1$H NMR (500 MHz, CDCl$_3$) δ 8.87 (t, J=4.5 Hz, 1H, NH), 8.60 (s, 1H, ArH-Coumarin), 7.00 (s, 1H, ArH-Coumarin), 6.68 (d, J=2.0 Hz, 1H, ArH), 6.41 (d, J=2.0 Hz, 1H, ArH), 3.45 (q, J=7.0 Hz, 2H, —CH$_2$—NH—C(O)—), 3.36-3.25 (overlapping multiples, 5H, 10eq-H, Coumarin —N—CH$_2$—), 2.88 (t, J=6.0 Hz, 2H, Coumarin —N—CH$_2$—CH$_2$—CH$_2$—), 2.77 (t, J=6.0 Hz, 2H, Coumarin —N—CH$_2$—CH$_2$—CH$_2$—), 2.69 (m as td, J=12.0 Hz, J=3.5 Hz, 1H, 10a-H), 2.59-2.52 (m, 1H, 8eq-H), 2.44-2.36 (m, 1H, 8ax-H), 2.24-2.10 (m, 2H, 10ax-H, 7eq-H), 2.10-1.92 (overlapping multiples, 5H, Coumarin —N—CH$_2$—CH$_2$—CH$_2$—, 6a-H), 1.80-1.63 (m, 4H, —NH—CH$_2$—CH$_2$—CH$_2$—CH$_2$), 1.52-1.46 (m, 6H, 7ax-H, 2'-H, especially 1.47, s, 6-Me), 1.38 (s, 3H, —C(O)O—C(CH$_3$)$_2$—), 1.33 (s, 3H, —C(O)O—C(CH$_3$)$_2$—), 1.23-1.14 (m, 14H, 3'-H, 4'-H, 5'-H, —NH—CH$_2$—CH$_2$—CH$_2$—CH$_2$, —C(CH$_3$)$_2$—, especially 1.21, s, —C(CH$_3$)$_2$—), 1.13 (s, 3H, 6-Me), 1.06 (sextet, J=7.5 Hz, 2H, 6'-H), 0.83 (t, J=6.5 Hz, 3H, 7'-H). $^{13}$C NMR (100 MHz, CDCl$_3$) δ 209.17 (>C=O), 176.01 (—C(O)—O), 163.34 (—C(O)—NH), 162.92 (—C(O)—O), 153.88 (ArC-1 or ArC-5), 150.79 (ArC-5 or ArC-1), 149.58 (tertiary aromatic), 147.88 (ArC-Coumarin), 126.87 (ArC-Coumarin), 119.43 (ArC-Coumarin), 114.18 (ArC-Coumarin), 112.81 (ArC-Coumarin), 112.09 (tertiary aromatic), 109.25 (ArC-2 and ArC-4), 108.20 (ArC-Coumarin), 105.58 (ArC-Coumarin), 50.13, 49.72, 47.81, 46.09, 44.24, 42.56, 40.63, 40.17, 39.37, 37.40, 34.81, 31.63, 30.23, 29.99, 29.85, 28.52, 28.42, 27.56, 27.38, 26.66, 25.15, 24.71, 24.43, 22.56, 22.35, 21.10, 20.16, 20.05, 18.74, 13.99. Mass spectrum (ESI) m/z (relative intensity) 781 (M$^+$+H, 100). Exact mass (ESI) calculated for $C_{34}H_{51}N_2O_5S$ (M$^+$+H), 781.4792; found 781.4772. LC/MS analysis (Waters MicroMass ZQ system) showed purity of 98.5% and retention time of 6.6 min for the title compound.

(6aR,10aR)-6,6-Dimethyl-3-(2-methyloctan-2-yl)-9-oxo-6a,7,8,9,10,10a-hexahydro-6H-benzo[c]chromen-1-yl 3-(7-methoxy-2-oxo-2H-chromene-3-carboxamido)-2,2-dimethylpropanoate (compound 9.13). The reaction was performed similar to as described for compound 9.9 using 7-methoxycoumarin-3-carboxylic acid (10 mg, 0.04 mmol), CDI (22 mg, 0.13 mmol), compound 9.5 (38 mg, 0.08 mmol) in dry DMF (1 ml) and gave 14 mg (78% yield) of compound 9.13 as a white crystalline solid. mp=119-120° C. IR (neat): 3358, 2930, 1725, 1618, 1537, 1413, 1372, 1219, 1118, 1026 cm$^{-1}$. $^1$H NMR (500 MHz, CDCl$_3$) δ 9.11 (t, J=3.0 Hz, 1H, NH), 8.85 (s, 1H, ArH-Coumarin), 7.59 (d, J=9.0 Hz, 1H, ArH-Coumarin), 6.94 (dd, J=8.5 Hz, J=2.5 Hz, 1H, ArH-Coumarin), 6.85 (d, J=2.5 Hz, 1H, ArH-Coumarin), 6.71 (d, J=1.5 Hz, 1H, ArH), 6.52 (d, J=2.0 Hz, 1H, ArH), 3.91 (s, 3H, O—CH$_3$), 3.82 (dd, J=8.5 Hz, J=2.5 Hz, 1H, —NH—CH$_2$—), 3.72 (dd, J=8.5 Hz, J=2.5 Hz, 1H, —NH—CH$_2$—), 3.20 (ddd, J=15.0 Hz, J=3.5 Hz, J=2.0 Hz, 1H, 10eq-H), 2.80 (m as td, J=12.0 Hz, J=2.5 Hz, 1H, 10a-H), 2.49-2.43 (m, 1H, 8eq-H), 2.38-2.29 (m, 1H, 8ax-H), 2.20-2.09 (m, 2H, 7eq-H, 10ax-H), 1.99-1.90 (m as td, J=12.0 Hz, J=3.0 Hz, 1H, 6a-H), 1.55-1.47 (m, 12H, 7ax-H, 2'-H, —C(O)O—C(CH$_3$)$_2$—, 6-Me, especially 1.49, s, 6-Me), 1.24-1.15 (m, 15H, 3'-H, 4'-H, 5'-H, —C(CH$_3$)$_2$—, especially 1.23, s, —C(CH$_3$)$_2$—, and 1.19, s, 6-Me), 1.06 (sextet, J=7.5 Hz, 2H, 6'-H), 0.83 (t, J=6.5 Hz, 3H, 7'-H). $^{13}$C NMR (100 MHz, CDCl$_3$) δ 209.06 (>C=O), 174.71 (C(O)—O), 164.64 (—C(O)—NH—), 162.33 (—C(O)—O), 161.59 (ArC-Coumarin), 156.60 (ArC-Coumarin), 153.90 (ArC-Coumarin), 150.90 (ArC-1 or ArC-5), 149.29 (ArC-5 or ArC-1), 148.26 (tertiary aromatic), 130.85 (ArC-Coumarin), 114.82 (tertiary aromatic), 114.36 (ArC-Coumarin), 113.74 (ArC-Coumarin), 113.08 (ArC-Coumarin), 112.42 (ArC-2 or ArC-4), 112.00 (ArC-4 or ArC-2), 100.16 (ArC-Coumarin), 55.88, 47.86, 47.02, 45.97, 44.22, 40.63, 37.46, 34.57, 31.62, 30.23, 29.83, 29.58, 28.47, 28.42, 27.55, 26.47, 24.43, 23.82, 22.58, 22.55, 18.72, 13.98. Mass spectrum (ESI) m/z (relative intensity) 674 (M$^+$+H, 100). Exact mass (ESI) calculated for $C_{40}H_{50}NO_8$ (M$^+$+H), 674.3693; found 674.3685. LC/MS analysis (Waters MicroMass ZQ system) showed purity of 99.2% and retention time of 6.2 min for the title compound.

(6aR,10aR)-6,6-Dimethyl-3-(2-methyloctan-2-yl)-9-oxo-6a,7,8,9,10,10a-hexahydro-6H-benzo[c]chromen-1-yl 4-(6-methoxy-2-oxo-2H-chromene-3-carboxamido)-2,2-dimethylbutanoate (compound 9.14). The reaction was performed similar to as described for compound 9.9 using 7-methoxycoumarin-3-carboxylic acid (10 mg, 0.04 mmol), CDI (22 mg, 0.13 mmol), compound 9.6 (39 mg, 0.08 mmol) in dry DMF (1 ml) and gave 15 mg (80% yield) of compound 9.14 as a white crystalline solid. mp=118-119° C. IR (neat): 3363, 2930, 1740, 1619, 1539, 1413, 1372, 1223, 1142, 1114, 1027 cm$^{-1}$. $^1$H NMR (500 MHz, CDCl$_3$) δ 8.84 (t, J=5.0 Hz, 1H, NH), 8.82 (s, 1H, ArH-Coumarin), 7.58 (d, J=9.0 Hz, 1H, ArH-Coumarin), 6.94 (dd, J=8.5 Hz, J=2.5 Hz, 1H, ArH-Coumarin), 6.86 (d, J=2.5 Hz, 1H, ArH-Coumarin), 6.70 (d, J=2.0 Hz, 1H, ArH), 6.51 (d, J=2.0 Hz, 1H, ArH), 3.91 (s, 3H, O—CH$_3$), 3.62-3.48 (m, 2H, —NH—CH$_2$—), 3.30 (ddd, J=15.0 Hz, J=3.5 Hz, J=2.0 Hz, 1H, 10eq-H), 2.72 (m as td, J=11.0 Hz, J=3.0 Hz, 1H, 10a-H), 2.59-2.52 (m, 1H, 8eq-H), 2.45-2.32 (m, 1H, 8ax-H), 2.25-2.10 (m, 2H, 7eq-H, 10ax-H), 2.09-1.92 (multiplet overlapping, 3H, —NH—CH$_2$—CH$_2$—, 6a-H), 1.54-1.46 (m, 9H, 7ax-H, 2'-H, —C(O)O—C(CH$_3$)$_2$—), 1.44 (s, 3H, 6-Me), 1.24-1.11 (m, 15H, 3'-H, 4'-H, 5'-H, —C(CH$_3$)$_2$—, especially 1.23, s, —C(CH$_3$)$_2$—, and 1.14, s, 6-Me), 1.07 (sextet, J=7.5 Hz, 2H, 6'-H), 0.83 (t, J=6.5 Hz, 3H, 7'-H). $^{13}$C NMR (100 MHz, CDCl$_3$) δ 209.20 (>C=O), 175.38 (C(O)—O), 164.68 (—C(O)—NH—), 161.82 (—C(O)—O), 161.66 (ArC-Coumarin), 156.56 (ArC-Coumarin), 153.90 (ArC-Coumarin), 150.95 (ArC-1 or ArC-5), 149.48 (ArC-5 or ArC-1), 148.01 (tertiary aromatic), 130.79 (ArC-Coumarin), 114.88 (tertiary aromatic), 114.11 (ArC-Coumarin), 113.86 (ArC-Coumarin), 112.96 (ArC-2 or ArC-4), 112.37 (ArC-4 or ArC-2), 112.16 (ArC-Coumarin), 100.22 (ArC-Coumarin), 55.91, 47.89, 46.22, 44.22, 41.71, 40.66, 39.49, 37.47, 36.23, 34.84, 32.13, 31.83, 31.64, 30.24, 29.86, 29.60, 29.27, 28.53, 28.44, 27.56, 26.71, 26.31, 25.22, 25.02, 24.46, 23.33, 22.57, 18.75, 13.99. Mass spectrum (ESI) m/z (relative intensity) 688 (M++H, 100). Exact mass (ESI) calculated for $C_{41}H_{54}NO_8$ (M++H), 688.3849; found 688.3842. LC/MS analysis (Waters MicroMass ZQ system) showed purity of 99.5% and retention time of 6.3 min for the title compound.

(6aS,10aR)-6,6-Dimethyl-3-(2-methyloctan-2-yl)-9-oxo-6a,7,8,9,10,10a-hexahydro-6H-benzo[c]chromen-1-yl 5-(7-methoxy-2-oxo-2H-chromene-3-carboxamido)-2,2-dimethylpentanoate (compound 9.15). The reaction was performed similar to as described for compound 9.9 using 7-methoxycoumarin-3-carboxylic acid (10 mg, 0.04 mmol), CDI (22 mg, 0.13 mmol), compound 9.7 (40 mg, 0.08 mmol) in dry DMF (1 ml) and gave 14 mg (78% yield) of compound 9.15 as a white crystalline solid. mp=120-121° C. IR (neat): 3737, 2930, 1746, 1618, 1540, 1413, 1370, 1218, 1116, 1028 cm$^{-1}$. $^1$H NMR (500 MHz, CDCl$_3$) δ 8.85 (t, J=5.5 Hz, 1H, NH), 8.83 (s, 1H, ArH-Coumarin), 7.58 (d, J=9.0 Hz, 1H, ArH-Coumarin), 6.94 (dd, J=8.5 Hz, J=2.5 Hz, 1H, ArH-Coumarin), 6.86 (d, J=2.5 Hz, 1H, ArH-Coumarin), 6.69 (d, J=2.0 Hz, 1H, ArH), 6.41 (d, J=2.0 Hz, 1H, ArH), 3.91 (s, 3H, O—CH$_3$), 3.57-3.46 (m, 2H, —NH—CH$_2$—), 3.30 (ddd, J=15.0 Hz, J=3.5 Hz, J=2.0 Hz, 1H, 10eq-H), 2.70 (m as td, J=13.0 Hz, J=2.5 Hz, 1H, 10a-H), 2.59-2.53 (m, 1H, 8eq-H), 2.44-2.33 (m, 1H, 8ax-H), 2.27-2.10 (m, 2H, 7eq-H, 10ax-H), 2.01-1.93 (m as td, J=12.0 Hz, J=3.0 Hz, 1H, 6a-H), 1.84-1.66 (m, 4H, —NH—CH$_2$—CH$_2$—CH$_2$—), 1.55-1.46 (m, 6H, 7ax-H, 2'-H, especially 1.48, s, 6-Me), 1.39 (s, 3H, —C(O)O—C(CH$_3$)$_2$—), 1.36 (s, 3H, —C(O)O—C(CH$_3$)$_2$—), 1.23-1.15 (m, 12H, 3'-H, 4'-H, 5'-H, —C(CH$_3$)$_2$—, especially 1.22, s, —C(CH$_3$)$_2$—), 1.13 (s, 3H, 6-Me), 1.06 (sextet, J=7.5 Hz, 2H, 6'-H), 0.83 (t, J=6.5 Hz, 3H, 7'-H). $^{13}$C NMR (100 MHz, CDCl$_3$) δ 209.30 (>C=O), 175.81 (C(O)—O), 164.64 (—C(O)—NH—), 161.88 (—C(O)—O), 161.88 (ArC-Coumarin), 161.67 (ArC-Coumarin), 156.54 (ArC-Coumarin), 153.91 (ArC-Coumarin), 150.84 (ArC-1 or ArC-5), 149.55 (ArC-5 or ArC-1), 148.04 (tertiary aromatic), 130.78 (ArC-Coumarin), 114.19 (tertiary aromatic), 113.82 (ArC-Coumarin), 112.89 (ArC-Coumarin), 112.38 (ArC-2 or ArC-4), 112.04 (ArC-4 or ArC-2), 100.21 (ArC-Coumarin), 55.90, 47.87, 46.15, 44.23, 42.39, 40.67, 39.94, 37.70, 37.42, 34.86, 31.63, 30.24, 29.84, 28.52, 28.41, 27.56, 26.71, 25.12, 24.88, 24.44, 22.56, 18.74, 13.99. LC/MS analysis (Waters MicroMass ZQ system) showed purity of 99.0% and retention time of 6.4 min for the title compound.

(6aS,10aR)-6,6-Dimethyl-3-(2-methyloctan-2-yl)-9-oxo-6a,7,8,9,10,10a-hexahydro-6H-benzo[c]chromen-1-yl 6-(7-methoxy-2-oxo-2H-chromene-3-carboxamido)-2,2-dimethylhexanoate (compound 9.16). The reaction was performed similar to as described for compound 9.9 using 7-methoxycoumarin-3-carboxylic acid (10 mg, 0.04 mmol), CDI (22 mg, 0.13 mmol), compound 9.8 (41 mg, 0.08 mmol) in dry DMF (1 ml) and gave 16 mg (81% yield) of compound 9.16 as a white crystalline solid. mp=121-122° C. IR (neat): 3352, 2927, 1731, 1619, 1540, 1463, 1372, 1224, 1141, 1115, 1026 cm$^{-1}$. $^1$H NMR (500 MHz, CDCl$_3$) δ 8.83 (s, 1H, ArH-Coumarin), 8.78 (t, J=5.5 Hz, 1H, NH), 7.59 (d, J=9.0 Hz, 1H, ArH-Coumarin), 6.94 (dd, J=8.5 Hz, J=2.5 Hz, 1H, ArH-Coumarin), 6.86 (d, J=2.5 Hz, 1H, ArH-Coumarin), 6.69 (d, J=2.0 Hz, 1H, ArH), 6.40 (d, J=2.0 Hz, 1H, ArH), 3.91 (s, 3H, O—CH$_3$), 3.51-3.44 (m, 2H, —NH—CH$_2$—), 3.30 (ddd, J=15.0 Hz, J=3.5 Hz, J=2.0 Hz, 1H, 10eq-H), 2.69 (m as td, J=14.0 Hz, J=3.5 Hz, 1H, 10a-H), 2.59-2.52 (m, 1H, 8eq-H), 2.45-2.35 (m, 1H, 8ax-H), 2.22-2.10 (m, 2H, 7eq-H, 10ax-H), 2.01-1.93 (m as td, J=12.0 Hz, J=3.0 Hz, 1H, 6a-H), 1.82-1.66 (m, 4H, —NH—CH$_2$—CH$_2$—CH$_2$—CH$_2$—), 1.54-1.44 (m, 8H, 7ax-H, 2'-H, —NH—CH$_2$—CH$_2$—CH$_2$—, especially 1.48, s, 6-Me), 1.38 (s, 3H, —C(O)O—C(CH$_3$)$_2$—), 1.34 (s, 3H, —C(O)O—C(CH$_3$)$_2$—), 1.24-1.11 (m, 12H, 3'-H, 4'-H, 5'-H, —C(CH$_3$)$_2$—, especially 1.21, s, —C(CH$_3$)$_2$—), 1.13 (s, 3H, 6-Me), 1.07 (sextet, J=7.5 Hz, 2H, 6'-H), 0.83 (t, J=6.5 Hz, 3H, 7'-H). $^{13}$C NMR (100 MHz, CDCl$_3$) δ 209.18 (>C=O), 176.23 (C(O)—O), 164.64 (—C(O)—NH—), 161.82 (—C(O)—O), 156.52 (ArC-Coumarin), 153.91 (ArC-Coumarin), 150.79 (ArC-1 or ArC-5), 149.56 (ArC-5 or ArC-1), 148.01 (tertiary aromatic), 130.78 (ArC-Coumarin), 114.91 (tertiary aromatic), 114.16 (ArC-Coumarin), 113.83 (ArC-Coumarin), 112.85 (ArC-2 or ArC-4), 112.04 (ArC-4 or ArC-2), 100.21 (ArC-Coumarin), 55.90, 47.81, 46.09, 44.23, 42.56, 40.64, 40.09, 39.59, 37.41, 34.84, 31.63, 29.85, 28.52, 28.41, 27.56, 26.70, 25.14, 24.75, 24.43, 22.56, 22.34, 18.74, 13.98. LC/MS analysis (Waters MicroMass ZQ system) showed purity of 99.6% and retention time of 6.2 min for the title compound.

H. 9-Keto-Hexahydrocannabinols Carrying Polar Moieties.

9-Keto-hexahydrocannabinols 10.1-10.14 (shown in Table 4) were synthesized by methods depicted in Scheme 10.

Scheme 10

Reagents and conditions: (a) EDCI, DMAP, R-OH, CH$_2$Cl$_2$, 0° C. to rt, 24 h, 58-91%; (d) TFA, CH$_2$Cl$_2$, rt, 1 h, 90-95%.

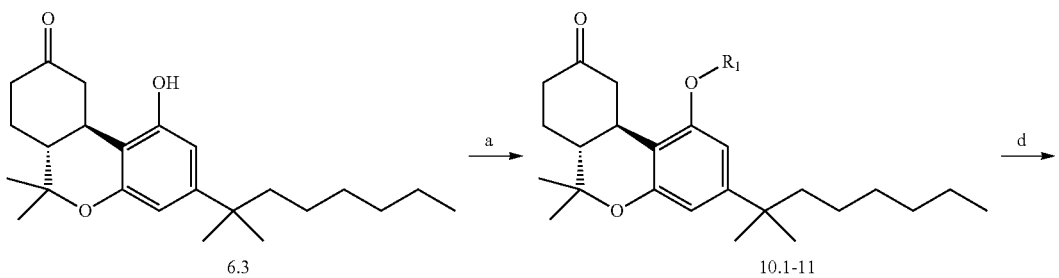

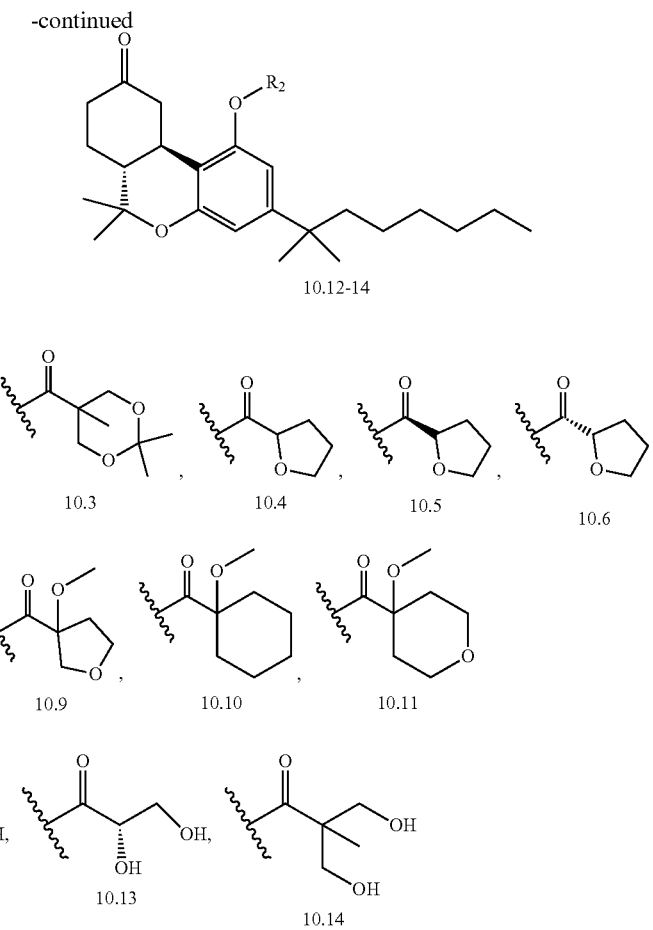

(6aR,10aR)-6,6-Dimethyl-3-(2-methyloctan-2-yl)-9-oxo-6a,7,8,9,10,10a-hexahydro-6H-benzo[c]chromen-1-yl (R)-2,2-dimethyl-1,3-dioxolane-4-carboxylate (compound 10.1). The reaction was performed using the standard procedure reported above using DMAP (100 mg, 0.8 mmol), EDCI (108 mg, 0.56 mmol), dry $CH_2Cl_2$ (2 ml), (R)-2,2-dimethyl-1,3-dioxolane-4-carboxylic acid (60 mg, 0.40 mmol) and compound 6.3 (50 mg, 0.14 mmol). The residue was chromatographed on silica gel (30% AcOEt in hexane) to give compound 10.1 as a colorless oil (61 mg, 91% yield). IR (neat): 2930, 1779, 1712, 1623, 1563, 1413, 1257, 1155, 1068 $cm^{-1}$. $^1H$ NMR (500 MHz, $CDCl_3$) δ 6.72 (d, J=1.5 Hz, 1H, ArH), 6.50 (d, J=1.4 Hz, 1H, ArH), 4.86 (dd, J=5.5 Hz, J=7.0 Hz, 1H, 3"-H), 4.21 (dd, J=5.5 Hz, J=7.0 Hz, 1H, 4"-H), 4.34 (dd, J=5.5 Hz, J=7.0 Hz, 1H, 4"-H), 3.23 (ddd, J=15.0 Hz, J=3.5 Hz, J=2.0 Hz, 1H, 10eq-H), 2.74 (m as td, J=12.4 Hz, J=3.4 Hz, 1H, 10a-H), 2.59-2.53 (m, 1H, 8eq-H), 2.44-2.35 (m, 1H, 8ax-H), 2.25-2.10 (m, 2H, 10ax-H, 7eq-H), 2.00-1.91 (m as td, J=12 Hz, J=3 Hz, 1H, 6a-H), 1.51-1.45 (m, 12H, 7ax-H, 2'-H, 6-Me, 5"-H especially 1.48, s, 6-Me, and 1.46, s, 5"-H), 1.23-1.16 (m, 12H, 3'-H, 4'-H, 5'-H, —$C(CH_3)_2$—, especially 1.22, s, —$C(CH_3)_2$—), 1.12 (s, 3H, 6-Me), 1.06 (sextet, J=7.5 Hz, 2H, 6'-H), 0.84 (t, J=6.5 Hz, 3H, 7'-H). $^{13}C$ NMR (100 MHz, $CDCl_3$) δ 209.2 (>C=O), 169.1 (—C(O)—O—), 154.1 (ArC-1 or ArC-5), 151.1 (ArC-5 or ArC-1), 148.7 (tertiary aromatic), 113.8 (tertiary aromatic), 113.5 (ArC-2 or ArC-4), 111.9 (ArC-4 or ArC-2), 111.8 (O—C—O), 74.1 (—CH—O—), 67.1 ($CH_2$—O—), 58.4, 47.5, 45.9, 44.3, 40.5, 37.5, 34.6, 31.7, 29.9, 28.5, 27.6, 26.4, 25.9, 25.4, 24.5, 22.6, 18.8, 14.0. Mass spectrum (ESI) m/z (relative intensity) 501 ($M^++H$, 100). Exact mass (ESI) calculated for $C_{30}H_{45}O_6$ ($M^++H$), 501.3216; found 501.3206. LC/MS analysis (Waters MicroMass ZQ system) showed purity of 99% and retention time of 6.0 min for the title compound.

(6aR,10aR)-6,6-Dimethyl-3-(2-methyloctan-2-yl)-9-oxo-6a,7,8,9,10,10a-hexahydro-6H-benzo[c]chromen-1-yl (S)-2,2-dimethyl-1,3-dioxolane-4-carboxylate (compound 10.2). The reaction was performed using the standard procedure reported above using DMAP (148 mg, 1.20 mmol), EDCI (158 mg, 0.80 mmol), dry $CH_2Cl_2$ (3 ml), (S)-2,2-dimethyl-1,3-dioxolane-4-carboxylic acid (88 mg, 0.60 mmol) and compound 6.3 (75 mg, 0.20 mmol). The residue was chromatographed on silica gel (30% AcOEt in hexane) to give compound 10.2 as a colorless oil (100 mg, 85% yield). LC/MS analysis (Waters MicroMass ZQ system) showed purity of 98.5% and retention time of 6.0 min for the title compound.

(6aR,10aR)-6,6-Dimethyl-3-(2-methyloctan-2-yl)-9-oxo-6a,7,8,9,10,10a-hexahydro-6H-benzo[c]chromen-1-yl 2,2,5-trimethyl-1,3-dioxane-5-carboxylate (compound 10.3). The reaction was performed using the standard procedure reported above using DMAP (98 mg, 0.80 mmol), EDCI (103 mg, 0.53 mmol), dry $CH_2Cl_2$ (2 ml), 2,2,5-trimethyl-1,3-dioxane-5-carboxylic acid (70 mg, 0.40 mmol) and compound 6.3 (50 mg, 0.13 mmol). The residue was chromatographed on silica gel (20% AcOEt in hexane) to give compound 10.3 as a colorless oil (70 mg, 80% yield). IR (neat): 2930, 1750, 1712, 1623, 1562, 1413, 1271, 1197, 1100 cm$^{-1}$. $^{1}$H NMR (500 MHz, CDCl$_3$) δ 6.73 (d, J=1.5 Hz, 1H, ArH), 6.49 (d, J=1.4 Hz, 1H, ArH), 4.37-4.33 (m as dd, J=12.0 Hz, J=7.0 Hz, 2H, —CH$_2$—O—), 3.83-3.77 (m as dd, J=12.0 Hz, J=7.0 Hz, 2H, —CH$_2$—O—) 3.28 (ddd, J=15.0 Hz, J=3.5 Hz, J=2.0 Hz, 1H, 10eq-H), 2.76 (m as td, J=12.4 Hz, J=3.4 Hz, 1H, 10a-H), 2.60-2.54 (m, 1H, 8eq-H), 2.45-2.38 (m, 1H, 8ax-H), 2.28-2.13 (m, 2H, 10ax-H, 7eq-H), 2.02-1.94 (m as td, J=12 Hz, J=3 Hz, 1H, 6a-H), 1.56-1.49 (m, 9H, 7ax-H, 2'-H, —O—C(CH$_3$)$_2$—O—, especially 1.50, s, —O—C(CH$_3$)$_2$—O—), 1.38 (s, 3H, C(CH$_3$)), 1.46 (s, 3H, 6-Me), 1.24-1.15 (m, 12H, 3'-H, 4'-H, 5'-H, —C(CH$_3$)$_2$—, especially 1.26, s, —C(CH$_3$)$_2$—), 1.15 (s, 3H, 6-Me), 1.08 (sextet, J=7.5 Hz, 2H, 6'-H), 0.86 (t, J=6.5 Hz, 3H, 7'-H). $^{13}$C NMR (100 MHz, CDCl$_3$) δ 209.3 (>C=O), 172.6 (—C(O)—O—), 154.0 (ArC-1 or ArC-5), 151.0 (ArC-5 or ArC-1), 149.3 (tertiary aromatic), 114.2 (tertiary aromatic), 113.2 (ArC-2 or ArC-4), 112.2 (ArC-4 or ArC-2), 98.2 (O—C—O), 66.2 (—CH—O—), 66.1 (CH—O—), 47.7, 46.2, 44.3, 42.4, 40.5, 37.5, 34.7, 31.7, 29.9, 28.6, 28.4, 27.6, 26.6, 25.5, 24.5, 22.6, 22.0, 18.7, 18.2, 14.0. Mass spectrum (ESI) m/z (relative intensity) 529 (M$^+$+H, 100). Exact mass (ESI) calculated for C$_{32}$H$_{49}$O$_6$ (M$^+$+H), 529.3529; found 529.3524. LC/MS analysis (Waters Micro-Mass ZQ system) showed purity of 99.2% and retention time of 6.1 min for the title compound.

(6aR,10aR)-6,6-Dimethyl-3-(2-methyloctan-2-yl)-9-oxo-6a,7,8,9,10,10a-hexahydro-6H-benzo[c]chromen-1-yl tetrahydrofuran-2-carboxylate (compound 10.4). The reaction was performed using the standard procedure reported above using DMAP (37 mg, 0.30 mmol), EDCI (38 mg, 0.20 mmol), dry CH$_2$Cl$_2$ (0.8 ml), tetrahydro-2-furoic acid (18 mg, 0.15 mmol) and compound 6.3 (25 mg, 0.05 mmol). The residue was chromatographed on silica gel (20% AcOEt in hexane) to give compound 10.4 as a colorless oil (25 mg, 80% yield). LC/MS analysis (Waters MicroMass ZQ system) showed purity of 98.7% and retention time of 5.9 min for the title compound.

(6aR,10aR)-6,6-Dimethyl-3-(2-methyloctan-2-yl)-9-oxo-6a,7,8,9,10,10a-hexahydro-6H-benzo[c]chromen-1-yl (R)-tetrahydrofuran-2-carboxylate (compound 10.5). The reaction was performed using the standard procedure reported above using DMAP (37 mg, 0.30 mmol), EDCI (38 mg, 0.20 mmol), dry CH$_2$Cl$_2$ (0.8 ml), (R)-tetrahydro-2-furoic acid (18 mg, 0.15 mmol) and compound 6.3 (25 mg, 0.05 mmol). The residue was chromatographed on silica gel (20% AcOEt in hexane) to give compound 10.5 as a colorless oil (22 mg, 78% yield). LC/MS analysis (Waters MicroMass ZQ system) showed purity of 99.2% and retention time of 5.9 min for the title compound. IR (neat): 2928, 1754, 1712, 1623, 1562, 1413, 1256, 1183, 1030 cm$^{-1}$. $^{1}$H NMR (500 MHz, CDCl$_3$) δ 6.71 (d, J=1.5 Hz, 1H, ArH), 6.52 (d, J=1.4 Hz, 1H, ArH), 4.20-4.15 (dd, J=2.5 Hz, J=9.0 Hz, 1H, furan ring), 4.16-4.10 (m, 1H, furan ring), 4.04-3.98 (m, 1H, furan ring), 3.29 (ddd, J=15.0 Hz, J=3.5 Hz, J=2.0 Hz, 1H, 10eq-H), 2.73 (m as td, J=12.4 Hz, J=3.4 Hz, 1H, 10a-H), 2.58-2.52 (m, 1H, 8eq-H), 2.46-2.36 (m, 1H, 8ax-H), 2.27-1.93 (m, 7H, 10ax-H, 7eq-H, 6a-H, furan ring), 1.52-1.47 (m, 6H, 7ax-H, 2'-H, 6-Me, especially 1.48, s, 6-Me), 1.25-1.15 (m, 12H, 3'-H, 4'-H, 5'-H, —C(CH$_3$)$_2$—, especially 1.22, s, —C(CH$_3$)$_2$—), 1.12 (s, 3H, 6-Me), 1.05 (sextet, J=7.5 Hz, 2H, 6'-H), 0.84 (t, J=6.5 Hz, 3H, 7'-H). $^{13}$C NMR (100 MHz, CDCl$_3$) δ 209.5 (>C=O), 171.3 (—C(O)—O—), 154.0 (ArC-1 or ArC-5), 151.0 (ArC-5 or ArC-1), 148.9 (tertiary aromatic), 113.6 (tertiary aromatic), 113.2 (ArC-2 or ArC-4), 112.4 (ArC-4 or ArC-2), 69.6, 47.6, 45.9, 44.3, 40.7, 37.5, 34.9, 31.7, 30.1, 29.9, 28.5, 27.6, 26.7, 25.6, 24.5, 22.6, 18.8, 14.0. Mass spectrum (ESI) m/z (relative intensity) 471 (M$^+$+H, 100). Exact mass (ESI) calculated for C$_{29}$H$_{43}$O$_5$ (M$^+$+H), 471.3110; found 471.3102. LC/MS analysis (Waters MicroMass ZQ system) showed purity of 99.0% and retention time of 5.9 min for the title compound.

(6aR,10aR)-6,6-Dimethyl-3-(2-methyloctan-2-yl)-9-oxo-6a,7,8,9,10,10a-hexahydro-6H-benzo[c]chromen-1-yl (S)-tetrahydrofuran-2-carboxylate (compound 10.6). The reaction was performed using the standard procedure reported above using DMAP (37 mg, 0.30 mmol), EDCI (38 mg, 0.20 mmol), dry CH$_2$Cl$_2$ (0.8 ml), (S)-tetrahydro-2-furoic acid (18 mg, 0.15 mmol) and compound 6.3 (25 mg, 0.05 mmol). The residue was chromatographed on silica gel (20% AcOEt in hexane) to give compound 10.6 as a colorless oil (23 mg, 79% yield). LC/MS analysis (Waters MicroMass ZQ system) showed purity of 98.9% and retention time of 5.9 min for the title compound.

(6aR,10aR)-6,6-Dimethyl-3-(2-methyloctan-2-yl)-9-oxo-6a,7,8,9,10,10a-hexahydro-6H-benzo[c]chromen-1-yl cyclopentanecarboxylate (compound 10.7). The reaction was performed using the standard procedure reported above using DMAP (37 mg, 0.30 mmol), EDCI (38 mg, 0.20 mmol), dry CH$_2$Cl$_2$ (0.8 ml), cyclopentanecarboxylic acid (17 mg, 0.15 mmol) and compound 6.3 (25 mg, 0.05 mmol). The residue was chromatographed on silica gel (20% AcOEt in hexane) to give compound 10.7 as a colorless oil (25 mg, 78% yield). IR (neat): 2929, 1752, 1713, 1622, 1563, 1413, 1257, 1182, 1086 cm$^{-1}$. $^{1}$H NMR (500 MHz, CDCl$_3$) δ 6.69 (d, J=1.5 Hz, 1H, ArH), 6.48 (d, J=1.4 Hz, 1H, ArH), 3.33 (ddd, J=15.0 Hz, J=3.5 Hz, J=2.0 Hz, 1H, 10eq-H), 2.99 (q, J=8.0 Hz, 1H, cyclopentane ring) 2.70 (m as td, J=12.4 Hz, J=3.4 Hz, 1H, 10a-H), 2.58-2.52 (m, 1H, 8eq-H), 2.45-2.36 (m, 1H, 8ax-H), 2.25-2.03 (m, 4H, 10ax-H, 7eq-H, cyclopentane ring), 1.99-1.85 (m, 3H, 6a-H, cyclopentane ring), 1.83-1.75 (m, 2H, cyclopentane ring), 1.71-1.62 (m, 2H, cyclopentane ring), 1.53-1.46 (m, 6H, 7ax-H, 2'-H, 6-Me, especially 1.48, s, 6-Me), 1.24-1.15 (m, 12H, 3'-H, 4'-H, 5'-H, —C(CH$_3$)$_2$—, especially 1.22, s, —C(CH$_3$)$_2$—), 1.12 (s, 3H, 6-Me), 1.07 (sextet, J=7.5 Hz, 2H, 6'-H), 0.84 (t, J=6.5 Hz, 3H, 7'-H). $^{13}$C NMR (100 MHz, CDCl$_3$) δ 209.5 (>C=O), 174.7 (—C(O)—O—), 154.0 (ArC-1 or ArC-5), 150.9 (ArC-5 or ArC-1), 149.4 (tertiary aromatic), 113.9 (tertiary aromatic), 112.9 (ArC-2 or ArC-4), 112.3 (ArC-4 or ArC-2), 47.6, 45.9, 44.3, 44.0, 40.7, 37.5, 34.9, 31.7, 30.1, 30.0, 29.9, 28.5, 27.6, 26.7, 25.9, 25.8, 24.5, 22.6, 18.8, 14.0. Mass spectrum (ESI) m/z (relative intensity) 469 (M$^+$+H, 100). Exact mass (ESI) calculated for C$_{30}$H$_{45}$O$_4$ (M$^+$+H), 469.3318; found 469.3310. LC/MS analysis (Waters MicroMass ZQ system) showed purity of 99.4% and retention time of 6.4 min for the title compound.

(6aR,10aR)-6,6-Dimethyl-3-(2-methyloctan-2-yl)-9-oxo-6a,7,8,9,10,10a-hexahydro-6H-benzo[c]chromen-1-yl 1-methoxycyclopentane-1-carboxylate (compound 10.8). The reaction was performed using the standard procedure reported above using DMAP (41 mg, 0.34 mmol), EDCI (43 mg, 0.28 mmol), dry CH$_2$Cl$_2$ (1 ml), 1-methoxycyclopentane-1-carboxylic acid (41 mg, 0.28 mmol) and compound 6.3 (25 mg, 0.05 mmol). The residue was chromatographed on silica gel (30% AcOEt in hexane) to give compound 10.8 as a colorless oil (20 mg, 60% yield). IR (neat): 2929, 1749, 1712, 1622, 1561, 1412, 1277, 1199, 1026 cm$^{-1}$. $^{1}$H NMR (500 MHz, CDCl3) δ 6.71 (d, J=1.5 Hz, 1H, ArH), 6.47 (d, J=1.4 Hz, 1H, ArH), 3.37 (s, 3H, O—CH$_3$), 3.33 (ddd, J=15.0 Hz, J=3.5 Hz, J=2.0 Hz, 1H, 10eq-H), 2.71 (m as td, J=12.4 Hz, J=3.4 Hz, 1H, 10a-H), 2.57-2.51 (m, 1H, 8eq-H), 2.44-2.36 (m, 1H, 8ax-H), 2.24-2.07 (m, 6H, 10ax-H, 7eq-H, cyclopentane ring), 2.00-1.94 (m as td, J=12 Hz, J=3 Hz, 1H, 6a-H), 1.88-1.82 (m, 4H, cyclohexane ring), 1.52-1.47 (m, 6H, 7ax-H, 2'-H, 6-Me, especially 1.48, s, 6-Me), 1.25-1.16 (m, 12H, 3'-H, 4'-H, 5'-H, —C(CH$_3$)$_2$—, especially 1.22, s, —C(CH$_3$)$_2$—), 1.13 (s, 3H, 6-Me), 1.06 (sextet, J=7.5 Hz, 2H, 6'-H), 0.84 (t, J=6.5 Hz, 3H, 7'-H). $^{13}$C NMR (100 MHz, CDCl$_3$) δ 209.2 (>C=O), 172.7 (—C(O)—O—), 154.1 (ArC-1 or ArC-5), 151.0 (ArC-5 or ArC-1), 149.3 (tertiary aromatic), 114.0 (tertiary aromatic), 113.1 (ArC-2 or ArC-4), 112.0 (ArC-4 or ArC-2), 88.6, 52.9, 47.7, 45.9, 44.3, 40.7, 37.5, 36.0, 35.0, 31.7, 29.9, 29.7, 28.6, 28.5, 27.6, 26.8, 24.5, 24.1, 24.0, 22.6, 18.8, 14.0. Mass spectrum (ESI) m/z (relative intensity) 499 (M$^+$+H, 100). Exact mass (ESI) calculated for C$_{31}$H$_{47}$O$_5$ (M$^+$+H), 499.3423; found 499.3421. LC/MS analysis (Waters MicroMass ZQ system) showed purity of 98.5% and retention time of 6.2 min for the title compound.

(6aR,10aR)-6,6-Dimethyl-3-(2-methyloctan-2-yl)-9-oxo-6a,7,8,9,10,10a-hexahydro-6H-benzo[c]chromen-1-yl 3-methoxytetrahydrofuran-3-carboxylate (compound 10.9). The reaction was performed using the standard procedure reported above using DMAP (41 mg, 0.34 mmol), EDCI (43 mg, 0.28 mmol), dry CH$_2$Cl$_2$ (1 ml), 3-methoxytetrahydrofuran-3-carboxylic acid (42 mg, 0.28 mmol) and compound 6.3 (25 mg, 0.05 mmol). The residue was chromatographed on silica gel (30% AcOEt in hexane) to give compound 10.9 as a colorless oil (18 mg, 58% yield). IR (neat): 2929, 1750, 1713, 1622, 1562, 1413, 1227, 1137, 1030 cm$^{-1}$. $^1$H NMR (500 MHz, CDCl$_3$) δ 6.73 (d, J=1.5 Hz, 1H, ArH), 6.48 (d, J=1.4 Hz, 1H, ArH), 4.20-4.15 (m, 2H, furan ring), 4.11-4.05 (m, 2H, furan ring), 3.46 (s, 3H, O—CH$_3$), 3.27 (ddd, J=15.0 Hz, J=3.5 Hz, J=2.0 Hz, 1H, 10eq-H), 2.69 (m as td, J=12.4 Hz, J=3.4 Hz, 1H, 10a-H), 2.60-2.38 (m, 4H, 8eq-H, 8ax-H, furan ring), 2.27-2.14 (m, 4H, 10ax-H, 7eq-H), 2.01-1.94 (m as td, J=12 Hz, J=3 Hz, 1H, 6a-H), 1.54-1.48 (m, 6H, 7ax-H, 2'-H, 6-Me, especially 1.49, s, 6-Me), 1.25-1.17 (m, 12H, 3'-H, 4'-H, 5'-H, —C(CH$_3$)$_2$—, especially 1.22, s, —C(CH$_3$)$_2$—), 1.13 (s, 3H, 6-Me), 1.06 (sextet, J=7.5 Hz, 2H, 6'-H), 0.84 (t, J=6.5 Hz, 3H, 7'-H). $^{13}$C NMR (100 MHz, CDCl$_3$) δ 209.1 (>C=O), 170.3 (—C(O)—O—), 154.2 (ArC-1 or ArC-5), 151.1 (ArC-5 or ArC-1), 149.0 (tertiary aromatic), 113.8 (tertiary aromatic), 113.5 (ArC-2 or ArC-4), 111.8 (ArC-4 or ArC-2), 88.0, 68.2, 53.7, 53.6, 47.7, 45.9, 44.3, 40.7, 37.5, 36.1, 35.0, 31.7, 29.9, 28.5, 28.5, 27.6, 26.8, 24.5, 22.6, 18.8, 14.0. Mass spectrum (ESI) m/z (relative intensity) 501 (M$^+$+H, 100). Exact mass (ESI) calculated for C$_{30}$H$_{45}$O$_6$ (M$^+$+H), 501.3216; found 501.3211. LC/MS analysis (Waters MicroMass ZQ system) showed purity of 98.9% and retention time of 5.9 min for the title compound.

(6aR,10aR)-6,6-Dimethyl-3-(2-methyloctan-2-yl)-9-oxo-6a,7,8,9,10,10a-hexahydro-6H-benzo[c]chromen-1-yl 1-methoxycyclohexane-1-carboxylate (compound 10.10). The reaction was performed using the standard procedure reported above using DMAP (50 mg, 0.40 mmol), EDCI (54 mg, 0.28 mmol), dry CH$_2$Cl$_2$ (1 ml), 1-methoxycyclohexane-1-carboxylic acid (45 mg, 0.28 mmol) and compound 6.3 (25 mg, 0.05 mmol). The residue was chromatographed on silica gel (30% AcOEt in hexane) to give compound 10.10 as a colorless oil (25 mg, 73% yield). IR (neat): 2930, 1748, 1713, 1622, 1562, 1412, 1261, 1120, 1007 cm$^{-1}$. $^1$H NMR (500 MHz, CDCl3) δ 6.70 (d, J=1.5 Hz, 1H, ArH), 6.44 (d, J=1.4 Hz, 1H, ArH), 3.37 (s, 3H, O—CH$_3$), 3.34 (ddd, J=15.0 Hz, J=3.5 Hz, J=2.0 Hz, 1H, 10eq-H), 2.71 (m as td, J=12.4 Hz, J=3.4 Hz, 1H, 10a-H), 2.57-2.51 (m, 1H, 8eq-H), 2.44-2.35 (m, 1H, 8ax-H), 2.24-2.07 (m, 4H, 10ax-H, 7eq-H, cyclohexane ring), 1.99-1.86 (m, 4H, 6a-H, cyclohexane ring), 1.70-1.60 (m, 6H, cyclohexane ring), 1.52-1.47 (m, 6H, 7ax-H, 2'-H, 6-Me, especially 1.48, s, 6-Me), 1.25-1.16 (m, 12H, 3'-H, 4'-H, 5'-H, —C(CH$_3$)$_2$—, especially 1.22, s, —C(CH$_3$)$_2$—), 1.13 (s, 3H, 6-Me), 1.06 (sextet, J=7.5 Hz, 2H, 6'-H), 0.84 (t, J=6.5 Hz, 3H, 7'-H). $^{13}$C NMR (100 MHz, CDCl$_3$) δ 209.2 (>C=O), 172.6 (—C(O)—O—), 154.0 (ArC-1 or ArC-5), 150.9 (ArC-5 or ArC-1), 149.4 (tertiary aromatic), 114.1 (tertiary aromatic), 113.1 (ArC-2 or ArC-4), 112.0 (ArC-4 or ArC-2), 79.5, 51.9, 47.7, 45.9, 44.2, 40.7, 37.5, 34.9, 32.0, 31.7, 31.3, 29.9, 28.6, 28.5, 27.6, 26.7, 25.2, 24.5, 22.6, 21.3, 21.2, 18.8, 14.0. Mass spectrum (ESI) m/z (relative intensity) 513 (M$^+$+H, 100). Exact mass (ESI) calculated for C$_{32}$H$_{49}$O$_5$ (M$^+$+H), 513.3580; found 513.3577. LC/MS analysis (Waters MicroMass ZQ system) showed purity of 99.5% and retention time of 6.4 min for the title compound.

(6aR,10aR)-6,6-Dimethyl-3-(2-methyloctan-2-yl)-9-oxo-6a,7,8,9,10,10a-hexahydro-6H-benzo[c]chromen-1-yl 4-methoxytetrahydro-2H-pyran-4-carboxylate (compound 10.11): The reaction was performed using the standard procedure reported above using DMAP (50 mg, 0.40 mmol), EDCI (54 mg, 0.28 mmol), dry CH$_2$Cl$_2$ (1 ml), 4-methoxytetrahydropyran-4-carboxylic acid (47 mg, 0.28 mmol) and compound 6.3 (25 mg, 0.05 mmol). The residue was chromatographed on silica gel (30% AcOEt in hexane) to give compound 10.11 as a colorless oil (22 mg, 70% yield). $^1$H NMR (500 MHz, CDCl$_3$) δ 6.72 (d, J=1.5 Hz, 1H, ArH), 6.44 (d, J=1.4 Hz, 1H, ArH), 3.84-3.79 (m, 4H, pyran ring), 3.40 (s, 3H, O—CH$_3$), 3.30 (ddd, J=15.0 Hz, J=3.5 Hz, J=2.0 Hz, 1H, 10eq-H), 2.69 (m as td, J=12.4 Hz, J=3.4 Hz, 1H, 10a-H), 2.57-2.51 (m, 1H, 8eq-H), 2.45-2.36 (m, 1H, 8ax-H), 2.28-2.12 (m, 4H, 10ax-H, 7eq-H, pyran ring), 2.09-2.01 (m, 2H, pyran ring), 2.00-1.94 (m as td, J=12 Hz, J=3 Hz, 1H, 6a-H), 1.52-1.48 (m, 6H, 7ax-H, 2'-H, 6-Me, especially 1.49, s, 6-Me), 1.26-1.17 (m, 12H, 3'-H, 4'-H, 5'-H, —C(CH$_3$)$_2$—, especially 1.22, s, —C(CH$_3$)$_2$—), 1.14 (s, 3H, 6-Me), 1.06 (sextet, J=7.5 Hz, 2H, 6'-H), 0.84 (t, J=6.5 Hz, 3H, 7'-H). $^{13}$C NMR (100 MHz, CDCl$_3$) δ 209.1 (>C=O), 171.2 (—C(O)—O—), 154.1 (ArC-1 or ArC-5), 151.1 (ArC-5 or ArC-1), 149.2 (tertiary aromatic), 114.0 (tertiary aromatic), 113.4 (ArC-2 or ArC-4), 111.8 (ArC-4 or ArC-2), 63.3, 52.1, 47.7, 45.9, 44.2, 40.7, 37.5, 35.0, 32.3, 31.7, 31.4, 29.9, 28.6, 28.5, 27.6, 26.8, 24.5, 22.6, 18.8, 14.0. Mass spectrum (ESI) m/z (relative intensity) 515 (M$^+$+H, 100). Exact mass (ESI) calculated for C$_{31}$H$_{47}$O$_6$ (M$^+$+H), 515.3373; found 515.3372. LC/MS analysis (Waters MicroMass ZQ system) showed purity of 99.1% and retention time of 5.9 min for the title compound.

(6aR,10aR)-6,6-Dimethyl-3-(2-methyloctan-2-yl)-9-oxo-6a,7,8,9,10,10a-hexahydro-6H-benzo[c]chromen-1-yl (R)-2,3-dihydroxypropanoate (compound 10.12). To a stirred solution of compound 10.1 (80 mg, 0.16 mmol) in CH$_2$Cl$_2$ (3.5 ml) at room temperature was added TFA (1 ml) under argon atmosphere. The reaction was stirred for 15 min to ensure complete formation of the product. The reaction was quenched using saturated aqueous NaHCO$_3$ and extracted using AcOEt. The organic phase was dried over MgSO$_4$, and the solvent was removed under reduced pressure. The residue was chromatographed on silica gel (40% AcOEt in hexane) to give compound 10.12 as colorless oil (70 mg, 95% yield). IR (neat): 3384, 2955, 1761, 1703, 1622, 1563, 1414, 1267, 1183, 1111 cm$^{-1}$. $^1$H NMR (500 MHz, CDCl$_3$) δ 6.73 (d, J=1.5 Hz, 1H, ArH), 6.57 (d, J=1.4 Hz, 1H, ArH), 4.53 (dd, J=5.5 Hz, J=7.0 Hz, 1H, —CH—OH), 4.14 (dd, J=5.5 Hz, J=7.0 Hz, 1H, —C(CH$_2$)—OH), 4.08 (dd, J=5.5 Hz, J=7.0 Hz, 1H, —C(CH$_2$)—OH), 3.29 (ddd, J=15.0 Hz, J=3.5 Hz, J=2.0 Hz, 1H, 10eq-H), 2.73 (m as td, J=12.4 Hz, J=3.4 Hz, 1H, 10a-H), 2.60-2.53 (m, 1H, 8eq-H), 2.47-2.40

(m, 1H, 8ax-H), 2.26-2.15 (m, 2H, 10ax-H, 7eq-H), 2.03-1.96 (m as td, J=12 Hz, J=3 Hz, 1H, 6a-H), 1.53-1.48 (m, 6H, 7ax-H, 2'-H, 6-Me, especially 1.49, s, 6-Me), 1.23-1.16 (m, 12H, 3'-H, 4'-H, 5'-H, —C(CH$_3$)$_2$—, especially 1.22, s, —C(CH$_3$)$_2$—), 1.12 (s, 3H, 6-Me), 1.06 (sextet, J=7.5 Hz, 2H, 6'-H), 0.84 (t, J=6.5 Hz, 3H, 7'-H). $^{13}$C NMR (100 MHz, CDCl$_3$) δ 212.1 (>C=O), 171.6 (—C(O)—O—), 154.2 (ArC-1 or ArC-5), 151.3 (ArC-5 or ArC-1), 148.9 (tertiary aromatic), 113.9 (tertiary aromatic), 113.7 (ArC-2 or ArC-4), 112.1 (ArC-4 or ArC-2), 72.2 (—CH—OH), 63.2 (CH$_2$—O—), 48.0, 46.5, 44.3, 40.7, 37.6, 35.3, 31.7, 29.9, 28.5, 27.6, 27.1, 24.5, 22.6, 18.7, 14.0. Mass spectrum (ESI) m/z (relative intensity) 461 (M$^+$+H, 100). Exact mass (ESI) calculated for C$_{27}$H$_{41}$O$_6$ (M$^+$+H), 461.2903; found 461.2895. LC/MS analysis (Waters MicroMass ZQ system) showed purity of 98.6% and retention time of 5.2 min for the title compound.

(6aR,10aR)-6,6-Dimethyl-3-(2-methyloctan-2-yl)-9-oxo-6a,7,8,9,10,10a-hexahydro-6H-benzo[c]chromen-1-yl (S)-2,3-dihydroxypropanoate (compound 10.13). To a stirred solution of compound 10.2 (15 mg, 0.03 mmol) in CH$_2$Cl$_2$ (0.5 ml) at room temperature was added TFA (0.1 ml). The reaction was stirred for 15 min to ensure complete formation of the product. The reaction was quenched using saturated aqueous NaHCO$_3$ and extracted using AcOEt. The organic phase was dried over MgSO$_4$, and the solvent was removed under reduced pressure. The residue was chromatographed on silica gel (40% AcOEt in hexane) to give compound 10.13 as colorless oil (10 mg, 92% yield). LC/MS analysis (Waters MicroMass ZQ system) showed purity of 98.9% and retention time of 5.2 min for the title compound.

(6aR,10aR)-6,6-Dimethyl-3-(2-methyloctan-2-yl)-9-oxo-6a,7,8,9,10,10a-hexahydro-6H-benzo[c]chromen-1-yl 3-hydroxy-2-(hydroxymethyl)-2-methylpropanoate (10.14). To a stirred solution of compound 10.3 (15 mg, 0.03 mmol) in CH$_2$Cl$_2$ (0.5 ml) at room temperature was added TFA (0.1 ml). The reaction was stirred for 15 min to ensure complete formation of the product. The reaction was quenched using saturated aqueous NaHCO$_3$ and extracted using AcOEt. The organic phase was dried over MgSO$_4$, and the solvent was removed under reduced pressure. The residue was chromatographed on silica gel (40% AcOEt in hexane) to give compound 10.14 as colorless oil (10 mg, 90% yield). IR (neat): 3394, 2928, 1746, 1705, 1623, 1562, 1412, 1259, 1198, 1099 cm$^{-1}$. $^1$H NMR (500 MHz, CDCl$_3$) δ 6.72 (d, J=1.5 Hz, 1H, ArH), 6.46 (d, J=1.4 Hz, 1H, ArH), 4.09 (d, J=10.5 Hz, 1H, —CH$_2$—O—), 4.00 (d, J=11.0 Hz, 1H, —CH$_2$—O—), 3.89-3.82 (m as dd, J=11.0 Hz, J=6.5 Hz, 2H, —CH$_2$—O—) 3.32 (ddd, J=15.0 Hz, J=3.5 Hz, J=2.0 Hz, 1H, 10eq-H), 2.75 (m as td, J=12.4 Hz, J=3.4 Hz, 1H, 10a-H), 2.58-2.52 (m, 1H, 8eq-H), 2.49-2.40 (m, 1H, 8ax-H), 2.27-2.14 (m, 2H, 10ax-H, 7eq-H), 2.04-1.97 (m as td, J=12 Hz, J=3 Hz, 1H, 6a-H), 1.53-1.46 (m, 6H, 7ax-H, 2'-H, 6-Me, especially 1.48, s, 6-Me), 1.33 (s, 3H, C(CH$_3$)), 1.24-1.15 (m, 12H, 3'-H, 4'-H, 5'-H, —C(CH$_3$)$_2$—, especially 1.22, s, —C(CH$_3$)$_2$—), 1.12 (s, 3H, 6-Me), 1.08 (sextet, J=7.5 Hz, 2H, 6'-H), 0.84 (t, J=6.5 Hz, 3H, 7'-H). $^{13}$C NMR (100 MHz, CDCl$_3$) δ 211.7 (>C=O), 174.2 (—C(O)—O—), 154.0 (ArC-1 or ArC-5), 151.2 (ArC-5 or ArC-1), 149.1 (tertiary aromatic), 114.0 (tertiary aromatic), 113.3 (ArC-2 or ArC-4), 112.2 (ArC-4 or ArC-2), 67.4 (—CH—OH), 67.3 (CH—OH), 50.2, 48.0, 46.5, 44.3, 40.8, 37.5, 35.2, 31.7, 29.9, 29.7, 28.6, 28.5, 27.6, 27.1, 24.5, 22.6, 18.8, 17.3, 14.0. Mass spectrum (ESI) m/z (relative intensity) 489 (M$^+$+H, 100). Exact mass (ESI) calculated for C$_{29}$H$_{45}$O$_6$ (M$^+$+H), 489.3216; found 489.3208. LC/MS analysis (Waters MicroMass ZQ system) showed purity of 98.4% and retention time of 5.3 min for the title compound.

I. Phenolic Substituted Triazole Derivatives

Phenolic substituted triazole derivative compound 11.2 (shown in Table 1) was synthesized from azido compound 1.21 by a method depicted in Scheme 11. Starting azido compound 1.21 and by using the same method and methods disclosed earlier, additional phenolic substituted triazole derivatives of 11.2 can be synthesized.

Scheme 11
Reagents and conditions: (a) (CH$_3$CO)$_2$O, DMAP, CH$_2$Cl$_2$ rt, 1 h, 89%; (b) 2.13, CuSO$_4$•5H$_2$O, sodium ascorbate, tert-BuOH/H$_2$O, rt, 24 h, 90%.

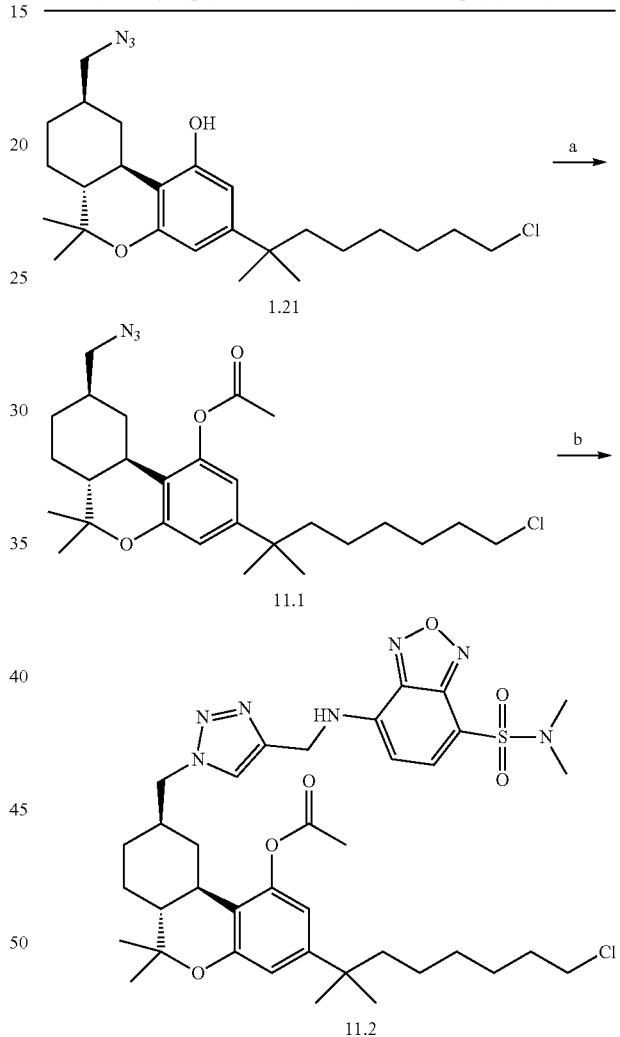

(6aR,9R,10aR)-9-(azidomethyl)-3-(8-chloro-2-methyloctan-2-yl)-6,6-dimethyl-6a,7,8,9,10,10a-hexahydro-6H-benzo[c]chromen-1-yl acetate (compound 11.1). To a solution of compound 1.21 (50 mg, 0.1 mmol) in anhydrous CH$_2$Cl$_2$ (1 mL), under an argon atmosphere at room temperature, were added acetic anhydride (0.04 mL, 0.4 mmol)) and DMAP (25 mg, 0.2 mmol) sequentially. Upon completion the reaction was poured into water and was stirred for 30 minutes before extracted with diethyl ether. The combined organic fragments were washed sequentially with 1N aqueous HCl, saturated aqueous NaHCO$_3$, water and brine, dried under MgSO$_4$ and evaporated under reduced pressure.

Purification by flash column chromatography (silica gel, 20% diethyl ether/hexanes) afforded the title compound 11.1 (48 mg, 89%) as a colorless oil. $^1$H NMR (500 MHz, CDCl$_3$) δ 6.65 (d, J=2.0 Hz, 1H), 6.48 (d, J=2.0 Hz, 1H), 3.49 (t, J=6.8 Hz, 2H), 3.28 (dd, J=12.0, 5.7 Hz, 1H), 3.09 (dd, J=12.0, 8.0 Hz, 1H), 2.84-2.77 (m, 1H), 2.36 (td, J=11.3, 2.8 Hz, 1H), 2.32 (s, 3H), 1.95-1.87 (m, 2H), 1.79-1.66 (dq, J=14.5, 7.0, 6.4 Hz, 3H), 1.55-1.45 (m, 3H), 1.40-1.31 (m, 5H), 1.27-1.16 (m, 9H), 1.16-1.03 (m, 6H), 0.89 (q, J=12.1 Hz, 1H).

(6aR,9R,10aR)-3-(8-chloro-2-methyloctan-2-yl)-9-((4-((7-(N,N-dimethylsulfamoyl)benzo [c][1,2,5]oxadiazol-4-yl)amino)-1H-1,2,3-triazol-1-yl)methyl)-6,6-dimethyl-6a,7,8,9,10,10a-hexahydro-6H-benzo[c]chromen-1-yl acetate (compound 11.2). To a solution of 11.1 (27 mg, 0.05 mmol) and 2.13 (14 mg, 0.05 mmol) in 1 mL 1:1 mixture of tert-BuOH:H$_2$O under Ar at room temperature was added aqueous solution of CuSO$_4$·5H$_2$O (0.6 mg, 0.0025 mmol) and 1M freshly prepared aqueous solution of sodium ascorbate (1 mg, 0.005 mmol). The reaction was left for 24 h. The mixture was diluted with CH$_2$Cl$_2$. The organic phase was washed with brine, dried over MgSO$_4$, concentrated under reduced pressure, and chromatographed (silica gel, 80% EtOAc/hexanes) to give 11.2 (38 mg, 90%) as yellow powder. $^1$H NMR (500 MHz, CDCl$_3$) δ 7.90 (d, J=7.8 Hz, 1H), 7.57 (s, 1H), 6.64 (d, J=1.9 Hz, 1H), 6.44 (d, J=1.9 Hz, 1H), 6.42-6.37 (m, 1H), 6.35-6.25 (m, 2H), 4.73 (d, J=5.2 Hz, 2H), 4.34 (dd, J=13.6, 5.7 Hz, 1H), 4.13 (td, J=8.7, 4.1 Hz, 1H), 3.79 (s, 1H), 3.48 (t, J=6.8 Hz, 2H), 2.88 (s, 6H), 2.49 (d, J=12.8 Hz, 1H), 2.40-2.28 (m, 1H), 2.23 (s, 1H), 2.04 (d, J=1.6 Hz, 3H), 1.91 (t, J=14.1 Hz, 2H), 1.73-1.59 (m, 3H), 1.54-1.42 (m, 4H), 1.36 (d, J=21.8 Hz, 4H), 1.30-1.12 (m, 9H), 1.06 (s, 4H), 0.94 (q, J=12.0 Hz, 1H).

It is to be understood that while embodiments of an invention have been shown and described in the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of formula I or a pharmaceutically acceptable salt thereof, and all stereoisomers and enantiomers:

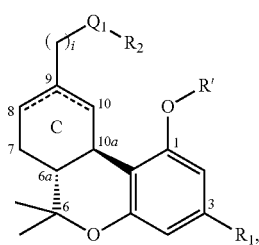

I wherein:

=== can be a single or a double bond between C$_8$-C$_9$ or C$_9$-C$_{10}$, provided that no more than one double bond is present in the C-ring of formula I;

Q$_1$ is selected from

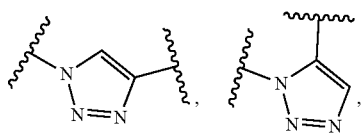 [SMILES: *c1cn(*)nn1 ; *c1cnnn1*]

i is an integer from 0 to 3;

R$_1$ is selected from:

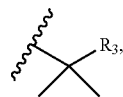

a$_1$

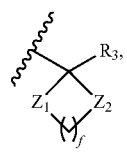

a$_2$

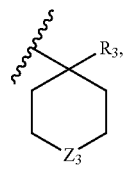

a$_3$

Z$_1$, Z$_2$, and Z$_3$ are independently selected from CH$_2$, O, S, NH and NMe;

R$_3$ is selected from —(CH$_2$)$_j$—R$_4$ and —(CH$_2$)$_j$—B—(CH$_2$)$_k$—R$_4$;

B is selected from CH$_2$—CH$_2$ and CH=CH, C≡C;

R$_4$ is selected from the group consisting of H, F, Cl, Br, I, NCS, N$_3$, CN, NO$_2$, ONO$_2$, SO$_2$F, OH, SH, NH$_2$, and —N(Alkyl)$_2$;

f is an integer from 0 to 3;

j is an integer from 0 to 7;

k is an integer from 0 to 7;

R' is selected from —H, —C(O)CH$_3$,

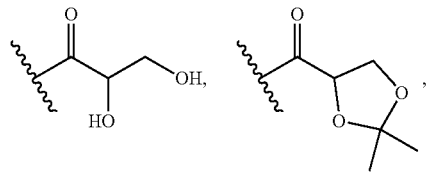

-continued

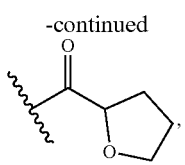

and all enantiomers;
$R_2$ is selected from $R_5$ and $T-R_5$;
T is a tether selected from

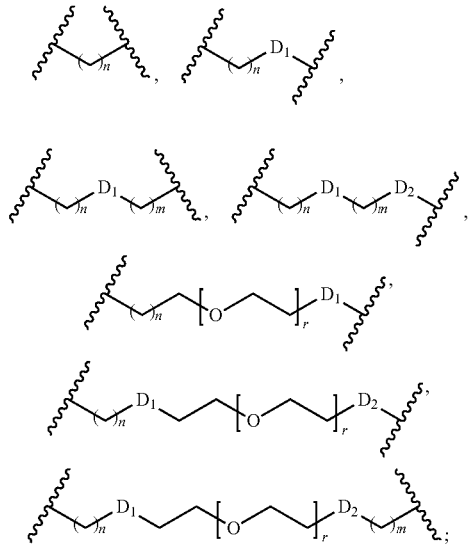

$D_1$ and $D_2$ are independently selected from the group consisting of —O—, —S—, —NH—, —OC(O)—, —C(O)O—, C(O)NH, —NHC(O)—, —NHSO$_2$—, and

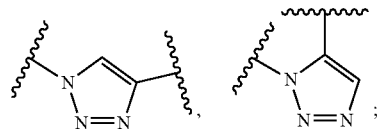 [SMILES: *c1cn(*)nn1 ; *c1cnnn1*]

n is an integer from 0 to 7;
m is an integer from 1 to 7;
r is an integer from 1 to 5;
$R_5$ is selected from the group consisting of fluorophore moieties, nitroxide spin labels, metal chelates, biotin, heterocyclic moieties, —(NH)-Alkyl, —N(Alkyl)$_2$, —O-Alkyl, F, Cl, Br, I, NCS, N$_3$, CN, NO$_2$, ONO$_2$, SO$_2$F, OH, SH, and NH$_2$, wherein fluorophore moieties, nitroxide spin labels, metal chelates, biotin, and heterocyclic moieties, if present, can be bonded to $Q_1$ or T from any possible position.

2. The compound or pharmaceutically acceptable salt thereof, and all stereoisomers and enantiomers of claim 1, wherein:
R' is H; and
$R_5$ is selected from the group consisting of —(NH)-Alkyl, —N(Alkyl)$_2$, —O-Alkyl, F, Cl, Br, I, NCS, N$_3$, CN, NO$_2$, ONO$_2$, SO$_2$F, OH, SH, and NH$_2$, fluorophore moieties, nitroxide spin labels, biotin, and heterocyclic moieties, wherein fluorophore moieties, nitroxide spin labels, biotin, and heterocyclic moieties, if present, can be bonded to $Q_1$ or T from any possible position.

3. The compound or pharmaceutically acceptable salt thereof, and all stereoisomers and enantiomers of claim 1, wherein
R' is H; and
$Q_1$ is selected from

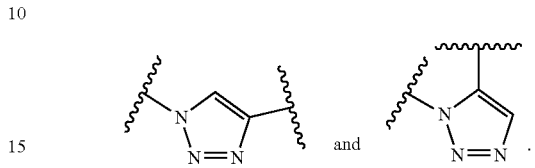

4. The compound or pharmaceutically acceptable salt thereof, and all stereoisomers and enantiomers of claim 1, wherein
R' is H; and
T is a tether selected from

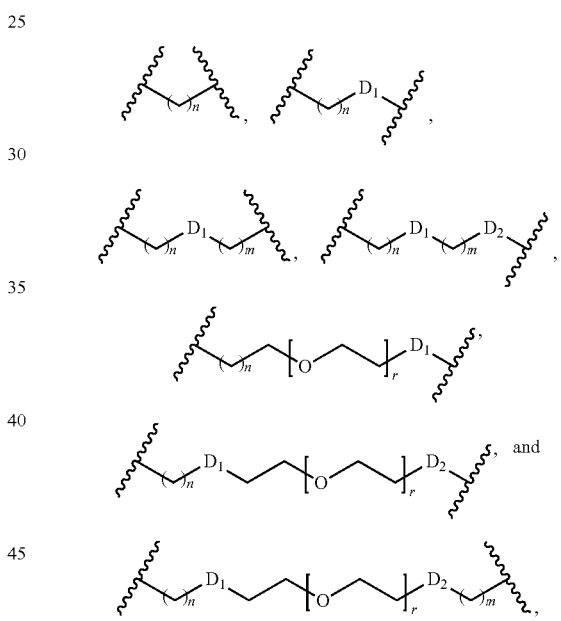

wherein
each of $D_1$ and $D_2$ is independently selected from the group consisting of —O—, —S—, —NH—, —OC(O)—, —C(O)O—, C(O)NH, —NHC(O)—, —NHSO$_2$—,

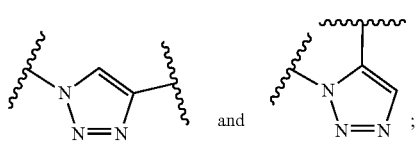 [SMILES: *c1cn(*)nn1 ; *c1cnnn1*]

n is an integer from 0 to 7;
m is an integer from 1 to 7; and
r is an integer from 1 to 5.

5. The compound or pharmaceutically acceptable salt thereof, and all stereoisomers and enantiomers of claim 1, wherein R' is H;

$R_1$ is selected from:

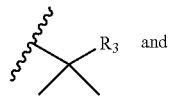 a₁ and

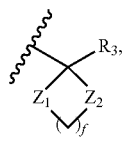 a₂ wherein each of $Z_1$ and $Z_2$ is $CH_2$;

$R_3$ is —$(CH_2)_j$—$R_4$;

$R_4$ is selected from the group consisting of H, Cl and F;

f is an integer from 0 to 3;

j is an integer from 3 to 7; and $R_5$ is selected from the group consisting of fluorophore moieties, nitroxide spin labels, metal chelates, biotin, and heterocyclic moieties wherein fluorophore moieties, nitroxide spin labels, metal chelates, biotin, and heterocyclic moieties, if present, can be bonded to $Q_1$ or T from any possible position.

6. The compound or pharmaceutically acceptable salt thereof, and all stereoisomers and enantiomers of claim 1, wherein R' is H, $R_1$ is:

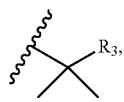 a₁

$R_3$ is —$(CH_2)_j$—$R_4$;

$R_4$ is selected from the group consisting of H, Cl, F, Br, I, and CN; and j is an integer from 3 to 7.

7. The compound or pharmaceutically acceptable salt thereof, and all stereoisomers and enantiomers of claim 1, wherein ═══ is a single bond between $C_8$-$C_9$ and $C_9$-$C_{10}$;

$Q_1$ is

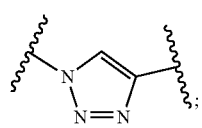;

i=1;

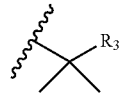

$R_1$ is $R_3$ is —$(CH_2)_j$—$R_4$;

j=6;

$R_4$ is Cl;

R' is H;

$R_2$ is T-$R_5$;

T is

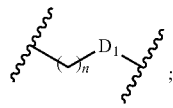;

$D_1$ is —NHC(O)—;

n=1; and $R_5$ is a fluorophore moiety.

8. The compound or pharmaceutically acceptable salt thereof, and all stereoisomers and enantiomers of claim 1, wherein ═══ is a single bond between $C_8$-$C_9$ and $C_9$-$C_{10}$;

$Q_1$ is

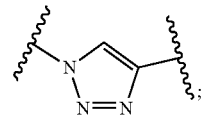 [SMILES: *c1cn(*)nn1];

i=1;

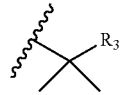

$R_1$ is $R_3$ is —$(CH_2)_j$—$R_4$;

j=6;

$R_4$ is Cl;

R' is H;

$R_2$ is T-$R_5$;

T is selected from

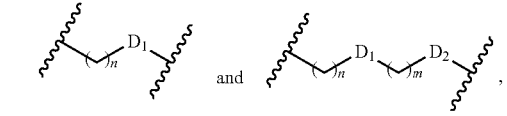, $D_1$ is —NHC(O)—, —NH—, O;

$D_2$ is —NHC(O)—;

n=1;

m=4; and $R_5$ is a fluorophore moiety.

9. The compound or pharmaceutically acceptable salt thereof, and all stereoisomers and enantiomers of claim 1, wherein ═ is a single bond between $C_5$-$C_9$ and $C_9$-$C_{10}$, $R_2$ is T-$R_5$;

T is selected from

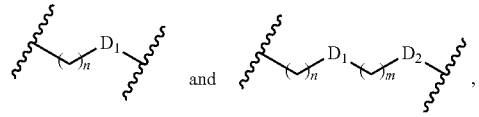

and $D_1$ is selected from —NHC(O)—, —NH— and O;

$D_2$ is —NHC(O)—;

n=1, m=4; and $R_5$ is a fluorophore moiety.

10. The compound or pharmaceutically acceptable salt thereof, and all stereoisomers and enantiomers of claim 1, wherein the compound is selected from the group consisting of:

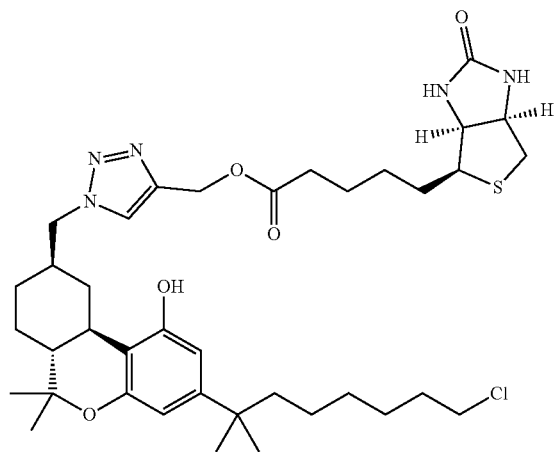

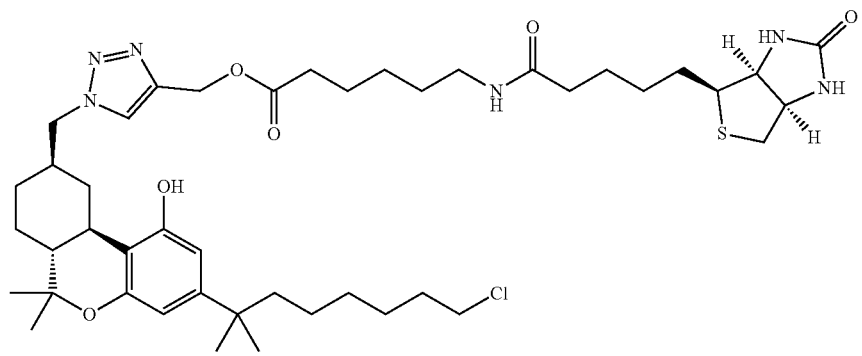

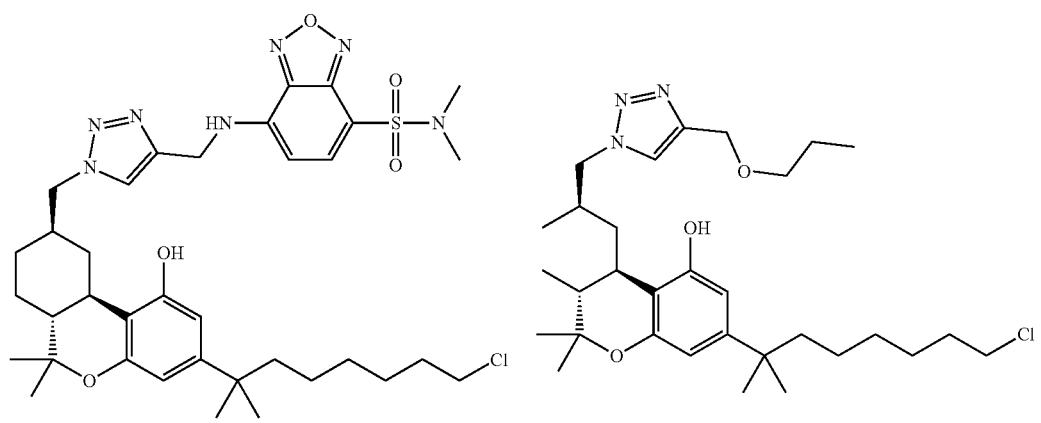

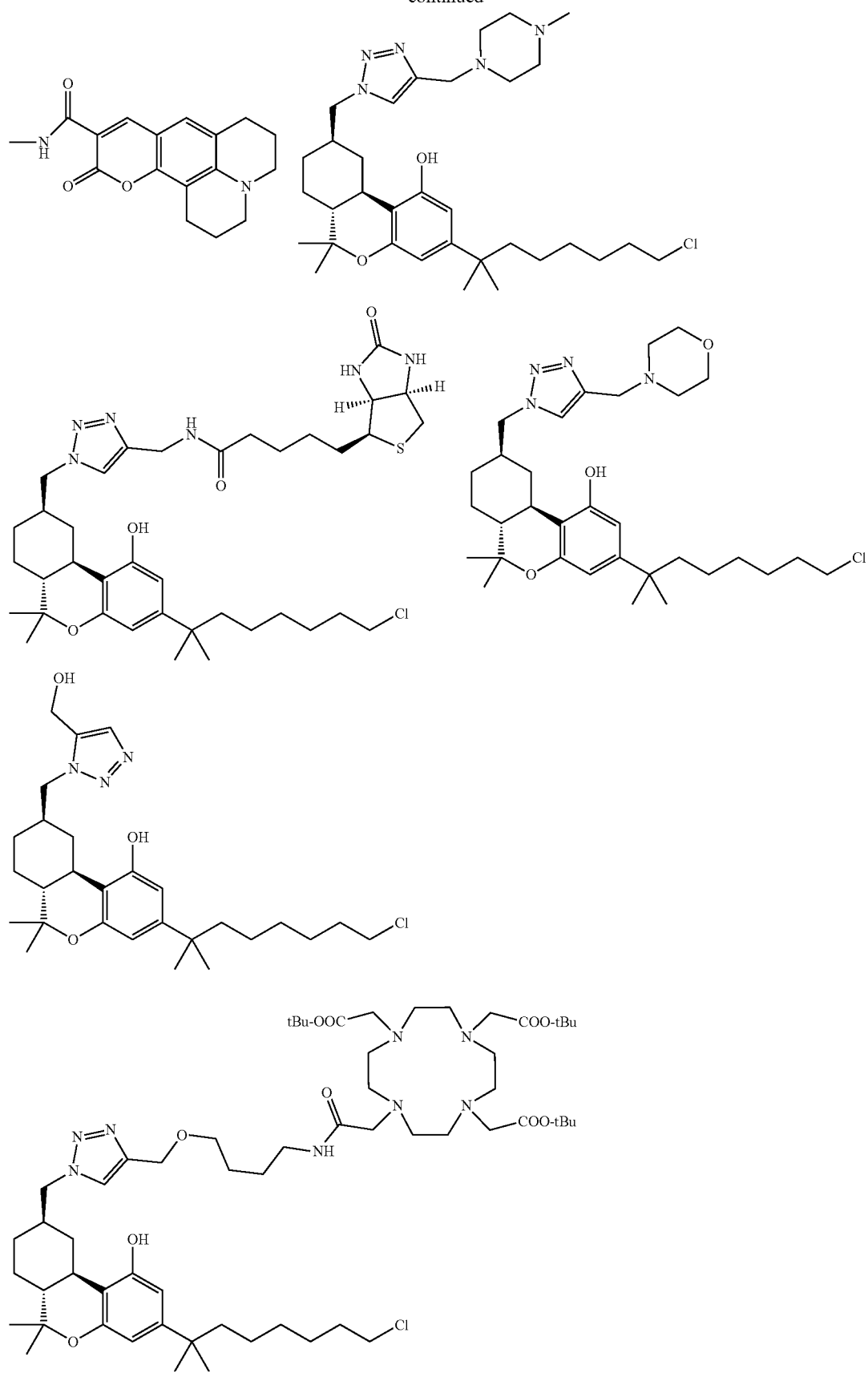

123
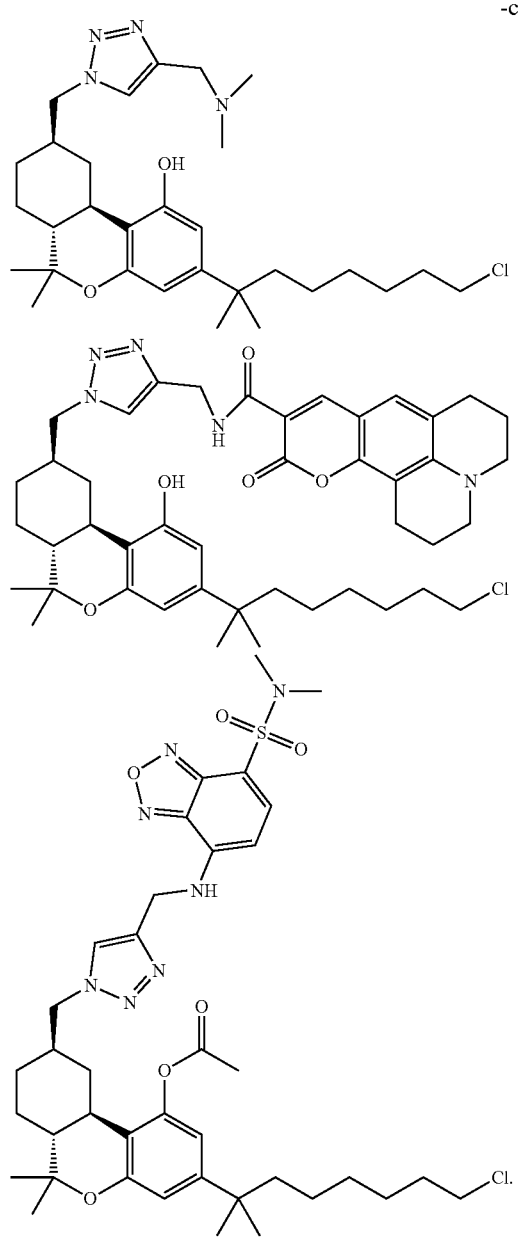
124
-continued
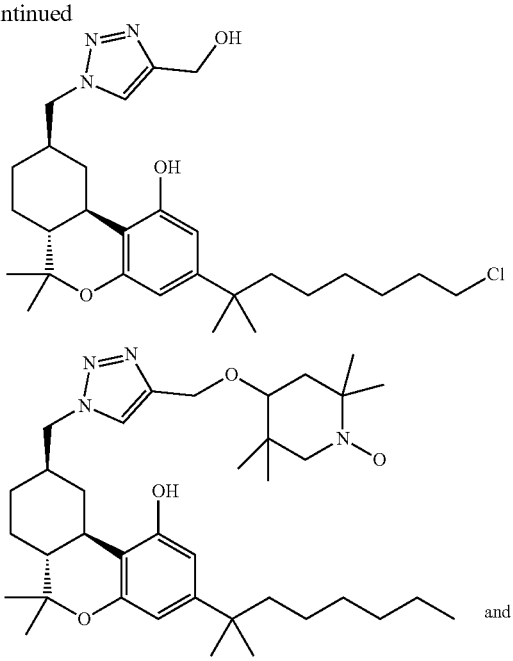
and
* * * * *

UNITED STATES PATENT AND TRADEMARK OFFICE
CERTIFICATE OF CORRECTION

PATENT NO. : 11,746,113 B2  
APPLICATION NO. : 17/205300  
DATED : September 5, 2023  
INVENTOR(S) : Alexandros Makriyannis et al.

Page 1 of 1

It is certified that error appears in the above-identified patent and that said Letters Patent is hereby corrected as shown below:

In the Claims

Claim 10, Columns 120-121:

Delete " 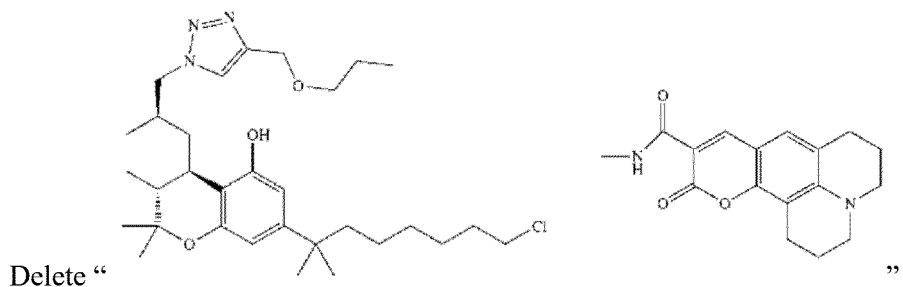 "

And insert --  --

Signed and Sealed this  
Twenty-ninth Day of October, 2024

Katherine Kelly Vidal  
*Director of the United States Patent and Trademark Office*